(12) United States Patent
LaVoie et al.

(10) Patent No.: US 8,741,917 B2
(45) Date of Patent: Jun. 3, 2014

(54) BENZO [C] PHENANTHRIDINES AS ANTIMICROBIAL AGENTS

(75) Inventors: Edmond J. LaVoie, New Brunswick, NJ (US); Ajit Parhi, New Brunswick, NJ (US); Daniel S. Pilch, Somerset, NJ (US); Malvika Kaul, Somerset, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 191 days.

(21) Appl. No.: 13/144,675

(22) PCT Filed: Jan. 15, 2010

(86) PCT No.: PCT/US2010/021237
§ 371 (c)(1),
(2), (4) Date: Jul. 14, 2011

(87) PCT Pub. No.: WO2010/083436
PCT Pub. Date: Jul. 22, 2010

(65) Prior Publication Data
US 2012/0022061 A1 Jan. 26, 2012

Related U.S. Application Data

(60) Provisional application No. 61/144,965, filed on Jan. 15, 2009, provisional application No. 61/171,720, filed on Apr. 22, 2009.

(51) Int. Cl.
*A01N 43/42* (2006.01)
*A61K 31/44* (2006.01)
*C07D 221/22* (2006.01)
*C07D 221/18* (2006.01)

(52) U.S. Cl.
USPC ............. 514/279; 514/280; 514/284; 546/38; 546/42; 546/61

(58) Field of Classification Search
USPC ................ 514/279, 280, 284; 546/38, 42, 61
See application file for complete search history.

(56) References Cited

U.S. PATENT DOCUMENTS

| | | | |
|---|---|---|---|
| 4,309,539 A | 1/1982 | Boller et al. | |
| 4,782,058 A | 11/1988 | Griffith | |
| 5,177,067 A | 1/1993 | Guerry et al. | |
| 5,177,075 A | 1/1993 | Suto et al. | |
| 2002/0035090 A1 | 3/2002 | Zeldis et al. | |
| 2002/0077333 A1 | 6/2002 | Dey et al. | |
| 2006/0183943 A1 | 8/2006 | Hu | |
| 2008/0027028 A1 | 1/2008 | Chichak | |
| 2008/0300239 A1 | 12/2008 | Adams et al. | |
| 2009/0076074 A1 | 3/2009 | Jung et al. | |
| 2009/0312319 A1 | 12/2009 | Ren et al. | |
| 2010/0120810 A1 | 5/2010 | Leblond et al. | |
| 2012/0059026 A1 | 3/2012 | LaVoie | |
| 2013/0109713 A1 | 5/2013 | Lavoie et al. | |
| 2013/0116278 A1 | 5/2013 | Lavoie et al. | |

FOREIGN PATENT DOCUMENTS

| | | |
|---|---|---|
| DE | 4327748 A1 | 2/1995 |
| EP | 0719764 A1 | 7/1996 |
| EP | 1078920 A1 | 2/2001 |
| EP | 1724262 A1 | 11/2006 |
| WO | WO 92/19242 A1 | 11/1992 |
| WO | WO 03/018017 A1 | 3/2003 |
| WO | WO 03/078397 A1 | 9/2003 |
| WO | WO 03/099274 A1 | 12/2003 |
| WO | WO 04/000814 A1 | 12/2003 |
| WO | WO 2004/005472 A2 | 1/2004 |
| WO | WO 2004/041210 A2 | 5/2004 |
| WO | WO 2004/087145 A2 | 10/2004 |
| WO | WO 2005/075428 A1 | 8/2005 |
| WO | WO 2006/067048 A1 | 6/2006 |
| WO | WO 2006/105289 A1 | 10/2006 |

(Continued)

OTHER PUBLICATIONS

Yamaguchi et. al., Chemical and Pharmaceutical Bulletin, 1983, Nihon Yakagakkai, vol. 31, issue 5, pp. 1601-1611.*
Ishii et. al., Chemical and Pharmaceutical Bulletin, 1984, Nihon Yakugakkai, vol. 32, No. 8, pp. 2984-2994.*
Cole et. al., Journal of Medicinal Chemistry, 2003, American Chemical Society, vol. 46, pp. 207-209.*
Okudaira et. al., The Journal of Pharmacology and Experimental Therapeutics, 2000, The American Society for Pharmacology and Experimental Therapeutics, vol. 294, No. 2, pp. 580-587.*

(Continued)

*Primary Examiner* — Sarah Pihonak
(74) *Attorney, Agent, or Firm* — Viksnins Harris & Padys PLLP

(57) ABSTRACT

The present invention provides compounds of formula I: formula (I) wherein $X^1$-$X^4$ and $R^1$-$R^{12}$ have any of the values defined in the specification, as well as salts and prodrugs thereof, which inhibit major molecular mechanisms associated with bacterial cell division and proliferation so as to be useful for the treatment and/or prevention of bacterial infections. The invention also provides compositions comprising these compounds as well as methods for using these compounds to inhibit bacterial cell division and proliferation and to treat bacterial infections.

20 Claims, 16 Drawing Sheets

(56) References Cited

FOREIGN PATENT DOCUMENTS

| WO | WO 2008/016596 A2 | 2/2008 |
|---|---|---|
| WO | WO 2010/127307 A1 | 11/2010 |
| WO | WO 2011/156626 A1 | 12/2011 |

OTHER PUBLICATIONS

Dykhuizen, Antonie van Leeuwenhoek, 1998, Kluwer Academic Publishers, vol. 73, pp. 25-33.*
Chen et. al., Journal of Medicinal Chemistry, 2001, American Chemical Society, vol. 44, pp. 2374-2377.*
Foroumadi et. al., European Journal of Medicinal Chemistry, 2003, Elsevier, vol. 38, pp. 851-854.*
Huecas et. al., The Journal of Biological Chemistry, 2007, American Society for Biochemistry and Molecular Biology, vol. 282, pp. 37515-37528.*
Smidrkal et. al., Collection of Czechoslovak Chemical Communications, 1985, Ceskoslovenska akademie ved, vol. 50, No. 4, pp. 861-868.*
Augstein et al., "Synthesis of 11-Hydroxy-2,3,9,10-tetramethoxy-5,6,13,13a-tetrahydro-8H-dibenzo[a,g]quinolizine. A Contribution to the Structure of Stepharotine", *Stepharotine*, vol. 34, No. 5, 1349-1352 (1969).
Beilstein, Database Beilstein Institute for Organic Chemistry, XP002591901, Database Accession No. 3834367 (BRN) abstract (1918).
Beilstein, Database Beilstein Institute for Organic Chemistry, XP002591900, Database Accession No. 3837583(BNR) abstract (1930).
Beuria, T.K. et al., "Sanguinarine Blocks Cytokinesis in Bacteria by Inhibiting FtsZ Assembly and Bundling", *Biochemistry*, 44, 16584-16593 (2005).
Database Registry [Online], Chemical Abstracts Service, XP002570845, Database accession No. 1043562-34-0/RN, abstract (2008).
Denes et al., "The chemistry of sanguinarine", XP002570844, Chemical Abstracts Service, Database accession No. 1960:91836, abstract, *Magyar Kemiai Folyoirat*, 64, 125-130 (1958).
Dyke et al., "The Chemistry of Cryptopine—I The Epicryptopines", *Tetrahedr0n*, vol. 24, No. 3, 1455-1465 (1968).
Dyke et al., "The Chemistry of Cryptopine—II Pseudocryptopine Chloride", *Tetrahedron*, vol. 25, 5375-5381 (1969).
Gopinath et al., "Dehydrogenation cyclization of 2-aryl-1-tetralone oxime acetates", XP002570843, Chemical Abstracts Service, Database accession No. 1960:23123, abstract, *Current Science*, 28, 241-242 (1959).

Patent Cooperation Treaty, International Searching Authority, Search Report and Written Opinion for PCT/US2010/021237, 19 pages, dated May 3, 2010.
Yaeko et al., "Studies of sanguinarine into *Bocconia cordata*. IV. Transformation of sanguinarine into bocconine", XP002570841, Chemical Abstracts Sservice, Database accession No. 1992:129332, abstract, *Journal of Heterocyclic Chemistry*, 28(8), 1841-1843 (1991).
Yamaguchi et al., "Utilization of Protopine and Related Alkaloids. XIV. Oxidation of the Photo-adduct of 1-Oxoanhydromethylberberine with Nitrosobenzene, and Synthesis of Ring C-Substituted Benzo[c]phenanthridines", *Chem. Pharm. Bull.*, 31(5), 1601-1611 (1983).
Akiba et al., "Preparation of 13-Substituted 8H-Dibenzo[a,g]quinolizin-8-onces by Intramolecular Wittig-Horner Reaction of Dialkyl 2-(o-Acyl-benzoyl)-1,2-dihydro-1-isoquinolylphosphonates", *Bull. Chem. Soc. Japan*, 57 (8), 2188-2192 (1984).
Bedi et al., "Synthesis and biological activity of novel antibacterial quinazolines", *Bioorganic & Medicinal Chemistry Letters*, vol. 14 (20), 5211-5213 (2004).
Bild et al., "Discovery of Inhibitors of MCF-7 Tumor Cells Adhesion to Endothelial Cells and Investigation on their Mode of Action", *Archiv Der Pharmazie*, vol. 337 (12), 687-694 (2004).
Ito et al., "A medium-term rat liver bioassay for rapid in vivo detection of carcinogenic potential of chemicals", *Cancer Sci*, vol. 94 (1), 3-8 (2003).
Jackson et al., "Non-Steroidal Aromatase Inhibitors Based on a Biphenyl Scaffod: Synthesis, in vitro SAR, and Molecular Modelling", *Chem. Med. Chem.*, vol. 3, (4), 603-618 (2008).
Kaul et al., "A Bactericidal Guanidinomethyl Biaryl That Alters the Dynamics of Bacterial FtsZ Polymerization", *Journal of Medicinal Chemistry*, 5(22), 10160-10176 (2012).
Leroux et al., "N-(4-Biphenylmethyl)imidazoles as Potential Therapeutics for the Treatment of Prostate Cancer: Metabolic Robustness Due to Fluorine Substituion?", *Helvetica Chimica Acta, Verlag Helvetica*, vol. 86, 2671-2686 (2003).
Sanders et al., "Selective Cytotoxicity of Topoisomerase-Directed Protoberberines against Glioblastoma Cells", *Biochemical Pharmacology*, vol. 56, 1157-1166 (1998).
Sethi, "Enzyme Inhibition VIII: Mode of Inhibition of Reverse Transcriptase Acitivity by Analogues, Isomers, and Related Alkaloids of Coralyne", *Journal of Phyarmaceutical Sciences*, vol. 74 (8), 889-891 (1985).
Wachall et al., "Imidazole Substitued Biphenyls: A new Class o Highly Potent and in Vivo Active Inhibitors of P450 17 as Potential Therapeutics for Treatment of Prostate Cancer", *Bioorganic & Medicinal Chemistry*, vol. 7 (9), 1913-1924 (1999).

* cited by examiner

BENZO [C] PHENANTHRIDINES AS ANTIMICROBIAL AGENTS

PRIORITY OF INVENTION

This application claims priority from U.S. Provisional Application No. 61/144,965, filed on 15 Jan. 2009 and from U.S. Provisional Application No. 61/171,720, filed on 22 Apr. 2009. The entire content of each of these provisional applications is hereby incorporated herein by reference.

FIELD OF THE INVENTION

The present invention relates to compounds, compositions and uses thereof for inhibiting bacterial cell cytokinesis, particularly FtsZ polymerization, Z-ring formation, and recruitment of divisome proteins.

BACKGROUND OF THE INVENTION

The emergence of multidrug resistant (MDR) bacterial pathogens (e.g. methicillin-resistant *Staphylococcus aureus* (MRSA), *Acinetobacter baumannii-calcoaceticus* complex (ABC), etc.) has added increasing concerns as to the adequacy of current antimicrobials and pathogen treatment methods. The lethality of such pathogens, particularly MRSA, has often led to treatment methods that are experimental or would otherwise normally be avoided in standard clinical practice. For example, the antibiotic colistin was traditionally considered too nephrotoxic and neurotoxic for clinical use, but is nevertheless used to treat many MDR bacterial infections due to a paucity of available active drugs. The growing threat from MDR pathogens highlights a critical need to expand currently available antimicrobials. In this connection, new antibiotics must be developed that exhibit novel mechanisms of action as well as the ability to circumvent known resistance pathways.

Elements of the bacterial cell division machinery present appealing targets for antimicrobial compounds because (i) they are essential for bacterial viability, (ii) they are widely conserved among bacterial pathogens, and (iii) they often have markedly different structures than their eukaryotic homologs. One such protein that has been identified as a potential target is the FtsZ protein. During the division process, FtsZ, along with approximately 15 other proteins, assemble at mid-cell into a large cell division complex (termed the divisome), ultimately facilitating cell cytokinesis. More importantly, FtsZ is widely conserved among many bacterial strains.

The appeal of FtsZ as a target has led to the identification of several FtsZ-directed inhibitors. Benzo[c]phenanthridines (e.g. sanguinarine and chelerythrine) present an emerging class of such inhibitors (Beuria, T. K., et al., *Biochemistry* 44:16584-16593). More specifically, benzo[c]phenanthridines (B[c]P compounds) prevent GTPase activity and FtsZ polymerization by competitively inhibiting the binding of GTP to FtsZ. Such competitive inhibition prevents FtsZ Z-ring formation and, ultimately, bacterial cell cytokinesis. Thus, these compounds are effective as antimicrobials.

Given the lethality of many MDR pathogens, an antimicrobial with heightened competitive inhibition of FtsZ GTPase activity is desirable. More specifically, an antimicrobial is desirable that increases the competitive inhibition of GTP binding to the FtsZ protein so as to effectively prevent FtsZ polymerization, FtsZ Z-ring formation, and bacterial cell division.

The present invention address one or more of the foregoing needs.

SUMMARY OF THE INVENTION

The present invention relates to compounds with antimicrobial activity. Representative compounds of formula I and II have demonstrated activity as antibiotic inhibitors of FtsZ polymerization, FtsZ Z-ring formation, and/or recruitment of divisome proteins.

In one embodiment the invention provides a compound of formula I:

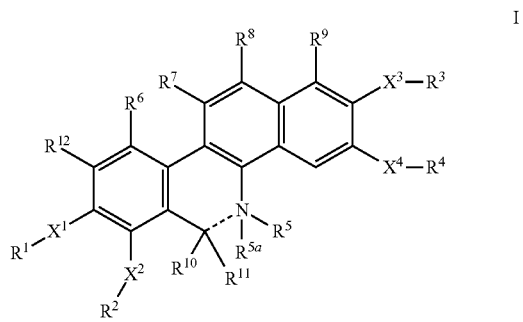

wherein:
the bond represented by - - - is a single or double bond;
when the bond represented by - - - is a single bond $R^5$, $R^{5a}$, $R^{10}$ and $R^{11}$ can have any of the values defined below; when the bond represented by - - - is a double bond $R^5$ can be absent or have any of the values defined below, $R^{10}$ can have any of the values defined below, and $R^{5a}$ and $R^{11}$ are absent;
$X^1$, $X^2$, $X^3$ and $X^4$ are each independently O, S or $NR^e$;
$R^1$ and $R^2$ are each independently, $(C_1-C_6)$alkyl, substituted $(C_1-C_6)$alkanoyl or —C(=O)$NR^fR^g$ or $R^1$ and $R^2$ together with the atoms to which they are attached form a 5 to 7 membered ring;
$R^3$ and $R^4$ are each independently, $(C_1-C_6)$alkyl, $(C_1-C_6)$alkanoyl or —C(=O)$NR^fR^g$ or $R^3$ and $R^4$ together with the atoms to which they are attached form a 5 to 7 membered ring;
$R^5$ is H, $(C_1-C_6)$alkyl, or substituted $(C_1-C_6)$alkyl; or $R^5$ and $R^{10}$ taken together with the atoms to which they are attached form an optionally substituted 5, 6, or 7 membered heterocyclic ring; and $R^{5a}$ is H, $(C_1-C_6)$alkyl, substituted $(C_1-C_6)$alkyl, or absent;
at least one of $R^6$, $R^7$, $R^8$, $R^9$ and $R^{12}$ is alkyl, substituted alkyl, optionally substituted alkenyl, optionally substituted alkynyl, optionally substituted cycloalkyl, optionally substituted arylalkyl, optionally substituted heteroarylalkyl, optionally substituted aryl, optionally substituted arylalkanoyl, $R^h$, or optionally substituted heteroaryl, wherein substituted alkyl is an alkyl group with 1 to 5 substituent groups independently selected from cycloalkyl, substituted cycloalkyl, alkoxycarbonyl, cyano, halo, hydroxyl, oxo, carboxy, aryloxy, heteroaryloxy, heterocyclooxy, nitro, and —$NR^aR^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic; and the remainder of $R^6$, $R^7$, $R^8$, $R^9$ and $R^{12}$ are independently H, halo, nitro, —$NR^cR^d$ optionally substituted alkyl, optionally substituted arylalkyl, optionally substituted heteroarylalkyl, optionally substituted aryl, or optionally substituted heteroaryl or $R^{12}$ is —$X^{13}$—$R^{13}$ wherein $X^{13}$ is O, S or $NR^e$ and $R^{13}$ is $(C_1-C_6)$ alkyl, substituted $(C_1-C_6)$alkyl, $(C_1-C_6)$ alkanoyl or $-C(=O)NR^fR^g$ or $R^{13}$ and $R^1$ together with the atoms to which they are attached form a 5 to 7 membered ring;

$R^{10}$ is H, optionally substituted $(C_1-C_6)$alkyl, optionally substituted $(C_1-C_6)$alkoxy, optionally substituted $(C_1-C_6)$alkyl-$S(=O)_n$—, optionally substituted aryloxy, optionally substituted aryl, CN, $NR^pR^q$, or optionally substituted aryl-S$(=O)_n$—, wherein n is 0, 1, or 2; and $R^{11}$ is H or optionally substituted $(C_1-C_6)$alkyl; or $R^{10}$ and $R^{11}$ together with the carbon to which they are attached form a carbonyl group; or $R^{10}$ and $R^5$ taken together with the atoms to which they are attached form an optionally substituted 5, 6, or 7 membered heterocyclic ring;

each $R^c$ and $R^d$ is independently H, $(C_1-C_6)$alkyl, aryl, heteroaryl, aryl$(C_1-C_6)$alkyl, or heteroaryl$(C_1-C_6)$alkyl; or $R^c$ and $R^d$ together with the nitrogen to which they are attached form a morpholino, piperazino, pyrrolidino or piperidino;

$R^e$ is H or $(C_1-C_6)$alkyl;

$R^f$ and $R^g$ are each independently H, aryl, heteroaryl, aryl$(C_1-C_6)$ alkyl, heteroaryl$(C_1-C_6)$ alkyl, or $(C_1-C_6)$ alkyl; or $R^f$ and $R^g$ together with the nitrogen to which they are attached form a morpholino, piperazino, pyrrolidino or piperidino;

each $R^h$ is independently selected from an aryl optionally substituted with one or more $R^k$, an alkyl substituted with one or more heterocycle, and an alkyl substituted with one or more substituted heterocycle;

each $R^k$ is independently alkyl, substituted alkyl, alkoxy, substituted alkoxy, heteroaryl, heterocycle, or $-S(O)_2 NR^mR^n$;

each $R^m$ and $R^n$ is independently H, $(C_1-C_6)$alkyl, aryl, heteroaryl, aryl$(C_1-C_6)$ alkyl, or heteroaryl$(C_1-C_6)$ alkyl; or $R^m$ and $R^n$ together with the nitrogen to which they are attached form a morpholino, piperazino, pyrrolidino or piperidino; and each $R^p$ and $R^q$ is independently H, $(C_1-C_6)$alkyl, aryl, heteroaryl, aryl$(C_1-C_6)$alkyl, or heteroaryl$(C_1-C_6)$alkyl; or $R^p$ and $R^q$ together with the nitrogen to which they are attached form a morpholino, piperazino, pyrrolidino or piperidino; and when the nitrogen attached to $R^5$ is a positively charged quaternary nitrogen, the compound is associated with a suitable counterion $X^-$;

or a salt or prodrug thereof.

In another embodiment, the invention provides a compound comprising the formula II:

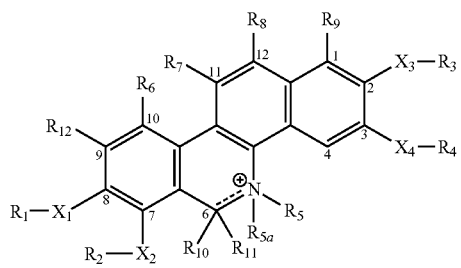

II wherein $X^1$, $X^2$, $X^3$, and $X^4$ are independently selected from the group consisting of an oxygen atom, a sulfur atom, and a nitrogen atom;

$R^1$ is comprised of an optionally substituted alkyl group having between 1-6 carbon atoms that, optionally, forms a heterocyclic ring with $R^2$;

$R^2$ is comprised of an optionally substituted alkyl group having between 1-6 carbon atoms that, optionally, forms a heterocyclic ring with $R^1$;

$R^3$ is comprised of an optionally substituted alkyl group having between 1-6 carbon atoms that, optionally, forms a heterocyclic ring with $R^4$;

$R^4$ is comprised of an optionally substituted alkyl group having between 1-6 carbon atoms that, optionally, forms a heterocyclic ring with $R^3$;

$R^5$ is comprised of an optionally substituted alkyl group having between 1-6 carbon atoms with the proviso that when the nitrogen atom adjacent to $R^5$ is double-bonded, $R^{5a}$ is absent from the formulation and when the nitrogen atom adjacent to $R^5$ is single-bonded, $R^{5a}$ is comprised of an optionally substituted alkyl group having 1-6 carbon atoms;

$R^6$, $R^7$, $R^8$, $R^9$, and $R^{12}$ are independently selected from the group consisting of a hydrogen atom, an optionally substituted alkyl group, an optionally substituted arylalkyl group, an optionally substituted heteroarylalkyl group, an optionally substituted aryl group, or an optionally substituted heteroaryl group; and $R^{10}$ is selected from the group consisting of a hydrogen atom, an optionally substituted alkyl group having 1-6 carbon atoms, and an optionally substituted alkoxy group having 1-6 carbon atoms; and $R^{11}$ is selected from the group consisting of a hydrogen atom or an optionally substituted alkyl group having 1-6 carbon atoms.

In another embodiment, the invention provides a method for treating a bacterial infection comprising: administering to a patient a composition having an antimicrobial compound of the formula I or II or a pharmaceutically acceptable salt or prodrug thereof.

In another embodiment, the invention provides a method for treating a bacterial infection in an animal (e.g. a mammal such as a human) comprising administering a compound of the formula I or II, or a pharmaceutically acceptable salt or prodrug thereof to the animal.

In another embodiment, the invention provides a method for inhibiting bacterial cell division comprising contacting a bacterial cell (in vitro or in vivo) with a compound of the formula I or II, or a pharmaceutically acceptable salt or prodrug thereof.

In another embodiment, the invention provides a method for inhibiting FtsZ Z-ring formation within a bacterial cell comprising contacting the bacterial cell (in vitro or in vivo) with a compound of the formula I or II, or a pharmaceutically acceptable salt or prodrug thereof.

In another embodiment, the invention provides a method for inhibiting polymerization of a FtsZ protein within a bacterial cell comprising contacting the bacterial cell (in vitro or in vivo) with a compound of the formula I or II, or a pharmaceutically acceptable salt or prodrug thereof.

In another embodiment, the invention provides a method for binding a compound of formula I or II, or a salt thereof to a GTP binding pocket of a FtsZ protein within a bacterial cell comprising contacting the bacterial cell (in vitro or in vivo) with the compound of formula I, or the pharmaceutically acceptable salt or a prodrug thereof. FtsZ proteins with compounds of formula I or II bound thereto can be used as pharmacological tools for further studying FtsZ protein structure and function.

In another embodiment, the invention provides a method for reducing GTPase activity and FtsZ polymerization within a bacterial cell comprising contacting the bacterial cell (in vitro or in vivo) with a compound of formula I or II, or a pharmaceutically acceptable salt or prodrug thereof.

In another embodiment, the invention provides a composition comprising a compound of formula I or II, or a pharmaceutically acceptable salt or prodrug thereof; and a pharmaceutically acceptable carrier.

In another embodiment, the invention provides a compound of the formula I or II, or a pharmaceutically acceptable salt or prodrug thereof for the prophylactic or therapeutic treatment of a bacterial infection.

In another embodiment, the invention provides a compound of the formula I or II, or a pharmaceutically acceptable salt or prodrug thereof for inhibiting bacterial cell division.

In another embodiment, the invention provides a compound of the formula I or II, or a pharmaceutically acceptable salt or prodrug thereof for inhibiting FtsZ Z-ring formation within a bacterial cell.

In another embodiment, the invention provides a compound of the formula I or II, or a pharmaceutically acceptable salt or prodrug thereof for inhibiting polymerization of a FtsZ protein within a bacterial cell.

In another embodiment, the invention provides a compound of the formula I or II, or a pharmaceutically acceptable salt or prodrug thereof for reducing GTPase activity and FtsZ polymerization within a bacterial cell.

In another embodiment, the invention provides the use of a compound of the formula I or II, or a pharmaceutically acceptable salt or prodrug thereof to prepare a medicament for treating a bacterial infection in an animal (e.g. a mammal such as a human).

In another embodiment, the invention provides the use of a compound of the formula I or II, or a pharmaceutically acceptable salt or prodrug thereof to prepare a medicament for inhibiting bacterial cell division in an animal (e.g. a mammal such as a human).

In another embodiment, the invention provides the use of a compound of the formula I or II, or a pharmaceutically acceptable salt or prodrug thereof to prepare a medicament for inhibiting FtsZ Z-ring formation within a bacterial cell in an animal (e.g. a mammal such as a human).

In another embodiment, the invention provides the use of a compound of the formula I or II, or a pharmaceutically acceptable salt or prodrug thereof to prepare a medicament for inhibiting polymerization of a FtsZ protein within a bacterial cell in an animal (e.g. a mammal such as a human).

In another embodiment, the invention provides the use of a compound of the formula I or II, or a pharmaceutically acceptable salt or prodrug thereof to prepare a medicament for reducing GTPase activity and FtsZ polymerization within a bacterial cell in an animal (e.g. a mammal such as a human).

The invention also provides processes and intermediates (e.g. a compound of formula X) disclosed herein that are useful for preparing compounds of formula I or II, or salts or prodrugs thereof.

Additional embodiments and limitations will be apparent to one of ordinary skill in the art based upon the disclosure provided herein.

DETAILED DESCRIPTION OF THE INVENTION

Definitions

Figure 1:
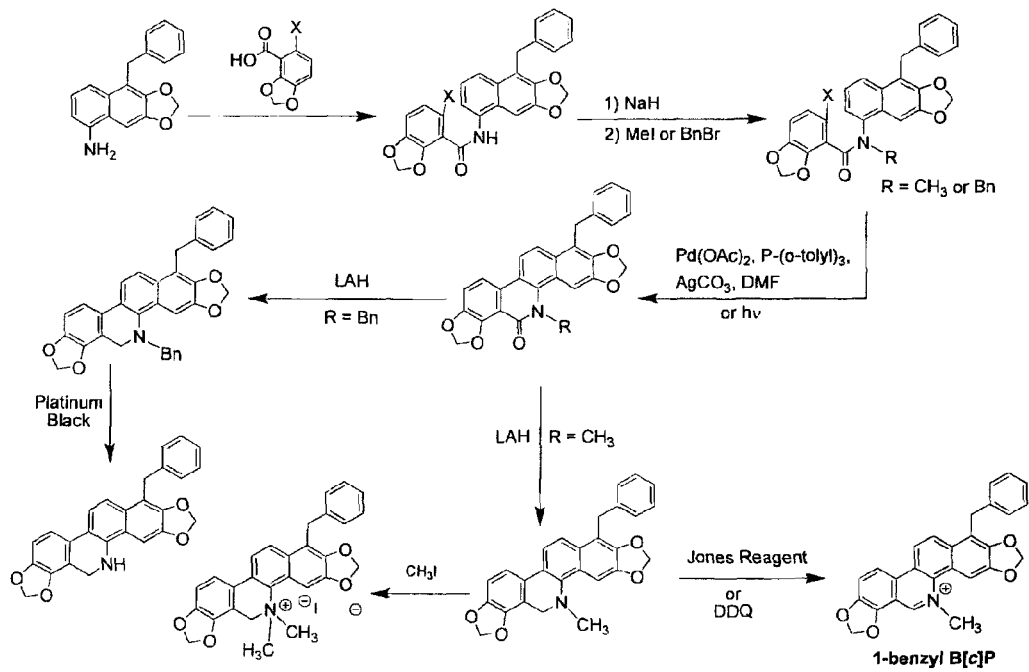
FIG. 1 illustrates one method for preparing core pentacyclic ring systems through the formation of benzophenanthridin-6-ones.

As used herein, "an alkyl group" denotes both straight and branched carbon chains with one or more carbon atoms, but reference to an individual radical such as "propyl" embraces only the straight chain radical, a branched chain isomer such as "isopropyl" specifically referring to only the branched chain radical.

As used herein, "substituted alkyl" is an alkyl group, as defined above, wherein one or more carbon atoms in the alkyl chain have been replaced with a heteroatom independently selected from —O—, —S— and NR— (where R is hydrogen or an alkyl group). Alternatively, a substituted alkyl refers to substitution of the hydrogens of the alkyl group with 1 to 5 substituent groups independently selected from the following: cycloalkyl, substituted cycloalkyl, alkoxycarbonyl (e.g. —CO$_2$Me), cyano, halo, hydroxyl, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, cycloalkyl, substituted cycloalkyl, aryl, heteroaryl and heterocyclic. Substituted alkyl groups are exemplified by, but not limited to, groups such as hydroxymethyl, hydroxyethyl, hydroxypropyl, 2-aminoethyl, 3-aminopropyl, 2-methylaminoethyl, 3-dimethylaminopropyl, 2-carboxyethyl, hydroxylated alkyl amines (e.g. 2-hydroxyaminoethyl) and the like. Alkyl groups substituted with one or more substituents of the formula —NR$^a$R$^b$ may also include, but are not limited to, embodiments where $R^a$, $R^b$, and N form a nitrogen containing heterocyclic ring. Specific examples of such heterocyclic rings include piperazino, pyrrolidino, piperidino, morpholino, or thiomorpholino. Other substituted alkyl groups include alkyl groups substituted with one or more carbon-linked oxygen atoms containing heterocyclic rings. Specific examples of such oxygenated heterocyclic rings include, but are not limited to, tetrahydrofuranyl, tetrahydropyranyl, 1,4-dioxanyl, and the like.

As used herein, "an alkoxy group" refers to a group of the formula alkyl-O—, where alkyl is as defined herein. Such alkoxy groups may include, but are not limited to, methoxy, ethoxy, propoxy, iso-propoxy, n-butoxy, tert-butoxy, sec-butoxy, n-pentoxy, n-hexoxy, 1,2-dimethylbutoxy, and the like.

As used herein, "an aryl group" denotes a structure derived from an aromatic ring such as a phenyl radical or an ortho-fused bicyclic carbocyclic radical having about nine to ten ring atoms in which at least one ring is aromatic. Non-limiting Examples of aryl group include a phenyl group, an indenyl group, a naphthyl group, a benzyl group and a biphenyl group.

As used herein, "a substituted aryl group" denotes an aryl group that is substituted with 1 to 5 substituent groups independently selected from the following: alkyl, substituted alkyl, cycloalkyl, substituted cycloalkyl, alkoxycarbonyl (e.g. —CO$_2$Me), cyano, halo, hydroxyl, carboxy (COOH), aryloxy, heteroaryloxy, heterocyclooxy, nitro, and —NR$^a$R$^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic. In one specific embodiment of the invention "a substituted aryl group" denotes an aryl group that is substituted with 1 to 5 substituent groups independently selected from the following: cycloalkyl, substituted cycloalkyl, alkoxycarbonyl (e.g. —CO$_2$Me), cyano, halo, hydroxyl, carboxy (COOH), aryloxy, heteroaryloxy, heterocyclooxy, nitro, and —NR$^a$R$^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic As used herein, "heteroaryl" encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. Examples of a heteroaryl group include furyl, imidazolyl, triazolyl, triazinyl, oxazoyl, isoxazoyl, thiazoly, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide), and a benzimidazole group.

As used herein, "a substituted heteroaryl group" denotes a heteroaryl group that is substituted with 1 to 5 substituent groups independently selected from the following: alkyl, substituted alkyl, cycloalkyl, substituted cycloalkyl, alkoxycarbonyl (e.g. —CO$_2$Me), cyano, halo, hydroxyl, carboxy (COOH), aryloxy, heteroaryloxy, heterocyclooxy, nitro, and —NR$^a$R$^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic. In one specific embodiment of the invention "a substituted heteroaryl group" denotes a heteroaryl group that is substituted with 1 to 5 substituent groups independently selected from the following: cycloalkyl, substituted cycloalkyl, alkoxycarbonyl (e.g. —CO$_2$Me), cyano, halo, hydroxyl, carboxy (COOH), aryloxy, heteroaryloxy, heterocyclooxy, nitro, and —NR$^a$R$^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic.

As used herein, "heterocycle" or "heterocyclic" refers to a monovalent saturated or partially unsaturated cyclic non-aromatic group which contains at least one heteroatom, preferably 1 to 4 heteroatoms, selected from nitrogen (NR$_x$, wherein R$_x$ is hydrogen, alkyl, or a direct bond at the point of attachment of the heterocycle group), sulfur, phosphorus, and oxygen within at least one cyclic ring and which may be monocyclic or multi-cyclic. Such heterocycle groups may contain from 3 to 10 atoms. The point of attachment of the heterocycle group may be a carbon or nitrogen atom. This term also includes heterocycle groups fused to an aryl or heteroaryl group, provided the point of attachment is on a non-aromatic heteroatom-containing ring. Representative heterocycle groups include, by way of example, pyrrolidinyl, piperidinyl, piperazinyl, imidazolidinyl, morpholinyl, indolin-3-yl, 2-imidazolinyl, 1,2,3,4-tetrahydroisoquinolin-2-yl, quinuclidinyl, benzimidazole, and the like.

As used herein, "substituted heterocycle" or "substituted heterocyclic" denotes a heterocycle or a heterocyclic that is substituted with 1 to 5 substituent groups independently selected from the following: alkyl, substituted alkyl, cycloalkyl, substituted cycloalkyl, alkoxycarbonyl (e.g. —CO$_2$Me), cyano, halo, hydroxyl, carboxy (COOH), aryloxy, heteroaryloxy, heterocyclooxy, nitro, and —NR$^a$R$^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic. In one specific embodiment of the invention "substituted heterocycle" or "substituted heterocyclic" denotes a heterocycle or a heterocyclic that is substituted with 1 to 5 substituent groups independently selected from the following: cycloalkyl, substituted cycloalkyl, alkoxycarbonyl (e.g. —CO$_2$Me), cyano, halo, hydroxyl, carboxy (COOH), aryloxy, heteroaryloxy, heterocyclooxy, nitro, and —NR$^a$R$^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic.

As used herein, "an aryloxy group" refers to a group of the formula aryl-O—, where aryl is as defined herein. Such aryloxy groups may include, but are not limited to, phenoxy, 4-phenylphenoxy, and naphthyloxy, and the like.

As used herein, "an heteroaryloxy group" refers to a group of the formula heteroaryl-O—, where heteroaryl is as defined herein.

As used herein, "a heterocyclooxy group" refers to a group of the formula heterocycle-O—, where heterocycle is as defined herein.

As used herein, "a arylalkyl group" refers to a group of the formula aryl-alkyl-, where aryl is as defined herein.

As used herein, "a heteroarylalkyl group" refers to a group of the formula heteroarylaryl-alkyl-, where heteroaryl is as defined herein.

As used herein, "an alkylthio group" refers to a group of the formula alkyl-S—, where alkyl is as defined herein. Such alkylthio groups may include, but are not limited to, methylthio, ethylthio, propylthio, iso-propylthio, n-butylthio, tert-butylthio, sec-butylthio, n-pentylthio, n-hexylthio, 1,2-dimethylbutylthio, and the like.

As used herein, "an arylthio group" refers to a group of the formula aryl-S—, where aryl is as defined herein. Such arylthio groups may include, but are not limited to, phenylthio, 4-phenylphenylthio, and naphthylthio, and the like.

As used herein, "an alkanoyl group" refers to a group of the formula alkyl-C(=O)—, where alkyl is as defined herein. Such alkanoyl groups may include, but are not limited to, formyl, ethanoyl, propanoyl, iso-propanoyl, n-butanoyl, tert-butanoyl, sec-butanoyl, n-pentanoyl, n-hexanoyl, 1,2-dimethylbutanoyl, and the like.

As used herein, "an alkoxycarbonyl group" refers to a group of the formula alkoxy-C(=O)—, where alkyl is as defined herein. Such alkoxycarbonyl groups may include, but are not limited to, methoxycarbonyl, ethoxycarbonyl, propoxycarbonyl, iso-propoxycarbonyl, n-butoxycarbonyl, tert-butoxycarbonyl, sec-butoxycarbonyl, n-pentoxycarbonyl, n-hexyloxycarbonyl, 1,2-dimethylbutoxycarbonyl, and the like.

As used herein, "an alkanoyloxy group" refers to a group of the formula alkanoyl-O—, where alkanoyl is as defined herein. Such alkanoyloxy groups may include, but are not limited to, formyloxy, ethanoyloxy, propanoyloxy, iso-propanoyloxy, n-butanoyloxy, tert-butanoyloxy, sec-butanoyloxy, n-pentanoyloxy, n-hexanoyloxy, 1,2-dimethylbutanoyloxy, and the like.

As used herein, "an arylalkanoyl group" refers to a group of the formula aryl-alkanoyl-, where aryl and alkanoyl are defined herein. Such arylalkanoyl groups may include, but are not limited to, benzoyl, 4-phenylbenzoyl, and naphthyoyl, and the like.

As used herein, "substituted alkoxy," "substituted alkylthio," "substituted arylalkanoyl," "substituted alkanoyl," "substituted alkoxycarbonyl," or "substituted alkanoyloxy," refers to an alkoxy, alkylthio, arylalkanoyl, alkanoyl, alkoxycarbonyl, or alkanoyloxy, group, respectively, which is substituted with 1 to 5 substituent groups independently selected from the following: cycloalkyl, substituted cycloalkyl, alkoxycarbonyl (e.g. —CO$_2$Me), cyano, halo, hydroxyl, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, cycloalkyl, substituted cycloalkyl, aryl, heteroaryl and heterocyclic.

As used herein, "substituted aryloxy," refers to an aryloxy group, which is substituted with 1 to 5 substituent groups independently selected from the following: alkyl, substituted alkyl, cycloalkyl, substituted cycloalkyl, alkoxycarbonyl (e.g. —CO$_2$Me), cyano, halo, hydroxyl, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, cycloalkyl, substituted cycloalkyl, aryl, heteroaryl and heterocyclic.

As used herein, "substituted heteroaryloxy," refers to a heteroaryloxy group, which is substituted with 1 to 5 substituent groups independently selected from the following: alkyl, substituted alkyl, cycloalkyl, substituted cycloalkyl, alkoxycarbonyl (e.g. —CO$_2$Me), cyano, halo, hydroxyl, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, cycloalkyl, substituted cycloalkyl, aryl, heteroaryl and heterocyclic.

As used herein, "cycloalkyl" denotes a saturated or partially unsaturated C3-C8 monocyclic carbon ring or a saturated or partially unsaturated C8-C15 bicyclic or tricyclic carbon ring system. Cycloalkyl includes but is not limited to cyclopropyl, cyclobutyl, cyclopentyl, cyclopentenyl, cyclohexyl, and cyclohexenyl.

As used herein, "a cycloalkyloxy group" refers to a group of the formula cycloalkyloxy-O—, where cycloalkyloxy is as defined herein.

As used herein, "substituted cycloalkyl" is a cycloalkyl group, as defined above, wherein 1 to 5 of the hydrogens have been replaced with 1 to 5 substituent groups independently selected from the following: alkyl, substituted alkyl, cycloalkyl, substituted cycloalkyl, alkoxycarbonyl (e.g. —CO$_2$Me), cyano, halo, hydroxyl, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, cycloalkyl, substituted cycloalkyl, aryl, heteroaryl and heterocyclic. In one specific embodiment of the invention "substituted cycloalkyl" is a cycloalkyl group, as defined above, wherein 1 to 5 of the hydrogens have been replaced with 1 to 5 substituent groups independently selected from the following: cycloalkyl, substituted cycloalkyl, alkoxycarbonyl (e.g. —CO$_2$Me), cyano, halo, hydroxyl, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, cycloalkyl, substituted cycloalkyl, aryl, heteroaryl and heterocyclic.

As used herein, "substituted heterocyclooxy" is a heterocyclooxy group, as defined above, wherein 1 to 5 of the hydrogens have been replaced with 1 to 5 substituent groups independently selected from the following: alkyl, substituted alkyl, cycloalkyl, substituted cycloalkyl, alkoxycarbonyl (e.g. —CO$_2$Me), cyano, halo, hydroxyl, oxo (=O), carboxy (COOH), aryloxy, heteroaryloxy, heterocyclooxy, nitro, and —NR$^a$R$^b$, wherein R$^a$ and R$^b$ may be the same or different and are chosen from hydrogen, alkyl, arylalkyl, heteroarylalkyl, cycloalkyl, substituted cycloalkyl, aryl, heteroaryl and heterocyclic.

As used herein, "solubilizing group(s)" are substituent groups that increase the water solubility of the compound, relative to the corresponding compound lacking the substituent. Examples of solubilizing groups include substituents independently selected from a substituted alkyl group, a alkoxycarbonyl group (e.g. —CO$_2$Me), a cyano group, a hydroxyl group, an oxo group (e.g. =O), a carboxy group (e.g. COOH), an aryloxy group, a heteroaryloxy group, a heterocyclooxy group, a nitro group, and —NR$^a$R$^b$, wherein R$_a$ and R$_b$ may be the same or different and are chosen from hydrogen, an alkyl group, an arylalkyl group, a heteroarylalkyl group, a cycloalkyl group, a substituted cycloalkyl group, an aryl group, a heteroaryl group and a heterocyclic group.

Specific Embodiments of the Invention

Specific embodiments, and values listed herein for radicals, substituents, and ranges, are for illustration only; they do not exclude other defined values or other values within defined ranges for the radicals and substituents.

In one embodiment the compounds of the present invention relate to derivatives of benzo[c]phenanthridine (B[c]P) compounds, particularly derivatives of sanguinarine or chelerythrine, having one or more substitution groups at positions 1, 9, 10, 11, and 12 of the core B[c]P structure. Specifically, at any one or more of these positions the hydrogen atoms are substituted with an aromatic ring containing a substituent group such as, but not limited to, a benzyl group, a benzoyl group, a biphenyl group, or a benzimidazole group. The addition of these groups is believed to provide for increased van der Waals interactions and bonding between the compound and the GTP binding domain of the FtsZ protein. This reduces GTPase activity within the GTP binding domain, thereby, reducing FtsZ polymerization, Z-ring formation, and recruitment of divisome proteins, all of which are critical molecular mechanisms associated with bacterial cell cytokinesis. Based on the foregoing, the compounds of the present invention may be formulated for administration to prevent and/or treat a bacterial infection by any one or more of the organisms discussed herein.

Compounds of Formula I

In one specific embodiment the invention provides a compound of formula I wherein:

the bond represented by - - - is a single or double bond;

when the bond represented by - - - is a single bond $R^5$, $R^{5a}$, $R^{10}$ and $R^{11}$ can have any of the values defined below; when the bond represented by - - - is a double bond $R^5$ can be absent or have any of the values defined below, $R^{10}$ can have any of the values defined below, and $R^{5a}$ and $R^{11}$ are absent;

$X^1$, $X^2$, $X^3$ and $X^4$ are each independently O, S or $NR^e$;

$R^1$ and $R^2$ are each independently, $(C_1-C_6)$alkyl, $(C_1-C_6)$alkanoyl or —C(=O)$NR^fR^g$ or $R^1$ and $R^2$ together with the atoms to which they are attached form a 5 to 7 membered ring;

$R^3$ and $R^4$ are each independently, $(C_1-C_6)$alkyl, $(C_1-C_6)$alkanoyl or —C(=O)$NR^fR^g$ or $R^3$ and $R^4$ together with the atoms to which they are attached form a 5 to 7 membered ring;

$R^5$ is H or $(C_1-C_6)$alkyl, which $(C_1-C_6)$alkyl is optionally substituted with one or more groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^aR^b$;

$R^{5a}$ is H, $(C_1-C_6)$alkyl, or absent, wherein the $(C_1-C_6)$alkyl is optionally substituted with one or more groups selected from halo, cyano, oxo (=O), $(C_1-C_6)$alkyl, $(C_2-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^aR^b$;

$R^{10}$ is H, $(C_1-C_6)$alkyl, $(C_1-C_6)$alkoxy, $(C_1-C_6)$ alkylthio, aryloxy, or aryl-S(=O)$_n$—, wherein n is 0, 1, or 2; and $R^{11}$ is H or $(C_1-C_6)$alkyl, wherein any $(C_1-C_6)$alkyl$(C_1-C_6)$alkoxy, and $(C_1-C_6)$alkylthio of $R^{10}$ and $R^{11}$ is optionally substituted with one or more groups selected from halo, cyano, oxo (=O), $(C_1-C_6)$alkyl, $(C_3-C_6)$ cycloalkyl, carboxy, $NO_2$, hydroxy, $(C_1-C_6)$ alkoxy, $(C_1-C_6)$alkoxycarbonyl, $(C_1-C_6)$alkanoyloxy, aryl, heteroaryl, aryloxy, heteroaryloxy, and —$NR^aR^b$, and wherein any wherein any aryloxy, or arylthio of $R^{10}$ and $R^{11}$ is optionally substituted with one or more groups selected from halo, cyano, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^aR^b$; or $R^{10}$ and $R^{11}$ together with the carbon to which they are attached form a carbonyl group;

at least one of $R^6$, $R^7$, $R^8$, $R^9$ and $R^{12}$ is aryl, heteroaryl, aryl($C_1-C_6$) alkyl, heteroaryl($C_1-C_6$) alkyl, or aryl($C_1-C_6$) alkanoyl; and the remainder of $R^6$, $R^7$, $R^8$, $R^9$ and $R^{12}$ are independently H, halo, nitro, —$NR^cR^d$, $(C_1-C_6)$alkyl, aryl, heteroaryl, aryl($C_1-C_6$) alkyl, heteroaryl($C_1-C_6$) alkyl, $(C_1-C_6)$alkanoyl or —C(=O)$NR^fR^g$, wherein the $(C_1-C_6)$alkyl, aryl, heteroaryl, aryl($C_1-C_6$)alkyl and heteroaryl($C_1-C_6$)alkyl of $R^6$, $R^7$, $R^8$, $R^9$ and $R^{12}$ are optionally substituted with or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^aR^b$;

each $R^a$ and $R^b$ is independently H, $(C_1-C_6)$alkyl, aryl, heteroaryl, aryl($C_1-C_6$) alkyl, or heteroaryl($C_1-C_6$) alkyl; or $R^a$ and $R^b$ together with the nitrogen to which they are attached form a morpholino, piperazino, pyrrolidino or piperidino;

each $R^c$ and $R^d$ is independently H, $(C_1-C_6)$alkyl, aryl, heteroaryl, aryl($C_1-C_6$)alkyl, or heteroaryl($C_1-C_6$)alkyl; or $R^a$ and $R^b$ together with the nitrogen to which they are attached form a morpholino, piperazino, pyrrolidino or piperidino;

$R^e$ is H or $(C_1-C_6)$alkyl;

$R^f$ and $R^g$ are each independently H, $(C_1-C_6)$alkyl, aryl, heteroaryl, aryl($C_1-C_6$)alkyl, or heteroaryl($C_1-C_6$)alkyl; or $R^f$ and $R^g$ together with the nitrogen to which they are attached form a morpholino, piperazino, pyrrolidino or piperidino; and when the nitrogen attached to $R^5$ is a positively charged quaternary nitrogen, the compound is associated with a suitable counterion $X^-$;

or a salt or prodrug thereof.

In one specific embodiment of the invention the compound of formula I is a compound of the following formula Ia:

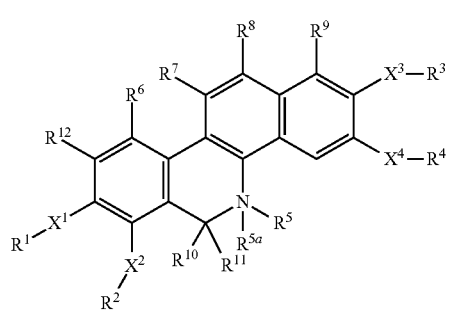

Ia or a salt or prodrug thereof.

In one specific embodiment of the invention the compound of formula I is a compound of the following formula Ib:

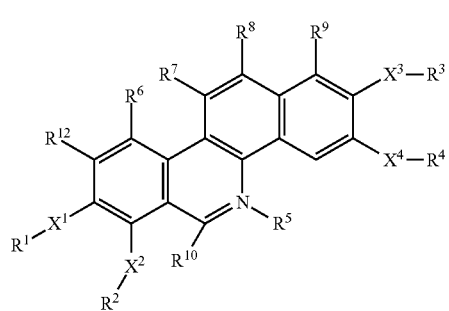

Ib or a salt or prodrug thereat.

In one specific embodiment of the invention the compound of formula I is a compound of the following formula Ic:

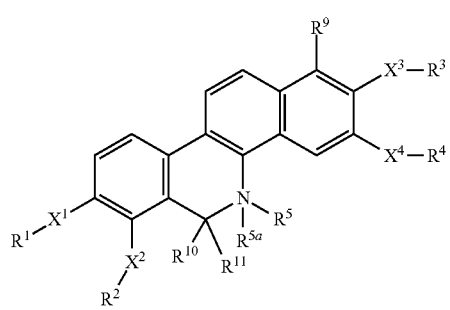

Ic or a salt or prodrug thereof.

In one specific embodiment of the invention the compound of formula I is a compound of the following formula Id:

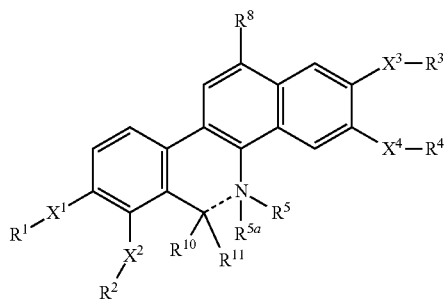

Id or a salt or prodrug thereof.

In one specific embodiment of the invention the compound of formula I is a compound of the following Ie:

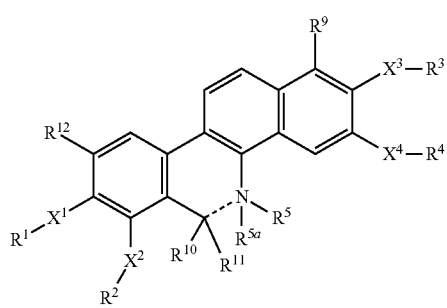

Ie or a salt or prodrug thereof.

In one specific embodiment of the invention the compound of formula I is a compound of the following formula If:

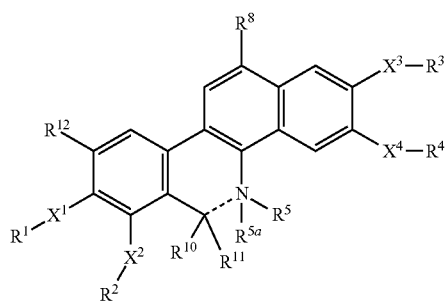

If or a salt or prodrug thereof.

In one specific embodiment of the invention the compound of formula I is a compound of the following formula Ig:

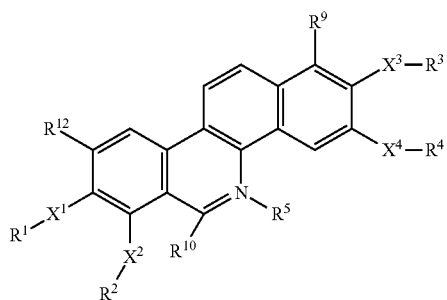

Ig or a salt or prodrug thereof.

In one specific embodiment of the invention the compound of formula I is a compound of the following formula Ih:

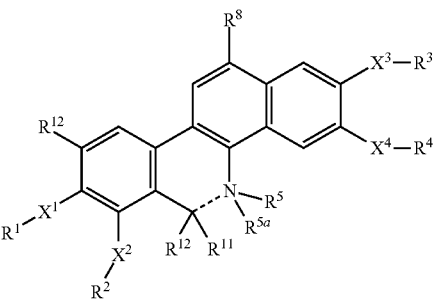

Ih or a salt or prodrug thereof.

In one specific embodiment of the invention the compound of formula I is a compound of the following formula Ij:

Ij or a salt or prodrug thereof.

In one specific embodiment the invention provides a compound of formula I wherein the bond represented by - - - is a single bond; $R^5$ is methyl; $R^{5a}$ is absent, hydrogen, or methyl.

In one specific embodiment the invention provides a compound of formula I wherein $R^{10}$ and $R^{11}$ are each hydrogen.

In one specific embodiment the invention provides a compound of formula I wherein the bond represented by - - - is a single bond; $R^5$ is methyl; $R^{5a}$ is absent; $R^{10}$ is methyl; and $R^{11}$ is hydrogen.

In one specific embodiment the invention provides a compound of formula I wherein the bond represented by - - - is a double bond; and $R^{10}$ is H, $(C_1-C_6)$alkyl, $(C_1-C_6)$alkoxy, $(C_1-C_6)$alkylthio, aryloxy, or aryl-S$(=O)_n$—, wherein n is 0, 1, or 2; wherein any $(C_1-C_6)$alkyl$(C_1-C_6)$alkoxy, and $(C_1-C_6)$alkylthio of $R^{10}$ is optionally substituted with one or more groups selected from halo, cyano, oxo (=O), $(C_3-C_6)$cycloalkyl, carboxy, $NO_2$, hydroxy, $(C_1-C_6)$ alkoxy, $(C_1-C_6)$alkoxycarbonyl, $(C_1-C_6)$alkanoyloxy, aryl, heteroaryl, aryloxy, heteroaryloxy, and —$NR^aR^b$, and wherein any aryloxy, or arylthio of $R^{10}$ is optionally substituted with one or more groups selected from halo, cyano, $C_1-C_6$)alkyl, $(C_3-C_6)$cycloalkyl, carboxy, $NO_2$, hydroxy, $(C_1-C_6)$alkoxy, $(C_1-C_6)$ alkoxycarbonyl, $(C_1-C_6)$ alkanoyloxy, aryl, heteroaryl, aryloxy, heteroaryloxy, and —$NR^aR^b$.

In one specific embodiment the invention provides a compound of formula I wherein the bond represented by - - - is a double bond; $R^5$ is hydrogen or methyl; and $R^{10}$ is H, $(C_1-C_6)$ alkyl, $(C_1-C_6)$alkoxy, $(C_1-C_6)$alkylthio, aryloxy, or aryl-S$(=O)_n$—, wherein n is 0, 1, or 2; wherein any $(C_1-C_6)$alkyl $(C_1-C_6)$alkoxy, and $(C_1-C_6)$alkylthio of $R^{10}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^a$R$^b$, and wherein any aryloxy, or arylthio of R$^{10}$ is optionally substituted with one or more groups selected from halo, cyano, C$_1$-C$_6$)alkyl, (C$_3$-C$_6$)cycloalkyl, carboxy, NO$_2$, hydroxy, (C$_1$-C$_6$)alkoxy, (C$_1$-C$_6$) alkoxycarbonyl, (C$_1$-C$_6$)alkanoyloxy, aryl, heteroaryl, aryloxy, heteroaryloxy, and —NR$^a$R$^b$.

In one specific embodiment the invention provides a compound of formula I wherein R$^{10}$ is (C$_1$-C$_6$)alkyl, (C$_1$-C$_6$)alkoxy, (C$_1$-C$_6$)alkylthio, or aryloxy, wherein any (C$_1$-C$_6$)alkyl(C$_1$-C$_6$)alkoxy, and (C$_1$-C$_6$)alkylthio of R$^{10}$ is optionally substituted with one or more groups selected from halo, cyano, oxo (=O), (C$_3$-C$_6$)cycloalkyl, carboxy, NO$_2$, hydroxy, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^a$R$^b$, and wherein any aryloxy of R$^{10}$ is optionally substituted with one or more groups selected from halo, cyano, (C$_3$-C$_6$) cycloalkyl, carboxy, NO$_2$, hydroxy, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^a$R$^b$.

In one specific embodiment the invention provides a compound of formula I wherein R$^{10}$ is (C$_1$-C$_3$)alkyl, (C$_1$-C$_3$)alkoxy, (C$_1$-C$_3$)alkylthio, or aryloxy, wherein any (C$_1$-C$_3$)alkyl(C$_1$-C$_3$)alkoxy, and (C$_1$-C$_3$)alkylthio of R$^{10}$ is optionally substituted with one or more groups selected from halo, cyano, oxo (=O), carboxy, NO$_2$, hydroxy, and —NR$^a$R$^b$, and wherein any aryloxy of R$^{10}$ is optionally substituted with one or more groups selected from halo, cyano, (C$_3$-C$_6$)cycloalkyl, carboxy, NO$_2$, hydroxy, (C$_1$-C$_6$) alkoxy, and —NR$^a$R$^b$.

In one specific embodiment the invention provides a compound of formula I wherein R$^{10}$ is methyl, ethyl, propyl, methoxy, ethoxy, propoxy, amino, methylthio, or nitromethyl.

In one specific embodiment the invention provides a compound of formula I wherein the bond represented by - - - is a double bond; R$^5$ is methyl; and R$^{10}$ is phenyl.

In one specific embodiment of the invention X$^1$ and X$^2$ are O.

In one specific embodiment of the invention R$^1$ and R$^2$ are each (C$_1$-C$_6$) alkyl.

In one specific embodiment of the invention R$^1$ and R$^2$ are each CH$_3$.

In one specific embodiment of the invention R$^1$ and R$^2$ together with the atoms to which they are attached form a five-membered ring.

In one specific embodiment of the invention R$^1$ and R$^2$ together form a methylenedioxy, which when taken together with the attached atoms forms a five-membered ring.

In one specific embodiment of the invention X$^3$ and X$^4$ are O.

In one specific embodiment of the invention R$^3$ and R$^4$ are each (C$_1$-C$_6$)alkyl.

In one specific embodiment of the invention R$^3$ and R$^4$ are each CH$_3$.

In one specific embodiment of the invention R$^3$ and R$^4$ together with the atoms to which they are attached form a five-membered ring.

In one specific embodiment of the invention R$^3$ and R$^4$ together form a methylenedioxy, which when taken together with the attached atoms forms a five-membered ring.

In one specific embodiment of the invention R$^{10}$ and R$^{11}$ are each independently H.

In one specific embodiment of the invention R$^{10}$ and R$^{11}$ together with the carbon to which they are attached form a carbonyl group.

In one specific embodiment of the invention at least one of R$^6$, R$^7$, R$^8$, R$^9$ and R$^{12}$ is benzyl.

In one specific embodiment of the invention at least one of R$^6$, R$^7$, R$^8$, R$^9$ and R$^{12}$ is benzimidazole.

In one specific embodiment of the invention at least one of R$^6$, R$^7$, R$^8$, R$^9$ and R$^{12}$ is 1,1'-biphenyl-4-yl.

In one specific embodiment of the invention the nitrogen attached to R$^5$ in formula I is a positively charged quaternary nitrogen, and X$^-$ is a pharmaceutically acceptable counterion.

In one specific embodiment of the invention at least one of R$^6$, R$^7$, R$^8$, R$^9$ and R$^{12}$ is phenyl, 4-pyridyl, 3-pyridyl, 2-pyridyl, 2-pyrmidinyl, cyclohexyl, 1-cyclohexenyl, piperidinomethyl, cyclopropyl, ethyl, vinyl, ethynyl, 3-furyl, 4-isooxazolyl, 4-hydroxyphenyl, 4-carboxyphenyl, 4-carboxymethylphenyl, dimethylamino)phenyl, 4-(N,N-dimethylaminomethyl)phenyl, 4-(aminosulfonyl)phenyl, 4-(N,N-dimethylaminosulfonyl)phenyl, 4-tetrazolylphenyl, 3,4,5-trimethoxyphenyl, biphenyl, 4-(N-methylpiperidin-4-yl)phenyl, 4-(4-methylpiperazin-1-yl)phenyl, 4-methoxyphenyl, benzyl, 4-(2-morpholinoethyl)phenyl, or phenyl.

In one specific embodiment of the invention R$^8$ is phenyl, 4-pyridyl, 3-pyridyl, 2-pyridyl, 2-pyrmidinyl, cyclohexyl, 1-cyclohexenyl, piperidinomethyl, cyclopropyl, ethyl, vinyl, ethynyl, 3-furyl, 4-isooxazolyl, 4-hydroxyphenyl, 4-carboxyphenyl, 4-carboxymethylphenyl, dimethylamino)phenyl, 4-(N,N-dimethylaminomethyl)phenyl, 4-(aminosulfonyl)phenyl, 4-(N,N-dimethylaminosulfonyl)phenyl, 4-tetrazolylphenyl, 3,4,5-trimethoxyphenyl, biphenyl, 4-(N-methylpiperidin-4-yl)phenyl, 4-(4-methylpiperazin-1-yl)phenyl 4-methoxyphenyl, benzyl, 4-(2-morpholinoethyl)phenyl, or phenyl.

In one specific embodiment of the invention R$^9$ is phenyl, 4-pyridyl, 3-pyridyl, 2-pyridyl, 2-pyrmidinyl, cyclohexyl, 1-cyclohexenyl, piperidinomethyl, cyclopropyl, ethyl, vinyl, ethynyl, 3-furyl, 4-isooxazolyl, 4-hydroxyphenyl, 4-carboxyphenyl, 4-carboxymethylphenyl, dimethylamino)phenyl, 4-(N,N-dimethylaminomethyl)phenyl, 4-(aminosulfonyl)phenyl, 4-(N,N-dimethylaminosulfonyl)phenyl, 4-tetrazolylphenyl, 3,4,5-trimethoxyphenyl, biphenyl, 4-(N-methylpiperidin-4-yl)phenyl, 4-methoxyphenyl, benzyl, 4-(4-methylpiperazin-1-yl)phenyl, 4-(2-morpholinoethyl)phenyl, or phenyl.

In one specific embodiment of the invention at least one of R$^6$, R$^7$, R$^8$, R$^9$ and R$^{12}$ is phenyl, 3-pyridyl, cyclohexyl, 1-cyclohexenyl, cyclopropyl, 3-furyl, dimethylaminomethyl)phenyl, 4-(N,N-dimethylamino-sulfonyl)phenyl, 3,4,5-trimethoxyphenyl, biphenyl, 4-(2-morpholinoethyl)phenyl, or phenyl.

In one specific embodiment of the invention R$^8$ is phenyl, 3-pyridyl, cyclohexyl, 1-cyclohexenyl, cyclopropyl, 3-furyl, 4-(N,N-dimethylaminomethyl)phenyl, dimethylaminosulfonyl)phenyl, 3,4,5-trimethoxyphenyl, biphenyl, 4-(2-morpholinoethyl)phenyl, or phenyl.

In one specific embodiment of the invention R$^9$ is phenyl, 3-pyridyl, cyclohexyl, 1-cyclohexenyl, cyclopropyl, 3-furyl, 4-(N,N-dimethylaminomethyl)phenyl, 4-(N,N-dimethylaminosulfonyl)phenyl, 3,4,5-trimethoxyphenyl, biphenyl, 4-(2-morpholinoethyl)phenyl, or phenyl.

In one specific embodiment the invention provides the compound:

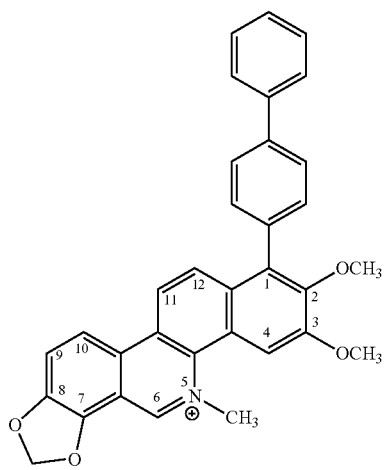
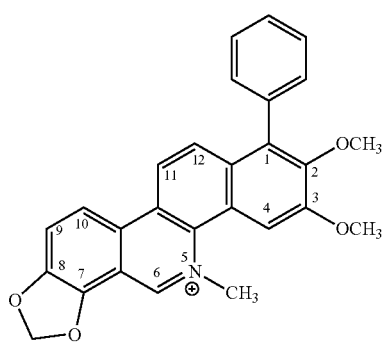
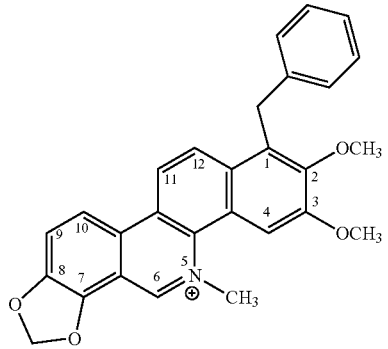
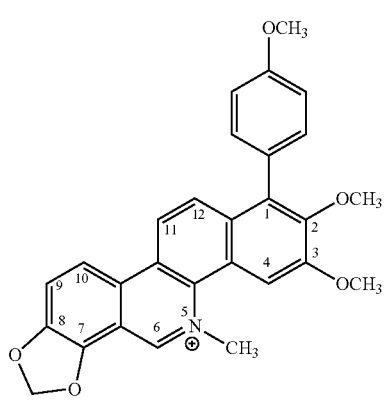
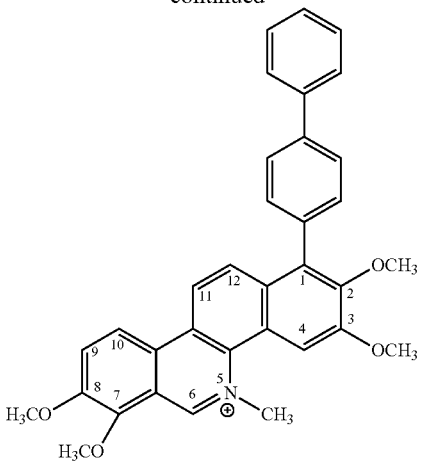
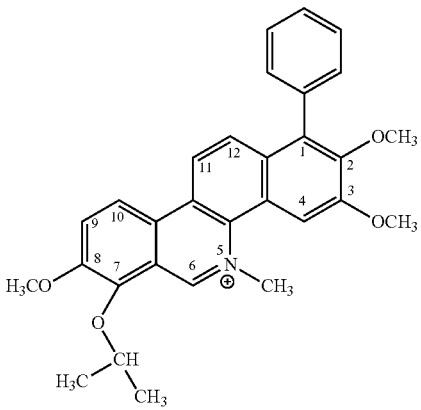
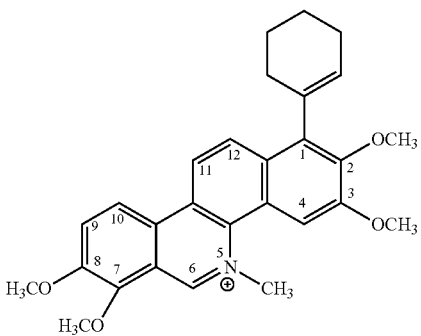
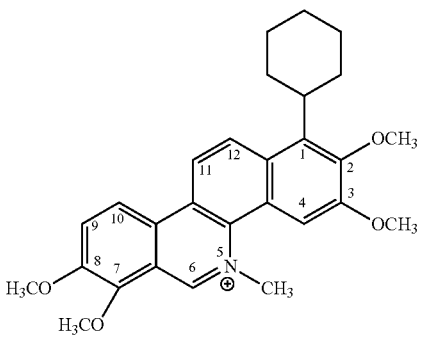

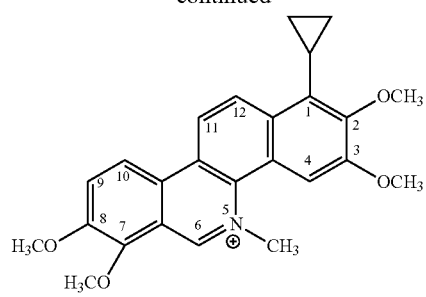
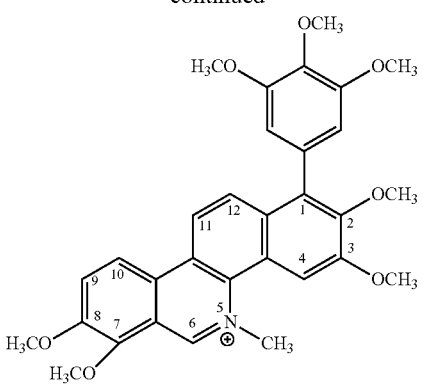
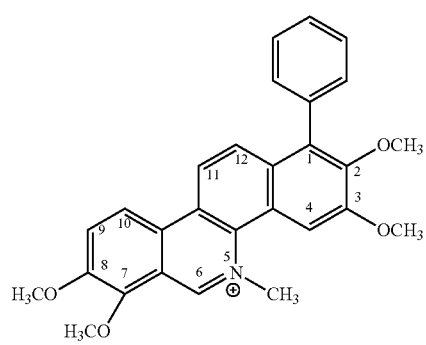
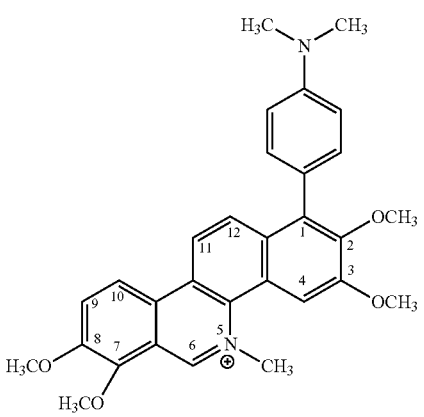
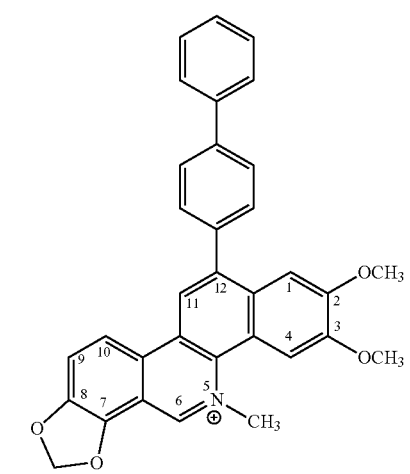
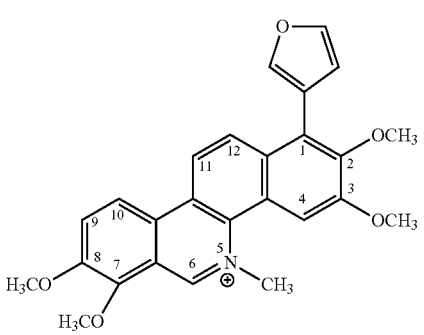
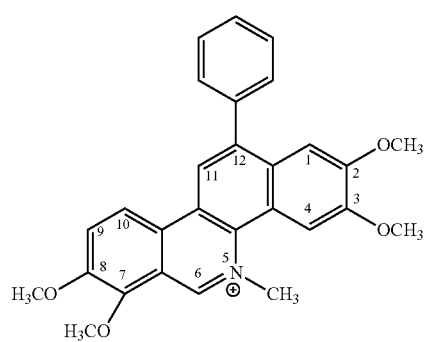
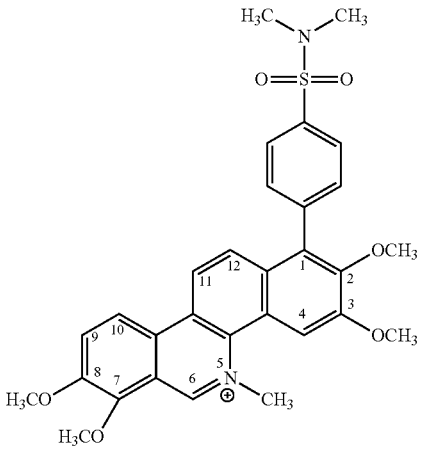

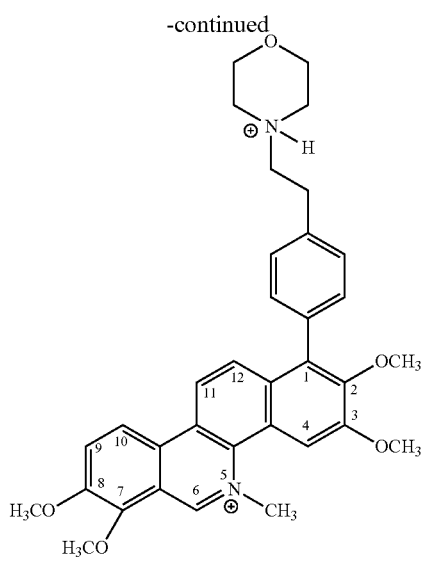
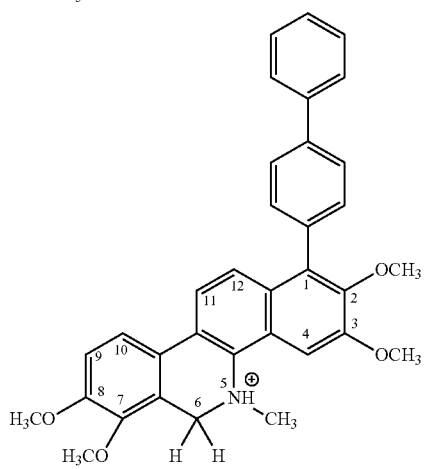
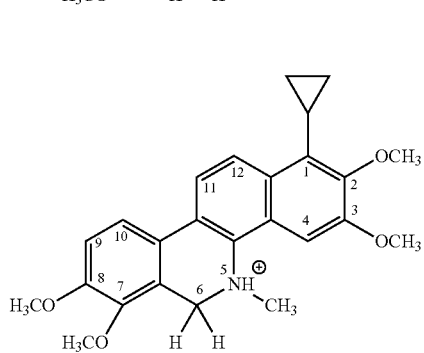
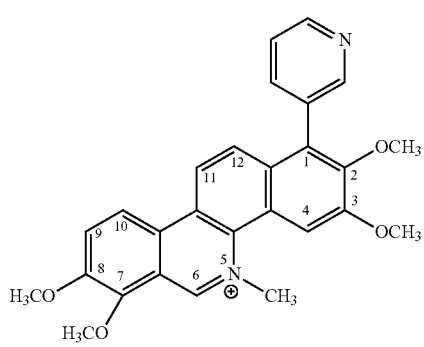
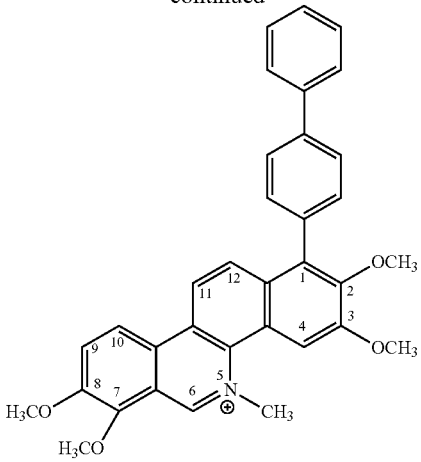
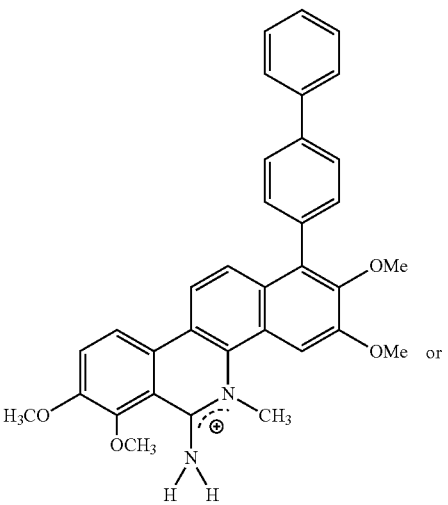
or
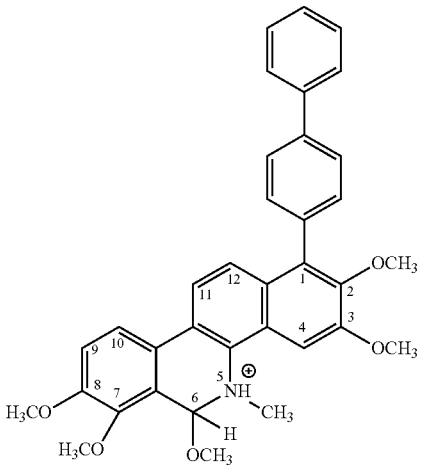
which is associated with a pharmaceutically acceptable counterion; or a prodrug thereof.
In one specific embodiment the invention provides the compound:

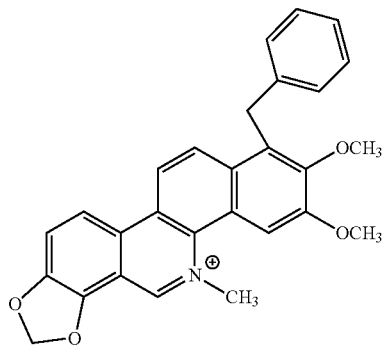
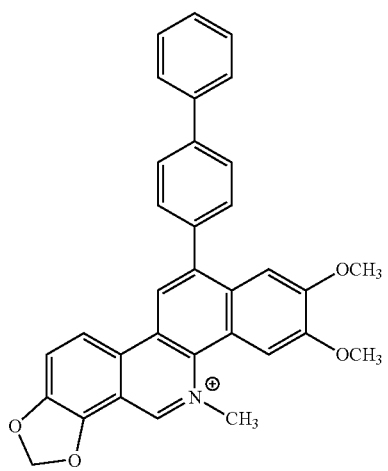
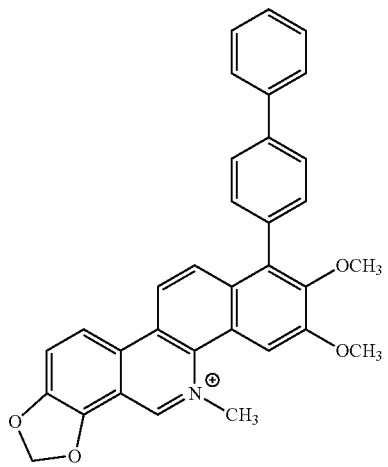
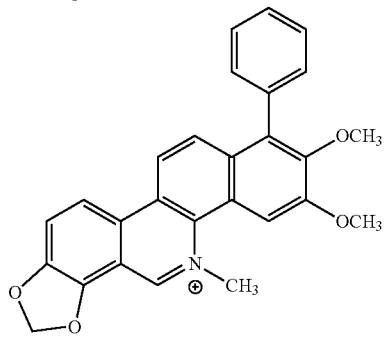

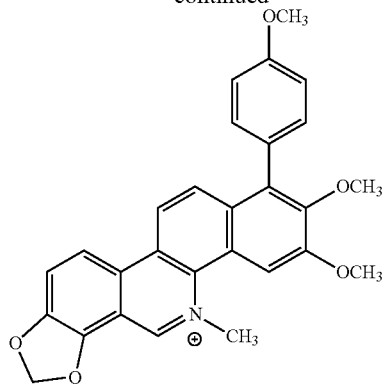
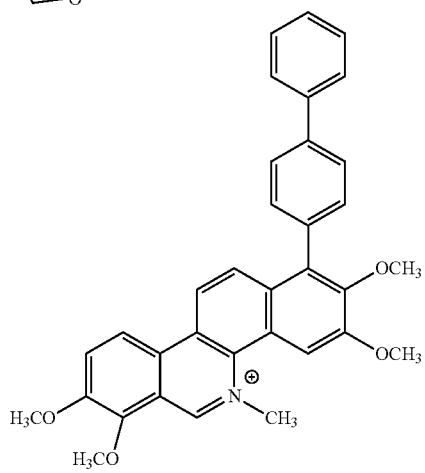

which is associated with a pharmaceutically acceptable counterion; or a prodrug thereof.

Compounds of Formula (II)

In one embodiment, the compounds of the present invention are comprised of the following formula II:

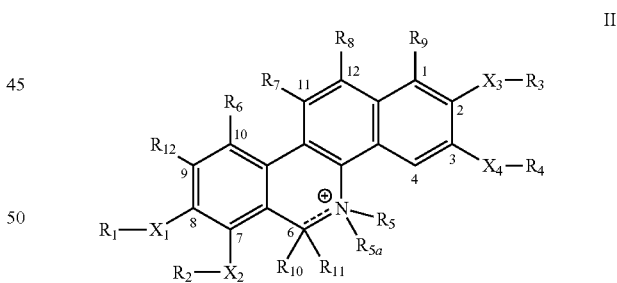

II wherein the numbers 1-12 represent the respective positions of the B[c]P compound core. It will be understood by one skilled in the art that the quaternary ammonium cation of formula II can be associated with a suitable counterion. $X^1$, $X^2$, $X^3$, and $X^4$ are independently comprised of an oxygen atom, a sulfur atom, or a nitrogen atom. In one non-limiting embodiment, each of $X^1$-$X^4$ are oxygen atoms.

$R^1$ is comprised of an alkyl group having between 1-6 carbon atoms, an optionally substituted alkyl group having between 1-6 carbon atoms or an alkyl group forming a heterocyclic ring with $R^2$. $R^2$ is similarly comprised of an alkyl group having between 1-6 carbon atoms, an optionally substituted alkyl group having between 1-6 carbon atoms or an alkyl group forming a heterocyclic ring with $R^1$. In one non-limiting embodiment, $R^1$ and $R^2$ are independently comprised of methylene groups. Alternatively, $R^1$ and $R^2$ may both be comprised of a single methylene, resulting in the formation of a five membered heterocyclic ring with $X^1$ and $X^2$ and carbon atoms at positions 7 and 8 of the B[c]P core. In embodiments where $R^1$ and $R^2$ are substituted, they may be substituted with any of the substituting groups provided herein (e.g. polarizing, cationic, solubilizing, etc.)

$R^3$ is an alkyl group having between 1-6 carbon atoms, an optionally substituted alkyl group having between 1-6 carbon atoms or an alkyl group forming a heterocyclic ring with $R^4$. $R^4$ is similarly an alkyl group having between 1-6 carbon atoms, an optionally substituted alkyl group having between 1-6 carbon atoms or an alkyl group forming a heterocyclic ring with $R^3$. In one non-limiting embodiment, $R^3$ and $R^4$ are independently comprised of methyl groups. Alternatively, $R^3$ and $R^4$ may be comprised of the same methylene group, thereby forming a five member heterocyclic ring with $X^3$ and $X^4$ and carbon atoms at positions 2 and 3 of the B[c]P core structure. In embodiments where $R^1$ and $R^2$ are substituted, they may be substituted with any of the substituting groups provided herein (e.g. polarizing, cationic, solubilizing, etc.)

$R^5$ is comprised of an optionally substituted alkyl group having between 1-6 carbon atoms. In one non-limiting embodiment, $R^5$ is comprised of a methyl group. In an alternative embodiment, the alkyl group of $R^5$ may be comprised of at least two carbon atoms substituted with a cationic substitution residue. Non-limiting examples of such cationic residues include amine, alkylamine, trialkylammonium, amidinium, or guanidinium substituent groups having an overall cationic charge.

As noted above, the nitrogen adjacent to the $R^5$ position is optionally double-bonded to the adjacent carbon (indicated by a broken line). In embodiments where this nitrogen atom is double-bonded, then $R^{5a}$ is absent from the formulation. However, if the nitrogen is only single-bonded to the adjacent carbon, then $R^{5a}$ may be comprised of any optionally substituted alkyl group having 1-6 carbon atoms. In embodiments where $R^{5a}$ is a substituted alkyl group, the alkyl group may be substituted with any cationic, solubility enhancing or other substituent group provided herein.

$R^6$, $R^7$, $R^8$, $R^9$, and $R^{12}$ are independently comprised of either a hydrogen, an alkyl group, an optionally substituted alkyl group, or a substituent group having at least one aromatic ring compound, with the proviso that at least one of $R^6$, $R^7$, $R^8$, $R^9$, and $R^{12}$ is not a hydrogen. More specifically, $R^6$, $R^7$, $R^8$, $R^9$, and $R^{12}$ may be independently comprised of one or any combination of a hydrogen atom, an alkyl group, an aryl group, an arylalkyl group, a heteroaryl group, or a heteroarylalkyl group, subject to the foregoing proviso. Each of the foregoing groups, except hydrogen, may be optionally substituted at one or more positions. For example, the aryl containing groups may be substituted at one or more positions with any one or combination of the following: a hydroxy group, a halo group, a nitro group, a trifluoromethyl group, a tetrazinyl group, a carboxy group, an amino group, an alkyl group having 1-6 carbons, an optionally substituted alkyl group having between 1-6 carbon atoms, a cycloalkyl group having from 3-6 carbons, and an alkoxy group having between 1-6 carbons. In an even further alternative, the aryl groups may be substituted with one or more polar substituent groups that are known in the art, with certain embodiments being comprised of polar substituent groups known to increase compound sensitivity to Gram-negative and/or Gram-positive bacteria. Non-limiting examples of such polar substituent groups include tetrazinyl groups, carboxy groups, urea substituents, amino groups, and other similar or otherwise known polar groups (e.g. sulfates and sulfonamides). In a further embodiment, the alkyl groups may be substituted at one or more positions with one or any combination of solubilizing groups, as defined herein. In an even further embodiment, and for purposes of improving aqueous solubility, a solubilizing group, as defined herein, can be added at positions 1, 9, 10, 11, or 12 that would otherwise be unsubstituted.

While not limited thereto, the aromatic ring containing compounds of positions $R^6$, $R^7$, $R^8$, $R^9$, and $R^{12}$ may include any one or more of a phenyl group, a biphenyl group, a benzyl group, or a benzimidazole group. The biphenyl group may be comprised of a (1,1'-Biphenyl)-4-yl group having the structure:

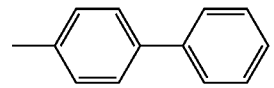

This structure is advantageous because it provides a substituent group of enhanced size, whereby enhancing van der Waals interactions with the target FtsZ protein.

The benzimidazole group may be comprised of a benzimidazole group either of the following structures:

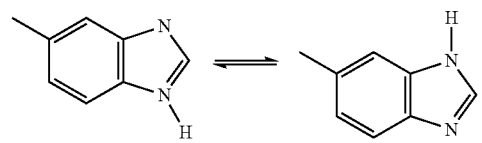

These structures are similarly advantageous because they provide for substituent groups of enhanced size and having hydrogen bond donor and acceptor atoms. Accordingly, the benzimidazole group offers enhanced Ftsz binding ability through a combination of both van der Waals and hydrogen bonding interactions.

$R^{10}$ is comprised of either a hydrogen atom, an alkyl group having 1-6 carbon atoms, or an alkoxy group having 1-6 carbon atoms, which may be bonded to a carbon atom at position 6 of the B[c]P core through a single bond. When $R^{10}$ is single-bonded to the carbon at position 6, then $R^{10}$ may be either a hydrogen atom or an alkyl group having 1-6 carbon atoms. In any of these embodiments of $R^{10}$ and $R^{11}$, the alkyl group or alkoxy group may, optionally, be substituted with one or more solubilizing groups, cationic groups, or other substitution groups defined herein.

In a further embodiment the invention provides a compound of formula,

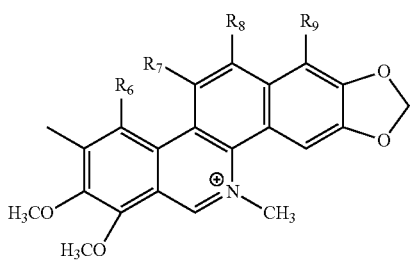

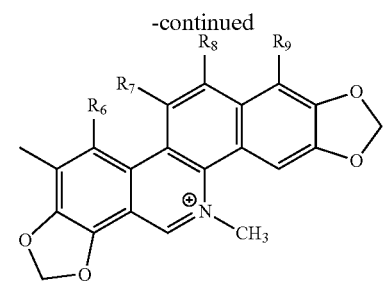
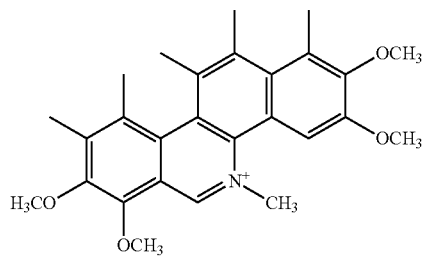
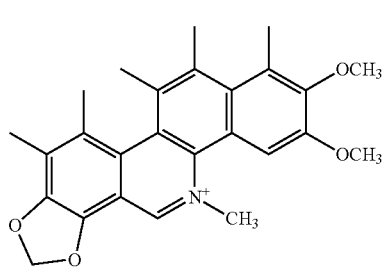
or
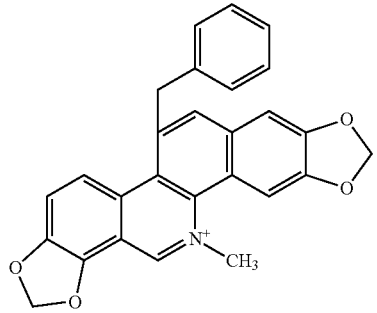
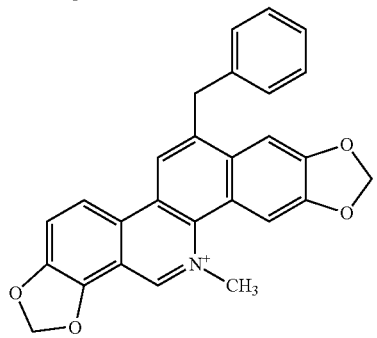
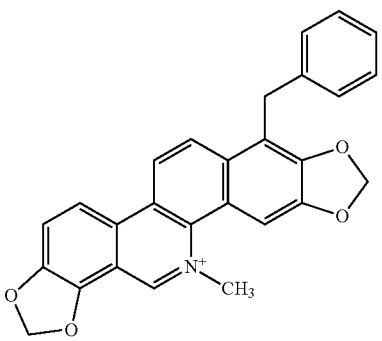
or a prodrug thereof. While also not limited thereto, these aromatic ring containing substitution groups, denoted as $R^6$-$R^9$ and $R^{12}$ may be any of the embodiments defined above such as, but not limited to, an optionally substituted benzyl group, biphenyl group, or benzimidazole group.
In a further embodiment the invention provides a compound of formula,
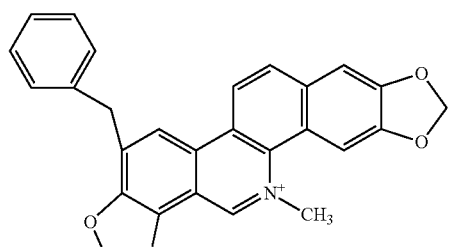
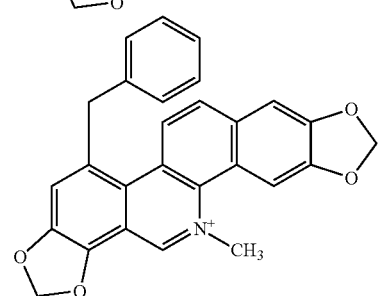
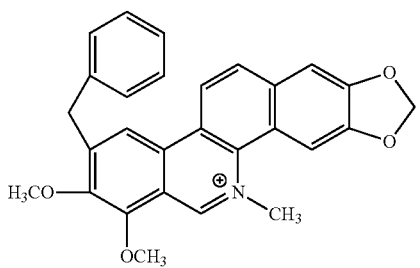
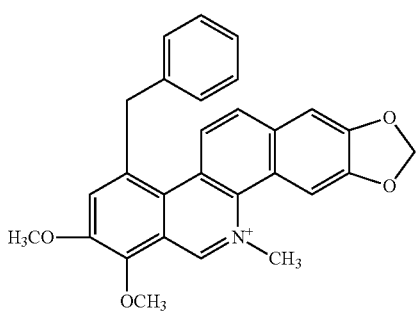

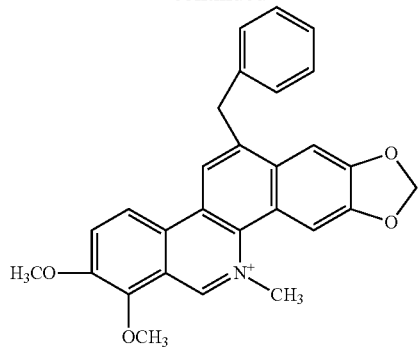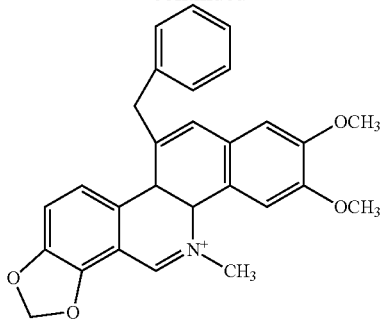

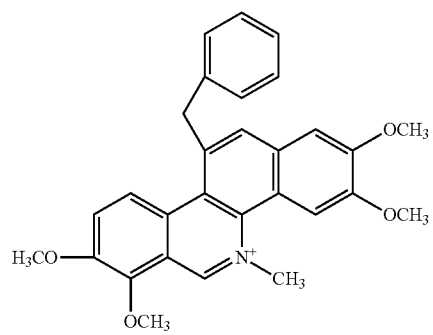
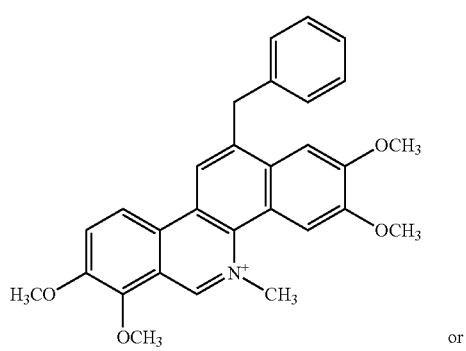
or
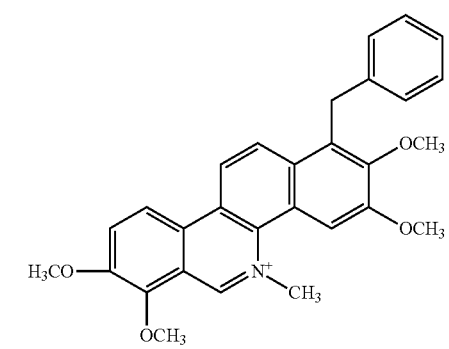 [SMILES: COc1cc2c(ccc3c4ccc(OC)c(OC)c4c[n+](C)c23)c(Cc2ccccc2)c1OC]
or a prodrug thereof.
In a further embodiment the invention provides a compound of formula,
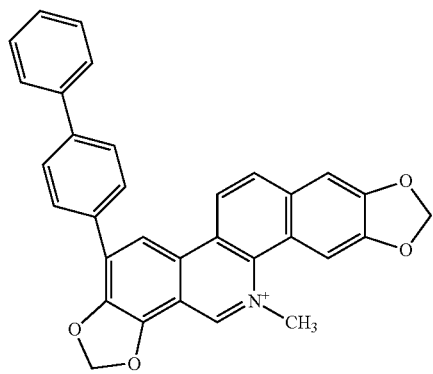
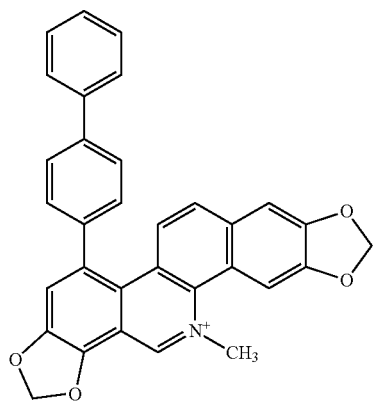
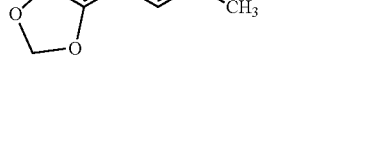
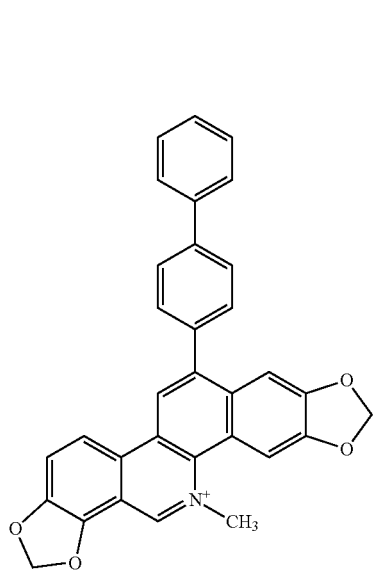

33
-continued
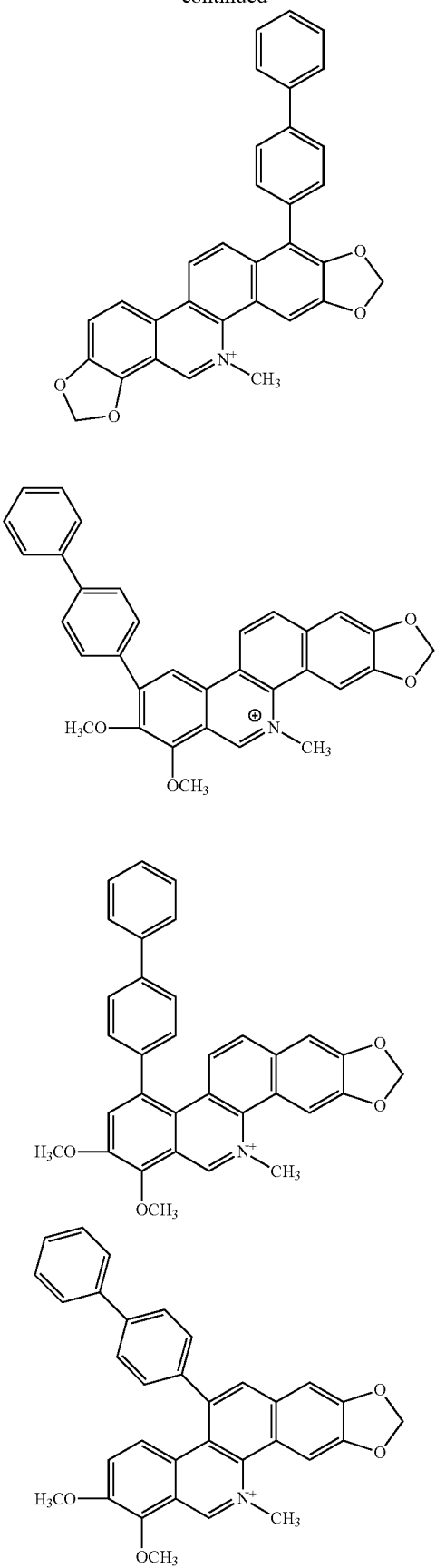
34
-continued
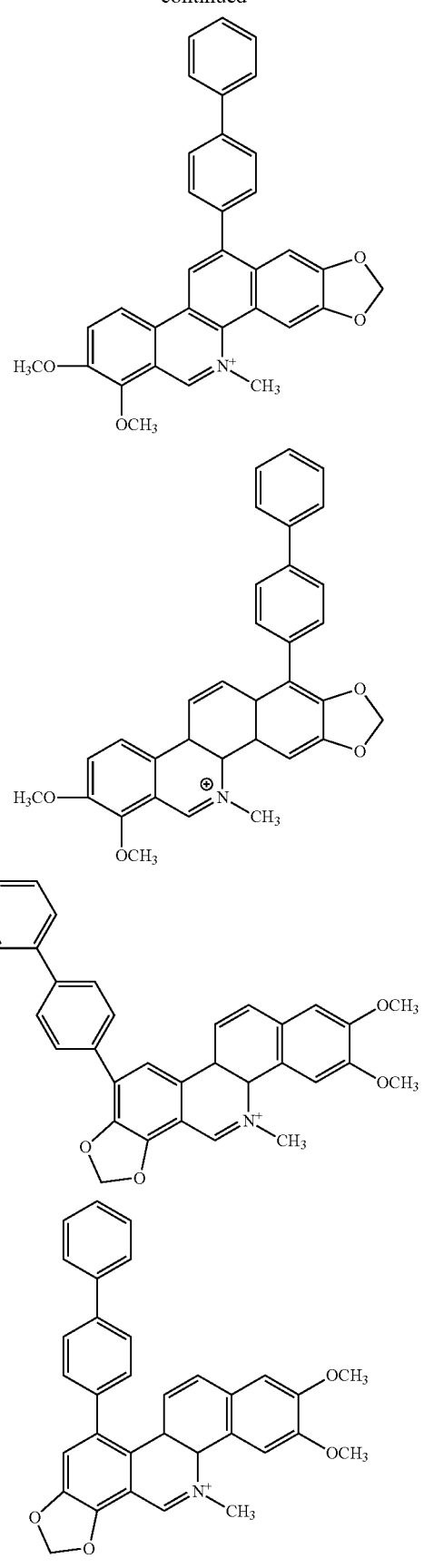

35
-continued
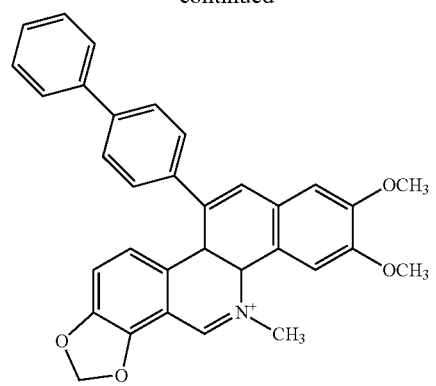
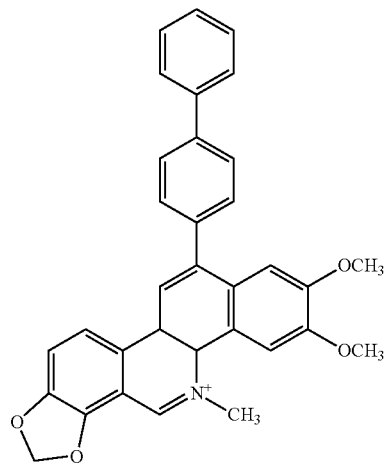
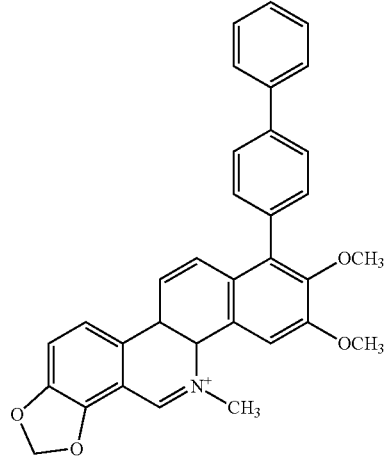
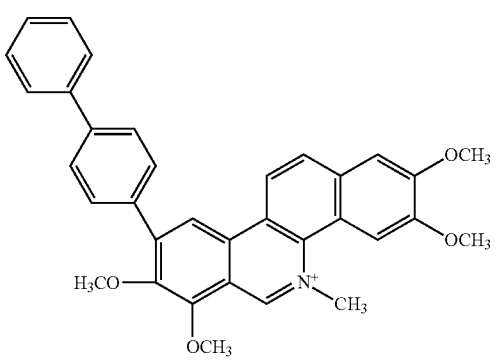
36
-continued
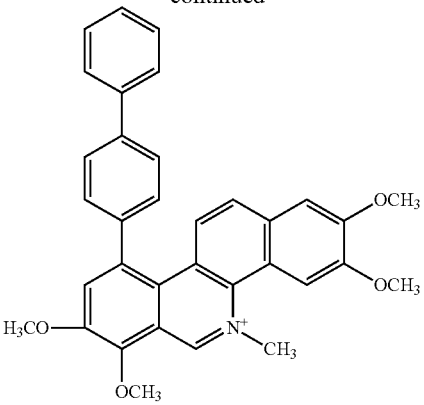
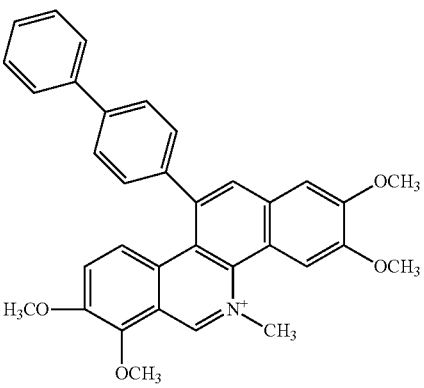
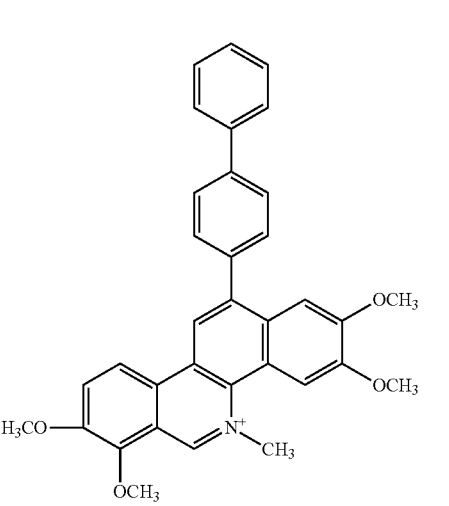
or

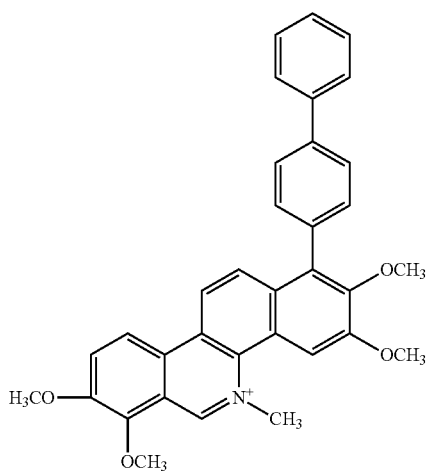 [SMILES: COc1cc2c(ccc3c4ccc(OC)c(OC)c4c[n+](C)c23)c(-c2ccc(-c3ccccc3)cc2)c1OC]
or a prodrug thereof.
In a further embodiment the invention provides a compound of formula,
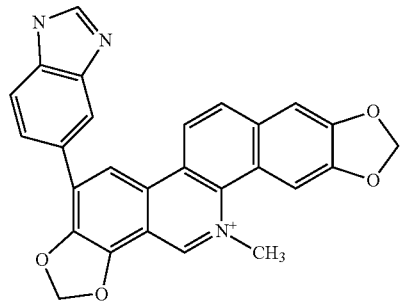
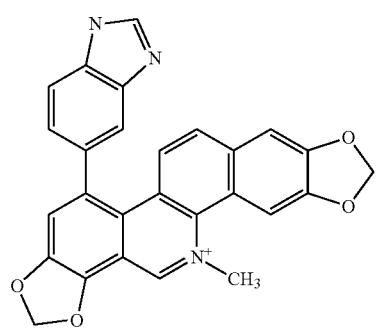
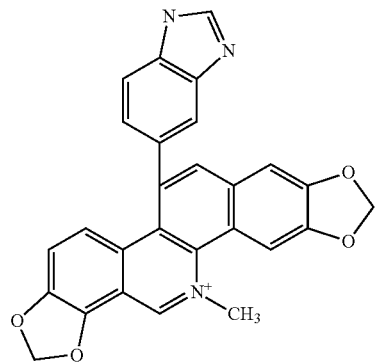
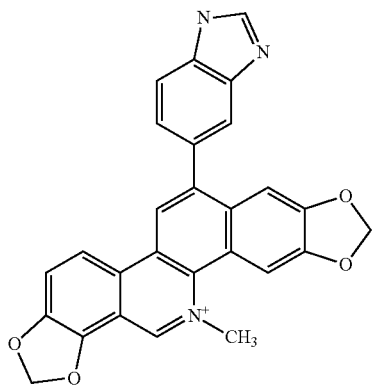
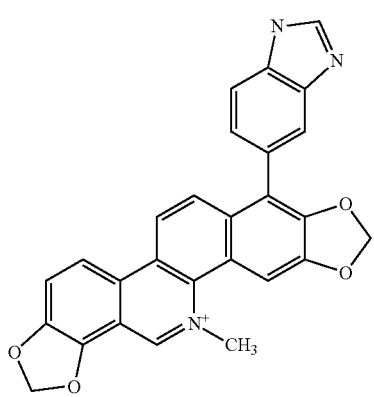
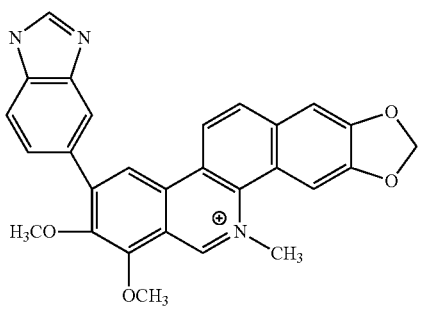
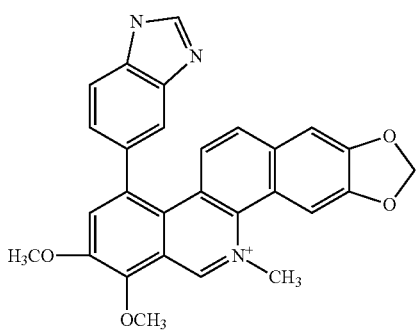

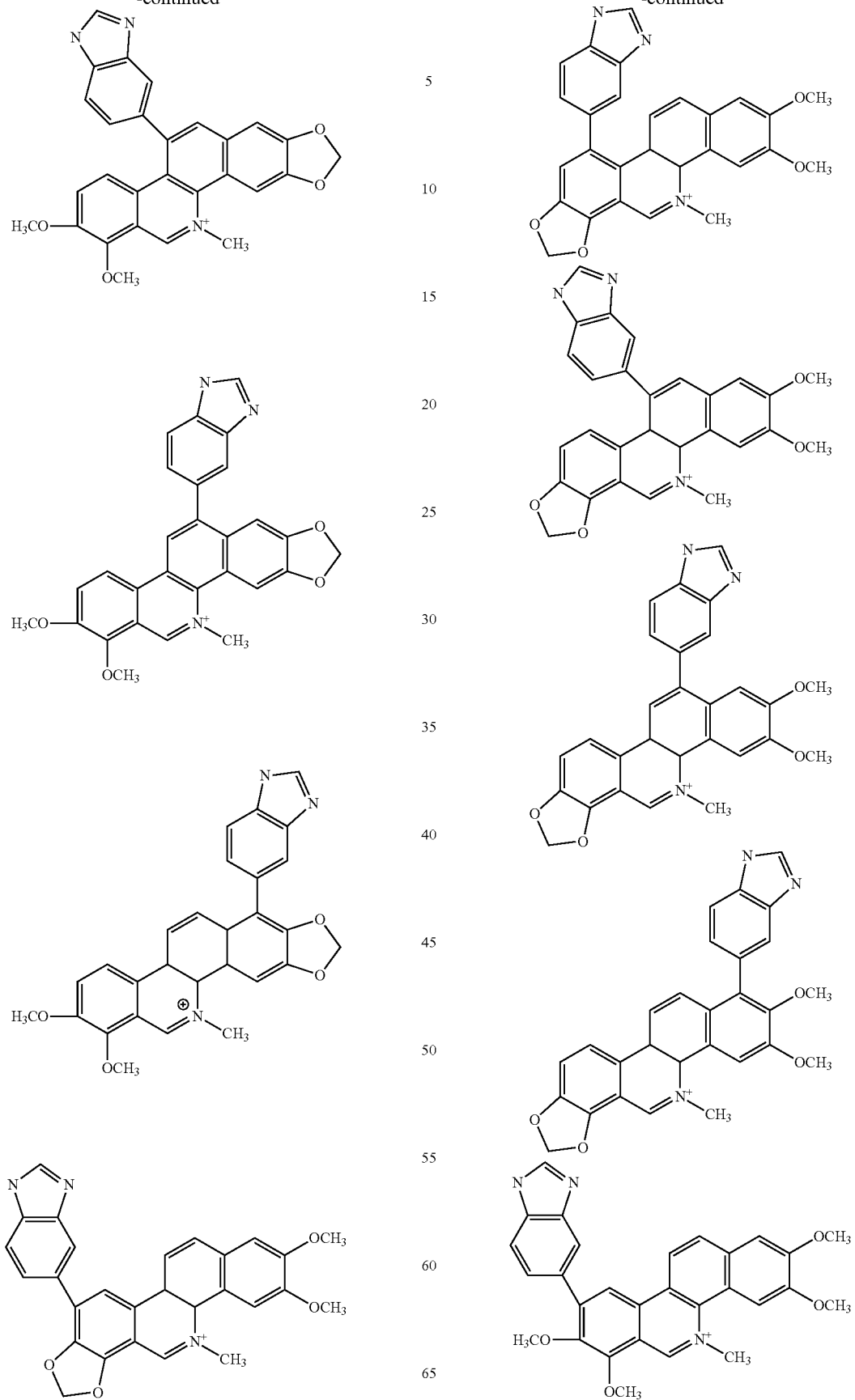

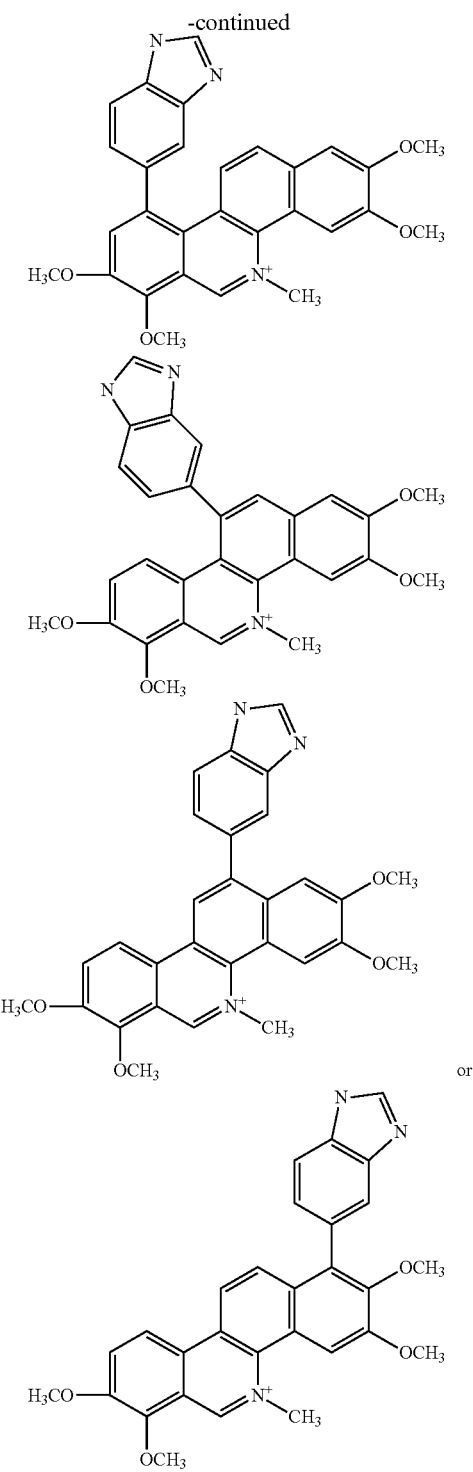

or a prodrug thereof.

In one specific embodiment the invention provides a compound of formula I or II as defined herein wherein "a substituted aryl group" denotes an aryl group that is substituted with 1 to 5 substituent groups independently selected from the following: cycloalkyl, substituted cycloalkyl, alkoxycarbonyl (e.g. —$CO_2Me$), cyano, halo, hydroxyl, carboxy (COOH), aryloxy, heteroaryloxy, heterocyclooxy, nitro, and —$NR^aR^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic; "a substituted heteroaryl group" denotes a heteroaryl group that is substituted with 1 to 5 substituent groups independently selected from the following: cycloalkyl, substituted cycloalkyl, alkoxycarbonyl (e.g. —$CO_2Me$), cyano, halo, hydroxyl, carboxy (COOH), aryloxy, heteroaryloxy, heterocyclooxy, nitro, and —$NR^aR^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic; "substituted heterocycle" or "substituted heterocyclic" denotes a heterocycle or a heterocyclic that is substituted with 1 to 5 substituent groups independently selected from the following: cycloalkyl, substituted cycloalkyl, alkoxycarbonyl (e.g. —$CO_2Me$), cyano, halo, hydroxyl, carboxy (COOH), aryloxy, heteroaryloxy, heterocyclooxy, nitro, and —$NR^aR^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic; a "substituted cycloalkyl" is a cycloalkyl group, as defined above, wherein 1 to 5 of the hydrogens have been replaced with 1 to 5 substituent groups independently selected from the following: cycloalkyl, substituted cycloalkyl, alkoxycarbonyl (e.g. —$CO_2Me$), cyano, halo, hydroxyl, oxo (=O), carboxy (COOH), aryloxy, heteroaryloxy, heterocyclooxy, nitro, and —$NR^aR^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic; and a "substituted aryloxy" is an aryloxy group, as defined above, wherein 1 to 5 of the hydrogens have been replaced with 1 to 5 substituent groups independently selected from the following: cycloalkyl, substituted cycloalkyl, alkoxycarbonyl (e.g. —$CO_2Me$), cyano, halo, hydroxyl, oxo (=O), carboxy (COOH), aryloxy, heteroaryloxy, heterocyclooxy, nitro, and —$NR^aR^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic.

provided $R^8$ is not 2-oxopropyl when $R^6$, $R^9$, and $R^{12}$ are each hydrogen, —$X^1$—$R^1$ and —$X^2$—$R^2$ are each methoxy, $X^3$ and $X^4$ are each O, $R^3$ and $R^4$ together form a methylenedioxy, which when taken together with the attached atoms forms a five-membered ring, and the bond represented - - - is a double bond;

In one specific embodiment the compound of the invention is a compound of formula I or II: provided $R^8$ is not 2-oxopropyl when $R^6$, $R^9$, and $R^{12}$ are each hydrogen, —$X^1$—$R^1$ and —$X^2$—$R^2$ are each methoxy, $X^3$ and $X^4$ are each O, $R^3$ and $R^4$ together form a methylenedioxy, which when taken together with the attached atoms forms a five-membered ring, and the bond represented by - - - is a double bond; and/or provided $R^7$ is not carboxy when $R^6$, $R^9$, and $R^{12}$ are each hydrogen, —$X^1$—$R^1$ and —$X^2$—$R^2$ are each methoxy, —$X^3$—$R^3$ and —$X^4$—$R^4$ are each methoxy, and the bond represented by - - - is a double bond.

In one specific embodiment the compound of the invention is a compound of formula I or II: provided $R^8$ is not 2-oxopropyl, when $R^6$, $R^9$, and $R^{12}$ are each hydrogen; and/or provided $R^7$ is not carboxy when $R^6$, $R^9$, and $R^{12}$ are each hydrogen.

The present invention, however, is not limited to the foregoing embodiments and may include alternative embodiments, as contemplated herein, or combinations of the foregoing embodiments.

Unless otherwise specified, a reference to a particular compound of the present invention includes all isomeric forms of the compound, to include all diastereomers, tautomers, enantiomers, racemic and/or other mixtures thereof. Unless otherwise specified, a reference to a particular compound also includes ionic, salt, solvate (e.g., hydrate), protected forms, and prodrugs thereof. For example, when a quaternary amonium cation is referred to, one skilled in the art will appreciate that the quaternary amonium cation can be associated with a suitable counterion (e.g. a pharmaceutically acceptable counterions such as Cl$^-$, Br$^-$, I$^-$, $CH_3SO_3^-$, $CF_3SO_3^-$, p-$CH_3C_6H_4SO_3^-$, citrate, tartrate, malate, fumarate, formate, or acetate). To this end, it may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19, the contents of which are incorporated herein by reference.

In one embodiment, any of the foregoing compounds may be administered as a prodrug, which is converted to a compound of formula (I) or (II) post-administration. For example, a compound of formula (I), wherein the bond between the 5- and 6-position on the ring system is saturated can function as a prodrug for a corresponding compound of formula (I), wherein the bond between the 5- and 6-position on the ring system is a double bond. Conversion of a dihydro derivative (a), to a corresponding unsaturated compound of formula (c) is illustrated below:

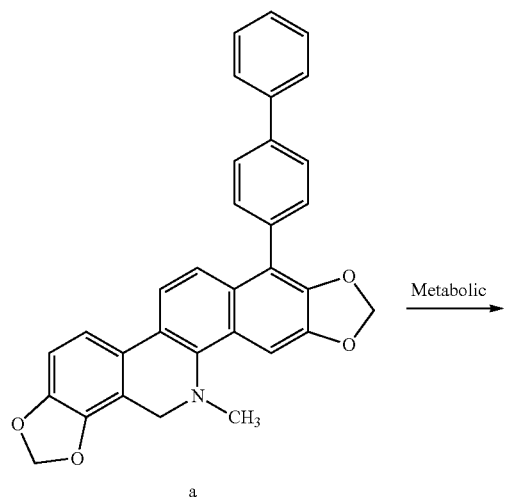

a

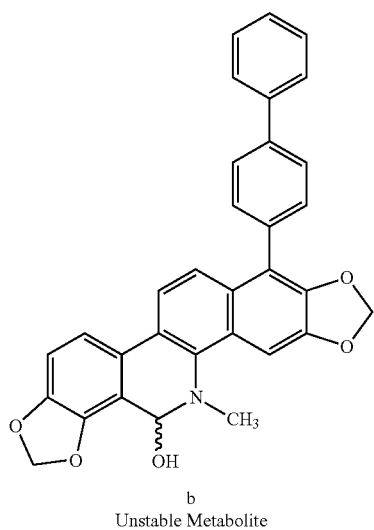

b
Unstable Metabolite

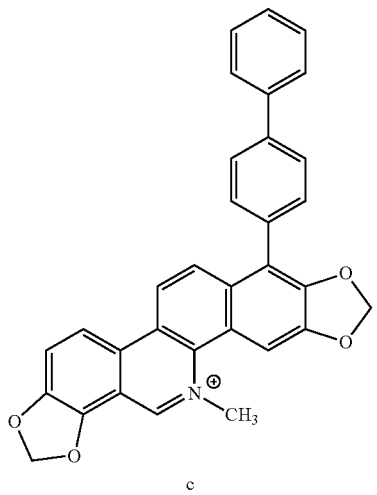

c

Figure 3:
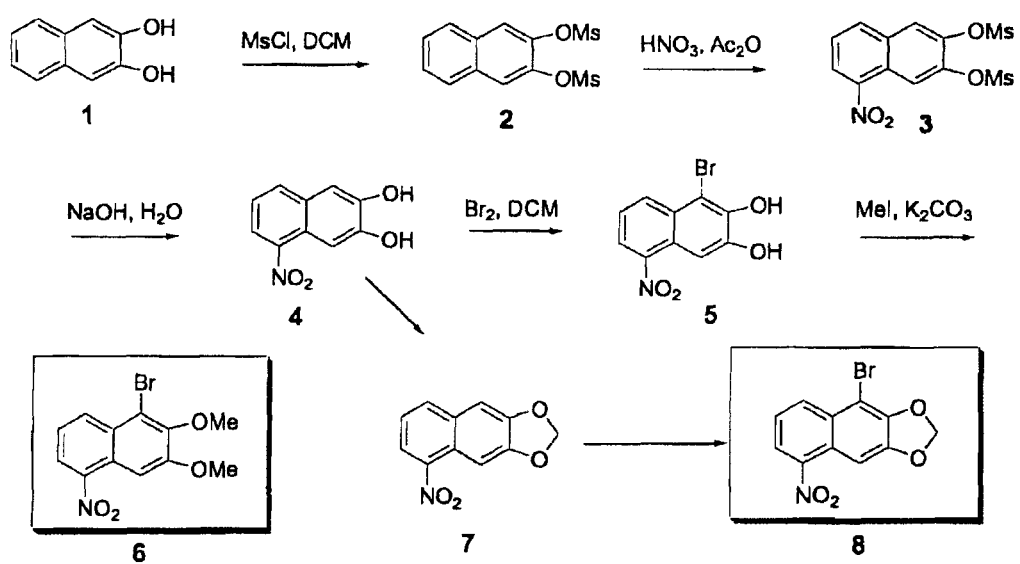
FIG. 3 illustrates a method for preparing the intermediates 1-bromo-2,3-dimethoxy-5-nitronaphthalene and 1-bromo-2,3-methylenedioxy-5-nitronaphthalene.

The present invention also relates to methods of preparing the compounds of the present invention. In one embodiment, the substituted B[c]P compounds of the present invention can be prepared using as a intermediate an appropriately substituted halogenated or triflate-substituted naphthalene. Referring to FIG. 3, a method for preparing the methylenedioxy intermediate is illustrated wherein commercially available 2,3-dihydroxynaphthalene 1 is converted to a dimesylate 2, which may be converted to a 5-nitro derivative 3 using nitric acid in acetic acid. These mesylate esters may be hydrolyzed using NaOH in water and the resulting dihydroxynaphthalene 4 may be converted to a 1-bromo derivative 5 using bromine in methylene chloride. Using methyl iodide, this dihydroxynaphthalene may be converted to 1-bromo-2,3-dimethoxy-5-nitronaphthalene 6. Compound 4 can be converted to its methylenedioxy derivative 7, which can then be brominated to provide the intermediate 8. Alternatively, 6 can be treated with borontribromide, which will provide the brominated derivative of 4, which can also be converted to its 2,3-methylenedioxy derivative 8. As illustrated below, either of the 1-bromo-2,3-dimethoxy-5-nitronaphthalene or 2,3-methylenedioxy derivatives are suitable intermediates.

Figure 4:
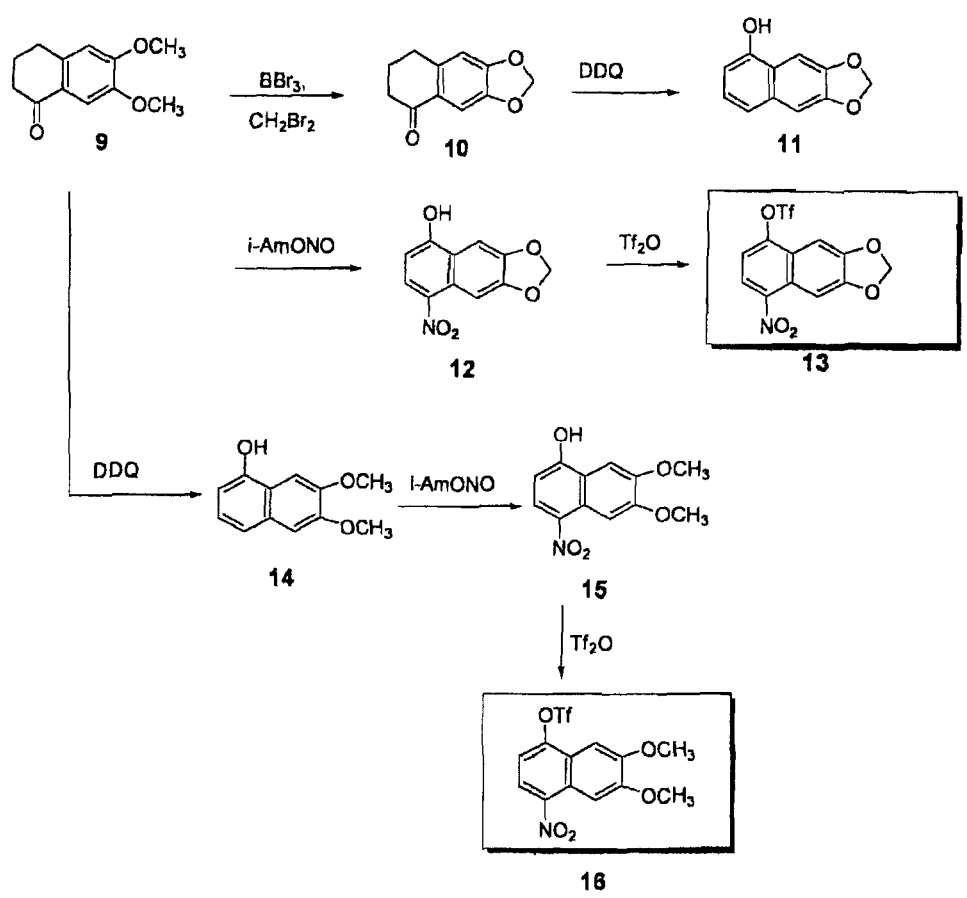
FIG. 4 illustrates the preparation of a triflate intermediate.

Referring to FIG. 4, the method for producing a triflate key intermediate is illustrated. Specifically, commercially available 6,7-dimethoxy-1-tetralone 9 can be converted using borontribromide to 6,7-dihydroxy-1-tetralone, which can be converted to a 6,7-methylenedioxy derivative 10 using dibromomethane. Treatment of the 6,7-methylenedioxy derivative with DDQ can provide a 1-hydroxy-6,7-methylenedioxynaphthalene 11. Nitration with isoamyl nitrite will provide the 1-hydroxy-4-nitro-6,7-methylenedioxynaphthalene 12, which can be converted to its triflate 13 using triflic anhydride.

In an alternative embodiment, 6,7-dimethoxy-1-tetralone 9 may be treated with DDQ to provide the naphthol 14, followed by nitration to form a 1-hydroxy-4-nitro-6,7-methylenedioxy derivative 15. Treatment of the 1-hydroxy-4-nitro-6,7-methylenedioxy derivative with triflic anhydride provides the triflate 16. Either triflate 13 or 16 is useful as a eferring to FIG. 5a or 5b, either the halogenated or triflate-substituted naphthalene intermediates may be treated intermediate.

Figure 5A:
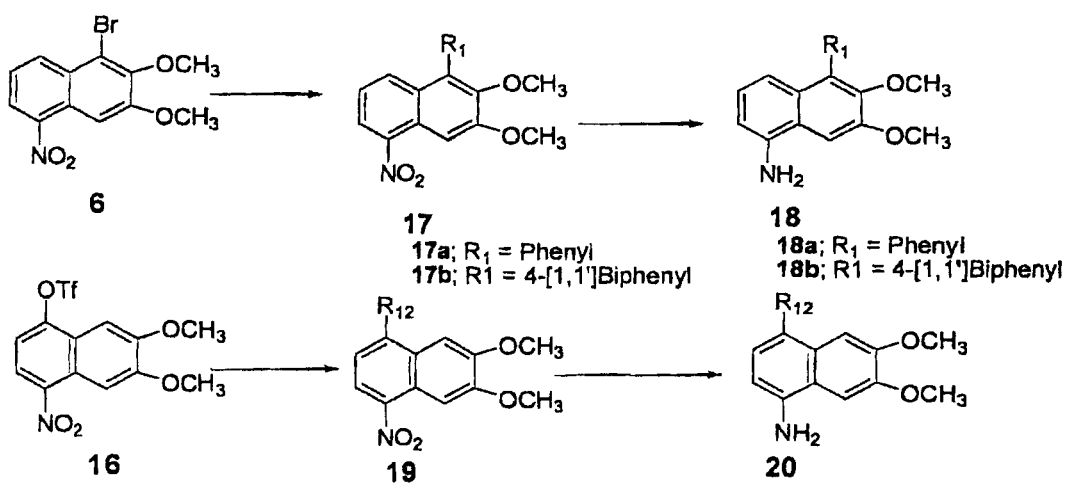
FIG. 5A illustrates the conversion of the intermediates of FIG. 3 and FIG. 4 to form a second intermediate 1- or 12-substituted-2,3-methoxy-5-aminonaphthalene.
Figure 5B:
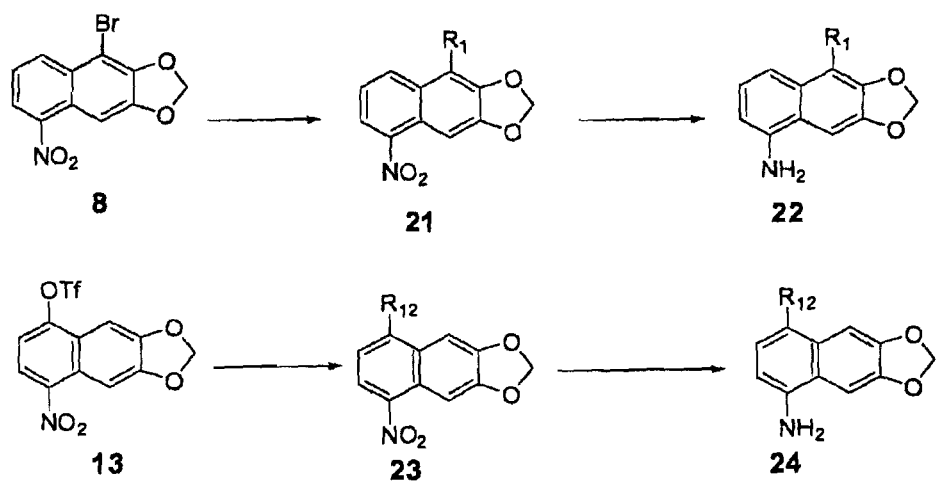
FIG. 5B illustrates the conversion of the intermediates of FIGS. 3 and 4 to form a second intermediate 1- or 12-substituted 2,3-methylenedixoy-5-aminonaphthalene.
Figure 7:
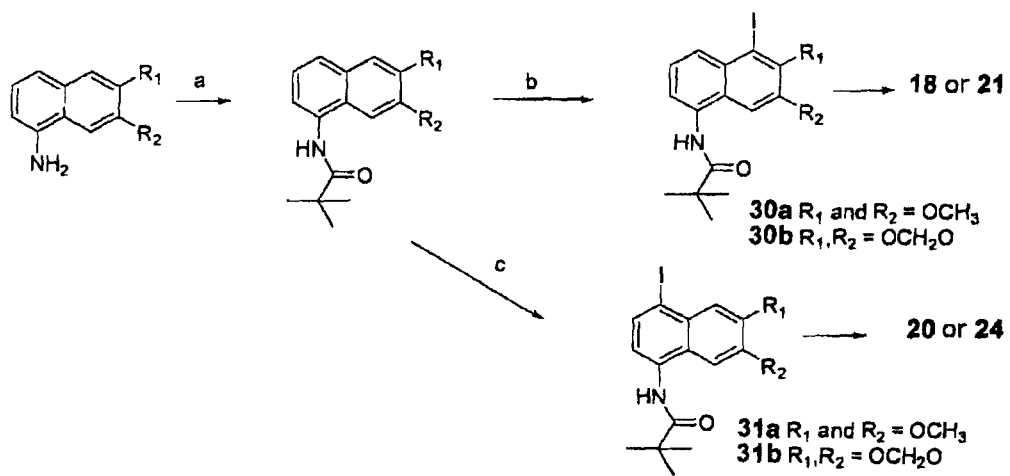
FIG. 7 illustrates a method of preparing alternative intermediates using pivalamide derivatives or N-boc protected naphthalylamines substituted with methoxyl substituents.

Rwith boronate to convert the intermediates to a corresponding alkyl, substituted alkyl, aryl, arylalkyl, heteroaryl, or heteroarylalkyl derivative, which is defined in FIGS. 5a and 5b as R. Also as illustrated in FIG. 7, similar derivatives may be prepared using a pivalamide derivative or N-boc protected naphthalylamine substituted with methoxyl substituents at both the 6- and 7-positions, which can be selectively lithiated at either the 1- or 12-position depending upon solvent conditions and reaction conditions and converted to their 1- and 12-iodo derivatives. The resulting structure provides an alternative approach to either 18 or 21 as well as to either 20 or 24 of FIG. 5.

Figure 6:
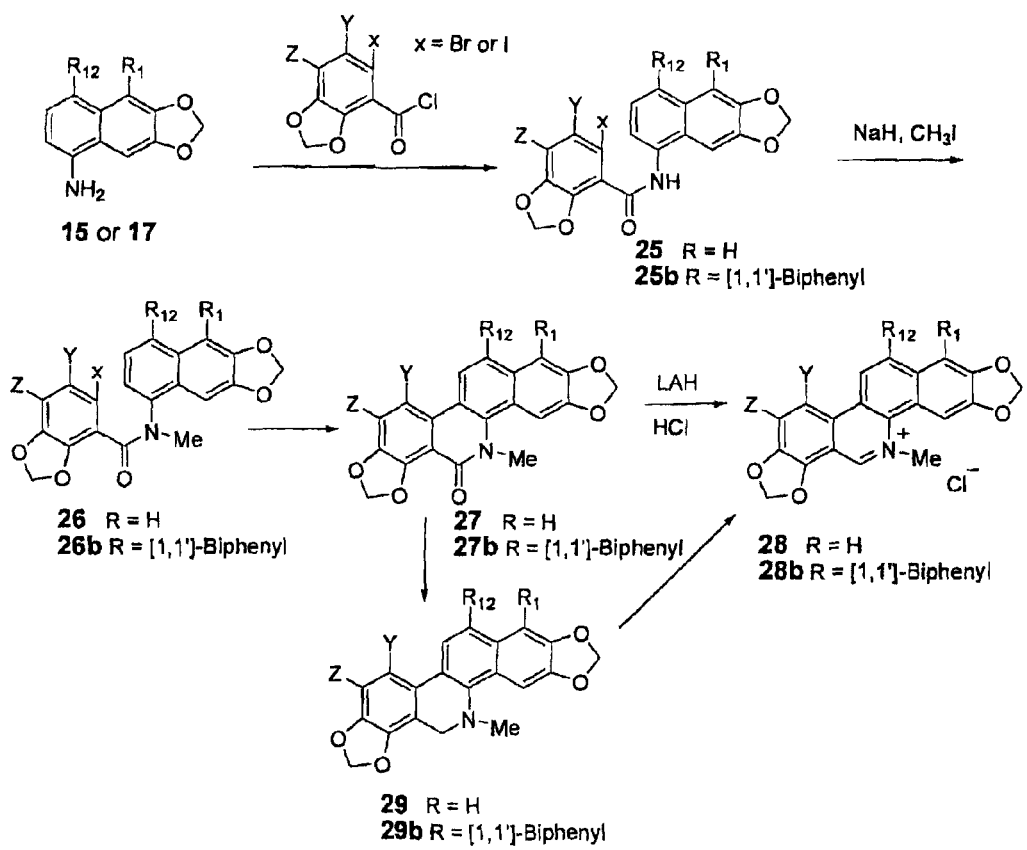
FIG. 6 illustrates a method for preparing 1- and 12-substituted 2,3-methylenedioxy-7,8-methylenedioxy-5-methylbenzo[c]phenanthridium salts from the intermediates of FIG. 5B.

Referring to FIG. 6, any of the final compounds of FIGS. 5 and 7 may then be converted to their final form. Specifically, the derivatives may be reacted with the acid chloride of either 2-bromo or 2-iodo-5,6-methylenebenzoic acid resulting in the formation of a secondary amide intermediate, which can be alkylated to form the tertiary amide. Heck cyclization of these tertiary amides will provide the benzo[c]phenathridin-6-one, which upon reduction with lithium aluminium hydride and treatment of the resultant product with aqueous HCl will provide the 5-alkyl 1- and 12-substituted 2,3-methylene-dioxy-7,8-methylenedioxy-5-alkylbenzo[c]phenanthridinium chloride.

The substituted benzo[c]phenanthridin-6-one formed by Heck cyclization of either appropriately substituted N-methyl or N-benzyl tertiary amide as outlined in FIG. 1 can be used as an intermediate for the preparation of 5,6-dihydrobenzo[c]phenanthridines. As shown in FIG. 1, the N-alkyl-5,6-dihydrobenzo[c]phenanthridines thus formed can be oxidized with Jones reagent or DDQ to provide the appropriately substituted 5-alkylbenzo[c]phenanthridinium derivative.

Figure 2:
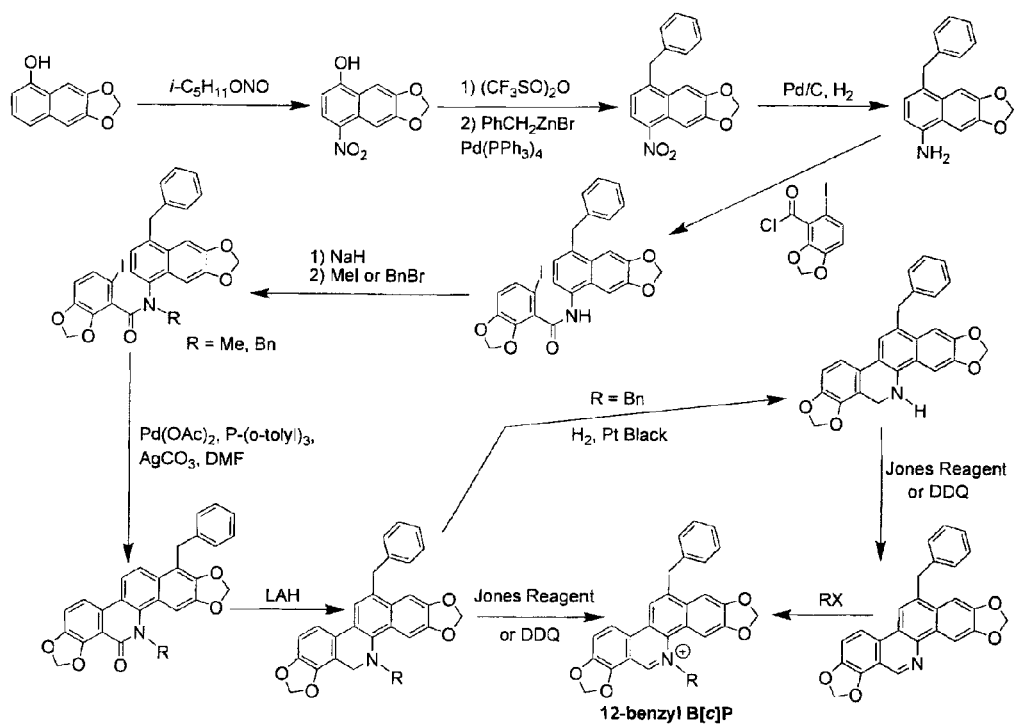
FIG. 2 illustrates a method for the preparation of a 12-substituted B[c]P compound wherein a benzyl group is substituted at the 12 position using a Negishi coupling of the triflate with the organozinc derivative of benzyl bromide.

An even further alternative to preparing the compounds of the present invention is provided in FIG. 2. Specifically, this reaction scheme couples the desired substitution group (e.g. benzyl, biphenyl, benzimidazole) to a 4-nitro derivative of 6,7-methylenedioxy-1-naphthol using a Negishi coupling, which is reduced to an aryl amine. This aryl amine is then reacted with an acid chloride or either 6-bromo or 6-iodo-2, 3-methylenedioxybenzoic acid. Cyclization of the resulting secondary amide could be problematic, as it would likely exist as a 6-hydroxy tautomeric form. Accordingly, prior to cyclization, the N-methyl and N-benzyl tertiary amides are formed. The resulting structures are then cyclized using Heck cyclization conditions. The resulting product is then reduced using LAH or oxidized with either Jones reagent or DDQ to provide the quaternary B[c]P derivative of the present invention.

Figure 9:
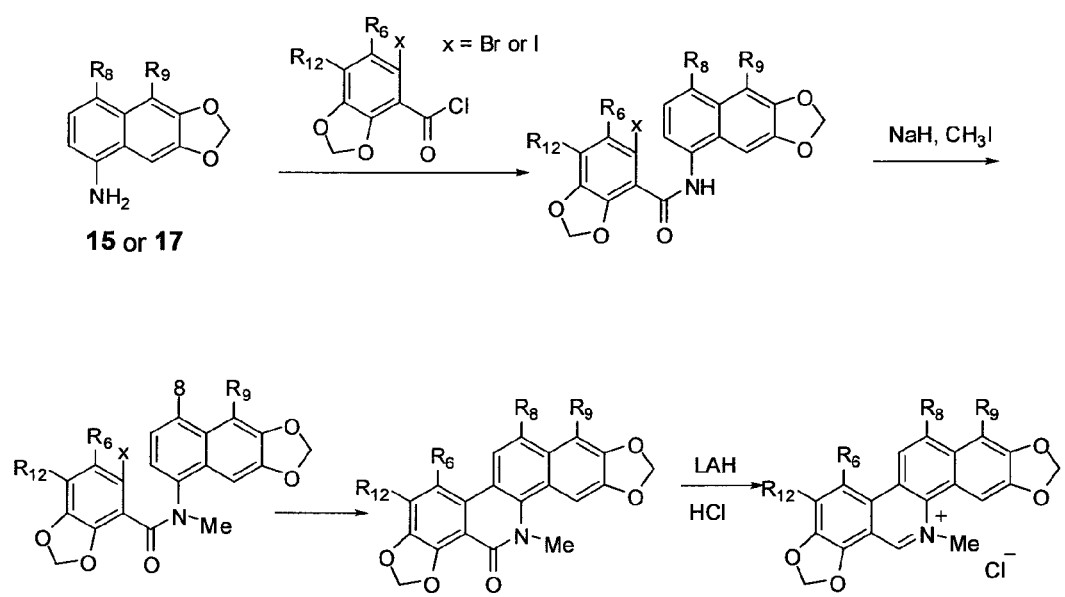
FIG. 9 illustrates the preparation of representative compounds of the invention.

FIG. 9 also illustrates the preparation of compounds of the invention.

Figure 10:
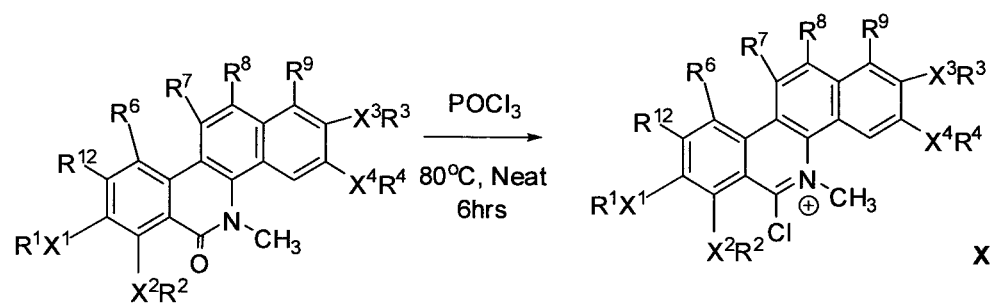
FIG. 10 illustrates the preparation of an intermediate compound of formula X which is a useful intermediate for preparing compounds of the invention wherein $R^{10}$ is other than H.

FIG. 10 and Example 24 illustrate the preparation of an intermediate compound of formula X which is a useful intermediate for preparing compounds of the invention wherein $R^{10}$ is other than H.

Figure 11:
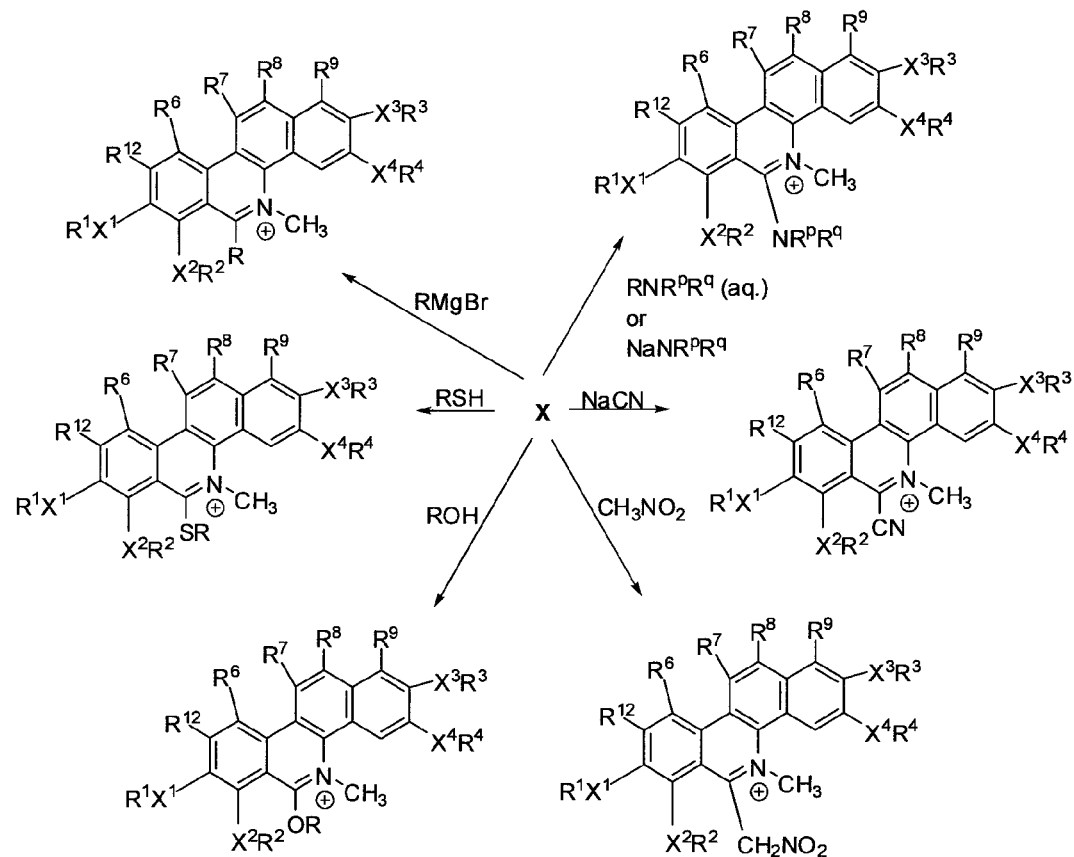
FIG. 11 illustrates the preparation of various compounds of the invention by the treatment of the compound of formula X (FIG. 10) with a variety of nucleophiles.
Figure 12:
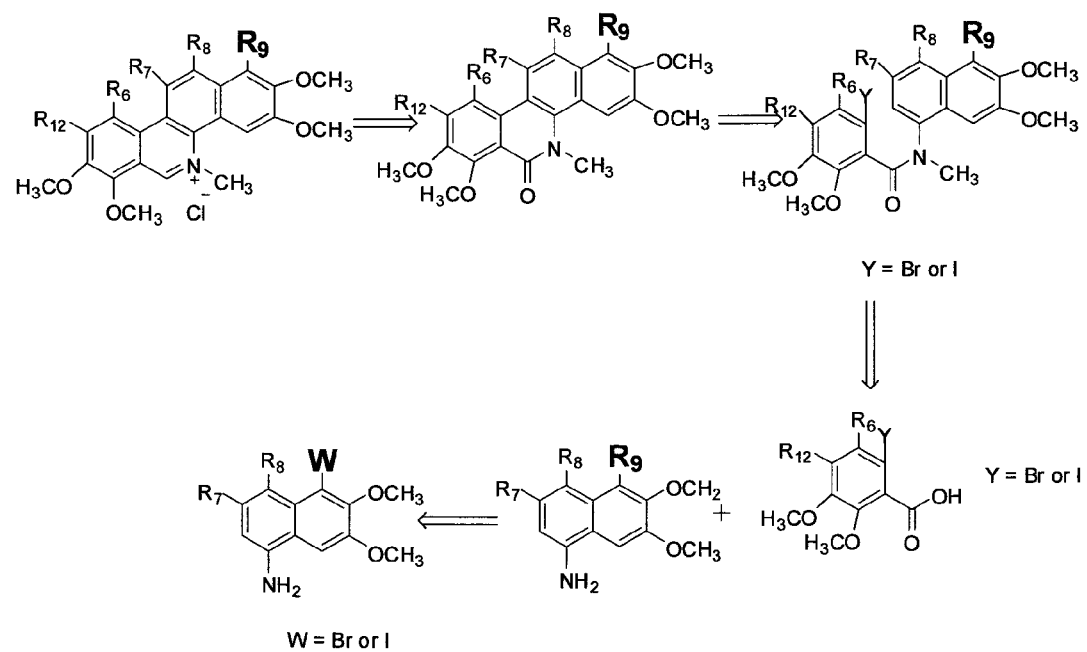
FIG. 12 illustrates a retrosynthetic scheme for varied 1-substituted 5-methyl-2,3,7,8,-Tetramethoxybenzo[c]-phenanthridines.
Figure 13:
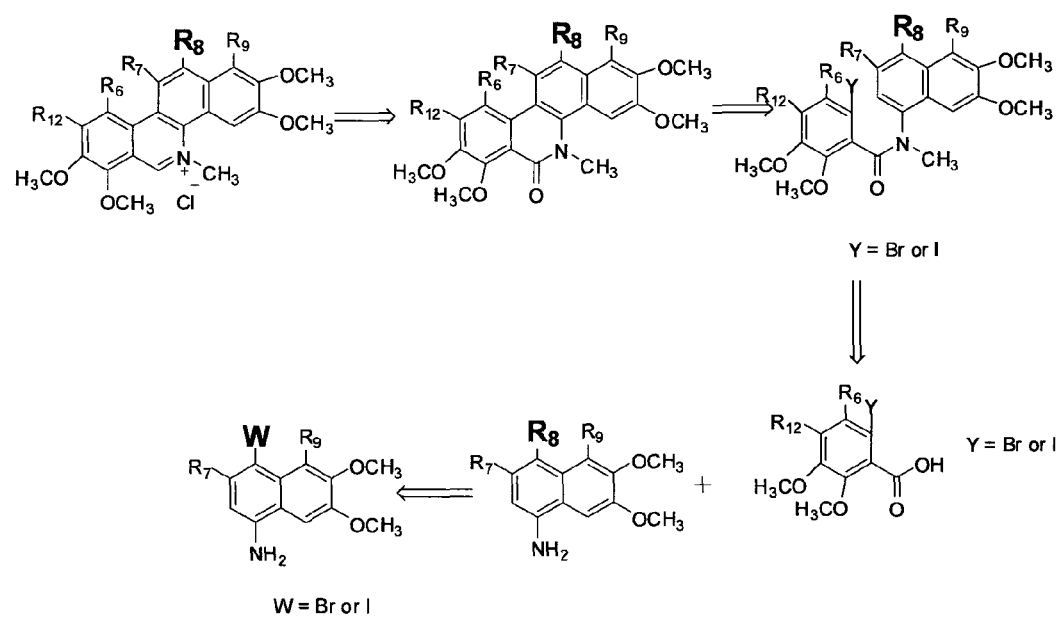
FIG. 13 illustrates a retrosynthetic scheme for varied 12-substituted 5-methyl-2,3,7,8,-Tetramethoxy-benzo[c] phenanthridines.
Figure 14:
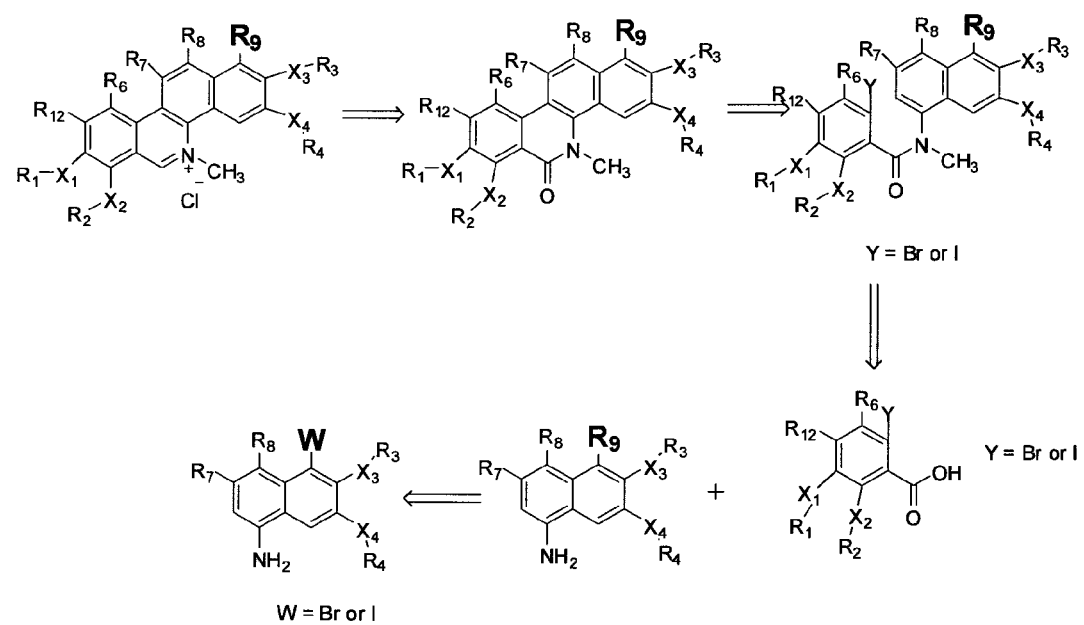
FIG. 14 illustrates a retrosynthetic scheme for varied 1-substituted 5-methylbenzo[c]phenanthrdine compounds.
Figure 15:
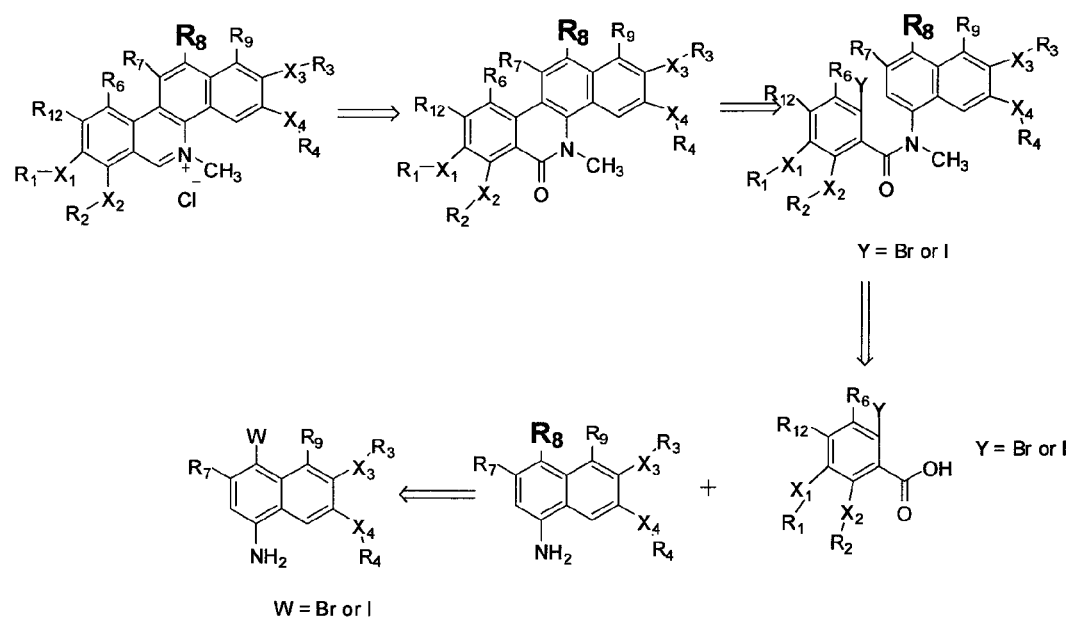
FIG. 15 illustrates a retrosynthetic scheme for varied 12-substituted 5-methylbenzo[c]phenanthrdine compounds.

FIG. 11 illustrates the preparation of various compounds of the invention by the treatment of the compound of formula X (FIG. 10) with a variety of representative nucleophiles.

In one embodiment the invention provides a compound of formula X:

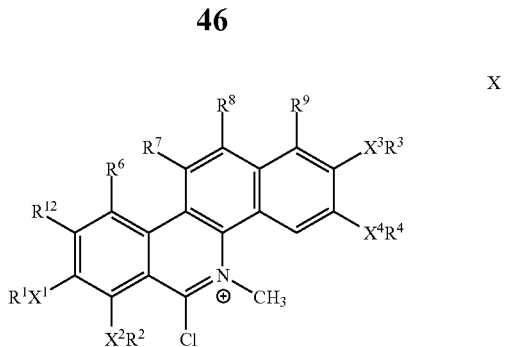

wherein $X^1$-$X^4$ and $R^1$-$R^{12}$ have any of the values or specific values defined herein.

In one specific embodiment the invention provides a method for preparing a compound of formula I or II where in the bond represented by - - - is a double bond, comprising reducing (e.g. with LAH) a corresponding compound of formula I or II wherein $R^{10}$ and $R^{11}$ taken together with the carbon to which they are attached form a carbonyl group and the bond represented by - - - is a single bond, to provide the corresponding compound of formula I or II where in the bond represented by - - - is a double bond.

In one specific embodiment the invention provides a method for preparing a salt of a compound of formula I or II comprising contacting a corresponding compound of formula I or II with a suitable acid or base to provide the salt of the compound of formula I or II.

The invention also provides an intermediate amide of formula XI that is useful for preparing a compound of formula I or II:

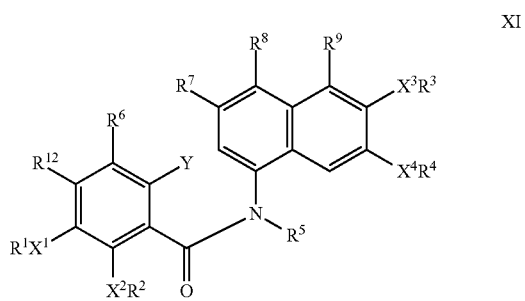

wherein $X^1$-$X^4$ and $R^1$-$R^{12}$ have any of the values or specific values defined herein; and Y is a suitable reactive group (e.g. chloro, bromo, or iodo).

The invention also provides a method for preparing a cyclic amide of formula XII:

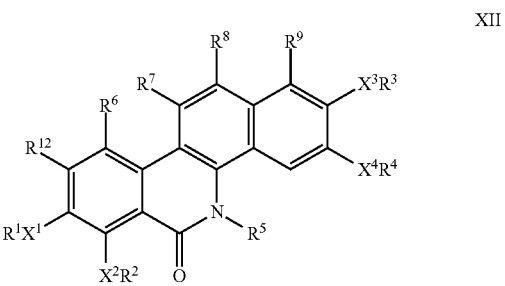

wherein $X^1$-$X^4$ and $R^1$-$R^{12}$ have any of the values or specific values defined herein; that comprises reacting a corresponding amide of formula XI:

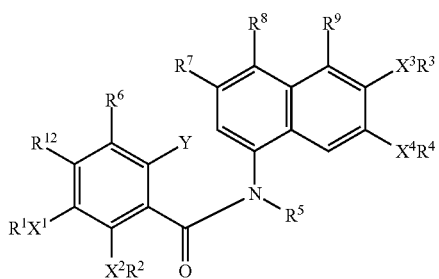

wherein Y is a suitable reactive group (e.g. chloro, bromo, or iodo) under conditions that are suitable to provide ring closure to the compound of formula XII.

While certain embodiments of the foregoing methods of preparation are provided as using a benzyl group at the 1 or 12 position, particularly FIGS. 1 and 2, one of ordinary skill in the art will understand that the foregoing methods may be adapted to provide for the addition of other groups (e.g. aromatic substituent groups) at any of positions 1, 9, 10, 11 and/or 12. To this end, the present invention is not limited to the foregoing schemes and methods of preparation may be devised or adapted using other similar methods or alternative methods otherwise known in the art.

The foregoing compounds of the present invention are advantageous because they more fully occupy the GTP binding pocket of FtsZ. These compounds thereby enhance van der Waals contacts, and in some cases hydrogen bonding contacts, with the FtsZ protein. To this end, the compounds of the present invention heighten the competitive inhibition of GTP binding, thereby, reducing GTPase activity and FtsZ polymerization. A reduction of FtsZ polymerization within bacterial cells prevents Z-ring formation and recruitment of the accompanying divisome proteins. Thus, the cell becomes ill-equipped to undergo cytokinesis and is unable to proliferate within the host organism.

Based on the foregoing, one or more small molecules, or pharmaceutical salts thereof, of the present invention may be synthesized and administered as a composition used to treat and/or prevent a bacterial infection wherein the bacterial cell uses polymerized FtsZ protein, or a homolog thereof, to facilitate cytokinesis. To this end, the compounds and compositions of the present invention may be administered to treat Staph Infections, Tuberculosis, Urinary Tract Infections, Meningitis, Enteric Infections, Wound Infections, Acne, Encephalitis, Skin Ulcers, Bed Sores, Gastric and Duodenal Ulcers, Eczema, Periodontal disease, Gingivitis, Halitosis, Anthrax, Tularemia, or Pneumonia, or the like.

The compounds and compositions of the present invention, therefore, may be administered as an antimicrobial to treat bacterial infections caused by FtsZ-expressing Gram-negative or Gram-positive bacteria. Such bacteria include Gram-negative strains such as, but are not limited to, *Escherchia coli, Caulobacter crescentus, Pseudomonas aeruginosa, Agrobacterium tumefaciens, Branhamella catarrhalis, Citrobacter diversus, Enterobacter aerogenes, Klebsiella pneumoniae, Proteus mirabilis, Pseudomonas aeruginosa, Salmonella typhimurium, Neisseria meningitidis, Serratia marcescens, Shigella sonnei, Neisseria gonorrhoeae, Acinetobacter baumannii, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis,* and *Haemophilus influenzae* among others. Alternatively, Gram-positive strains include, but are not limited to, *Staphylococcus aureus, Streptococcus pyogenes, Streptococcus faecalis, Enterococcus faecalis, Enterococcus faecium, Bacillus subtilis, Micrococcus luteus, Mycobacterium tuberculosis, Bacillus anthracis, Clostridium difficile, Propionibacterium acnes, Streptococcus mutans, Actinomyces viscosus, Actinomyces naeslundii, Streptococcus sanguis, Streptococcus pneumoniae* and *Streptococcus salivarius* among others. In even further embodiments, the compositions of the present invention may be administered to treat MDR bacterial strains such as, but not limited to, MRSA, vancomycin-resistant *Enterococcus* (VRE), MDR tuberculosis, *Clostridium difficile* and the like.

The compounds and compositions of the present invention may be administered to the patient at therapeutically effective dosage levels to treat the targeted bacterial infection. The dosage is preferably administered as a unit dosage form and may be dependant upon the genus, species, or strain of the bacteria treated. The unit dosage form for oral or parenteral use may be varied or adjusted according to the particular application and the potency of the active ingredient, as determined by factors such as the compound's Minimum Inhibitory Concentration (MIC), absorption rates, toxicity, the patient's age, weight, sex, general physical condition and the like. Using factors such as this, a therapeutically effective amount may be administered so as to ameliorate the symptoms of and/or treat or prevent microbial infections or diseases related thereto. Determination of a therapeutically effective amount is well within the capabilities of those skilled in the art, especially in light of the detailed disclosure and examples provided herein.

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, other antimicrobial (for example, an aminoglycoside, an antifungal, an antiparasitic, an antiviral, a carbapenem, a cephalosporin, a fluororquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropieitin (for example, epoetin alpha), a filgrastim (for example, G-CSF, Neupogen), a sargramostim (GM-CSF, Leukine), an immunization, an immuno-globulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

The composition containing the compound of the present invention may comprise a pharmaceutically acceptable carrier and may include other optional components. Such pharmaceutically acceptable carriers can be either solid or liquid, where solid form preparations may include powders, tablets, dispersable granules, capsules, cachets, suppositories or other well known carriers. To this end, the present invention is not limited by the selection of the carrier and may include any carrier known in the art to administer an antimicrobial agent to a mammal. The composition or formulation may also include diluents, flavoring agents, solubilizers, lubricants, suspending agents, binders, disintegrating agents, encapsulating materials, adjuvants, buffers, preservatives, and other additional excipients and other agents known to one of ordinary skill in the art. The compound may also be contained within known alternative carriers such as, but not limited to, soaps, disinfectants, topical ointments, toothpaste, mouthwash, breath strips, hand sanitizers, and the like.

The pharmaceutical compositions may also be formulated to suit a selected route of administration, and may contain ingredients specific to the route of administration. Routes of administration of such pharmaceutical compositions are usually split into five general groups: inhaled, oral, transdermal, parenteral and suppository. In the present invention, any of these routes may be utilized so long as the compound of the present invention is placed into contact with the targeted bacteria, such as by way of the blood stream of the mammal. In one embodiment, the pharmaceutical compositions of the present invention may be suited for parenteral administration by way of injection such as intravenous, intradermal, intramuscular, intrathecal, or subcutaneous injection. Alternatively, the composition of the present invention may be formulated for oral administration as provided herein or otherwise known in the art.

The following examples illustrate particular methods for preparing and characterizing compounds in accordance with this invention. These examples are thus not to be read as limiting the scope of the invention.

EXAMPLES

Example 1

Determining the FtsZ-Targeting Activities of B[c]P Compounds

A. Method for Characterizing B[c]P Binding to FtsZ

B[c]P binding to FtsZ can be tested using a fluorescence-based competition binding assay using purified FtsZ and a commercially available GTPγS analog where the nucleotide is covalently conjugated via its sulfur atom to the fluorescent dye BODIPY (DIPYrromethene BOron difluoride). Upon binding to FtsZ, BODIPY-GTPγS undergoes a dramatic increase in fluorescence emission intensity (I) at 510 nm. This binding-induced change in BODIPY-GTPγS fluorescence provides the dissociation constant ($K_{d-GTP}$) of the nucleotide for the protein through analysis of fluorescence titration profiles with the following formalism, which is predicated on a one-to-one binding stoichiometry:

$$I = I_0 + \frac{I_\infty - I_0}{2[FtsZ]_{tot}}[([GTP]_{tot} + [FtsZ]_{tot} + K_{d-GTP}) - (([GTP]_{tot} + [FtsZ]_{tot} + K_{d-GTP})^2 - 4[GTP]_{tot}[FtsZ]_{tot})^{1/2}]$$

$I_0$ and $I$ are the fluorescence emission intensities of BODIPY-GTPγS in the absence and presence of a given FtsZ concentration, respectively, $I_\infty$ is the fluorescence emission intensity of BODIPY-GTPγS in the presence of an infinite FtsZ concentration, and $[GTP]_{tot}$ and $[FtsZ]_{tot}$ are the total concentrations of BODIPY-GTPγS and FtsZ, respectively.

Figure 8:
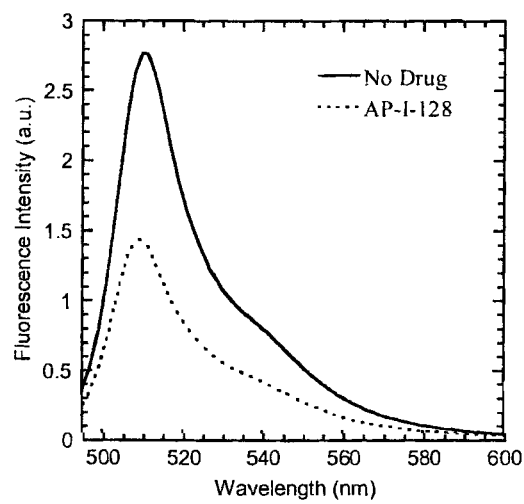
FIG. 8 illustrates the reduction in fluorescence that accompanies the displacement of BODIPY-GTPγS from *Bacillus subtilis* FtsZ as a consequence of the binding of a representative compound of the invention.

As shown in FIG. 8, the fluorescence of FtsZ-bound BODIPY-GTPγS decreases upon addition of a salt of the compound of Example 3, which is illustrated below:

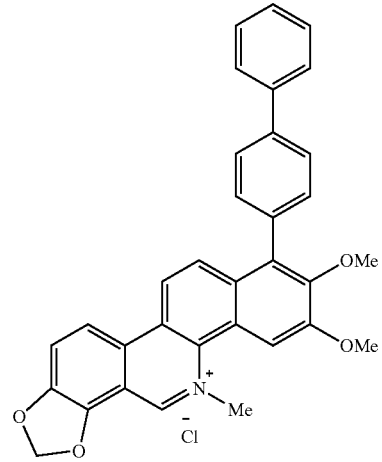 [SMILES: COc1cc2c(ccc3c4ccc5c(c4c[n+](C)c23)OCO5)c(-c2ccc(-c3ccccc3)cc2)c1OC ; [Cl-]]

This reduction in fluorescence reflects the binding of the compound to the target FtsZ protein and the concomitant release of the FtsZ-bound BODIPY-GTPγS.

The effective compound concentrations at which 50% of the FtsZ-bound BODIPY-GTPγS is released ($EC_{50}$) can be determined by fitting the fluorescence profiles with the following sigmoidal relationship:

$$I = I_\infty + \frac{I_0 - I_\infty}{\left(1 + \frac{[Compd]_{tot}}{EC_{50}}\right)^p}$$

$I_0$ and $I$ are the fluorescence emission intensities of the FtsZ-BODIPY-GTPγS complex in the absence and presence of a given compound concentration, respectively, $I_\infty$ is the fluorescence emission intensity of the FtsZ-BODIPY-GTPγS complex in the presence of infinite compound concentration, $[Compd]_{tot}$ is the total compound concentration, and p is the Hill slope. Using the $EC_{50}$ values so determined, the dissociation constants ($K_{d-Compd}$) for the compounds can be calculated using the well-established Cheng-Prusoff formalism:

$$K_{d-Compd} = \frac{ED_{50}}{1 + \frac{[GTP]_{tot}}{K_{d-GTP}}}$$

B. Method for Characterizing the Inhibition of FtsZ GTPase Activity by B[c]P Compounds.

GTPase activity can be tested using a GTPase assay in which FtsZ-mediated hydrolysis of GTP to GDP and inorganic phosphate ($P_i$) is measured spectrophotometrically through reaction of the released $P_i$ with malachite green and molybdate under acidic conditions to form a ternary complex that absorbs light at 650 nm. The reactions are incubated and assayed in 96-well microtiter plates.

Compound concentrations at which GTPase activity is inhibited by 50% ($IC_{50}$) can be determined by fitting semilogarithmic GTPase profiles with the following sigmoidal relationship:

$$\% \text{ GTPase Activity} = \frac{100}{\left(1 + \left(\frac{[Compd]_{tot}}{IC_{50}}\right)\right)^p}$$

TABLE 1

Bacillus subtilis FtsZ GTPase Inhibitory Activities of Compounds of the Invention

| Compound | Relative IC$_{50}$* |
|---|---|
| Example 3 | 0.5 |
| Sanguinarine | 1.0 |
| Chelerythrine | 1.0 |

*Relative IC$_{50}$ reflects the concentration relative to sanguinarine (whose value is set to 1) that is able to produce 50% inhibition of B. subtilis FtsZ GTPase activity.

C. Method for Characterizing the Inhibition of FtsZ Polymerization by B[c]P Compounds.

B[c]P inhibition of FtsZ polymerization can be tested using a 90°-angle light scattering assay for monitoring drug impact on FtsZ polymerization. This assay is premised on the increased light scattering properties of polymeric FtsZ relative to the monomeric form of the protein. To this end, the light scattering at 600 nm of 5 μM FtsZ is continuously monitored under polymerization conditions in the absence or presence of a B[c]P compound at concentrations ranging from 40 to 80 μM.

Polymerization is initiated by addition of 0.5 mM GTP. The rate and extent of FtsZ polymerization can be quantified by analyzing the light scattering profiles to derive maximal light scattering values (which provide a readout of the extent of polymerization) as well as the times required to reach half-maximal light scattering values (which provide a readout of the rate of polymerization).

TABLE 2

Inhibitory Activities of Compounds of the Invention Versus Bacillus subtilis FtsZ Polymerization

| Compound* | Maximal Light Scattering (a.u.)# | Time to Reach Half-Maximal Light Scattering (seconds) |
|---|---|---|
| None | 3.40 | 91.6 |
| Example 3 | 1.76 | 600.5 |
| Sanguinarine | 3.06 | 216.4 |
| Chelerythrine | 2.83 | 205.3 |

*When present, the concentration of all compounds was 40 μM.
a.u. denotes arbitrary units.

Example 2

Determining the Antibacterial Activities of B[c]P Compounds

A. Planktonic (Free-Living) Antibacterial Assay

Planktonic antibacterial activity can be determined using a broth microdilution assay in which log-phase bacteria are grown at 37° C. in appropriate medium containing two-fold serial dilutions of a compound to yield a final concentration ranging from 256 to 0.1 μg/ml. For determination of minimal inhibitory concentration (MIC) values, bacterial growth is monitored after 24 hours by measuring optical density at 600 nm. MIC values reflect the minimal compound concentrations at which bacterial growth is completely inhibited.

TABLE 3

Planktonic Antibacterial Activities of Compounds of the Invention*

| Compound | Staphylococcus aureus MIC (μg/ml) | MRSA MIC (μg/ml) | Mycobacterium tuberculosis MIC (μg/ml) |
|---|---|---|---|
| Example 3 | 2.0 | 8.0 | 4.0 |
| Sanguinarine | 8.0 | 16.0 | 8.0 |
| Chelerythrine | 8.0 | 16.0 | 8.0 |

*MIC values, which reflect the minimum inhibitory concentrations of compound at which bacterial growth is completely inhibited, have been determined after 24 hours of continuous drug exposure using a broth microdilution assay.

TABLE 4

Planktonic Antibacterial Activities of Compounds of the Invention*

| Compound | Enterococcus faecalis MIC (μg/ml) | Bacillus subtilis MIC (μg/ml) |
|---|---|---|
| Example 3 | 16.0 | 2.0 |
| Sanguinarine | 32.0 | 4.0 |
| Chelerythrine | 32.0 | 4.0 |

*MIC values, which reflect the minimum inhibitory concentrations of compound at which bacterial growth is completely inhibited, have been determined after 24 hours of continuous drug exposure using a broth microdilution assay.

The minimal inhibitory concentration against MRSA for each of the following representative compounds of the invention was determined to be less than 16 μg/ml.

TABLE 5

Minimal Inhibitory Concentrations against MRSA for Representative Compounds of the Invention

| Example | Structure | MIC vs. MRSA (μg/ml) |
|---|---|---|
| Example 3 | 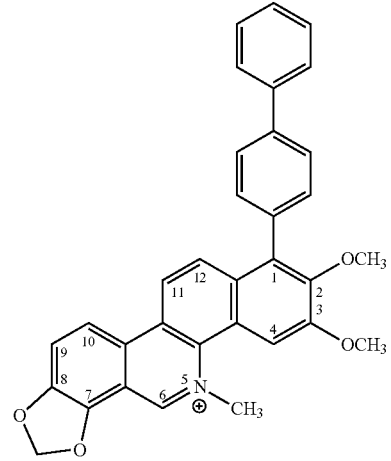 [SMILES: COc1cc2c(ccc3c4ccc5c(c4c[n+](C)c23)OCO5)c(-c2ccc(-c3ccccc3)cc2)c1OC] | <16 |

TABLE 5-continued

Minimal Inhibitory Concentrations against MRSA for Representative Compounds of the Invention

| Example | Structure | MIC vs. MRSA (μg/ml) |
|---|---|---|
| Example 4 | 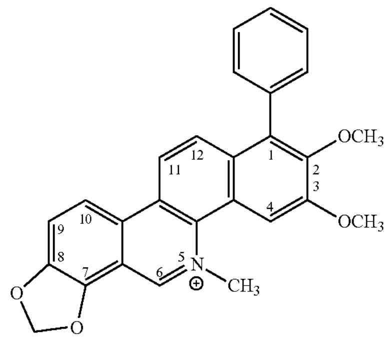 [SMILES: COc1cc2c(ccc3c4ccc5c(c4c[n+](C)c23)OCO5)c(-c2ccccc2)c1OC] | <16 |
| Example 5 | 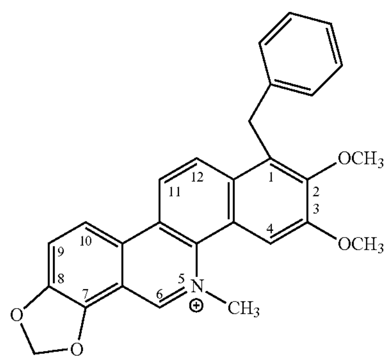 [SMILES: COc1cc2c(ccc3c4ccc5c(c4c[n+](C)c23)OCO5)c(Cc2ccccc2)c1OC] | <16 |
| Example 6 | 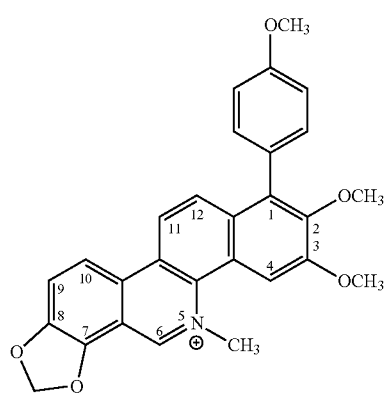 [SMILES: COc1ccc(-c2c(OC)c(OC)cc3c2ccc2c4ccc5c(c4c[n+](C)c32)OCO5)cc1] | <16 |
| Example 7 | | <16 |
| Example 8 | | <16 |
| Example 9 | | <16 |

TABLE 5-continued

Minimal Inhibitory Concentrations against MRSA for Representative Compounds of the Invention

| Example | Structure | MIC vs. MRSA (µg/ml) |
|---|---|---|
| Example 10 | [cyclohexyl-substituted phenanthridinium with OCH3 groups at positions 2,3 and H3CO at positions 7,8; N-CH3] | <16 |
| Example 11 | [cyclopropyl-substituted phenanthridinium with OCH3 groups at positions 2,3 and H3CO at positions 7,8; N-CH3] | <16 |
| Example 12 | [phenyl-substituted phenanthridinium with OCH3 groups at positions 2,3 and H3CO at positions 7,8; N-CH3] | <16 |
| Example 13 | [biphenyl-substituted phenanthridinium with OCH3 groups at positions 2,3 and methylenedioxy at positions 7,8; N-CH3] | <16 |
| Example 14 | [phenyl-substituted phenanthridinium at position 11 with OCH3 groups at positions 2,3 and H3CO at positions 7,8; N-CH3] | <16 |
| Example 15 | [3,4,5-trimethoxyphenyl-substituted phenanthridinium with OCH3 groups at positions 2,3 and H3CO at positions 7,8; N-CH3] | <16 |
| Example 16 | [4-(dimethylamino)phenyl-substituted phenanthridinium with OCH3 groups at positions 2,3 and H3CO at positions 7,8; N-CH3] | <16 |
| Example 17 | [furan-3-yl-substituted phenanthridinium with OCH3 groups at positions 2,3 and H3CO at positions 7,8; N-CH3] | <16 |

TABLE 5-continued
Minimal Inhibitory Concentrations against MRSA for Representative Compounds of the Invention
| Example | Structure | MIC vs. MRSA (µg/ml) |
|---|---|---|
| Example 18 | 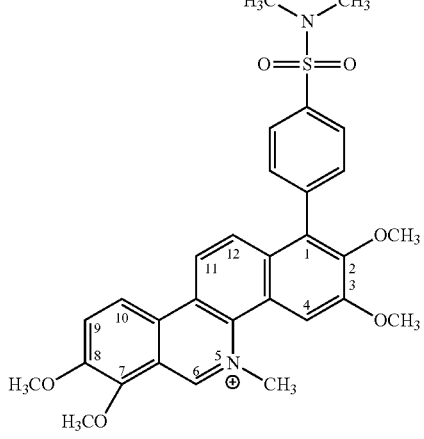 | <16 |
| Example 19 | 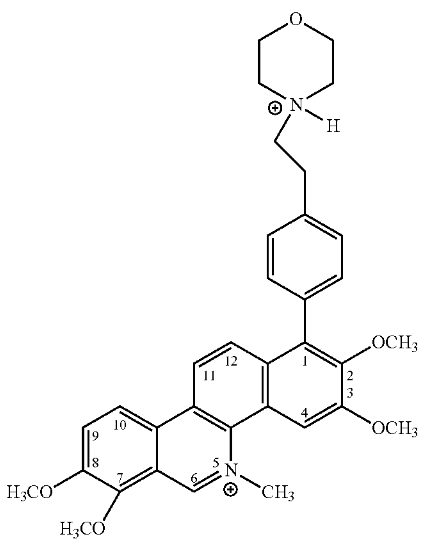 [SMILES: COc1cc2c(ccc3c4ccc(OC)c(OC)c4c[n+](C)c23)c(-c2ccc(CC[NH+]3CCOCC3)cc2)c1OC] | <16 |
| Example 20 | 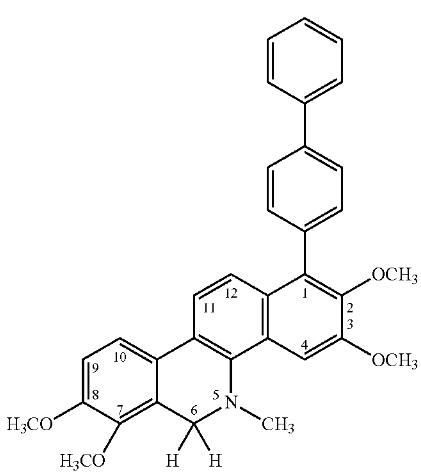 [SMILES: COc1ccc2c(c1OC)CN(C)c1c-2ccc2c(-c3ccc(-c4ccccc4)cc3)c(OC)c(OC)cc12] | <16 |
| Example 21 | 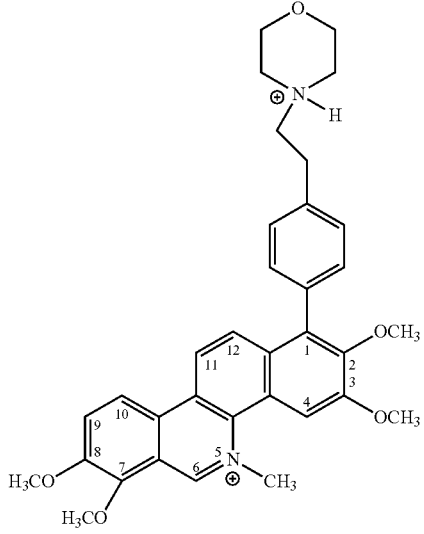 | <16 |
| Example 22 | | <16 |
| Example 23 | 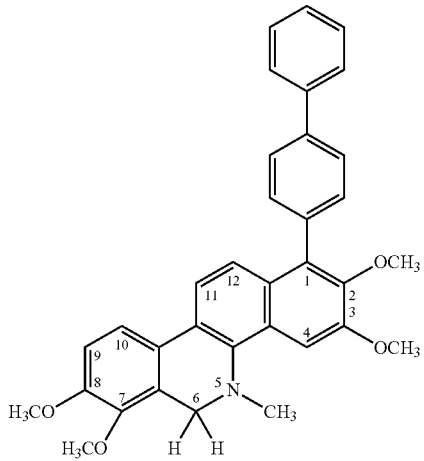 | <16 |

TABLE 5-continued

Minimal Inhibitory Concentrations against MRSA for Representative Compounds of the Invention

| Example | Structure | MIC vs. MRSA (µg/ml) |
|---|---|---|
| Example 24 | (structure) | <16 |
| Example 25 | (structure) | <16 |
| Comparative Example 1 | (structure) | 32.0 |
| Comparative Example 2 | (structure) | 64.0 |

Representative compounds of the invention were also tested against Methicillin-Sensitive *Staphylococcus aureus*, Vancomycin-Resistant *Enterococcus faecalis*, Vancomycin-Sensitive *Enterococcus faecalis Propionibacterium acnes, Clostridium difficile*, and *Bacillus subtilis* and they were found to have significant antibacterial activity.

B. Biofilm Antibacterial Assay

Bacteria growing in biofilms frequently exhibit altered sensitivities to antimicrobial agents relative to free-living bacteria. It is therefore important to assess the antibacterial activities of the compounds against bacteria growing as biofilms. Toward this end, well-established protocols can be used to determine biofilm susceptibilities to compounds. The biofilms are prepared by seeding overnight cultures of bacteria on top of sterile polycarbonate membranes resting on Tryptic Soy Agar (TSA) plates. The plates are inverted and incubated for 48 hours at 37° C. After 48 hours of incubation in the absence of antibiotic, colony biofilms are transferred to fresh TSA plates containing differing concentrations. These plates are incubated at 37° C. and the biofilms sampled every hour for four hours and after 24 hours. The biofilms are sampled by placing the membrane and associated bacteria into a tube containing phosphate-buffered water and vortexing at high speed. The resulting cell suspensions are serially diluted and the viable bacteria counted by drop-plating on R2A agar plates. The extent of bacterial killing is calculated relative to the cell count at time zero. Antibacterial potencies are defined by the minimum drug concentrations that eradicate the biofilm (i.e., minimum biofilm eradication concentrations, MBEC).

Preparation of Compounds

Melting points were determined with a Meltemp capillary melting point apparatus. Column chromatography refers to flash chromatography conducted on SiliTech 32-63 µm, (ICN Biomedicals, Eschwege, Ger.) using the solvent systems indicated. Infrared spectral data were obtained using a Thermo-Nicolet Avatar 360 Fourier transform spectrometer and are reported in $cm^{-1}$. Proton ($^1$H NMR) nuclear magnetic resonance spectra were recorded either on a 200 MHz Varian Gemini-200 Fourier Transform spectrometer or a 400 MHz NMR Bruker Avance III spectrometer. Chemical shifts reported in δ units downfield from tetramethylsilane (TMS). Coupling constants are reported in hertz (Hz). Mass spectra were obtained from Washington University Resource for Biomedical and Bio-organic Mass Spectrometry within the Department of Chemistry at Washington University, St. Louis, Mo. with the exception of Example 24. The mass spectrum of Example 24 was obtained from Princeton University. Most commercially available starting materials and reagents were purchased from Aldrich. Solvents were generally purchased from Fisher Scientific, and were A.C.S. grade or HPLC grade. Methylene chloride was freshly distilled from calcium hydride. All other solvents were used as provided without further purification.

Example 3

Preparation of Compound

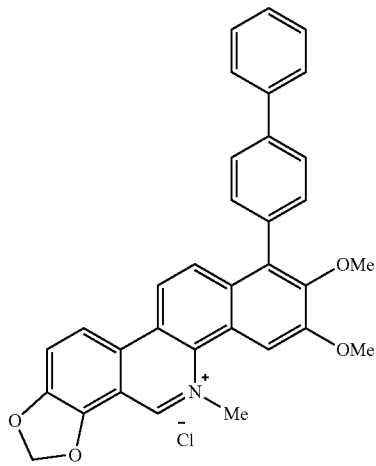 [SMILES: COc1cc2c(ccc3c4ccc5c(c4c[n+](C)c23)OCO5)c(-c2ccc(-c3ccccc3)cc2)c1OC ; [Cl-]]

LAH (0.9 mmol) was added to a solution of Heck cyclization product (0.3 mmol) in dry THF (5 mL) in a stream of $N_2$ at 0° C. The reaction mixture was stirred for 30 min at room temperature after which it was diluted with water and filtered. The filtrate was concentrated to give the amino alcohol and it was treated with 10% HCl (0.5 mL) at room temperature to provide the quaternized salt. The resulting mixture included 8-Biphenyl-4-yl-9,10-dimethoxy-12-methyl-1,3-dioxa-12-azoniacyclopenta[a]chrysene chloride; ($^1$H NMR (DMSO-$d_6$) δ 3.70 (s, 3H), 4.15 (s, 3H), 5.01 (s, 3H), 6.60 (s, 2H), 7.39-7.54 (m, 5H), 7.71-7.88 (m, 5H), 8.11 (d, J=8.8, 1H), 8.20 (s, 1H), 8.53 (d, J=8.8, 1H), 8.65 (d, J=8.8, 1H), 10.2 (s, 1H)

The intermediate Heck cyclization product was prepared as follows.

a. Preparation of Compound

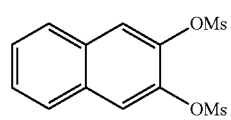 [SMILES: CS(=O)(=O)Oc1cc2ccccc2cc1OS(C)(=O)=O]

A solution of 5.0 g of 2,3-dihydroxynaphthalene in 50 ml of dichloromethane and 20 ml of triethylamine was treated drop-wise with 10 ml of methanesulfonyl chloride. After stirring for two hours, the white precipitate was collected by filtration and washed with ethanol to yield the 2,3-dihydroxynaphthalene dimesitylate as colorless solid. (Yield=9.5 g (96%). mp 160-163° C. $^1$H NMR (DMSO-$d_6$) δ 3.53 (s, 6H), 7.80 (m, 5H), 8.10 (s, 1H).)

b. Preparation of Compound

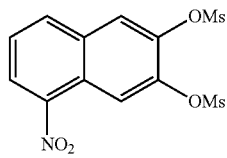 [SMILES: CS(=O)(=O)Oc1cc2cccc([N+](=O)[O-])c2cc1OS(C)(=O)=O]

A suspension of 5.0 g of the resulting product from step a in 50 ml of acetic anhydride was treated with 12 ml of 70% $HNO_3$ at such a rate as to keep the temperature between 37-40° C. A cooling bath was kept under the flask, ready to be raised if necessary, as the temperature was not allowed to exceed 45° C. The 12.0 ml of nitric acid was added to the reaction mixture over a period of 1-2 h. After 2 h, the reaction mixture was cooled to 5° C. in an ice bath and the precipitate, 5-nitro-2,3-dihydroxynaphthalene dimesitylate, was collected by filtration and washed with ether. (Yield 70%; mp 199-201° C., $^1$H NMR (DMSO-$d_6$) δ 3.58 (s, 6H), 7.76 (t, J=8.0 Hz, 1H), 8.25-8.65 (m, 4H).)

c. Preparation of Compound

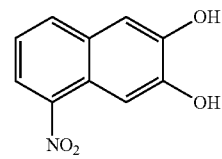 [SMILES: O=[N+]([O-])c1cccc2cc(O)c(O)cc12]

2,3-Dimethanesulfonyloxy-5-nitronaphthalene (3.0 g) was added to a solution of NaOH in water (58 ml) and the mixture was refluxed under nitrogen for 1.5 h. After cooling and acidification with (1:1) HCl, the mixture was extracted with ether and the combined extracts were dried over $Na_2SO_4$. Evaporation of the solvent afforded the dihydroxy derivative as dark yellow needles. Mp 206-208° C.

d. Preparation of Compound

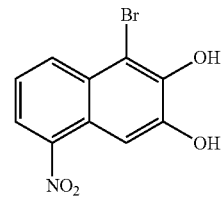 [SMILES: O=[N+]([O-])c1cccc2c(Br)c(O)c(O)cc12]

To a solution of 2,3-dihydroxy-5-nitronaphthalene (165 mg) in 3 ml of dichloromethane at 0° C. was added 0.05 ml of bromine in 1.5 ml of dichloromethane. The reaction mixture was allowed to stir for 10 minutes at room temperature. The reaction mixture was evaporated to give 235 mg of product, 1-bromo-5-nitro-2,3-dihydroxynaphthalene, as yellow solid. The product was pure enough to proceed to the next step and further purification was not attempted. ($^1$H NMR (DMSO-$d_6$) δ 7.52 (t, J=8.0 Hz, 1H), 7.78 (s, 1H), 8.13 (d, J=7.6 Hz, 1H), 8.33 (d, J=8.0 Hz, 1H), 10.4 (s, 1H), 11.34 (s, 1H); $^{13}$C NMR (DMSO-$d_6$) δ 103.7, 106.0, 121.1, 122.0, 123.4, 128.4, 133.7, 145.0, 146.3, 150.0.)

e. Preparation of Compound

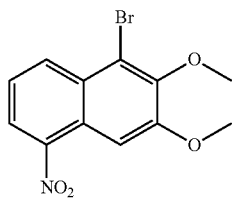 [SMILES: COc1cc2c([N+](=O)[O-])cccc2c(Br)c1OC]

To a solution of 75 mg of 1-bromo-2,3-dihydroxy-5-nitronaphthalene in 3.0 ml of DMF was added $K_2CO_3$ and Methyl iodide. The resulting solution was heated at 50° C. overnight after which the reaction mixture was diluted with water and extracted with ethyl acetate. Column chromatography using 30% ethyl acetate in hexane afforded the product, 1-bromo-5-nitro-2,3-dimethoxynaphthalene as a yellow solid. (Yield: 60 mg; $^1$H NMR (CDCl$_3$) δ 3.99 (s, 3H), 4.04 (s, 3H), 7.45-7.53 (m, 1H), 7.98 (s, 1H), 8.21 (dd, J=6.0 Hz, 1.2 Hz, 1H), 8.51 (dd, J=6.0 Hz, 1.2 Hz, 1H).

f. Preparation of Compound

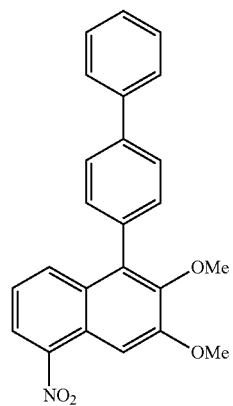

1-Bromo-2,3-dimethoxy-5-nitronaphthalene (1.0 mmol), 4-biphenyl boronic acid (Sigma-Aldrich, 1.5 equiv.), tetrakis(triphenylphosphine)palladium (0.2 mmol) and triphenylphosphine (1.5 equiv) were evacuated under vacuum. To this mixture were added Na$_2$CO$_3$ (2.0 equiv), degassed toluene and methanol (5:1) and was heated at 80° C. for 14 h. The reaction mixture was filtered through a plug of silica gel on celite using EtOAc as elutant. After concentration, the crude product was purified by flash column chromatography using a gradient of 30% hexane in dichloromethane gave the pure product 1-(biphenyl[1,1']-4-yl)-2,3-dimethoxy-5-nitronaphthalene ($^1$H NMR (CDCl$_3$) δ 3.70 (s, 3H), 4.09 (s, 3H), 7.25-7.54 (m, 6H), 7.69-7.82 (m, 5H), 8.09 (s, 1H), 8.18 (dd, J=7.8 Hz, 1.0 Hz, 1H); $^{13}$C NMR (CDCl$_3$) δ 56.0, 61.3, 102.6, 122.2, 123.8, 127.2, 127.3, 127.7, 129.0, 130.6, 131.0, 132.6, 134.3, 140.8, 145.7, 147.7, 155.2.)

g. Preparation of Compound

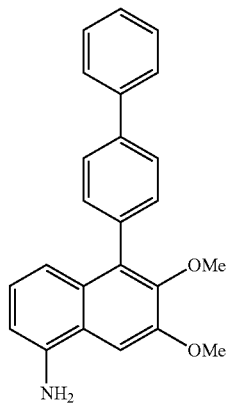 [SMILES: COc1cc2c([N+](=O)[O-])cccc2c(-c2ccc(-c3ccccc3)cc2)c1OC]

The nitro compound from step f (0.483 mmol) was dissolved in 4.0 ml of ethanol. The resulting solution was admixed with 0.18 ml of hydrazine hydrate and 18.5 mg of 10% palladium/carbon catalyst, and heated under reflux for 80 minutes. After cooling, the palladium/carbon catalyst was filtered off, and the filtrate was concentrated. The crude material, 1-amino-5-(biphenyl[1,1']-4-yl-2,3-dimethoxynaphthalene, thus formed was not purified further and was used as such for the next step. ($^1$H NMR (CDCl$_3$) δ 3.68 (s, 3H), 3.90 (bs, 2H), 4.06 (s, 3H), 6.77 (d, J=7.0 Hz, 1H), 7.01-7.09 (m, 2H), 7.19 (s, 1H), 7.38-7.71 (m, 5H), 7.74 (m, 4H); $^{13}$C NMR (CDCl$_3$) δ 55.9, 61.1, 100.7, 110.3, 117.8, 121.5, 124.5, 126.8, 127.2, 127.4, 128.9, 129.9, 131.1, 132.6, 135.6, 140.0, 140.9, 141.1, 146.8, 151.8.)

h. Preparation of Compound

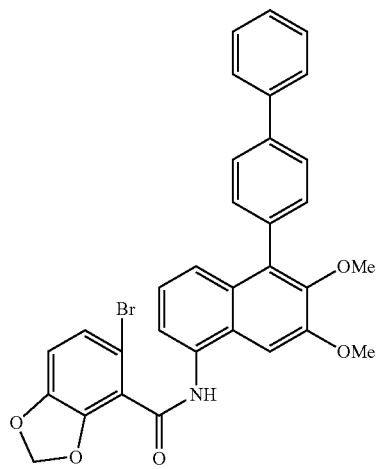 [SMILES: COc1cc2c(NC(=O)c3c(Br)ccc4c3OCO4)cccc2c(-c2ccc(-c3ccccc3)cc2)c1OC]

Oxalyl chloride (6.13 mmol) was added to a solution of the acid (5-bromobenzo[1,3]dioxole-4-carboxylic acid) (3.25 mmol) in anhyd CH$_2$Cl$_2$ (30 ml) and the stirred mixture was refluxed for 2 h. Then the mixture was concentrated to dryness under reduced pressure. To this residue was added a solution of amine from step g (2.45 mmol) in anhyd CH$_2$Cl$_2$ (15 ml) and anhyd Et$_3$N (3.67 mmol) and the mixture was stirred overnight at room temperature. The mixture was concentrated to dryness and diluted with CH$_2$Cl$_2$, then washed with 10% HCl, aq NaHCO$_3$ solution and brine. The residue was dissolved in chloroform and subjected to flash chromatography to provide 5-bromobenzo[1,3]dioxole-4-carboxamide), N-(5-(biphenyl[1,1']-4-yl)-6,7-dimethoxynaphthalen-1-yl) (¹H NMR (CDCl₃) δ 3.66 (s, 3H), 4.04 (s, 3H), 6.16 (s, 2H), 7.47-7.50 (m, 10H), 7.70-7-74 (m, 6H)).

i. Preparation of Compound

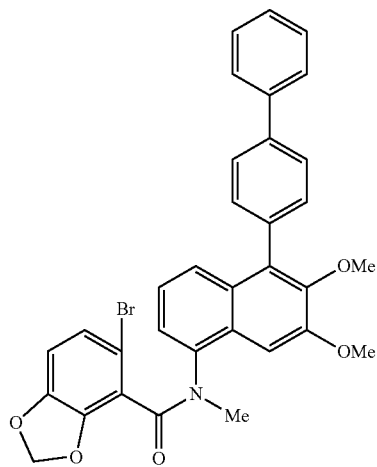 [SMILES: COc1cc2c(N(C)C(=O)c3c(Br)ccc4c3OCO4)cccc2c(-c2ccc(-c3ccccc3)cc2)c1OC]

To a suspension of the benzamide from step h (1.73 mmol), NaH (6.3 mmol) in dry DMF (20 mL) was added MeI (2 equiv). The reaction mixture was stirred over night, diluted with ether and then washed with 10% HCl and brine. The residue was subjected to column chromatography on silica using 2% methanol in chloroform to provide N-[(5-biphenyl[1,1']-4-yl)-6,7-dimethoxynaph-thalen-1-yl]-N-methyl-5-bromobenzo[1,3]dioxole-4-carboxamide; (¹H NMR (CDCl₃) δ 3.39-3.60 (m, 3H, N—CH₃), 3.66-3.68 (m, 3H, OCH₃), 4.04-4.08 (m, 3H, OCH₃), 5.10-6.18 (m, 2H, OCH₂O), 6.38-7.76 (m, 15H, aromatic).

j. Preparation of Compound

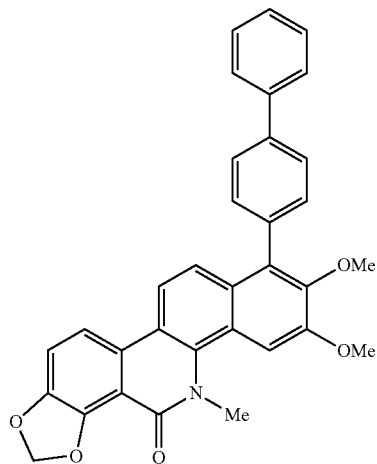 [SMILES: COc1cc2c(ccc3c4ccc5c(c4c(=O)n(C)c23)OCO5)c(-c2ccc(-c3ccccc3)cc2)c1OC]

A mixture of N-methyl benzamide (1 equiv), Pd(OAc)₂ (0.2 equiv), P(o-tolyl)₃ (0.4 equiv), Ag₂CO₃ (2 equiv) was evacuated under vacuum. To this mixture DMF (8 mL/0.3 mmol) was added under nitrogen and then heated at 160° C. overnight. After cooling to room temperature, reaction mixture was diluted with ether and washed with brine. The organic layer was dried over Na₂SO₄, filtered and concentrated under vacuum to get a brown residue. The residue was purified by flash chromatography eluting with 0.5 methanol/chloroform to provide the Heck cyclization product 8-biphenyl-4-yl-9,10-dimethoxy-12-methyl-12H-1,3-dioxa-12-azacyclopenta[a]chrysene-13-one (¹H NMR (CDCl₃) δ 3.71 (s, 3H), 4.00 (s, 3H), 4.07 (s, 3H), 6.29 (s, 2H), 7.24 (d, J=8.0, 1H), 7.28-7.54 (m, 6H), 7.59 (s, 1H), 7.71-7.78 (m, 5H), 7.88 (d, J=9.0, 1H).)

Example 4

Preparation of Compound

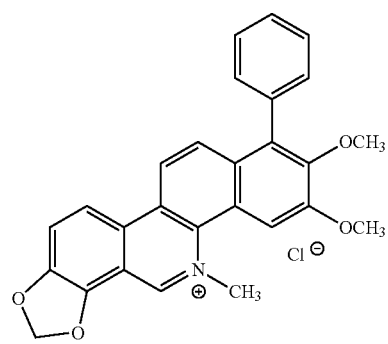 [SMILES: COc1cc2c(ccc3c4ccc5c(c4c[n+](C)c23)OCO5)c(-c2ccccc2)c1OC ; [Cl-]]

Using a reduction procedure similar to that described in Example 3, the title compound was prepared from the cyclic amide of sub-part e below. ¹H NMR (400 MHz) (DMSO-d₆) δ 3.76 (s, 3H), 4.24 (s, 3H), 5.11 (s, 3H), 6.70 (s, 2H), 7.47 (d, J=8.0 Hz, 2H), 7.60-7.69 (m, 3H), 7.77 (d, J=8.0 Hz, 1H), 8.22 (d, J=8.0 Hz, 1H), 8.29 (s, 1H), 8.64 (d, J=8.0 Hz, 1H), 8.74 (d, J=12.0 Hz, 1H), 10.33 (s, 1H). HRMS calculated: $C_{27}H_{22}NO_4$, 424.1549. found: 424.1542.

The starting cyclic amide material for the above reduction was prepared as follows.

a. Preparation of Compound

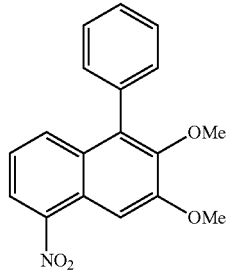 [SMILES: COc1cc2c([N+](=O)[O-])cccc2c(-c2ccccc2)c1OC]

1-Bromo-2,3-dimethoxy-5-nitronaphthalene from Example 3 sub-part e (1.0 mmol), phenyl boronic acid (Sigma-Aldrich, 1.5 equiv.), tetrakis(triphenylphosphine)-palladium (0.2 mmol) and triphenylphosphine (1.5 equiv) were evacuated under vacuum. To this mixture were added Na₂CO₃ (2.0 equiv), degassed toluene and methanol (5:1) and was heated at 80° C. for 14 h. The reaction mixture was filtered through a plug of silica gel on celite using EtOAc as elutant. After concentration, the crude product was purified by flash column chromatography using a gradient of 30% hexane in dichloromethane gave the pure product as yellow solid. Exemplified structures include 2,3-dimethoxy-5-nitro-1-phenylnaphthalene (¹H NMR (CDCl₃) δ 3.65 (s, 3H), 4.08

(s, 3H), 7.30-7.36 (m, 3H), 7.46-7.52 (m, 3H), 7.70 (dd, J=8.4 Hz, 1.2 Hz, 1H), 8.07 (s, 1H), 8.17 (dd, J=7.8 Hz, 1.6 Hz, 1H).

b. Preparation of Compound

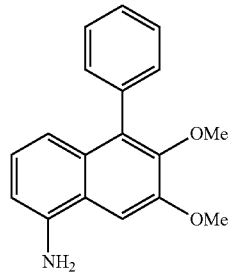

Using a precedure similar to that described in Example 3, sub-part g the nitro compound from step a was converted to the corresponding amine; $^1$H NMR (CDCl$_3$) δ 3.62 (s, 3H), 4.0 (s, 3H), 4.05 (bs, 2H), 6.70 (d, J=8.0. 1H), 7.20-7.35 (m, 7H) 7.7 (d, J=8.0, 1H).

c. Preparation of Compound

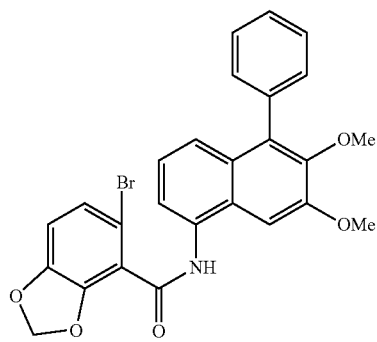 [SMILES: COc1cc2c(NC(=O)c3c(Br)ccc4c3OCO4)cccc2c(-c2ccccc2)c1OC]

Using a precedure similar to that described in Example 3, sub-part h the amine compound from step b was converted to the corresponding amide which was used in the next step.

d. Preparation of Compound

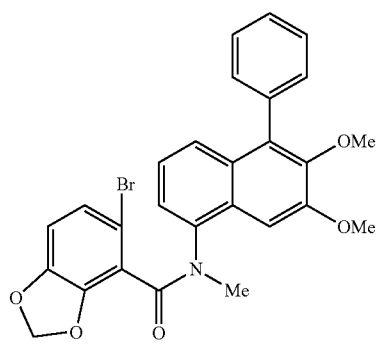 [SMILES: COc1cc2c(N(C)C(=O)c3c(Br)ccc4c3OCO4)cccc2c(-c2ccccc2)c1OC]

Using a precedure similar to that described in Example 3, sub-part i the amide step c was methylated to provide the corresponding methyl amide; $^1$H NMR (400 MHz) (CDCl$_3$) δ 3.30-4.00 (m, 12H), 5.00-7.43 (m, 13H).

e. Preparation of Compound

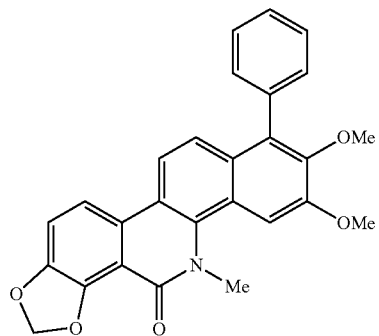 [SMILES: COc1cc2c(ccc3c4ccc5c(c4c(=O)n(C)c23)OCO5)c(-c2ccccc2)c1OC]

Using a precedure similar to that described in Example 3, sub-part j the methyl amide from step d was cyclized to provide the corresponding cyclic amide; $^1$H NMR (CDCl$_3$) δ 3.7 (s, 3H) 4.00 (s, 3H), 4.08 (s, 3H) 6.28 (s, 2H), 7.26 (d, J=8.0, 1H), 7.3 (m, 7H), 7.5 (s 1H) 7.8 (d, J=8.0 1H).

Example 5

Preparation of Compound

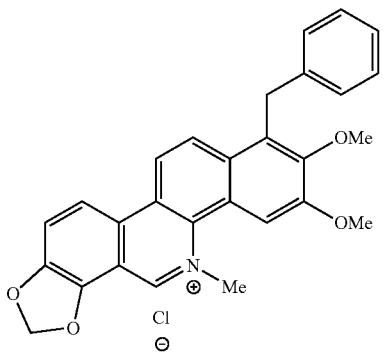 [SMILES: COc1cc2c(ccc3c4ccc5c(c4c[n+](C)c23)OCO5)c(Cc2ccccc2)c1OC ; [Cl-]]

Using a reduction procedure similar to the one described in Example 3, the title compound was prepared from the corresponding cyclic amide; $^1$H NMR (400 MHz) (DMSO-d$_6$) δ 3.87 (s, 3H), 4.10 (s, 3H), 4.57 (s, 1H), 4.95 (s, 3H), 6.58 (s, 2H), 7.09-7.23 (m, 5H), 8.07 (s, 1H), 8.08 (d, J=8.0 Hz, 1H), 8.34 (d, J=8.0 Hz, 1H), 8.59 (d, J=8.0 Hz, 1H), 8.67 (d, J=8.0 Hz, 1H), 10.18 (s, 1H). calculated: C$_{28}$H$_{24}$NO$_4$, 438.1705. found: 438.1700.

The intermediate cyclic amide was prepared as follows.

a. Preparation of Compound

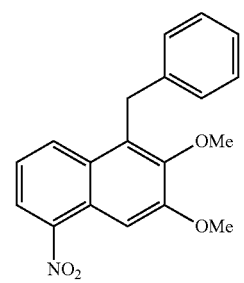

Using a precedure similar to that described in Example 3, sub-part f the nitro compound from Example 1 sub-part e was converted to the corresponding nitro benzyl compound; ¹H NMR (400 MHz) (CDCl₃) δ 3.93 (s, 3H), 4.12 (s, 3H), 4.60 (s, 2H), 7.16-7.41 (m, 6H), 8.02 (s, 1H), 8.17 (m, 2H).

b. Preparation of Compound

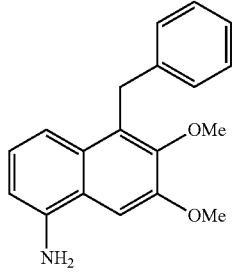 [SMILES: COc1cc2c([N+](=O)[O-])cccc2c(Cc2ccccc2)c1OC]

Using a precedure similar to that described in Example 3, sub-part g the nitro benzyl compound from sub-part a was converted to the corresponding amine; ¹H NMR (400 MHz) (CDCl₃) δ 3.84 (s, 3H), 3.99 (d, 2H), 4.02 (s, 3H), 4.51 (s, 2H), 6.72 (d, J=8.0 Hz, 1H), 7.10 (s, 1H), 7.13-7.23 (m, 6H), 7.36 (d, J=8.0 Hz, 1H).

c. Preparation of Compound

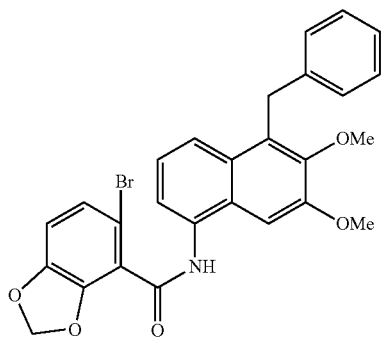 [SMILES: COc1cc2c(NC(=O)c3c(Br)ccc4c3OCO4)cccc2c(Cc2ccccc2)c1OC]

Using a precedure similar to that described in Example 3, sub-part h the amino compound from sub-part b was converted to the corresponding amide; ¹H NMR (400 MHz) (CDCl₃) δ 3.81 (s, 3H), 3.99 (s, 3H), 4.50 (s, 2H), 6.10 (s, 2H), 6.77 (d, J=8.0 Hz, 1H), 7.12-7.33 (m, 7H), 7.39 (s, 1H), 7.74 (m, 3H).

d. Preparation of Compound

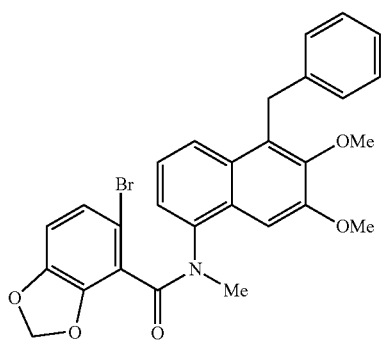 [SMILES: COc1cc2c(N(C)C(=O)c3c(Br)ccc4c3OCO4)cccc2c(Cc2ccccc2)c1OC]

Using a precedure similar to that described in Example 3, sub-part i the amide from sub-part c was converted to the corresponding methyl amide; ¹H NMR (400 MHz) (CDCl₃) δ 3.34-4.39 (m, 11H), 5.72-7.71 (m, 13H).

e. Preparation of Compound

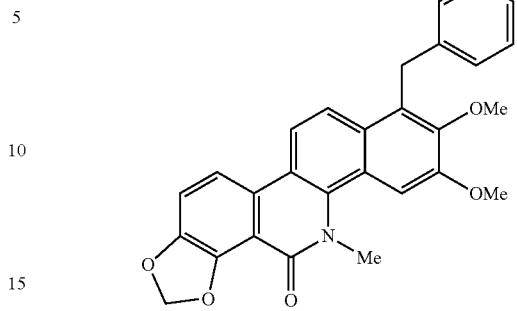

Using a precedure similar to that described in Example 3, sub-part j the methyl amide from sub-part d was converted to the corresponding cyclic amide; ¹H NMR (400 MHz) (CDCl₃) δ 3.87 (s, 3H), 3.96 (s, 3H), 4.04 (s, 3H), 4.54 (s, 2H), 6.27 (s, 2H), 7.17-7.24 (m, 6H), 7.50 (s, 1H), 7.71 (m, 2H), 7.88 (d, J=8.0 Hz, 1H).

Example 6

Preparation of Compound

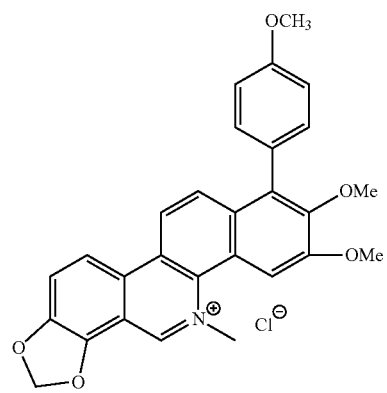 [SMILES: COc1ccc(-c2c(OC)c(OC)cc3c2ccc2c4ccc5c(c4c[n+](C)c32)OCO5)cc1 ; [Cl-]]

Using a reduction procedure similar to the one described in Example 3, the title compound was prepared from the corresponding cyclic amide; HRMS calculated: C₂₈H₂₄NO₅, 454.1654. found: 454.1649.

The intermediate cyclic amide was prepared as follows.

a. Preparation of Compound

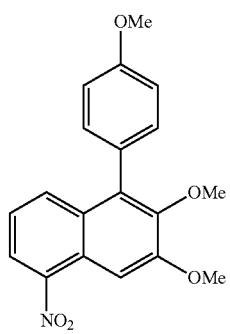 [SMILES: COc1ccc(-c2c(OC)c(OC)cc3c([N+](=O)[O-])cccc23)cc1]

Using a precedure similar to that described in Example 3, sub-part f the nitro compound from Example 1 sub-part e was converted to the corresponding 4-methoxtphenyl compound; ¹H NMR (CDCl₃) δ 3.64 (s, 3H), 3.95 (s, 3H) 4.05 (s 3H) 7.2-7.6 (m, 5H) 7.7 (d, J=8 1H) 8.1 (s 1H) 8.18 (d, J=8.0, 1H).

b. Preparation of Compound

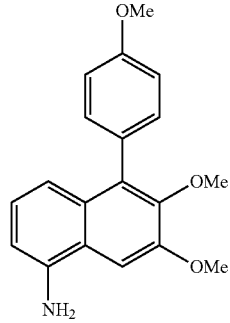

Using a precedure similar to that described in Example 3, sub-part g the 4-methoxyphenyl compound from sub-part a was converted to the corresponding amine; ¹H NMR (400 MHz) (CDCl₃) δ 3.64 (s, 3H), 3.92 (s, 3H), 4.05 (s, 3H), 6.77 (d, J=8.0 Hz, 1H), 6.98 (d, J=8.0 Hz, 1H), 7.04-7.09 (m, 3H), 7.11 (s, 1H), 7.30 (m, 2H).

c. Preparation of Compound

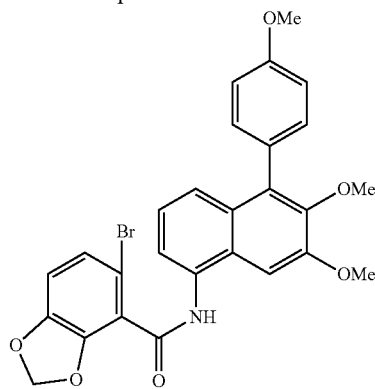

Using a precedure similar to that described in Example 3, sub-part h the amino compound from sub-part b was converted to the corresponding amide; ¹H NMR (400 MHz) (CDCl₃) δ 3.64 (s, 3H), 3.93 (s, 3H), 4.02 (s, 3H), 4.08 (s, 3H), 6.94 (d, J=8.0 Hz, 1H), 7.07 (m, 2H), 7.25-7.35 (m, 3H), 7.39 (d, J=8.0 Hz, 1H), 7.48 (d, J=8.0 Hz, 1H), 7.54 (bs, 1H), 7.60 (s, 1H), 7.66 (d, J=8.0 Hz, 1H).

d. Preparation of Compound

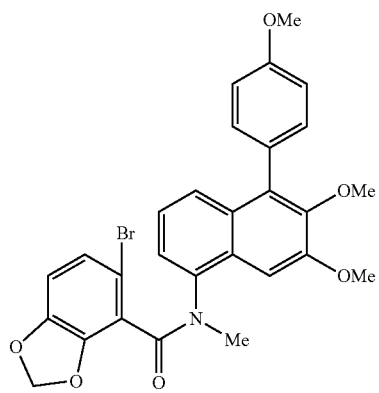 [SMILES: COc1ccc(-c2c(OC)c(OC)cc3c(N(C)C(=O)c4c(Br)ccc5c4OCO5)cccc23)cc1]

Using a precedure similar to that described in Example 3, sub-part i the amide from sub-part c was converted to the corresponding methyl amide; ¹H NMR (400 MHz) (CDCl₃) δ 3.17-4.17 (m, 18H), 6.80 7.62 (m, 10H).

e. Preparation of Compound

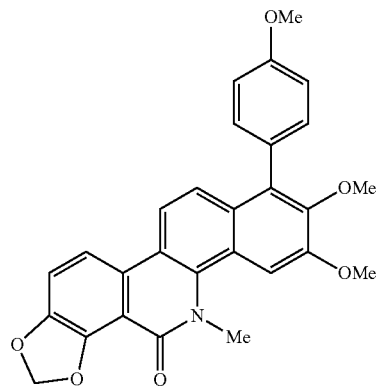 [SMILES: COc1ccc(-c2c(OC)c(OC)cc3c2ccc2c4ccc5c(c4c(=O)n(C)c32)OCO5)cc1]

Using a precedure similar to that described in Example 3, sub-part j the methyl amide from sub-part d was converted to the corresponding cyclic amide; ¹H NMR (400 MHz) (CDCl₃) δ 3.65 (s, 3H), 3.82 (s, 3H), 3.97 (s, 3H), 4.05 (s, 3H), 6.20 (s, 2H), 6.98 (d, J=8.0 Hz, 1H), 7.18 (d, J=8.0 Hz, 1H), 7.22 (m, 3H), 7.44 (s, 1H), 7.65 (d, J=8.0 Hz, 1H), 7.78 (d, J=8.0 Hz, 1H).

Example 7

Preparation of Compound

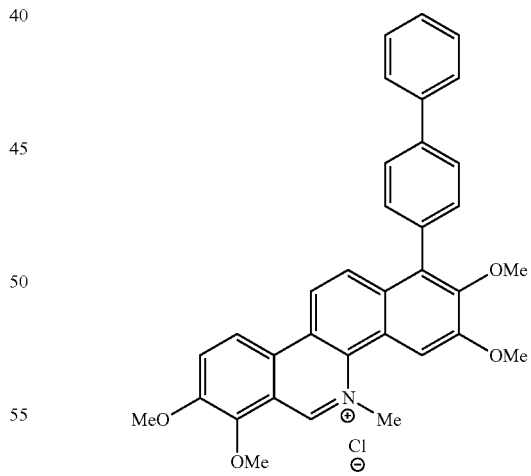

Using a reduction procedure similar to the one described in Example 3, the title compound was prepared from the corresponding cyclic amide; ¹H NMR (400 MHz) (DMSO-d₆) δ 3.76 (s, 3H), 4.13 (s, 3H), 4.20 (s, 3H), 4.21 (s, 3H), 5.13 (s, 3H), 7.46 (m, 2H), 7.51-7.58 (m, 3H), 7.79-7.85 (m, 3H), 7.92 (d, J=8.0 Hz, 2H), 8.30 (s, 1H), 8.33 (d, J=8.0 Hz, 1H), 8.78 (m, 2H), 10.21 (s, 1H). HRMS calculated: $C_{34}H_{30}NO_4$, 516.2175. found: 516.2168.

The intermediate cyclic amide was prepared as follows.

a. Preparation of Compound

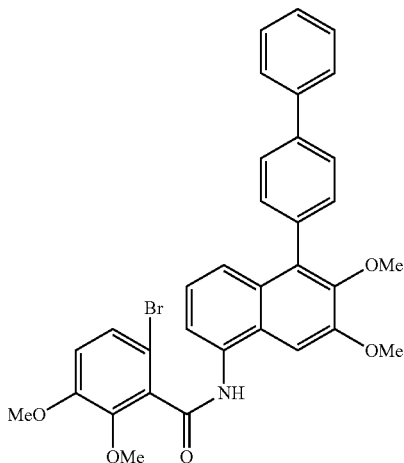 [SMILES: COc1ccc(Br)c(C(=O)Nc2cccc3c(-c4ccc(-c5ccccc5)cc4)c(OC)c(OC)cc23)c1OC]

Using a precedure similar to that described in Example 3, sub-part h the amino compound from Example 1 sub-part g and 6-bromo-2,3-dimethoxybenzoic acid (APIN Chemicals LTD.) were converted to the corresponding amide; $^1$H NMR (400 MHz) (CDCl$_3$) δ 3.60 (s, 3H), 3.86 (s, 3H), 3.93 (s, 3H), 4.00 (s, 3H), 6.84 (d, J=8.0 Hz, 1H), 7.20-7.25 (m, 1H), 7.29-7.32 (m, 2H), 7.36-7.41 (m, 6H), 7.41 (s, 1H), 7.45 (d, J=8.0 Hz, 1H), 7.56 (m, 4H).

b. Preparation of Compound

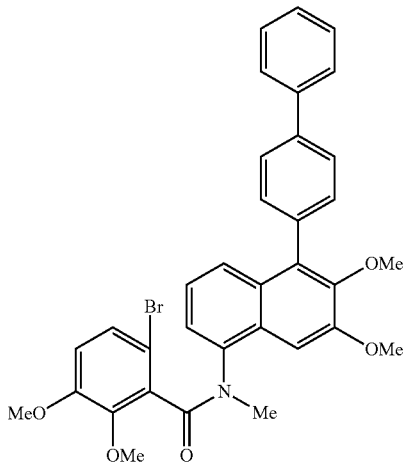 [SMILES: COc1ccc(Br)c(C(=O)N(C)c2cccc3c(-c4ccc(-c5ccccc5)cc4)c(OC)c(OC)cc23)c1OC]

Using a precedure similar to that described in Example 3, sub-part i the amide from sub-part a was converted to the corresponding methyl amide; $^1$H NMR (400 MHz) (CDCl$_3$) δ 3.1-4.02 (m, 15H), 6.74-7.67 (m, 15H).

c. Preparation of Compound

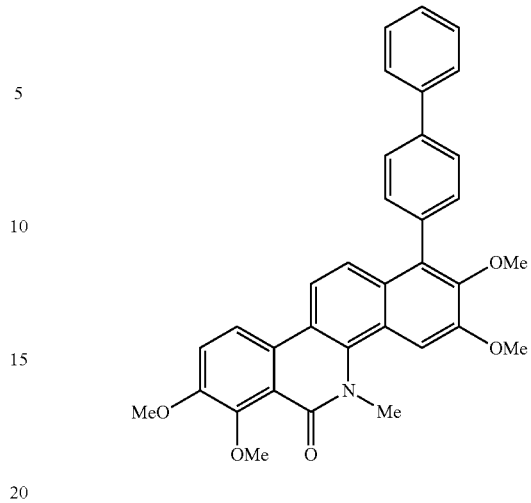

Using a precedure similar to that described in Example 3, sub-part j the methyl amide was converted to the corresponding cyclic amide; $^1$H NMR (400 MHz) (CDCl$_3$) δ 3.65 (s, 3H), 3.91 (s, 3H), 3.93 (s, 3H), 4.00 (s, 3H), 4.03 (s, 3H), 7.30-7.34 (m, 3H), 7.40-7.45 (m, 4H), 7.51 (s, 1H), 7.66 (d, J=8.0 Hz, 1H), 7.69 (d, J=8.0 Hz, 1H), 7.82 (d, J=8.0 Hz, 1H), 7.89 (d, J=8.0 Hz, 1H).

Example 8

Preparation of Compound

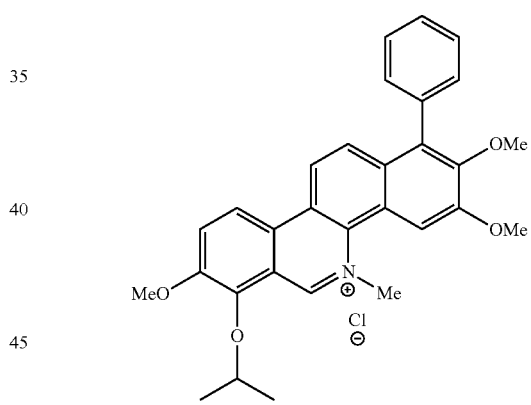

Using a reduction procedure similar to the one described in Example 3, the title compound was prepared from the corresponding cyclic amide; $^1$H NMR (400 MHz) (DMSO-d$_6$) δ 1.44 (d, J=8.0 Hz, 6H), 3.71 (s, 3H), 4.11 (s, 3H), 4.19 (s, 3H), 5.03 (m, 1H), 5.12 (s, 3H), 7.42 (d, J=8.0 Hz, 1H), 7.57-7.64 (m, 3H), 7.70 (d, J=8.0 Hz, 1H), 8.28 (s, 1H), 8.31 (d, J=8.0 Hz, 1H), 8.75 (t, J=8.0 Hz, 2H), 10.04 (s, 1H).

The intermediate cyclic amide was prepared as follows.

a. Preparation of Compound

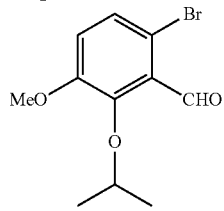

A mixture of 2-hydroxy-3-methoxy-6-bromobenzaldehyde, isopropyl bromide, (2 equiv.) and K₂CO₃ (4 equiv.) in DMF was stirred at 75° C. overnight. The reaction mixture was diluted with H₂O and extracted with EtOAc. The organic layer was dried with Na₂SO₄, concentrated to a solid residue, and chromatographed on silica to provide the desired compound in 90% yield ¹H NMR (400 MHz) (CDCl₃) δ 1.22 (s, 3H), 1.24 (s, 3H), 3.79 (s, 3H), 4.53 (t, 1H), 6.86 (d, J=8.0 Hz, 1H), 7.24 (d, J=8.0 Hz, 1H), 10.31 (s, 1H).

b. Preparation of Compound

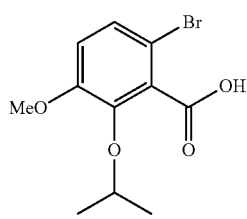

A suspension of the benzaldehyde intermediate (3.6 mmol) in water (30 ml) was stirred at 75° C., and a solution of KMnO₄ (5.5 mol) in water (20 ml) was added dropwise over a period of 20 min. The reaction mixture had been stirred at 75° C. for an additional 2 h and then allowed to cool to room temperature. Aqueous KOH (20%) was added until the solution was at a pH of 12 and the reaction mixture was filtered through Celite. The filtrate was then acidified (HCl 10%) until pH 2, and the mixture was then extracted with Et₂O. The ethyl layer was dried and concentrated to provide the benzoic acid derivative ¹H NMR (400 MHz) (CDCl₃) δ 1.32 (s, 6H), 3.87 (s, 3H), 4.71 (m, 1H), 6.85 (d, J=8.0 Hz, 1H), 7.26 (d, J=8.0 Hz, 1H), 10.1 (bs, 1H).

c. Preparation of Compound

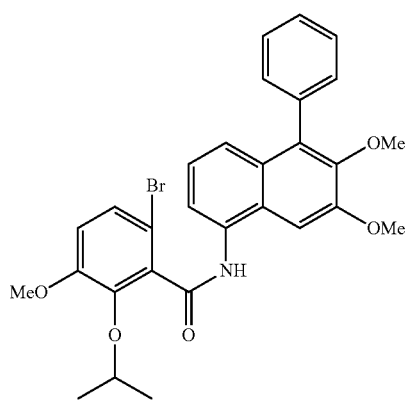 [SMILES: COc1ccc(Br)c(C(=O)Nc2cccc3c(-c4ccccc4)c(OC)c(OC)cc23)c1OC(C)C]

Using a precedure similar to that described in Example 3, sub-part h the amino compound from Example 4 sub-part b and the acid from sub-part b were converted to the corresponding amide; ¹H NMR (400 MHz) (CDCl₃) δ 1.25 (s, 3H), 1.26 (s, 3H), 3.55 (s, 3H), 3.83 (s, 3H), 3.98 (s, 3H), 4.61 (m, 1H), 6.81 (d, J=8.0 Hz, 1H), 7.18-7.22 (m, 2H), 7.26-7.31 (m, 4H), 7.35-7.45 (m, 3H), 7.48 (s, 1H), 7.78 (d, J=8.0 Hz, 1H).

d. Preparation of Compound

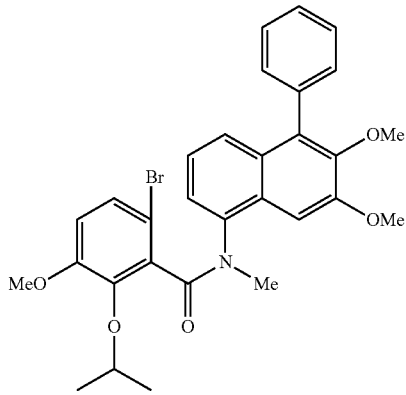 [SMILES: COc1ccc(Br)c(C(=O)N(C)c2cccc3c(-c4ccccc4)c(OC)c(OC)cc23)c1OC(C)C]

Using a precedure similar to that described in Example 3, sub-part i the amide from sub-part c was converted to the corresponding methyl amide; ¹H NMR (400 MHz) (CDCl₃) δ 1.13-1.37 (m, 6H), 3.14-4.03 (m, 12H), 4.64-4.73 (m, 1H), 6.44-7.68 (m, 11H).

e. Preparation of Compound

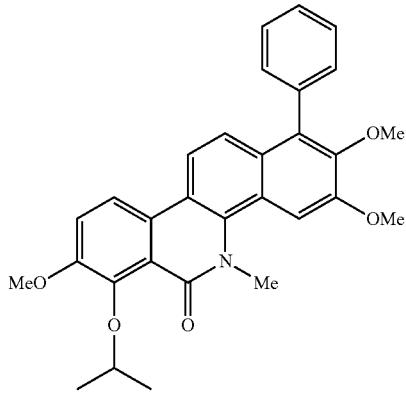 [SMILES: COc1cc2c(ccc3c4ccc(OC)c(OC(C)C)c4c(=O)n(C)c23)c(-c2ccccc2)c1OC]

Using a precedure similar to that described in Example 3, sub-part j the methyl amide from sub-part d was converted to the corresponding cyclic amide; ¹H NMR (400 MHz) (CDCl₃) δ 1.19 (d, 6H), 3.59 (s, 3H), 3.87 (s, 3H), 3.90 (s, 3H), 3.98 (s, 3H), 4.58 (m, 1H), 7.21 (d, J=8.0 Hz, 1H), 7.28-7.34 (m, 3H), 7.40-7.47 (m, 3H), 7.50 (s, 1H), 7.80 (d, J=8.0 Hz, 1H), 7.86 (d, J=8.0 Hz, 1H).

Example 9

Preparation of Compound

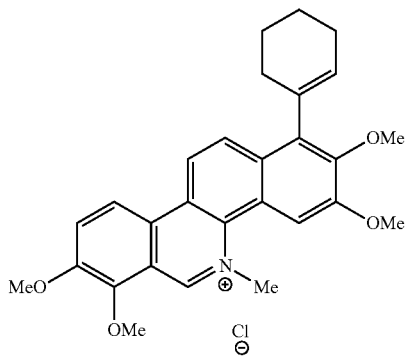 [SMILES: COc1cc2c(ccc3c4ccc(OC)c(OC)c4c[n+](C)c23)c(C2=CCCCC2)c1OC ; [Cl-]]

Using a reduction procedure similar to the one described in Example 3, the title compound was prepared from the corresponding cyclic amide; ¹H NMR (400 MHz) (DMSO-d₆) 5.1.80-1.85 (m, 4H), 2.18-2.39 (m, 4H), 3.89 (s, 3H), 4.12 (s, 3H), 4.13 (s, 3H), 4.20 (s, 3H), 5.07 (s, 3H), 5.73 (m, 1H), 8.14 (s, 1H), 8.25 (d, J=8.0 Hz, 1H), 8.33 (d, J=8.0 Hz, 1H), 8.33 (m, 2H), 10.17 (s, 1H).

The intermediate cyclic amide was prepared as follows.

a. Preparation of Compound

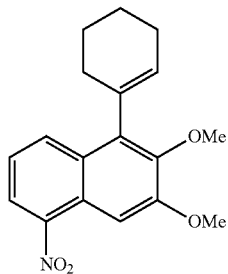 [SMILES: COc1cc2c([N+](=O)[O-])cccc2c(C2=CCCCC2)c1OC]

Using a precedure similar to that described in Example 3, sub-part f the nitro compound from Example 1 sub-part e was converted to the corresponding 1-cyclohexenyl compound; ¹H NMR (400 MHz) (CDCl₃) δ 1.60-1.80 (m, 4H), 2.02-2.25 (m, 4H), 3.80 (s, 3H), 3.98 (s, 3H), 5.60 (m, 1H), 7.26 (t, J=8.0 Hz, 1H), 7.86 (s, 1H), 8.07 (d, J=8.0 Hz, 2H).

b. Preparation of Compound

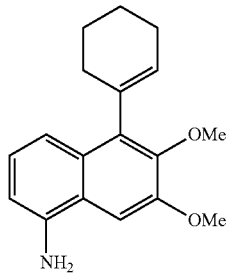

Using a precedure similar to that described in Example 3, sub-part g the nitro compound from sub-part a was converted to the corresponding amino compound; ¹H NMR (400 MHz) (CDCl₃) --- 1.69-1.80 (m, 4H), 2.06-2.28 (m, 4H), 3.59-3.80 (bs, 2H), 3.80 (s, 3H), 3.95 (s, 3H), 5.58 (m, 1H), 6.66 (d, J=8.0 Hz, 1H), 6.95 (s, 1H), 7.06 (m, 1H), 7.28 (d, J=8.0 Hz, 1H).

c. Preparation of Compound

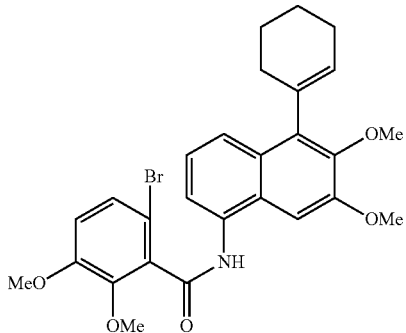 [SMILES: COc1ccc(Br)c(C(=O)Nc2cccc3c(C4=CCCCC4)c(OC)c(OC)cc23)c1OC]

Using a precedure similar to that described in Example 3, sub-part h the amino compound from sub-part b was converted to the corresponding amide; ¹H NMR (400 MHz) (CDCl₃) δ. 1.71-1.80 (m, 4H), 2.06-2.35 (m, 4H), 3.74 (s, 3H), 3.84 (s, 3H), 3.90 (s, 3H), 3.97 (s, 3H), 5.60 (m, 1H), 6.81 (d, J=8.0 Hz, 1H), 7.17 (d, J=8.0 Hz, 1H), 7.26-7.30 (m, 2H), 7.38 (s, 1H), 7.46 (s, 1H), 7.56 (d, J=8.0 Hz, 1H), 7.75 (d, J=8.0 Hz, 1H).

d. Preparation of Compound

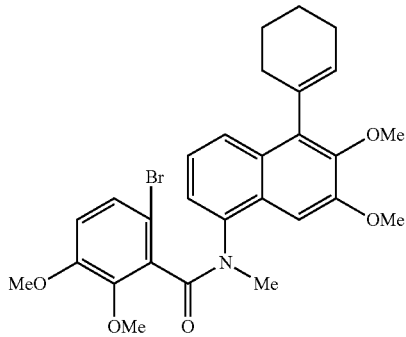 [SMILES: COc1ccc(Br)c(C(=O)N(C)c2cccc3c(C4=CCCCC4)c(OC)c(OC)cc23)c1OC]

Using a precedure similar to that described in Example 3, sub-part i the amide from sub-part c was converted to the corresponding methyl amide; ¹H NMR (400 MHz) (CDCl₃) δ 1.70-1.81 (m, 4H), 2.06-2.35 (m, 4H), 3.14-3.92 (m, 15H), 5.55-5.62 (m, 1H), 6.43-7.80 (m, 6H).

e. Preparation of Compound

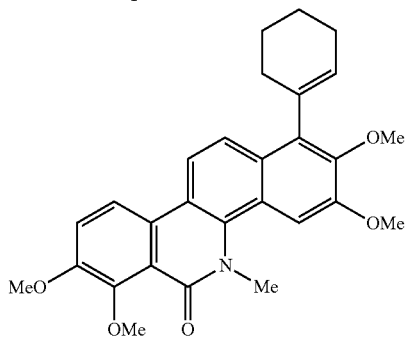

Using a precedure similar to that described in Example 3, sub-part j the methyl amide from sub-part d was converted to the corresponding cyclic amide; ¹H NMR (400 MHz) (CDCl₃) δ. 1.53-1.82 (m, 4H), 2.09-2.42 (m, 4H), 3.60-4.01 (m, 15H), 5.65 (m, 1H), 7.31-7.37 (m, 2H), 7.66 (d, J=8.0 Hz, 1H), 7.88-7.93 (m, 2H).

Example 10

Preparation of Compound

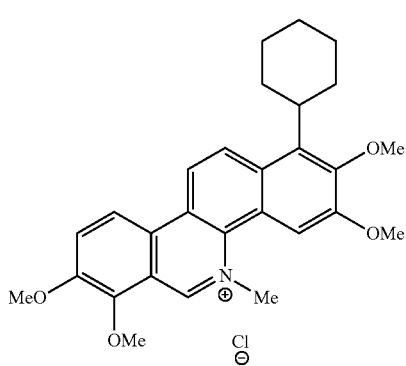 [SMILES: COc1cc2c(ccc3c4ccc(OC)c(OC)c4c[n+](C)c23)c(C2CCCCC2)c1OC ; [Cl-]]

Using a reduction procedure similar to the one described in Example 3, the title compound was prepared from the corresponding cyclic amide; ¹H NMR (400 MHz) (DMSO-d₆) δ 1.77 (m, 4H), 2.30 (m, 4H), 3.89 (s, 3H), 4.16 (s, 3H), 4.20 (s, 3H), 4.35 (s, 3H), 5.16 (s, 3H), 8.23 (s, 1H), 8.34 (d, J=8.0 Hz, 1H), 8.43 (d, J=8.0 Hz, 1H), 8.87 (d, J=8.0 Hz, 1H), 8.95 (d, J=8.0 Hz, 1H), 10.25 (s, 1H).

The intermediate cyclic amide was prepared as follows.

a. Preparation of Compound

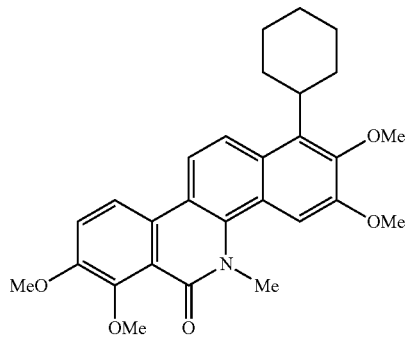 [SMILES: COc1cc2c(ccc3c4ccc(OC)c(OC)c4c(=O)n(C)c23)c(C2CCCCC2)c1OC]

Cataylic hydrogenation using $H_2$ and Pd/C of the compound of Example 9, sub-part e in ethanol provide the desired the cyclohexyl derivative in quantitative yield. The catalyst was removed by filtration through Celite and the ethanol solution was concentrated under reduced pressure. $^1$H NMR (400 MHz) (CDCl$_3$) δ. 1.15-1.18 (m, 3H), 1.33-1.53 (m, 3H), 1.74-1.88 (m, 3H), 2.13-2.42 (m, 2H), 3.79-4.08 (m, 15H), 7.19 (s, 1H), 7.29-7.37 (m, 2H), 7.88-7.94 (m, 2H).

Example 11

Preparation of Compound

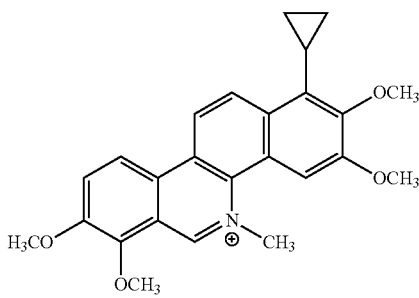 [SMILES: COc1cc2c(ccc3c4ccc(OC)c(OC)c4c[n+](C)c23)c(C2CC2)c1OC]

Using a reduction procedure similar to the one described in Example 3, the title compound was prepared from the corresponding cyclic amide; $^1$H NMR (DMSO-d$_6$) δ 0.8-0.82 (m, 2H), 1.14-1.19 (m, 2H), 1.92-1.98 (m, 1H) 3.97 (s, 3H), 4.09 (s, 3H), 4.14 (s, 3H) 4.20 (s, 3H), 5.03 (s, 3H) 7.82 (d, J=8.0, 1H) 8.15 (s, 1H) 8.3 (d, J=8.0, 1H), 8.8-8.9 (m, 2H), 10.15 (s, 1H).

The intermediate cyclic amide was prepared as follows.

a. Preparation of Compound

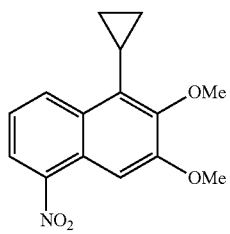 [SMILES: COc1cc2c([N+](=O)[O-])cccc2c(C2CC2)c1OC]

Using a precedure similar to that described in Example 3, sub-part f the nitro compound from Example 1 sub-part e was converted to the corresponding cyclopropyl compound; $^1$H NMR (400 MHz) (CDCl$_3$) δ. 0.75-0.79 (m, 2H), 1.12-1.17 (m, 2H), 1.93 (m, 1H), 3.88 (s, 3H), 3.90 (s, 3H), 7.34 (t, J=8.0 Hz, 1H), 7.79 (s, 1H), 8.06 (d, J=8.0 Hz, 1H), 8.64 (d, J=8.0 Hz, 1H).

b. Preparation of Compound

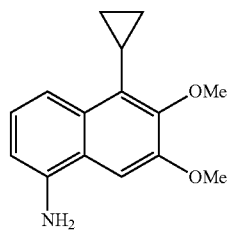 [SMILES: COc1cc2c(N)cccc2c(C2CC2)c1OC]

Using a precedure similar to that described in Example 3, sub-part g the nitro compound from sub-part a was converted to the corresponding amino compound; $^1$H NMR (400 MHz) (CDCl$_3$) δ. 0.89-0.93 (m, 2H), 1.18-1.23 (m, 2H), 2.02 (m, 1H), 4.01 (s, 3H), 4.05 (s, 3H), 6.80 (d, J=8.0 Hz, 1H), 7.06 (s, 1H), 7.26 (dd, J=8.0 Hz, 1H), 7.94 (d, J=8.0 Hz, 1H).

c. Preparation of Compound

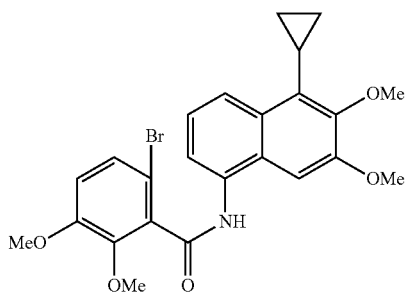 [SMILES: COc1ccc(Br)c(C(=O)Nc2cccc3c(C4CC4)c(OC)c(OC)cc23)c1OC]

Using a precedure similar to that described in Example 3, sub-part h the amino compound from sub-part b was converted to the corresponding amide; $^1$H NMR (400 MHz) (CDCl$_3$) δ. 0.77-0.80 (m, 2H), 1.07-1.19 (m, 2H), 1.93 (m, 1H), 3.77 (s, 3H), 3.85 (s, 3H), 3.88 (s, 3H), 3.92 (s, 3H), 6.80 (d, J=8.0 Hz, 1H), 7.26 (d, J=8.0 Hz, 1H), 7.33 (m, 2H), 7.47 (s, 1H), 7.57 (d, J=8.0 Hz, 1H), 8.29 (d, J=8.0 Hz, 1H).

d. Preparation of Compound

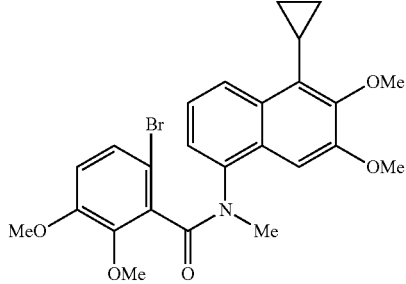 [SMILES: COc1ccc(Br)c(C(=O)N(C)c2cccc3c(C4CC4)c(OC)c(OC)cc23)c1OC]

Using a precedure similar to that described in Example 3, sub-part i the amide compound from sub-part c was converted to the corresponding methyl amide; $^1$H NMR (400 MHz) (CDCl$_3$) δ. 0.73-0.84 (m, 2H), 1.04-1.12 (m, 2H), 1.93 (m, 1H), 3.15-3.95 (m, 15H), 6.44-6.39 (m, 6H).

e. Preparation of Compound

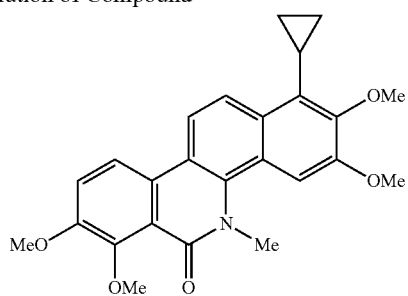

Using a precedure similar to that described in Example 3, sub-part j the methyl amide compound from sub-part d was converted to the corresponding cyclic amide; $^1$H NMR (400 MHz) (CDCl$_3$) δ. 0.79 (m, 2H), 1.15 (m, 2H), 1.95 (m, 1H), 3.76 (s, 3H), 3.91 (s, 3H), 3.92 (s, 3H), 3.96 (s, 3H), 4.04 (s, 3H), 7.33 (m, 2H), 7.96 (m, 2H), 8.19 (d, J=8.0 Hz, 1H).

Example 12

Preparation of Compound

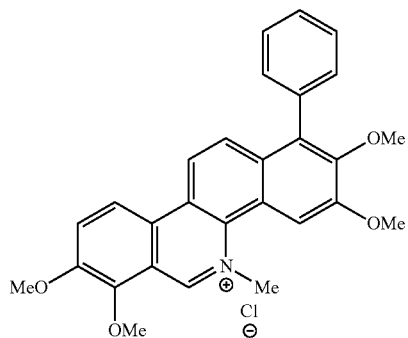 [SMILES: COc1cc2c(ccc3c4ccc(OC)c(OC)c4c[n+](C)c23)c(-c2ccccc2)c1OC ; [Cl-]]

Using a reduction procedure similar to the one described in Example 3, the title compound was prepared from the corresponding cyclic amide; $^1$H NMR (400 MHz) (DMSO-d$_6$) δ 3.71 (s, 3H), 4.13 (s, 3H), 4.19 (s, 3H), 4.21 (s, 3H), 5.12 (s, 3H), 7.41-7.43 (m, 2H), 7.55-7.63 (m, 3H), 7.69 (d, J=12.0 Hz, 1H), 8.28 (s, 1H), 8.33 (d, J=8.0 Hz, 1H), 8.76 (dd, J=8.0 Hz, 2H), 10.24 (s, 1H).

The intermediate cyclic amide was prepared as follows.

a. Preparation of Compound

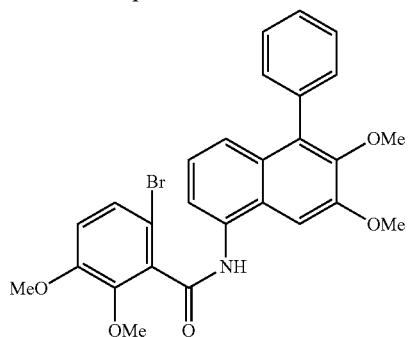

Using a precedure similar to that described in Example 3, sub-part h the amino compound from Example 4 sub-part b and 6-bromo-2,3-dimethoxybenzoic acid (APIN Chemicals LTD.) were converted to the corresponding amide; $^1$H NMR (400 MHz) (CDCl$_3$) δ. 3.54 (s, 3H), 3.85 (s, 3H), 3.91 (s, 3H), 3.98 (s, 3H), 6.82 (d, J=8.0 Hz, 1H), 7.18 (m, 2H), 7.30 (m, 4H), 7.38 (m, 1H), 7.44 (m, 1H), 7.52 (s, 1H), 7.55 (d, J=8.0 Hz, 1H).

b. Preparation of Compound

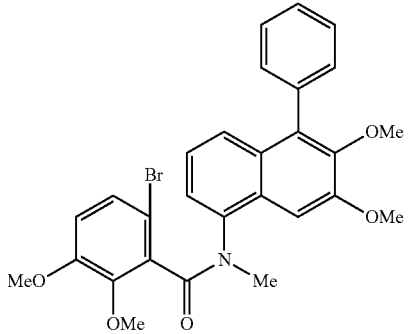 [SMILES: COc1ccc(Br)c(C(=O)N(C)c2cccc3c(-c4ccccc4)c(OC)c(OC)cc23)c1OC]

Using a precedure similar to that described in Example 3, sub-part i the amide from sub-part a was converted to the corresponding methyl amide; $^1$H NMR (400 MHz) (CDCl$_3$) δ. 3.20-4.02 (m, 15H), 6.46-7.32 (m, 11H).

c. Preparation of Compound

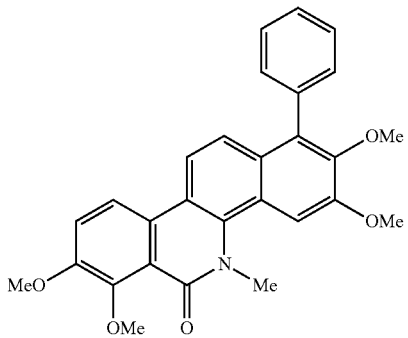 [SMILES: COc1cc2c(ccc3c4ccc(OC)c(OC)c4c(=O)n(C)c23)c(-c2ccccc2)c1OC]

Using a precedure similar to that described in Example 3, sub-part j the methyl amide was converted to the corresponding cyclic amide; $^1$H NMR (400 MHz) (CDCl$_3$) δ. 3.60 (s, 3H), 3.90 (s, 3H), 3.92 (s, 3H), 3.98 (s, 3H), 4.02 (s, 3H), 7.21 (d, J=8.0 Hz, 1H), 7.29-7.34 (m, 3H), 7.39-7.47 (m, 3H), 7.50 (s, 3H), 7.79 (d, J=8.0 Hz, 1H), 7.87 (d, J=8.0 Hz, 1H).

Example 13

Preparation of Compound

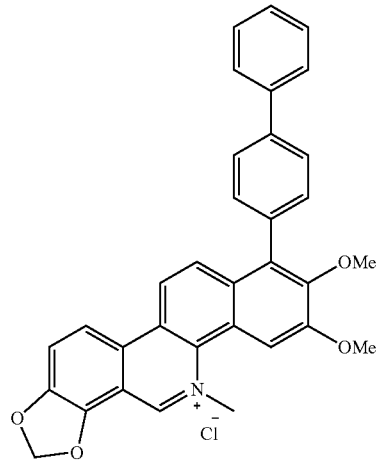 [SMILES: COc1cc2c(ccc3c4ccc5c(c4c[n+](C)c23)OCO5)c(-c2ccc(-c3ccccc3)cc2)c1OC ; [Cl-]]

LAH (0.9 mmol) was added to a solution of 7-(biphenyl-4-yl)-9,10-dimethoxy-12-methylbenzo[1,3]dioxolo[4,5]-phenanthridin-13(12H)-one (0.3 mmol) in dry THF (5 mL) in a stream of $N_2$ at 0° C. The reaction mixture was stirred for 30 minutes at room temperature after which it was diluted with water and filtered. The filtrate was concentrated to give the amino alcohol and it was treated with 10% HCl (0.5 mL) at room temperature to provide the quaternized salt. $^1$H NMR (400 MHz) (DMSO-$d_6$) δ 3.73 (s, 3H), 4.02 (s, 3H), 4.94 (s, 3H), 6.54 (s, 2H), 7.36 (m, 1H), 7.40 (s, 1H), 7.47 (m, 2H), 7.74 (d, J=8.0 Hz, 4H), 7.87 (d, J=8.0 Hz, 2H), 8.01 (d, J=8.0 Hz, 1H), 8.08 (s, 1H), 8.63 (s, 1H), 8.71 (d, J=8.0 Hz, 1H), 10.12 (s, 1H).

The intermediate 7-(biphenyl-4-yl)-9,10-dimethoxy-12-methylbenzo[1,3]dioxolo[4,5]phenanthridin-13(12H)-one was prepared as follows.

a. 2,3-Dihydroxynaphthalene dimesitylate

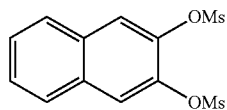

A solution of 10 g of 2,3-dihydroxynaphthalene in 50 ml of dichloromethane and 20 ml of triethylamine was treated drop-wise with 10 ml of methanesulfonyl chloride. After stirring for two hour, the white precipitate was collected by filtration and washed with ethanol to yield the product as colorless solid. Yield=9.5 g (96%). mp 160-163° C. $^1$H NMR (DMSO-$d_6$) δ 3.53 (s, 6H), 7.80 (m, 5H), 8.10 (s, 1H).

b. 5-Nitro-2,3-dihydroxynaphthalene dimesitylate

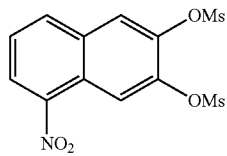 [SMILES: CS(=O)(=O)Oc1cc2cccc([N+](=O)[O-])c2cc1OS(C)(=O)=O]

A suspension of 5.0 g of 2,3-Dihydroxynaphthalene dimesitylate in 50 ml of acetic anhydride was treated with 12 ml of 70% $HNO_3$ at such a rate as to keep the temperature between 37-40° C. A cooling bath should be kept under the flask, ready to be raised if necessary, as the temperature should not be allowed to exceed 45° C. The 12.0 ml of nitric acid was added to the reaction mixture over a period of 1-2 h. After 2 h, the reaction mixture was cooled to 5° C. in an ice bath and the precipitate was collected by filtration and washed with ether. Yield 5-Nitro-2,3-dihydroxynaphthalene dimesitylate 70%; mp 199-201° C., $^1$H NMR (DMSO-$d_6$) δ 3.58 (s, 6H), 7.76 (t, J=8.0 Hz, 1H), 8.25-8.65 (m, 4H)

c. 5-nitro-2,3-dihydroxynaphthalene

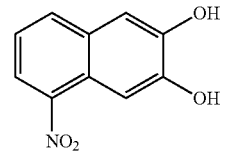 [SMILES: O=[N+]([O-])c1cccc2cc(O)c(O)cc12]

2,3-dimethanesulfonyloxy-5-nitronaphthalene (3.0 g) was added to a solution of NaOH (2.0 g) in water (58 ml) and the mixture was refluxed under nitrogen for 1.5 h. After cooling and acidification with (1:1) HCl, the mixture was extracted with ether and the combined extracts were dried over $Na_2SO_4$. Evaporation of the solvent afforded the dihydroxy derivative 5-nitro-2,3-dihydroxynaphthalene as dark yellow needles. Mp 206-208° C.

d. 5-nitro-2,3-dimethoxynaphthalene

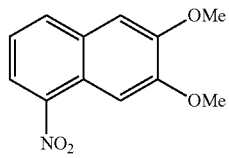 [SMILES: COc1cc2cccc([N+](=O)[O-])c2cc1OC]

Dimethyl sulfate was added to the solution of 5-nitro-2,3-dihydroxynaphthalene and NaOH in water. After being stirred for overnight at room temperature, the yellow solid was filtered off while the filtrate was checked for no product. The yellow solid was dried under vacuum to furnish the desired 5-nitro-2,3-dimethoxynaphthalene. $^1$H NMR (200 MHz) (CDCl$_3$) δ 4.04 (s, 3H), 4.06 (s, 3H), 7.20 (s, 1H), 7.39 (m, 1H), 7.96 (dd, J=8.0 Hz, 1.4 Hz, 1H), 8.05 (s, 1H), 8.18 (dd, J=8.0 Hz, 1.4 Hz, 1H).

e. 1-amino-6,7-dimethoxynapthylamine

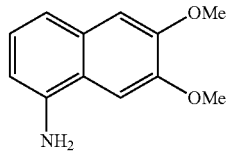 [SMILES: COc1cc2cccc(N)c2cc1OC]

5-Nitro-2,3-dimethoxynaphthalene (0.483 mmol) was dissolved in 4.0 ml of ethanol. The resulting solution was admixed with 0.18 ml of hydrazine hydrate and 18.5 mg of 10% palladium/carbon catalyst, and heated under reflux for 80 minutes. After cooling, the palladium/carbon catalyst was filtered off, and the filtrate was concentrated. The crude material thus formed was not purified further and was used as such for the next step.

f. 1-(N-tert-Butoxycarbonylamino)-6,7-dimethoxynaphthalene

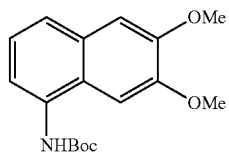 [SMILES: COc1cc2cccc(NC(=O)OC(C)(C)C)c2cc1OC]

Di-tert-butyl dicarbonate (0.15 mol) was added to a solution of 1-amino-6,7-dimethoxynapthylamine (0.13 mol) in THF (25 mL) and the resulting solution stirred under reflux for 2 h. The cooled mixture was concentrated in vacuo, then dissolved in ethyl acetate and washed twice with 1M HCl, then with water, dried, filtered and evaporated to leave a pink solid. The product 1-(N-tert-Butoxycarbonylamino)-6,7-dimethoxynaphthalene was purified by column chromatography on silica gel, eluting with 1; 1 ethyl acetate/hexane. $^1$H NMR (200 MHz) (DMSO-$d_6$) δ 1.51 (s, 9H), 3.88 (s, 3H), 3.90 (s, 3H), 7.26 (m, 1H), 7.29 (s, 1H), 7.35 (s, 1H), 7.44 (d, J=8.0 Hz, 1H), 7.53 (d, J=8.0 Hz, 1H), 9.13 (s, 1H).

g. 1-(N-tert-Butoxycarbonylamino)-6,7-dimethoxy-4-iodonaphthalene

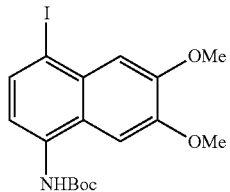 [SMILES: COc1cc2c(I)ccc(NC(=O)OC(C)(C)C)c2cc1OC]

t-Buthyllithium (2.7 mL of a 1.7 M solution in pentane, 4.61 mmol) was added to a solution of 1-(N-tert-Butoxycarbonylamino)-6,7-dimethoxynaphthalene (0.50 g, 1.65 mmol) in dry diethyl ether (5.0 mL) and dry DME (2.5 mL) at −40° C. under nitrogen. The resulting mixture was stirred at −20° C. for 5 h and then cooled to −78° C. A solution of 1,2-diiodoethane (1.30 g, 4.61 mmol) in dry DME was added and the resulting solution was allowed to warm to ambient temperature over several hours. Aq. NH4Cl was added, and the mixture was extracted twice with DCM. The combined organic extracts were washed with water, dried, filtered and evaporated to leave a dark glass. The compound was purified by column chromatography to give the pure product 1-(N-tert-Butoxycarbonylamino)-6,7-dimethoxy-4-iodonaphthalene. $^1$H NMR (200 MHz) (DMSO-$d_6$) δ 1.51 (s, 9H), 3.82 (s, 3H), 3.97 (s, 3H), 7.42 (t, J=8.5 Hz, 1H), 7.48 (s, 1H), 7.57 (d, J=8.5 Hz, 1H), 7.79 (d, J=8.5 Hz, 1H), 9.28 (s, 1H).

h. 1-(N-tert-Butoxycarbonylamino)-4-biphenyl-6,7-dimethoxynaphthalene

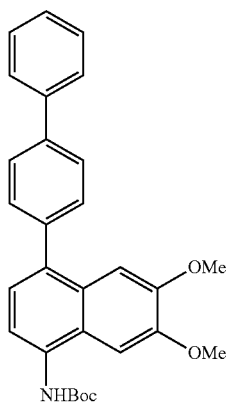 [SMILES: COc1cc2c(NC(=O)OC(C)(C)C)ccc(-c3ccc(-c4ccccc4)cc3)c2cc1OC]

1-(N-tert-Butoxycarbonylamino)-6,7-dimethoxy-4-iodonaphthalene (1.0 mmol), 4-biphenyl boronic acid (Sigma-Aldrich, 1.5 equiv.), tetrakis(triphenylphosphine)-palladium (0.2 mmol), triphenylphosphine (1.5 equiv) were evacuated under vacuum. To this mixture were added $Na_2CO_3$ (aq) (2.0 equiv), degassed toluene and methanol (5:1) and was heated at 80° C. for 14 h. The reaction mixture was filtered through a plug of silica gel on celite using EtOAc as elutant. After concentration, the crude product was purified by flash column chromatography using a gradient of 30% hexane in dichloromethane gave the pure product 1-(N-tert-Butoxycarbonylamino)-4-biphenyl-6,7-dimethoxynaphthalene as yellow solid. (yield; 85%). $^1$H NMR (400 MHz) (CDCl$_3$) δ 1.51 (s, 9H), 3.75 (s, 3H), 3.98 (s, 3H), 7.12 (s, 1H), 7.18 (s, 1H), 7.23 (d, J=8.0 Hz, 2H), 7.30 (m, 1H), 7.41 (m, 2H), 7.49 (d, J=8.0 Hz, 2H), 7.55 (m, 1H), 7.63 (m, 3H).

i. 4-(biphenyl-4-yl)-6,7-dimethoxynaphthalen-1-amine

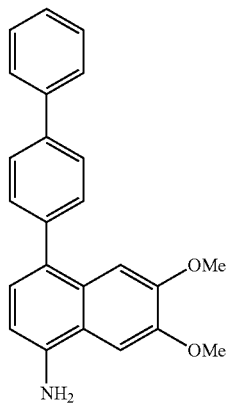 [SMILES: COc1cc2c(N)ccc(-c3ccc(-c4ccccc4)cc3)c2cc1OC]

55 mg of 4-(biphenyl-4-yl)-6,7-dimethoxynaphthaleneamine was heated in 3 mL of THF and 0.36 mL of water with 0.36 mL of concentrated hydrochloric acid under argon atmosphere of 40 minutes. After evaporation of the THF, the aqueous solution was basified at 0° C. with 3N NH$_4$OH and extracted with DCM. The combined organic extracts were washed with brine, dried and evaporated. Silica gel chromatography eluting with 2% MeOH in DCM gave the pure product 4-(biphenyl-4-yl)-6,7-dimethoxynaphthalen-1-amine (46 mg) as off white solid. $^1$H NMR (400 MHz) (CDCl$_3$) δ 3.76 (s, 3H), 3.97 (s, 3H), 3.96 (bs, 2H), 6.72 (d, J=8.0 Hz, 1H), 7.05 (s, 1H), 7.10 (d, J=8.0 Hz, 1H), 7.18 (s, 1H), 7.30 (d, J=8.0 Hz, 1H), 7.40 (m, 2H), 7.49 (d, J=8.0 Hz, 2H), 7.63 (m, 4H).

j. N-(4-(biphenyl-4-yl)-6,7-dimethoxynaphthalen-1-yl)-5-bromobenzo[1,3]dioxole-4-carboxamide

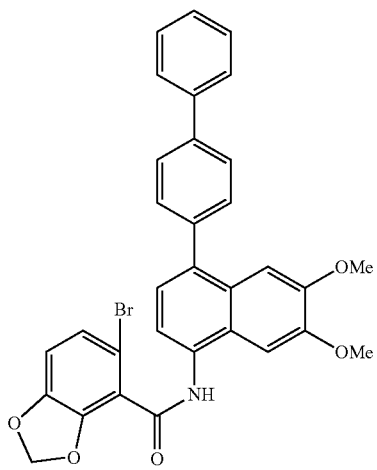 [SMILES: COc1cc2c(NC(=O)c3c(Br)ccc4c3OCO4)ccc(-c3ccc(-c4ccccc4)cc3)c2cc1OC]

Oxalyl chloride (6.13 mmol) was added to a solution of the acid (5-Bromobenzo[1,3]dioxole-4-carboxylic acid) (3.25 mmol) in anhyd $CH_2Cl_2$ (30 ml) and the stirred mixture was refluxed for 2 h. Then the mixture was concentrated to dryness under reduced pressure. To this residue was added a solution of amine (2.45 mmol) in anhyd CH₂Cl₂ (15 ml) and anhyd Et₃N (3.67 mmol) and the mixture was stirred overnight at room temperature. The mixture was concentrated to dryness and diluted with CH₂Cl₂, then washed with 10% HCl, aq NaHCO₃ solution and brine. The residue was dissolved in chloroform and subjected to flash chromatography to provide compound N-(4-(biphenyl-4-yl)-6,7-dimethoxynaphthalen-1-yl)5-bromobenzo[1,3]dioxole-4-carboxamide. $^1$H NMR (400 MHz) (CDCl₃) δ 3.77 (s, 3H), 3.96 (s, 3H), 6.08 (s, 2H), 6.74 (d, J=8.0 Hz, 1H), 7.12 (d, J=8.0 Hz, 1H), 7.25 (s, 1H), 7.30 (m, 2H), 7.38 (s, 1H), 7.44 (m, 2H), 7.51 (d, J=8.0 Hz, 2H), 7.68 (m, 5H), 7.78 (bs, 1H).

k. N-(4-(biphenyl-4-yl)-6,7-dimethoxynaphthalen-1-yl)-5-bromo-N-methylbenzo[1,3]dioxole-4-carboxamide

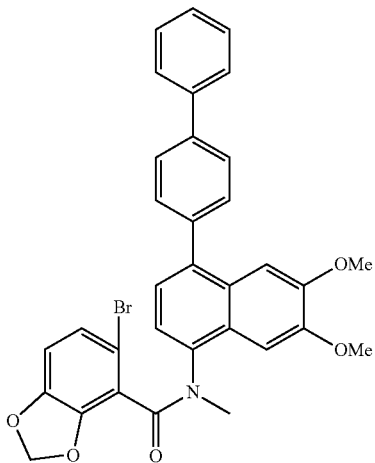 [SMILES: COc1cc2c(-c3ccc(-c4ccccc4)cc3)ccc(N(C)C(=O)c3c(Br)ccc4c3OCO4)c2cc1OC]

To a suspension of benzamide N-(4-(biphenyl-4-yl)-6,7-dimethoxynaphthalen-1-yl)5-bromobenzo[1,3]dioxole-4-carboxamide (1 mmol), and NaH (3 mmol) in dry DMF (20 mL) was added MeI (2 equiv). The reaction mixture was stirred over night, diluted with ether and then washed with 10% HCl and brine. The residue was subjected to column chromatography on silica using 2% methanol in chloroform to provide product N-(4-(biphenyl-4-yl)-6,7-dimethoxynaphthalen-1-yl)5-bromo-N-methylbenzo[1,3]dioxole-4-carboxamide as an off white solid. $^1$H NMR (400 MHz) (CDCl₃) δ 3.39-3.60 (m, 3H, N—CH₃), 3.66-3.80 (m, 3H, O—CH₃), 3.96-4.00 (m, 3H, O—CH₃), 5.03-6.18 (m, 2H, O—CH₂O), 6.30-7.69 (m, 15H, aromatic).

l. 7-(biphenyl-4-yl)-9,10-dimethoxy-12-methylbenzo[1,3]dioxolo[4,5]phenanthridin-13(12H)-one

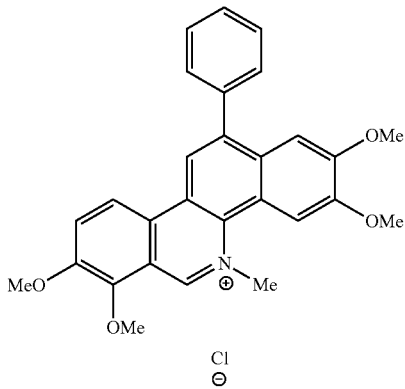 [SMILES: COc1cc2c(-c3ccccc3)cc3c4ccc(OC)c(OC)c4c[n+](C)c3c2cc1OC ; [Cl-]]

A mixture of N-methyl benzamide N-(4-(biphenyl-4-yl)-6,7-dimethoxynaphthalen-1-yl)5-bromo-N-methylbenzo[1,3]-dioxole-4-carboxamide (1 equiv), Pd(OAc)₂ (0.2 equiv), P(o-tolyl)₃ (0.4 equiv), Ag₂CO₃ (2 equiv) was evacuated under vacuum. To this mixture DMF (8 mL/0.3 mmol) was added under nitrogen and then heated at 160° C. overnight. After cooling to room temperature, reaction mixture was diluted with ether and washed with brine. The organic layer was dried over Na₂SO₄, filtered and concentrated under vacuum to get a brown residue 7-(biphenyl-4-yl)-9,10-dimethoxy-12-methylbenzo[1,3]dioxolo[4,5]phenanthridin-13(12H)-one. The residue was purified by flash chromatography eluting with 0.5 methanol/chloroform. $^1$H NMR (400 MHz) (CDCl₃) δ 3.79 (s, 3H), 3.94 (s, 3H), 3.99 (s, 3H), 6.22 (s, 2H), 7.17 (d, J=8.0 Hz, 2H), 7.24 (s, 1H), 7.35 (m, 1H), 7.44 (m, 2H), 7.51 (s, 1H), 7.57 (d, J=8.0 Hz, 2H), 7.66 (d, J=8.0 Hz, 2H), 7.72 (m, 3H), 7.91 (s, 1H).

Example 14

Preparation of Compound

Using a reduction procedure similar to the one described in Example 3, the title compound was prepared from the corresponding cyclic amide; $^1$H NMR (400 MHz) (DMSO-d₆) δ: 3.79 (s, 3H), 4.11 (s, 3H), 4.13 (s, 3H), 5.08 (s, 3H), 7.47 (s, 1H), 7.61-7.44 (m, 5H), 8.21 (s, 1H), 8.26 (d, J=8.0 Hz, 1H), 8.72 (s, 1H), 8.99 (d, J=8.0 Hz, 1H), 10.15 (s, 1H).

The intermediate cyclic amide was prepared as follows.

a. Preparation of 4-iodo-6,7-dimethoxynaphthylen-1-amine

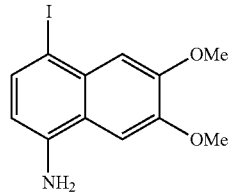 [SMILES: COc1cc2c(N)ccc(I)c2cc1OC]

Dimethoxynapthalenamine (1 mmol) was dissolved in dioxane (6.0 mL) and pyridine (6.0 mL) and the solution was cooled to 0° C. Iodine (3.0 mmol) was added in one portion. The solution progressively took a dark brown color. After 1-1.5 h, the ice bath was removed and a supplementary portion of Iodine (1 mmol) was added if needed. The solution was further stirred for one hour at room temperature. A saturated solution of sodium thiosulfate was then added until the brown color disappeared. The mixture was extracted with DCM (40 mL) and washed with water (40 ml). After evaporation the product was purified by column chromatography. (Chloroform or 1-2% methanol in chloroform was used). Note—some decomposition occurred during purification, there is a spot just under the desired product). $^1$NMR (400 MHz) (CDCl$_3$) δ 3.95 (s, 3H), 3.99 (s, 3H), 6.41 (d, J=8.0 Hz. 1H), 6.99 (s, 1H), 7.32 (s, 1H), 7.63 (d, J=8.0 Hz, 1H).

b. Preparation of Compound

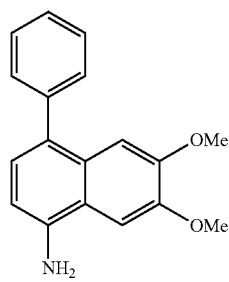 [SMILES: COc1cc2c(N)ccc(-c3ccccc3)c2cc1OC]

Using a procedure similar to the one described in Example 13 sub-part h, the iodo compound from sub-part a was converted to the corresponding phenyl compound; $^1$H NMR (400 MHz) (CDCl$_3$) δ 3.76 (s, 3H), 3.96 (s, 3H), 6.74 (d, J=8.0 Hz, 1H), 7.06 (d, J=8.0 Hz, 1H), 7.07 (s, 1H), 7.19 (s, 1H), 7.29-7.32 (m, 1H), 7.37-7.42 (m, 4H).

c. Preparation of Compound

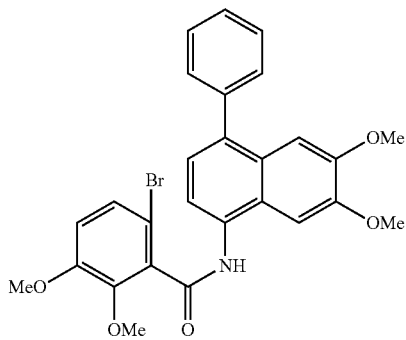 [SMILES: COc1cc2c(NC(=O)c3c(Br)ccc(OC)c3OC)ccc(-c3ccccc3)c2cc1OC]

Using a precedure similar to that described in Example 3, sub-part h the amino compound from sub-part b was converted to the corresponding amide; $^1$H NMR (400 MHz) (CDCl$_3$) δ 3.74 (s, 3H), 3.85 (s, 3H), 3.91 (s, 3H), 3.98 (s, 3H), 6.83 (d, J=8.0 Hz, 1H), 7.17 (d, J=8.0 Hz, 1H), 7.27 (dd, J=8.0 Hz, 4.0 Hz, 1H), 7.37 (m, 2H), 7.42 (m, 4H), 7.47 (m, 2H), 7.61 (d, J=8.0 Hz, 1H).

d. Preparation of Compound

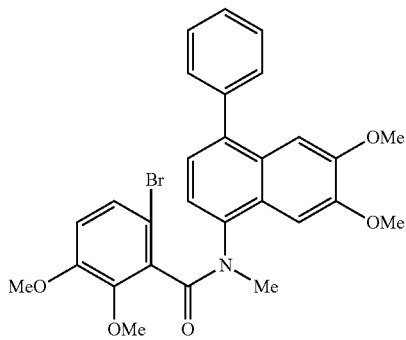 [SMILES: COc1cc2c(-c3ccccc3)ccc(N(C)C(=O)c3c(Br)ccc(OC)c3OC)c2cc1OC]

Using a precedure similar to that described in Example 3, sub-part i the amide from sub-part c was converted to the corresponding methyl amide; $^1$H NMR (400 MHz) (CDCl$_3$) δ 3.31-4.01 (m, 15H), 6.45-7.31 (m, 11H).

e. Preparation of Compound

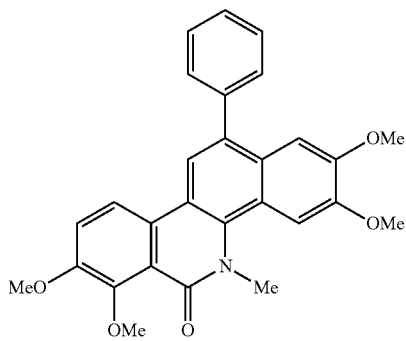 [SMILES: COc1cc2c(-c3ccccc3)cc3c4ccc(OC)c(OC)c4c(=O)n(C)c3c2cc1OC]

Using a precedure similar to that described in Example 3, sub-part j the methyl amide from sub-part d was converted to the corresponding cyclic amide; $^1$H NMR (400 MHz) (CDCl$_3$) δ 3.75 (s, 3H), 3.91 (s, 3H), 3.97 (s, 3H), 4.02 (s, 3H), 7.15 (s, 1H), 7.30 (d, J=8.0 Hz, 1H), 7.41 (m, 2H), 7.48 (m, 4H), 7.87 (s, 1H), 7.92 (d, J=8.0 Hz, 1H).

Example 15

Preparation of Compound 107

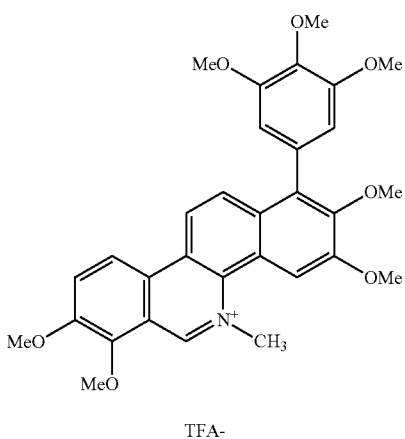

107

TFA-

To a solution of cyclic amide 106 (110 mg, 0.198 mmoles) in 4 mL of THF was added a 2 M solution of LAH in THF (0.2 mL). The mixture was stirred for 45 min. and then cooled in an ice bath and quenched with 3 drops of water. Solids were removed by filtration and the solvent was evaporated under vacuum. The residue was taken up in 50% $CH_3CN/H_2O$ and purified by reverse phase chromatography (VYDAC C18, 2 cm×20 cm, gradient 20% $CH_3CN/0.2\%$ TFA $H_2O$ to 90% $CH_3CN/0.2\%$ TFA $H_2O$. 20 mL/min.) affording 107 39 mg (0.061 mmoles, 30%) as the TFA salt; $^1$H NMR (CDCl$_3$) δ 3.85 (s, 3H), 3.90 (s, 3H), 4.02 (s, 3H), 4.14 (s, 3H), 4.22 (s, 3H), 4.36 (s, 3H), 4.36 (s 3H), 5.25 (s, 3H), 6.64 (s, 2H), 7.96-7.98 (m, 2H), 8.08 (s, 1H), 8.31 (d, J=8.0, 1H), 8.40 (d, J=8.0, 1H), 10.33 (s, 1H).

The intermediate cyclic amide 106 was prepared as follows.

a. Preparation of Compound 102

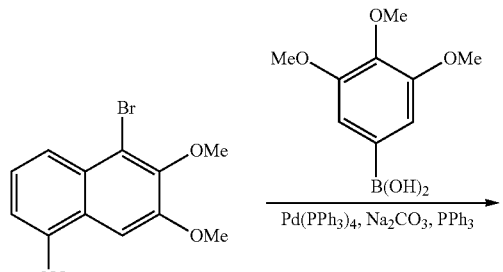

101

-continued

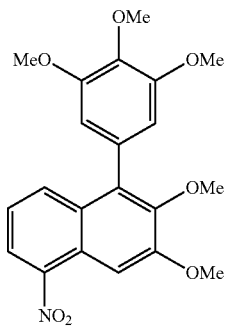

102

An aluminum multi vial reaction block was pre heated to 80° C. Intermediate 101 (100 mg, 0.32 mmoles), 3,4,5-trimethoxyphenylboronic acid (136 mg, 0.64 mmoles), triphenylphosphine (100 mg, 0.38 mmoles) and tetrakistriphenylphosphine palladium (77 mg, 0.067 mmoles) were added to a reaction vial along with a stirring magnet. A rubber septum was placed over the top and argon gas was passed through for 5 min. A degassed mixture of toluene/MeOH (5:1) was introduced via syringe (1.5 mL) followed by degassed 2M $Na_2CO_3$ (0.5 mL). The mixture was stirred vigorously under argon for several minutes and then the septum was replaced with a screw cap and the vial was placed in the reaction block. Stirring and heating was continued for 17.5 hrs. TLC (25% hexane/$CH_2Cl_2$) showed nearly complete reaction. The vial was cooled to room temp., filtered and solvent was evaporated. A concentrated solution of the crude residue in 20% hexane/DCM was applied to a short silica gel column and eluted with 20% hexane/DCM (100 ml), then 100% DCM (100 mL), then 20% EtOAc/DCM. Product was eluted with 20% EtOAc/DCM. Yield of 102: 110 mg (86%); $^1$H NMR (CDCl$_3$) δ 3.68 (s, 3H), 3.85 (s, 6H), 4.97 (s, 3H), 4.05 (s, 3H) 6.66 (s, 2H), 7.2 (m 1H), 7.8 (m, 1H), 8.1 (s, 1H) 8.2 (m, 1H).

b. Preparation of Compound 103

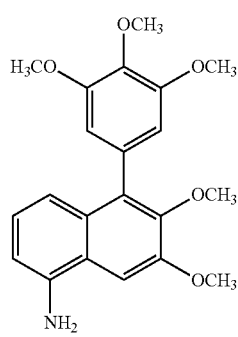

103

To a suspension 102 (200 mg, 0.5 mmoles) in EtOH (5 mL) in a screw cap vial fitted with a septum, was added 10% Pd/C (20 mg) in 1 ml EtOH. The mixture was degassed under argon then 0.2 mL of hydrazine hydrate was added via syringe. The vial was capped and heated in a reaction block at 80° C. for 3 hrs., cooled to room temp and filtered. The filter cake was washed with 10 mL of hot toluene and EtOH and then solvent was evaporated to give 180 mg of product 103, which was not purified. Crude yield: 89%; $^1$H NMR (CDCl$_3$) δ 3.67 (s, 3H) 3.84 (s, 6H), 4.98 (s 3H) 4.01 (s, 3H) 4.02-4.06 (bs 2H), 6.6 (s 2H) 6.8 (d, J=8.0 1H), 7.0 (J=8.0 1H) 7.1 (m 1H) 7.18 (s 1H).

c. Preparation of Compound 104

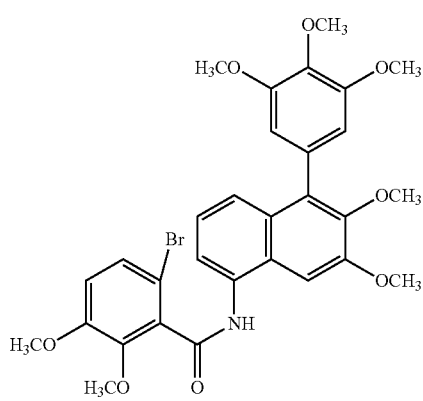

To a solution of 103 (170 mg, 0.46 mmoles) in DCM (3 mL) was added a solution of the acid chloride (160 mg, 0.54 mmoles) in 2 mL of DCM followed by TEA (0.1 mL) and a catalytic amt. of DMAP. The reaction was stirred overnight at room temp. TLC (10% EtOAc/DCM) showed nearly complete reaction. Solvent was evaporated. The residue was dissolved in DCM and washed with 10% HCl followed by sat aq. NaHCO$_3$ and finally, brine. Solvent was evaporated and the residue was purified by column chromatography on silica gel (100% DCM→20% EtOAc/DCM), yielding 220 mg (0.36 mmoles, 78%) of product 104; $^1$H NMR (CDCl$_3$) δ 3.7-4.1 (7 singlets, 21H), 6.6 (s, 2H), 6.9 (m, 1H), 7.1-7.2 (m, 3H), 7.5 (d, J=8, 1H), 7.6 (m, 2H).

d. Preparation of Compound 105

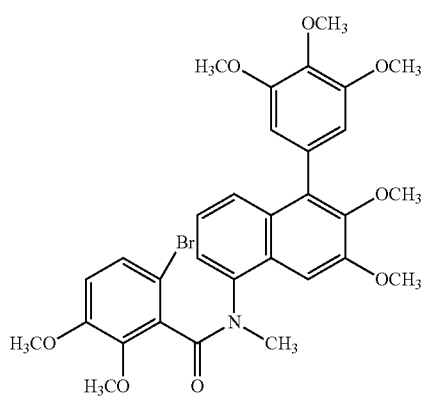

To a 10% DMF solution of benzamide 104 (220 mg, 0.36 mmoles) was added a suspension of NaH (3 eq., pre-washed with hexane) in DMF (1.5 mL). After stirring for 10 min., a solution of MeI (78 mg, 0.55 mmoles) in 0.5 mL DMF was added and the mixture was stirred for 19 hrs. at room temp. TLC (10% EtOAc/DCM) of a small aliquot, which had been treated with water and washed with 10% HCl and brine and extracted into EtOAC showed complete reaction. The entire reaction was then treated in a similar manner. The organic layer was washed rigorously with brine, dried over Na$_2$SO$_4$, filtered and concentrated to an oil which was purified by chromatography on silica gel (100% DCM→10% EtOAc/DCM). Yield of 105: 200 mg (0.32 mmoles, 89%) as a mixture of rotmers; $^1$H NMR (CDCl$_3$) δ 3.1-4.1 (m, 24H), 6.5-7.6 (m, 8H).

e. Preparation of Compound 106

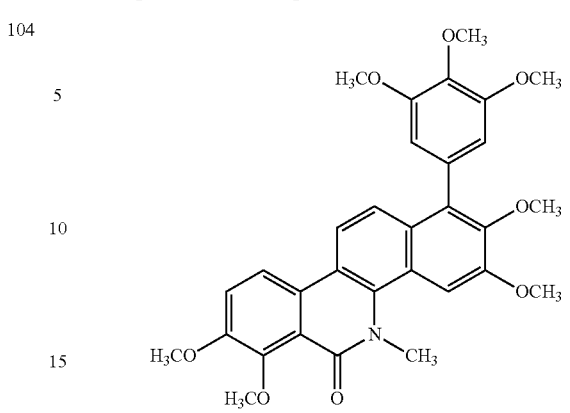

To a 25 mL pressure vessel was added Pd(OAc)$_2$ (14 mg, 0.062 mmoles), P(o-tolyl)$_3$ (37.7 mg, 0.124 mmoles), and AgCO$_3$ (178 mg, 0.65 mmoles), fitted with a septum and purged with argon for 15 min. A solution of 105 (200 mg, 0.32 mmoles) in 10 mL of DMF was prepared and flushed with argon. The solution was transferred to the pressure vessel via syringe. The vessel was capped and heated with stirring in a temperature regulated oil bath at 155-168° C. over night. The reaction vessel was allowed to cool to room temp. and diluted with 50 mL of EtOAc and filtered through filter paper. The filtrate was washed with brine (3×50 mL) and dried over Na$_2$SO$_4$. The solvent was evaporated and the residue was purified by chromatography on silica gel (10% EtOAc/DCM→20% EtOAc/DCM) yielding 110 mg (0.20 mmoles, 62%) of product 106; $^1$H NMR (CDCl$_3$) δ 3.70 (s, H), 3.82 (s, 6H), 3.98 (s, 9H), 4.02 (s, 3H), 4.05 (s, 3H), 6.6 (2H), 7.37 (m, 2H), 7.50 (s, 1H), 7.9 (m 2H).

Example 16

Preparation of Compound 113

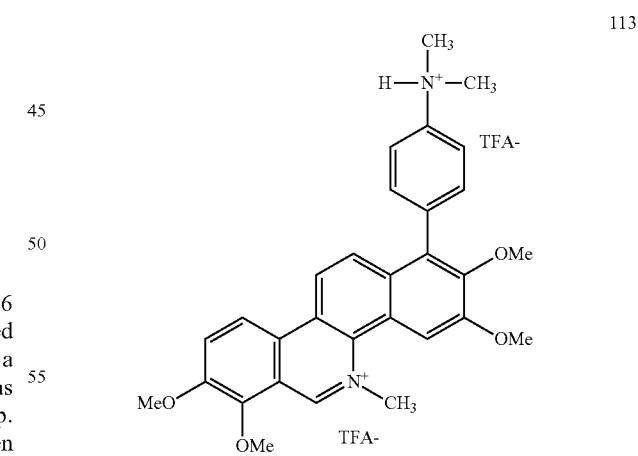

To a solution of cyclic amide 112 (80 mg, 0.16 mmoles) in 4 mL of THF was added a 2 M solution of LAH in THF (0.2 mL). The mixture was stirred for 45 min. and then cooled in an ice bath and quenched with 3 drops of water. Solids were removed by filtration and the solvent was evaporated under vacuum. The residue was taken up in 50% CH$_3$CN/H$_2$O and purified by reverse phase chromatography (VYDAC C18, 2 cm×20 cm, gradient 20% CH$_3$CN/0.2% TFA H$_2$O to 90%

CH$_3$CN/0.2% TFA H$_2$O, 20 mL/min.). To yield 59 mg (0.083 mmoles, 52%) of 113 as the bis-TFA salt; $^1$H NMR (CDCl$_3$) δ 3.40 (s, 6H), 3.83 (s, 3H) 4.06 (s, 3H), 4.11 (s, 3H), 4.18 (3 3H) 5.2 (s 3H), 7.6 (d, J=8.0, 1H), 7.78 (m 3H) 8.06 (d, J=8.0 1H), 8.15 (s, 1H), 8.36 (d, J=8.0, 1H), 8.40 (d, J=1, 1H), 10.2 (s, 1H).

The intermediate cyclic amide 112 was prepared as follows.

a. Preparation of Compound 108

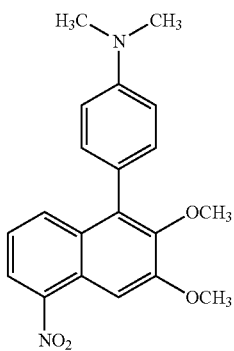

108

An aluminum multi vial reaction block was pre heated to 80° C. Intermediate 101 (200 mg, 0.64 mmoles), 4-N,N-dimethylaminophenylboronic acid (212 mg, 1.28 mmoles), triphenylphosphine (100 mg, 0.38 mmoles) and tetrakistriphenylphosphine palladium (155 mg, 0.134 mmoles) were added to a reaction vial along with a stirring magnet. A rubber septum was placed over the top and argon gas was passed through for 5 min. A degassed mixture of toluene/MeOH (5:1) was introduced via syringe (1.5 mL) followed by degassed 2M Na$_2$CO$_3$ (0.5 mL). The mixture was stirred vigorously under argon for several minutes and then the septum was replaced with a screw cap and the vial was placed in the reaction block. Stirring and heating was continued for 17.5 hrs. TLC (25% hexane/CH$_2$Cl$_2$) showed nearly complete reaction. The vial was cooled to room temp., filtered and solvent was evaporated. A concentrated solution of the crude residue in 20% hexane/DCM was applied to a short silica gel column and eluted with 20% hexane/DCM (100 ml), then 100% DCM (100 mL), then 20% EtOAc/DCM. Product was eluted with 20% EtOAc/DCM. Yield of pure 108: 206 mg (0.58 mmoles, 91%); $^1$H NMR (CDCl$_3$) δ 3.10 (s, 6H), 4.10 (s, 3H) 6.84 (d, J=8.0, 1H), 7.2 (m, 4H), 7.9 (d, J=8.0, 1H) 8.1 (s, 1H) 8.2 (d, J=8.0, 1H).

b. Preparation of Compound 109

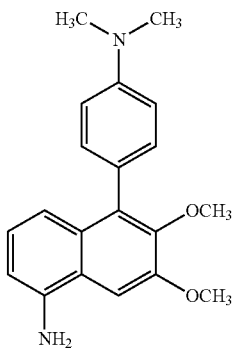

109

To a suspension 108 (200 mg, 0.56 mmoles) in EtOH (5 mL) in a screw cap vial fitted with a septum, was added 10% Pd/C (20 mg) in 1 ml EtOH. The mixture was degassed under argon then 0.2 mL of hydrazine hydrate was added via syringe. The vial was capped and heated in a reaction block at 80° C. for 3 hrs., cooled to room temp and filtered. The filter cake was washed with 10 mL of hot toluene and EtOH and then solvent was evaporated to give 188 mg of crude product 109, which was not purified; $^1$H NMR (CDCl$_3$) δ 2.91 (s, 6H), 3.62 (s, 3H), 4.10 (s 3H), 7.25 (m, 2H) 7.55 (m 2H), 7.8 (m 1H), 7.98 (d, J=8.0, 1H), 8.1 (s 1H), 8.2 (d, J=8.0, 1H).

c. Preparation of Compound 110

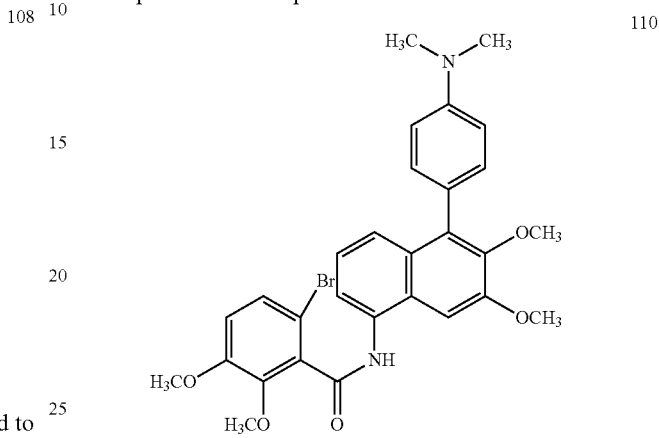

110

To a solution of 109 (180 mg, 0.56 mmoles) in DCM (3 mL) was added a solution of the acid chloride (180 mg, 0.64 mmoles) in 2 mL of DCM followed by TEA (0.1 mL) and a catalytic amt. of DMAP. The reaction was stirred overnight at room temp. TLC (10% EtOAc/DCM) showed nearly complete reaction. Solvent was evaporated and the residue was dissolved in DCM, washed with 10% HCl followed by sat aq. NaHCO$_3$ and finally, brine. Solvent was evaporated and the residue was purified by column chromatography on silica gel (100% DCM→20% EtOAc/DCM), crude yield 320 mg of product. Purification by prep tlc (20% EtOAc/CH$_2$Cl$_2$) gave 240 mg (0.42 mmoles) of 110, 76%; $^1$H NMR (CDCl$_3$) δ 3.01 (s, 6H), 3.60 (s, 3H), 4.97 (s, 3H) 4.99 (s, 3H) 5.04 (s, 3H), 6.94 (m, 2H), 7.24 (m, 3H), 7.4 (d, J=8.0, 1H), 7.6-7.8 (m, 4H).

d. Preparation of Compound 111

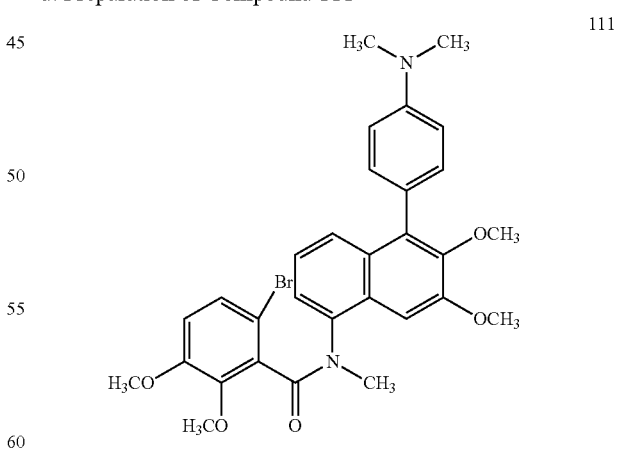

111

To a 10% DMF solution of benzamide 110 (240 mg, 0.42 mmoles) was added a suspension of NaH (3 eq., pre-washed with hexane) in DMF (1.5 mL). After stirring for 10 min., a solution of MeI (156 mg, 1.1 mmoles) in 0.5 mL DMF was added and the mixture was stirred for 19 hrs. at room temp. TLC (10% EtOAc/DCM) of a small aliquot, treated with water, 10% HCl, aq. Na$_2$CO$_3$ and brine and extracted into EtOAC showed complete reaction. The entire reaction was then treated in a similar manner. The organic layer was washed rigorously with brine, dried over Na$_2$SO$_4$, filtered and concentrated to an oil which was purified by chromatography on silica gel (100% DCM→10% EtOAc/DCM) to yield 111 (150 mg, 0.26 mmoles, 62%); $^1$H NMR (CDCl$_3$) δ 2.9-3.1 (m, 6H), 3.1-4.1 (m, 15H) 6.58-8.1M, 10H).

e. Preparation of Compound 112

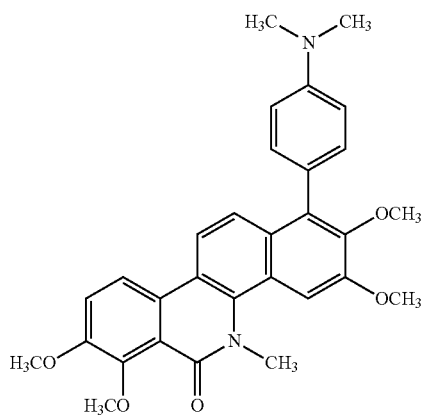

112

To a 25 mL pressure vessel was added Pd(OAc)$_2$ (3.8 mg, 0.017 mmoles, P(o-tolyl)$_3$ (10.6 mg, 0.035 mmoles), and AgCO$_3$ (48 mg, 0.174 mmoles) fitted with a septum and purged with argon for 15 min. A solution of 111 (50 mg, 0.087 mmoles) in 2 mL of DMF was prepared and flushed with argon. The solution was transferred to the pressure vessel via syringe. The vessel was capped and heated with stirring in a temperature regulated oil bath at 155-168° C. over night. The reaction vessel was allowed to cool to room temp. and diluted with 50 mL of EtOAc and filtered through filter paper. The filtrate was washed with brine (3×50 mL) and dried over Na$_2$SO$_4$. The solvent was evaporated and the residue was purified by chromatography on silica gel (10% EtOAc/DCM→20% EtOAc/DCM) yielding 27 mg of product 112 (0.054 mmoles, 63%); $^1$H NMR (CDCl$_3$) δ 3.15 (s 6H), 3.62 (s, 3H) 3.98 (s, 3H) 3.99 (s 3H) 4.01 (s, 3H), 4.5 (s, 3H), 6.95 (d, J=8 2H, 2H), 7.28 (m, 2H) 7.4 (d, J=8.0 1H), 7.44 (d, J=8 1H), 7.5 (s, 1H), 7.86 (d, J=8.0, 1H) 7.96 (d, J=8, 1H).

Example 17

Preparation of Compound 119

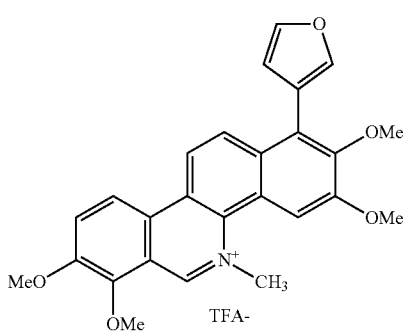

119

To a solution of the cyclic amide 118 (80 mg, 0.19 mmoles) in 4 mL of THF was added a 2 M solution of LAH in THF (0.2 mL). The mixture was stirred for 45 min. and then cooled in an ice bath and quenched with 3 drops of water. Solids were removed by filtration and the solvent was evaporated under vacuum. The residue was taken up in 50% CH$_3$CN/H$_2$O and purified by reverse phase chromatography (VYDAC C18, 2 cm×20 cm, gradient 20% CH$_3$CN/0.2% TFA H$_2$O to 90% CH$_3$CN/0.2% TFA H$_2$O. 20 mL/min.). To yield 29 mg (0.053 mmoles, 28%) of 119 as the TFA salt.

The starting cyclic amide 118 was prepared as follows.

a. Preparation of Compound 114

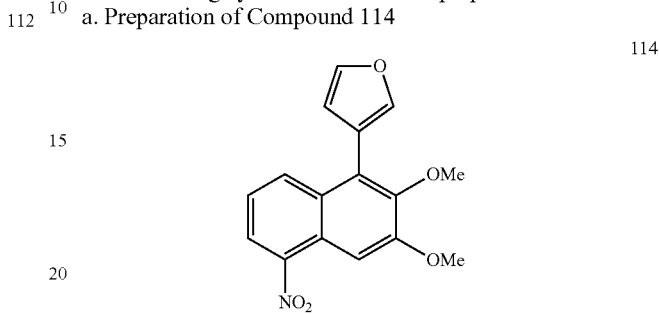

114

An aluminum multi vial reaction block was pre heated to 80° C. Compound 101 (200 mg, 0.64 mmoles), furan-3-boronic acid (143.2 mg, 1.28 mmoles), triphenylphosphine (200 mg, 1.36 mmoles) and tetrakistriphenylphosphine palladium (155 mg, 0.134 mmoles) were added to a reaction vial along with a stirring magnet. A rubber septum was placed over the top and argon gas was passed through for 5 min. A degassed mixture of toluene/MeOH (5:1) was introduced via syringe (1.5 mL) followed by degassed 2M Na$_2$CO$_3$ (0.5 mL). The mixture was stirred vigorously under argon for several minutes and then the septum was replaced with a screw cap and the vial was placed in the reaction block. Stirring and heating was continued for 17.5 hrs. TLC (25% hexane/CH$_2$Cl$_2$) showed nearly complete reaction. The vial was cooled to room temp., filtered and solvent was evaporated. A concentrated solution of the crude residue in 20% hexane/DCM was applied to a short silica gel column and eluted with 20% hexane/DCM (100 ml), then 100% DCM (100 mL), then 20% EtOAc/DCM. Product was eluted with 20% EtOAc/DCM. Yield of pure 114: 180 mg (0.60 mmoles, 94%); $^1$H NMR (CDCl$_3$) δ 3.75 (s, 3H), 6.60 (s, 1H) 7.3 (m, 1H), 7.65 (d, J=8.0, 2H), 8.05 (s, 1H), 8.10 (d, J=8.0, 1H), 8.2 (d, J=8.0, 1H).

b. Preparation of Compound 115

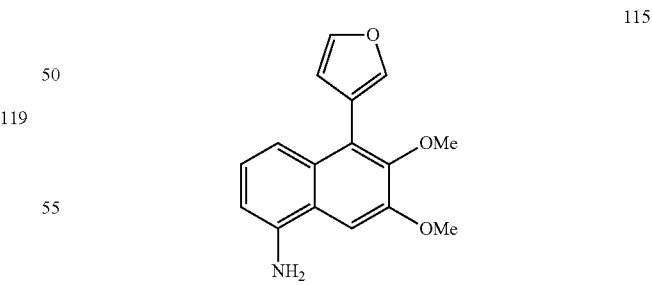

115

To a suspension 114 (190 mg, 0.64 mmoles) in EtOH (5 mL) in a screw cap vial fitted with a septum, was added 10% Pd/C (20 mg) in 1 ml EtOH. The mixture was degassed under argon then 0.21 mL of hydrazine hydrate was added via syringe. The vial was capped and heated in a reaction block at 80° C. for 3 hrs., cooled to room temp and filtered. The filter cake was washed with 10 mL of hot toluene and EtOH and then solvent was evaporated to give 180 mg of crude product 115, which was purified by silica gel chromatography (100% DCM→20% EtOAc/DCM). Yield of 115: 150 mg (0.56 mmoles, 87%); $^1$H NMR (CDCl$_3$) δ 3.75 (s 3H), 4.05 (s, 3H), 6.60 (s, 1H), 7.4 (m, 2H0, 7.64 (m, 2H), 8.05 (s 1H), 8.1 (d, J=8.0, 1H), 8.15 (d, J=8, 1H).

c. Preparation of Compound 116

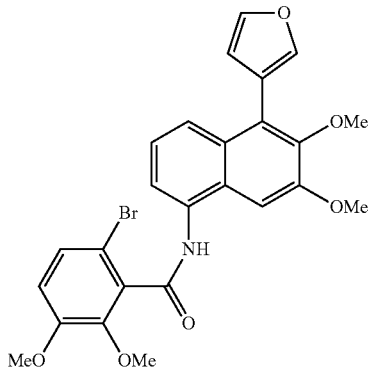

116

To a solution of 115 (130 mg, 0.48 mmoles) in DCM (3 mL) was added a solution of the acid chloride (155 mg, 0.56 mmoles) in 2 mL of DCM followed by TEA (0.1 mL) and a catalytic amt. of DMAP. The reaction was stirred overnight at room temp. TLC (10% EtOAc/DCM) showed nearly complete reaction. Solvent was evaporated and the residue was dissolved in DCM, washed with 10% HCl followed by sat aq. NaHCO$_3$ and finally, brine. Solvent was evaporated and the residue was purified by column chromatography on silica gel (100% DCM→20% EtOAc/DCM). Crude yield 270 mg of crude product 116. Purification by prep tlc (20% EtOAc/CH$_2$Cl$_2$) gave 190 mg (0.37 mmoles, 77%) of 116; $^1$H NMR (CDCl$_3$) δ 3.70 (s, 3H), 3.90 (s, 3H) 3.95 (s 3H), 4.05 (s, 3H), 6.60 (s 1H) 6.90 (d, J=8.0, 1H), 7.37 (m, 2H), 7.60 (m, 5H) 7.80 (d, J=8.0, 1H).

d. Preparation of Compound 117

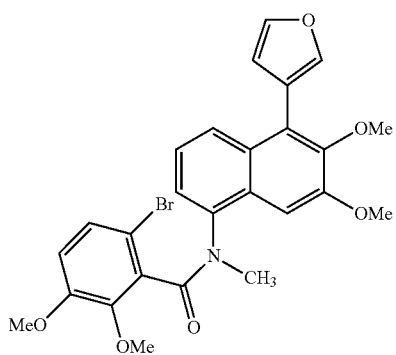

117

To a 10% DMF solution of benzamide 116 (160 mg, 0.31 mmoles) was added a suspension of NaH (3 eq., pre-washed with hexane) in DMF (1.5 mL). After stirring for 10 min., a solution of MeI (88 mg, 0.62 mmoles) in 0.5 mL DMF was added and the mixture was stirred for 19 hrs. at room temp. TLC (10% EtOAc/DCM) of a small aliquat, treated with water, 10% HCl and brine and extracted into EtOAC showed complete reaction. The entire reaction was then treated in a similar manner. The organic layer was washed rigorously with brine, dried over Na$_2$SO$_4$, filtered and concentrated to an oil which was purified by chromatography on silica gel (100% DCM→10% EtOAc/DCM) to yield 117 (155 mg, 0.29 mmoles, 95%); $^1$H NMR (CDCl$_3$) δ 3.0-4.1 (m 15H) 6.5-8.1 (m, 9H).

e. Preparation of Compound 118

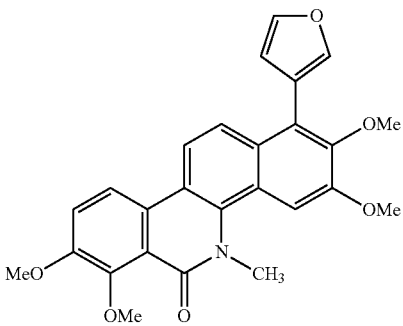

118

To a 25 mL pressure vessel was added Pd(OAc)$_2$ (15 mg, 0.067 mmoles, P(o-tolyl)$_3$ (39 mg, 0.128 mmoles), and AgCO$_3$ (182 mg, 0.66 mmoles), fitted with a septum and purged with argon for 15 min. A solution of 117 (170 mg, 0.33 mmoles) in 10 mL of DMF was prepared and flushed with argon. The solution was transferred to the pressure vessel via syringe. The vessel was capped and heated with stirring in a temperature regulated oil bath at 155-168° C. over night. The reaction vessel was allowed to cool to room temp. and diluted with 50 mL of EtOAc and filtered through filter paper. The filtrate was washed with brine (3×50 mL) and dried over Na$_2$SO$_4$. The solvent was evaporated and the residue was purified by chromatography on silica gel (10% EtOAc/DCM→20% EtOAc/DCM) yielding 80 mg (0.185 mmoles, 56%) of cyclic amide product 118; $^1$H NMR (CDCl$_3$) δ 3.78 (s, 3H) 4.05 (s, 3H) 4.08 (s 3H) 4.10, (s, 3H), 4.15 (s, 3H) 6.7 (s, 1H), 7.42 (m, 1H), 7.55 (s, 1H), 7.7 (m, 2H), 7.78 (d, J=8.0, 1H), 8.05 (m, 2H).

Example 18

Preparation of Compound 125

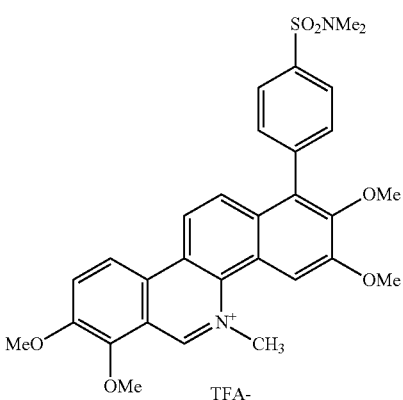

125

To a suspension of cyclic amide 124 (106 mg, 0.194 mmoles) in 4 mL of THF was added a 2 M solution of LAH in THF (0.2 mL). Starting material remained undissolved. The mixture was stirred for 45 min. at room temperature after which it was apparent that the starting material had not gone into solution. Two mL of dichloromethane and a additional 0.2 mL of LAH solution were added in an attempt to effect dissolution of the starting material without success. Two mL of toluene were added along with another 0.2 mL of LAH solution. The starting material finally dissolved and reaction was allowed to proceed for 30 min. The reaction mixture was cooled in ice water and quenched with 4 drops of water. Solids were removed by filtration and the solvent was evaporated under vacuum. TLC of the residue did not generate the characteristic yellow color of the phenanthridine salt. H$^1$NMR indicated that over reduction of the amide had occurred. In an attempt to regenerate the desired phenanthridine salt by air oxidation, the material was dissolved in CDCl$_3$ and several drops of TFA were added. The solution was stirred in air overnight and the following day, NMR showed the appearance of a peak at 10.2 ppm, characteristic of the phenanthridine methine along with unreacted reduced material. Presence of the phenanthridine salt was confirmed by prep tlc isolation of the MeOH adduct which, upon treatment with TFA produced the characteristic yellow color and an NMR spectrum consistent with the phenanthridine. Exposure of the prep tlc plate to light and air for three days converted a colorless upper band to a deep yellow color. Isolation of this band and treatment with TFA afforded additional quantities of the phenanthridine. Final purification was affected by flash silica gel chromatography (CombiFlash Companion System) eluting with 2:18:80 MeOH/EtOAc/DCM to yield 31 mg (0.049 mmoles, 31%) of 125 as the TFA salt.

The intermediate cyclic amide 124 was prepared as follows.

a. Preparation of Compound 120

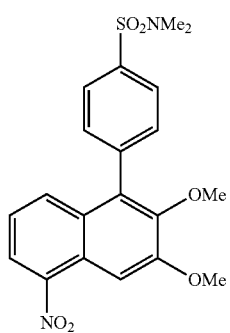

120

An aluminum multi vial reaction block was pre heated to 80° C. Compound 101 (200 mg, 0.64 mmoles), 4-N,N-dimethylaminosulfonylphenylboronic acid pinicol ester (398.3 mg, 0.1.28 mmoles), triphenylphosphine (100 mg, 0.38 mmoles) and tetrakistriphenylphosphine palladium (155 mg, 0.134 mmoles) were added to a reaction vial along with a stirring magnet. A rubber septum was placed over the top and argon gas was passed through for 5 min. A degassed mixture of toluene/MeOH (5:1) was introduced via syringe (1.5 mL) followed by degassed 2M Na$_2$CO$_3$ (0.5 mL). The mixture was stirred vigorously under argon for several minutes and then the septum was replaced with a screw cap and the vial was placed in the reaction block. Stirring and heating was continued for 17.5 hrs. TLC (25% hexane/CH$_2$Cl$_2$) showed nearly complete reaction. The vial was cooled to room temp., filtered and solvent was evaporated. A concentrated solution of the crude residue in 20% hexane/DCM was applied to a short silica gel column and eluted with 20% hexane/DCM (100 ml), then 100% DCM (100 mL), then 20% EtOAc/DCM. Product was eluted with 20% EtOAc/DCM. Yield of pure 120: 206 mg (0.50 mmoles, 77%); $^1$H NMR (CDCl$_3$) δ 2.85 (s, 6H), 3.60 (s, 3H), 4.1 (s, 3H), 7.25 (m, 1H), 7.29 (m, 1H), 7.48 (d, J=8.0, 1H), 7.52 (d, J=8, 1H), 7.75 (m, 2H) 8.00 (m 2H), 8.15 (s 1H) 8.22 (d, J=8.0, 1H).

b. Preparation of Compound 121

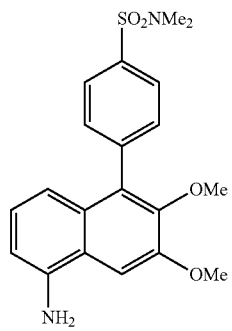

121

To a suspension 120 (200 mg, 0.48 mmoles) in EtOH (5 mL) in a screw cap vial fitted with a septum, was added 10% Pd/C (20 mg) in 1 ml EtOH. The mixture was degassed under argon then 0.2 mL of hydrazine hydrate was added via syringe. The vial was capped and heated in a reaction block at 80° C. for 3 hrs., cooled to room temp and filtered. The filter cake was washed with 10 mL of hot toluene EtOH and then solvent was evaporated to give 180 mg of crude product 21, which was purified by silica gel chromatography (100% DCM→20% EtOAc/DCM) affording 140 mg, (0.36 mmoles, 75%) of pure 121; $^1$H NMR (CDCl$_3$) δ 2.80 (s, 6H), 3.60 (s 3H), 4.10 (s, 3H), 4.7 (bs 2H) 6.9 (m, 2H) 7.15 (m, 1H) 7.25 (d, J=8, 1H) 7.6 (d J=8, 2H) 7.96 (d J=8, 2H).

c. Preparation of Compound 122

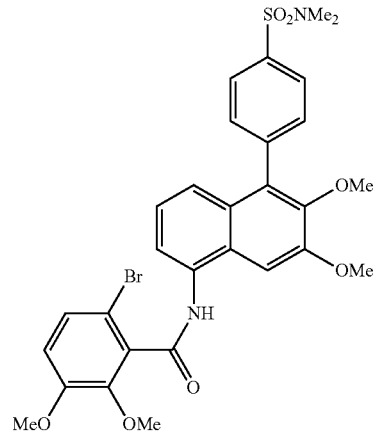

122

To a solution of 121 (185 mg, 0.57 mmoles) in DCM (3 mL) was added a solution of the acid chloride (143 mg, 0.51 mmoles) in 2 mL of DCM followed by TEA (1 mL) and a catalytic amt. of DMAP. The reaction was stirred overnight at room temp. TLC (10% EtOAc/DCM) showed nearly complete reaction. Solvent was evaporated and the residue was dissolved in DCM, washed with 10% HCl followed by sat aq. NaHCO$_3$ and finally, brine. Solvent was evaporated and the residue was purified by column chromatography on silica gel (100% DCM→20% EtOAc/DCM, crude yield 320 mg of crude product. Purification by prep tlc (20% EtOAc/CH$_2$Cl$_2$) gave 240 mg (0.42 mmoles, 74%) of 122.

d. Preparation of Compound 123

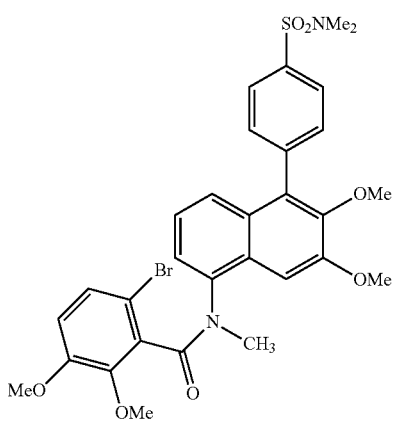

123

To a 10% DMF solution of benzamide 122 (130 mg, 0.21 mmoles) was added a suspension of NaH (3 eq., pre-washed with hexane) in DMF (1.5 mL). After stirring for 10 min., a solution of MeI (61 mg, 0.43 mmoles) in 0.5 mL DMF was added and the mixture was stirred for 19 hrs. at room temp. TLC (10% EtOAc/DCM) of a small aliquot, treated with water, 10% HCl and brine and extracted into EtOAC showed complete reaction. The entire reaction was then treated in a similar manner. The organic layer was washed rigorously with brine, dried over Na$_2$SO$_4$, filtered and concentrated to an oil which was purified by chromatography on silica gel (100% DCM→10% EtOAc/DCM) to yield 123 (130 mg, 0.21 mmoles, 100%); $^1$H NMR (CDCl$_3$) δ 2.8 (m, 6H), 3.15-4.20 (m, 15H), 6.6 (m, 10H).

e. Preparation of Compound 124

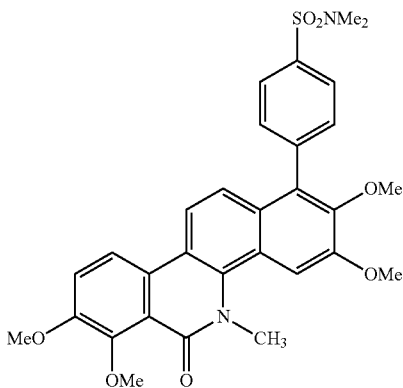

124

To a 25 mL pressure vessel was added Pd(OAc)$_2$ (9.3 mg, 0.042 mmoles, P(o-tolyl)$_3$ (25.5 mg, 0.084 mmoles), and AgCO$_3$ (115.7 mg, 0.42 mmoles) fitted with a septum and purged with argon for 15 min. A solution of 123 (130 mg, 0.21 mmoles) in 2 mL of DMF was prepared and flushed with argon. The solution was transferred to the pressure vessel via syringe. The vessel was capped and heated with stirring in a temperature regulated oil bath at 155-168° C. over night. The reaction vessel was allowed to cool to room temp. and diluted with 50 mL of EtOAc and filtered through filter paper. The filtrate was washed with brine (3×50 mL) and dried over Na$_2$SO$_4$. The solvent was evaporated and the residue was purified by chromatography on silica gel (10% EtOAc/ DCM→20% EtOAc/DCM) yielding 106 mg (0.194 mmoles, 92%) of the cyclic amide product 124; $^1$H NMR (CDCl$_3$) δ 2.8 (s, 6H), 3.6 (s, 3H) 3.95 (s, 6H), 4.02 (s, 3H) 4.05 (s, 3H), 7.1 (d, J=8.0, 1H), 7.3 (d, J=8.0, 1H) 7.58 (m, 3H), 7.9 (m, 4H).

Example 19

Preparation of Compound 131

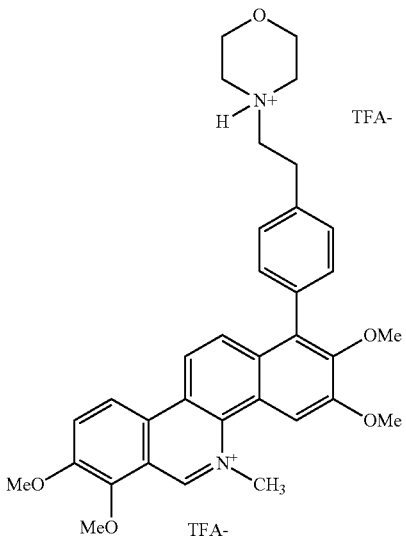

131

To a solution of the cyclic amide 130 (50 mg, 0.085 mmoles) in 4 mL of THF was added a 2 M solution of LAH in THF (0.1 mL). The mixture was stirred for 45 min. and then cooled in an ice bath and quenched with 3 drops of water. Solids were removed by filtration and the solvent was evaporated under vacuum. The residue was taken up in 50% CH$_3$CN/H$_2$O and purified by reverse phase chromatography (VYDAC C18, 2 cm×20 cm, gradient 20% CH$_3$CN/0.2% TFA H$_2$O to 90% CH$_3$CN/0.2% TFA H$_2$O. 20 mL/min.). To yield 29 mg, 0.038 mmoles (44.7%) of 131 as the bis-TFA salt.

The intermediate cyclic amide 130 was prepared as follows.

a. Preparation of Compound 126

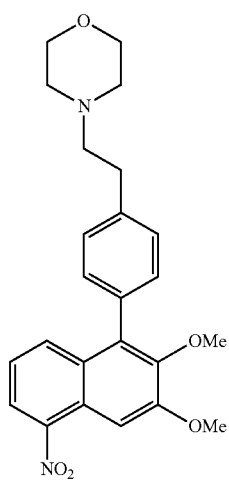

126

An aluminum multi vial reaction block was pre heated to 85° C. Compound 101 (400 mg, 1.28 mmoles), 4-(2-morpholinoethyl)phenylboronic acid (500 mg, 2.12 mmol), and tetrakistriphenylphosphine palladium (144 mg, 0.17 mmoles) were added to a reaction vial along with a stirring magnet. A rubber septum was placed over the top and argon gas was passed through for 5 min. A degassed mixture of Dioxane (10.5 mL) was introduced via syringe (2.5 mL) followed by degassed 2M Na$_2$CO$_3$ (0.5 mL). The mixture was stirred vigorously under argon for several minutes and then the septum was replaced with a screw cap and the vial was placed in the reaction block. Stirring and heating was continued for 27.5 hrs. TLC (5% MeOH/CH$_2$Cl$_2$) showed nearly complete reaction. The vial was cooled to room temp., filtered and solvent was evaporated. A concentrated solution of the crude residue in DCM was applied to a short silica gel column (Radii, Isco,) and eluted with 5% MeOH/DCM on combiflash system. Product was eluted with 5% MeOH/DCM. Yield: 210 mg of 126; $^1$H NMR (CDCl$_3$) δ 2.6 (m, 4H) 2.95 (m 2H) 3.6 (s, 3H), 3.8 (m 4H) 4.05 (s, 3H), 7.25 (m, 2H) 7.36 (d, J=8.0, 1H), 7.5 (m, 3H), 8.06 (s 1H) 8.18 (d, J=8.0, 1H).

b. Preparation of Compound 127

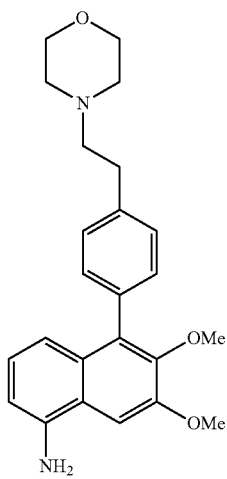

127

To a suspension 126 (365 mg, 0.864 mmoles) in EtOH (12 mL) in a screw cap vial fitted with a septum, was added 10% Pd/C (40 mg) in 1 ml EtOH. The mixture was degassed under argon then 0.5 mL of hydrazine hydrate was added via syringe. The vial was capped and heated in a reaction block at 80° C. for 3 hrs., cooled to room temp and filtered. The filter cake was washed with 10 mL of hot toluene and EtOH and then solvent was evaporated to give 350 mg of crude product 127, which was purified by silica gel chromatography (100% DCM→40% EtOAc/DCM) to afford 127: 310 mg (0.79 mmoles, 91%); $^1$H NMR (CDCl$_3$) δ 2.6 (m 4H) 2.7 (m, 2H) 2.95 (m, 2H), 3.6 (s 3H) 3.8 (m, 4H), 4.05 (s, 3H) 4.1 (bs, 2H), 6.8 (d J=8.0, 1H), 6.9 (d, J=8.0, 1H) 7.15 (m, 1H) 7.4 (m, 2H), 7.5 (m, 1H) 7.6 (m, 1H) 7.75 (m, 1H).

c. Preparation of Compound 122

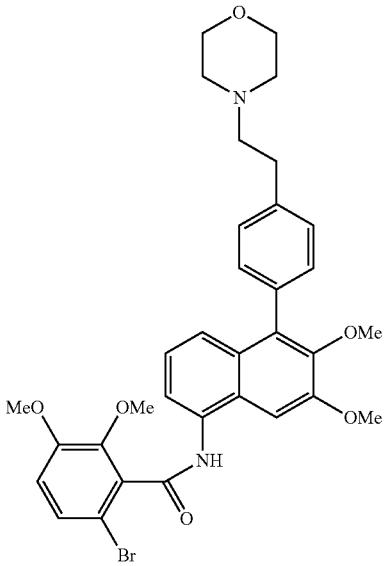

128

To a solution of 127 (310 mg, 0.79 mmoles) in DCM (3 mL) was added a solution of the acid chloride (251 mg, 0.90 mmoles) in 2 mL of DCM followed by TEA (0.42 mL) and a catalytic amt. of DMAP. The reaction was stirred overnight at room temp. TLC (10% EtOAc/DCM) showed nearly complete reaction. Solvent was evaporated and the residue was dissolved in DCM, washed with 10% HCl followed by sat aq. Na$_2$CO$_3$ and finally, brine. Solvent was evaporated and the residue was purified by column chromatography on silica gel (100% DCM→MeOH/EtOAc/DCM, 2:18:80) affording 200 mg of product 128 (0.31 mmoles, 40%); $^1$H NMR (CDCl$_3$) δ 2.6 (m, 4H) 2.7 (m, 2H), 2.95 (m, 2H) 3.6 (s 3H) 3.85 (m, 4H), 3.98 (s 3H), 4.01 (s 3H), 4.1 (s, 3H), 6.98 (d, J=8.0, 1H) 7.25-7.8 (m, 10H).

d. Preparation of Compound 129

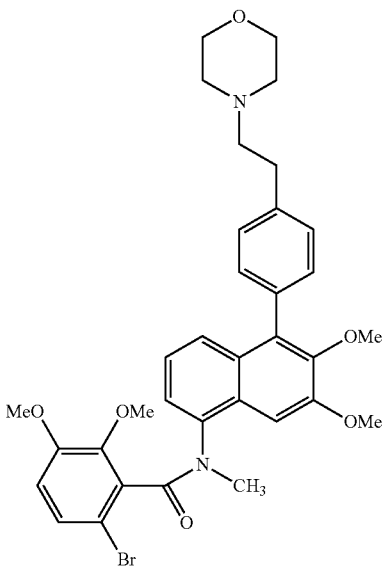

129

To a 10% DMF solution of benzamide 128 (200 mg, 0.315 mmoles) was added a suspension of NaH (3 eq., pre-washed with hexane) in DMF (1.5 mL). After stirring for 10 min., a solution of MeI (44 mg, 0.31 mmoles) in 0.5 mL DMF was added and the mixture was stirred for 19 hrs. at room temp. TLC (2.5% MeOH/DCM) of a small aliquot, treated with water, 10% HCl, aq. Na$_2$CO$_3$ and brine and extracted into EtOAC showed complete reaction. The entire reaction was then treated in a similar manner. The organic layer was washed rigorously with brine, dried over Na$_2$SO$_4$, filtered and concentrated to an oil which was purified by chromatography on silica gel (100% DCM→15% MeOH/DCM) to yield 129 (180 mg, 0.277 mmoles, 88%); $^1$H NMR (CDCl$_3$) δ 2.8-4.1 (m, 27H), 6.65-8.1 (m 9H).

e. Preparation of Compound 130

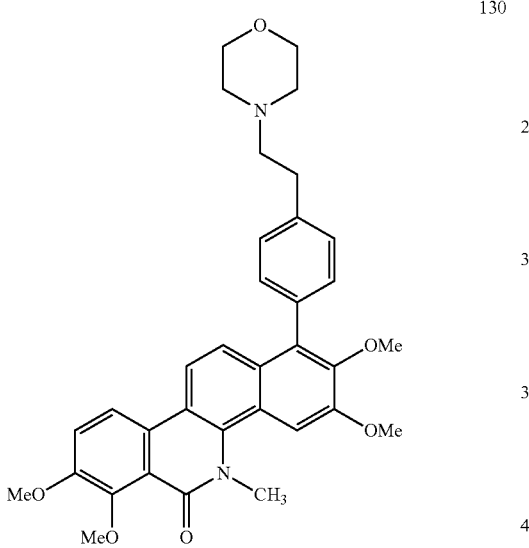

130

To a 25 mL pressure vessel was added Pd(OAc)$_2$ (12.3 mg, 0.056 mmoles), P(o-tolyl)$_3$ (32 mg, 0.112 mmoles), and AgCO$_3$ (155.7 mg, 0.56 mmoles) fitted with a septum and purged with argon for 15 min. A solution of 129 (180 mg, 0.28 mmoles) in 10 mL of DMF was prepared and flushed with argon. The solution was transferred to the pressure vessel via syringe. The vessel was capped and heated with stirring in a temperature regulated oil bath at 155-168° C. over night. The reaction vessel was allowed to cool to room temp. and diluted with 50 mL of EtOAc and filtered through filter paper. The filtrate was washed with brine (3×50 mL) and dried over Na$_2$SO$_4$. The solvent was evaporated and the residue was purified by chromatograph on silica gel (10% EtOAc/DCM→15% MeOH/DCM) yielding 50 mg (0.085 mmoles, 30%) of product 130; $^1$H NMR (CDCl$_3$) δ 2.56 (m, 4H), 2.71 (m, 2H), 2.94 (m, 2H), 3.6 (s, 3H) 3.8 (m, 4H) 3.98 (s, 3H) 4.04 (s, 3H) 4.12 (s, 3H) 7.38-7.44 (m, 6H), 7.6 (s, 1H), 7.91 (d, J=8, 1H) 8.0 (d, J=8.0, 1H).

Example 20

Preparation of Compound

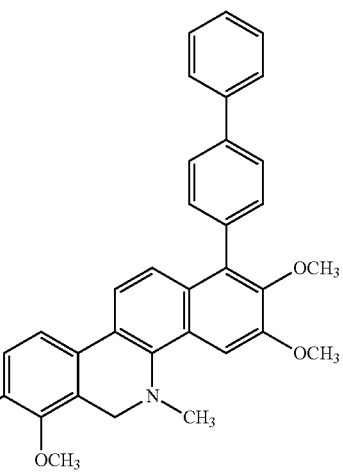

The product from Example 3 (15 mg) was dissolved in methanol and sodium borohydride (19 mg) was added at room temperature. After one hour, the reaction mixture was diluted with water and extracted with chloroform to provide the title compound; $^1$H NMR (CDCl$_3$) δ 2.60 (s 3H), 3.81 (s 3H), 3.83 (s, 3H), 4.03 (s, 3H), 4.26 (s, 2H), 6.87 (d, J=8.0, 1H) 7.15 (d, J=8.0, 1H), 7.30 (m, 2H), 7.42 (m 5H) 7.56 (d, J=8, 1H), 7.65 (m, 4H), 7.68 (s 1H).

Example 21

Preparation of Compound

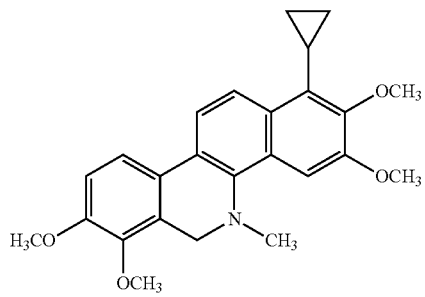 [SMILES: COc1ccc2c(c1OC)CN(C)c1c-2ccc2c(C3CC3)c(OC)c(OC)cc12]

The product from Example 11 was dissolved in methanol and treated with sodium borohydride as described in Example 20 to provide the title compound; $^1$H NMR (CDCl$_3$) δ 0.75-0.79 (m 2H), 1.13-1.17 (m, 2H), 1.90-1.96 (m 1H), 2.58 (s, 3H), 3.80 (s 3H) 3.83 (s, 3H) 4.01 (s, 3H) 4.2 (s 2H), 6.84 (d, J=8.0, 1H), 7.2 (d, J=8.0, 1H), 7.28-7.31 (m 1H), 7.40 (m, 5H), 7.54 (d, J=8.0, 1H), 7.62-7.66 (m, 4H), 7.71 (s, 1H).

Example 22

Preparation of Compound

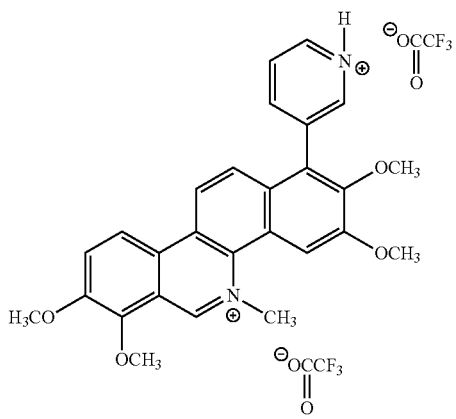

To a solution of the corresponding cyclic amide (77 mg, 0.147 mmoles) in 4 mL of THF was added a 2 M solution of LAH in THF (0.2 mL). The mixture was stirred for 45 min. and then cooled in an ice bath and quenched. Solids were removed by filtration and the solvent was evaporated under vacuum. The residue was taken up in 50% $CH_3CN/H_2O$ and purified by reverse phase chromatography (VYDAC C18, 2 cm×20 cm, gradient 20% $CH_3CN/0.2\%$ TFA $H_2O$ to 90% $CH_3CN/0.2\%$ TFA $H_2O$. 20 mL/min.) affording 52 mg of the title compound; $^1H$ NMR ($D_2O$) δ 3.57 (s 3H) 3.8 (s 3H), 3.95 (s, 3H) 4.02 (s, 3H), 4.8 (s, 3H) 7.5 (d, J=8, 1H), 7.78 (d, J=8.0, 1H), 7.95 (S, 1H) 8.15-8.22 (m, 3H), 8.6 (d, J=8.0 1H), 8.95 (m, 2H), 9.6 (s 1H).

The intermediate cyclic amide was prepared as follows.

a. Preparation of Compound

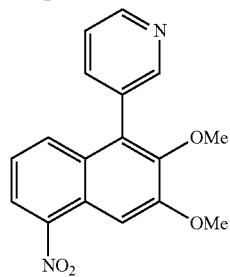 [SMILES: COc1cc2c([N+](=O)[O-])cccc2c(-c2cccnc2)c1OC]

An aluminum multi vial reaction block was pre heated to 80° C. The compound from Example 3 sub-part e (400 mg, 1.28 mmoles), 3-pyridine boronic acid (549 mg, 2.56 mmoles), and tetrakistriphenylphosphine palladium (144 mg, 0.17 mmoles) were added to a reaction vial along with a stirring magnet. A rubber septum was placed over the top and argon gas was passed through for 5 min. A degassed mixture of Dioxane (10.5 mL) was introduced via syringe (2.5 mL) followed by degassed 2M $Na_2CO_3$ (0.5 mL). The mixture was stirred vigorously under argon for several minutes and then the septum was replaced with a screw cap and the vial was placed in the reaction block. Stirring and heating was continued for 27.5 hrs. TLC (20% $EtOAc/CH_2Cl_2$) showed nearly complete reaction. The vial was cooled to room temp., filtered and solvent was evaporated. A concentrated solution of the crude residue in 20% hexane/DCM was applied to a short silica gel column and eluted with 20% EtOAc/DCM (100 ml), then 100% DCM (100 mL), then 30% EtOAc/DCM. Product was eluted with 30% EtOAc/DCM. Yield: 210 mg of the nitro compound; $^1H$ NMR (CDCl$_3$) δ 3.62 (s, 3H) 4.10 (s, 3H), 7.25 (m, 1H) 7.26 (m 1H) 77 (m, 2H) 8.1 (s, 1H), 8.2 (d, J=8.0, 1H) 8.6 (s 1H), 8.76 (d, J=8.0, 1H).

b. Preparation of Compound

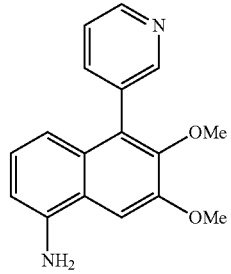 [SMILES: COc1cc2c(N)cccc2c(-c2cccnc2)c1OC]

To a suspension of the nitro compound 210 mg, 0.67 mmoles) in MeOH (5 mL) in a screw cap vial fitted with a septum, was added 2.8 μm of SnCl2. The mixture was heated under argon at 80° C. for 20 min then 20 mL of Na2CO3 the reaction mixture was extracted by ethyl acetate and purified on SiO2 using CH2Cl2/MeOH (95:4) to yield 141 mg of corresponding amine; $^1H$ NMR (CDCl$_3$) δ 3.60 (s 3H), 4.08 (s, 3H), 3.9 (bs, 2H) 6.8 (m 2H) 7.1 (m 1H) 7.5 (m 1H) 7.8 (m, 2H) 8.6 (s 1H), 8.7 (d J=8.0, 1H).

c. Preparation of Compound

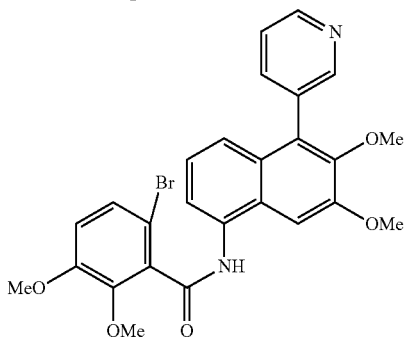 [SMILES: COc1ccc(Br)c(C(=O)Nc2cccc3c(-c4cccnc4)c(OC)c(OC)cc23)c1OC]

To a solution of the amine (105 mg, 0.375 mmoles) in DCM (3 mL) was added a solution of the 6-bromo-2,3-dimethoxybenzoic acid chloride (320 mg, 1.08 mmoles) in 4 mL of DCM followed by TEA (1 mL) and a catalytic amount of DMAP. The reaction was stirred for five days at room temp. TLC (40% EtOAc/DCM) showed nearly 50% complete reaction. Solvent was evaporated. The residue was dissolved in DCM and washed by sat aq. NaHCO$_3$(NaHCO3, Saturated, aq.). Solvent was evaporated and the residue was purified by column chromatography on silica gel (100% DCM→40% EtOAc/DCM, yielding 106 mg of the amide.

d. Preparation of Compound

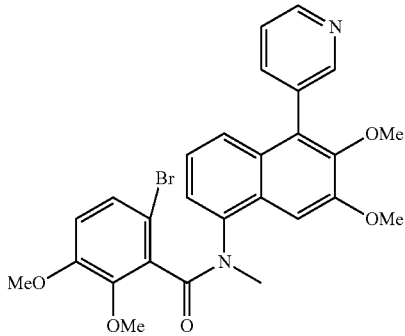 [SMILES: COc1ccc(Br)c(C(=O)N(C)c2cccc3c(-c4cccnc4)c(OC)c(OC)cc23)c1OC]

Using a precedure similar to that described in Example 3, sub-part i the amide from sub-part c was converted to the corresponding methyl amide.

e. Preparation of Compound

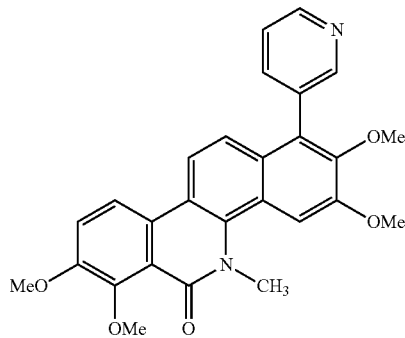 [SMILES: COc1cc2c(ccc3c4ccc(OC)c(OC)c4c(=O)n(C)c23)c(-c2cccnc2)c1OC]

To a 25 mL pressure vessel was added Pd(OAc)$_2$ (14 mg, 0.062 mmoles), P(o-tolyl)$_3$ (37.7 mg, 0.124 mmoles), and AgCO$_3$ (178 mg, 0.65 mmoles) and purged with argon for 15 min. A solution of the methyl amide (98 mg, 0.182 mmol) in 10 mL of DMF was prepared and flushed with argon. The solution was transferred to the pressure vessel via syringe. The vessel was capped and heated with stirring in a temperature regulated oil bath at 155-168° C. over night. The reaction vessel was allowed to cool to room temp. and diluted with 50 mL of EtOAc and filtered through filter paper. The filtrate was washed with brine (3×50 mL) and dried over Na$_2$SO$_4$. The solvent was evaporated and the residue was purified by chromatograph on silica gel (40% EtOAc/DCM→40% EtOAc/DCM) yielding 80 mg of the corresponding cyclic amide; $^1$H NMR (CDCl$_3$) δ 3.6 (s 3H) 3.95 (s, 3H), 3.96 (s 3H), 4.02 (s 3H) 4.05 (s, 3H) 6.8 (m 2H) 7.25 (m, 3H), 7.4 (d, J=8.0, 1H) 7.55 (m, 2H), 7.6 (d, J=8.0, 1H).

Example 23

Preparation of Compound

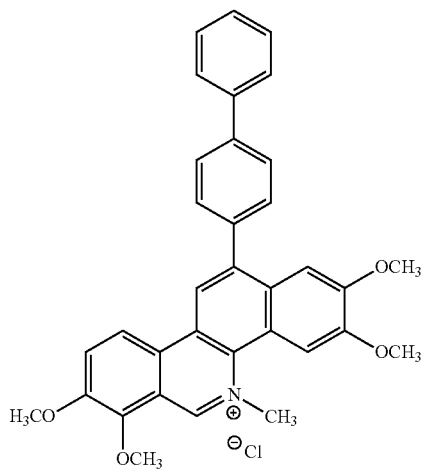 [SMILES: COc1cc2c(-c3ccc(-c4ccccc4)cc3)cc3c4ccc(OC)c(OC)c4c[n+](C)c3c2cc1OC ; [Cl-]]

Using a reduction procedure similar to the one described in Example 3, the title compound was prepared from the corresponding cyclic amide; $^1$H NMR (DMSO-d$_6$) δ 3.96 (s, 3H), 4.25 (s, 3H), 4.26 (s 3H), 4.34 (s, 3H), 5.22 (s, 3H) 7.56 (m 2H), 7.64 (s, 1H) 7.69 (m 2H) 7.98 (m, 3H), 8.10 (d, J=8.0 2H), 8.35 (s, 1H) 8.39 (d, J=8.0, 1H), 8.91 (s 1H), 9.14 (d, J=8.0, 1H), 10.29 (s, 1H).

The intermediate cyclic amide was prepared as follows.

a. Preparation of Compound

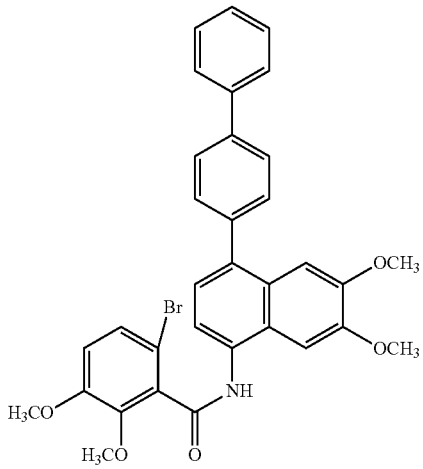 [SMILES: COc1cc2c(NC(=O)c3c(Br)ccc(OC)c3OC)ccc(-c3ccc(-c4ccccc4)cc3)c2cc1OC]

Using a precedure similar to that described in Example 13, sub-part j the amino compound from Example 13 sub-part i and 6-bromo-2,3-dimethoxybenzoic acid (APIN Chemicals LTD.) were converted to the corresponding amide, which was used in the next reaction.

b. Preparation of Compound

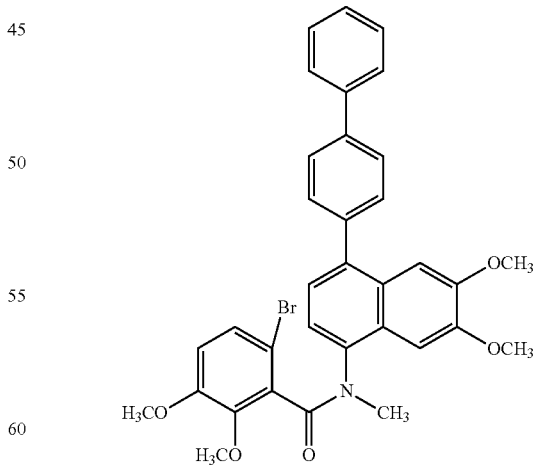

Using a precedure similar to that described in Example 3, sub-part i the amide was converted to the corresponding methyl amide; $^1$H NMR (400 MHz) (CDCl$_3$) δ 3.1-4.02 (m, 15H), 6.74-7.67 (m, 15H).

c. Preparation of Compound

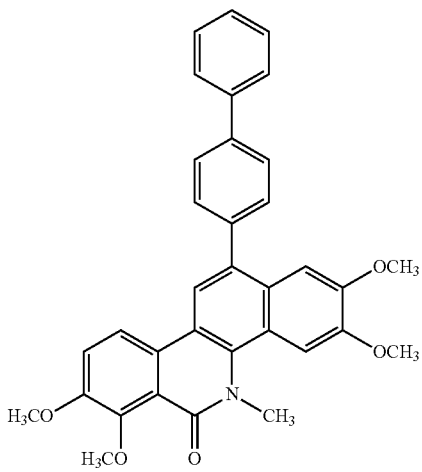 [SMILES: COc1cc2c(-c3ccc(-c4ccccc4)cc3)cc3c4ccc(OC)c(OC)c4c(=O)n(C)c3c2cc1OC]

Using a precedure similar to that described in Example 3, sub-part j the methyl amide was converted to the corresponding cyclic amide; $^1$H NMR (CDCl$_3$) δ 3.78 (s, 3H), 3.95 (s 3H), 3.96 (s, 3H), 4.01 (s, 3H) 4.05 (s, 3H) 7.23 (s, 1H) 7.28 (d, J=8.0, 1H) 7.34 (m, 1H), 7.43 (m, 2H), 7.48 (s, 1H) 7.57 (m, 2H), 7.66 (d, J=8.0, 2H), 7.71 (m 2H), 7.91 (s, 1H) 7.93 (d, J=8.0, 1H).

Example 24

Preparation of Compound

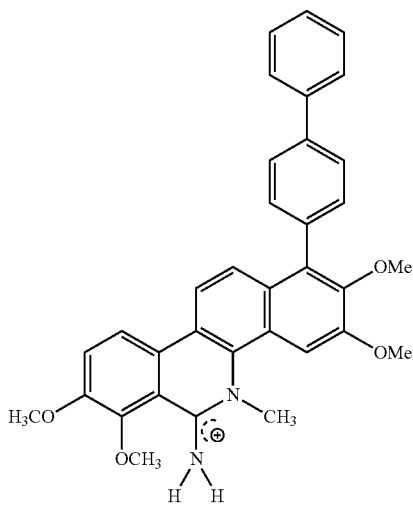 [SMILES: COc1ccc2c(c1OC)C(N)N(C)c1c-2ccc2c(-c3ccc(-c4ccccc4)cc3)c(OC)c(OC)cc12]

The chloro compound from sub-part a below was diluted with 4 ml of dry dioxanes within a in a screw cap reaction vial fitted with a septum and 4 ml of concentrated ammonia solution in water was added. The vial was capped again and heated in a reaction block at 70° C. for 1 hrs. Again the reaction mixture was concentrated and purified by reverse phase chromatography (VYDAC C18, 2 cm×20 cm, gradient 20% CH$_3$CN/0.2% TFA H$_2$O to 90% CH$_3$CN/0.2% TFA H$_2$O. 20 mL/min.) to yield 26 mg of the title compound; $^1$H NMR (CDCl$_3$+1% TFA, 300 MHz) δ 10.16 (bs, 1H, D$_2$O exchangeable, 8.24 (d, J=6 Hz, 1H), 8.15 (bs, 1H, D$_2$O exchangeable, 8.13 (d, J=6 Hz, 1H), 7.26-7.84 (m, 12H), 4.42 (S, 3H), 4.24 (s, 3H), 4.18 (s, 6H), 3.8 (s, 3H). HRMS m/e (100%) calculated for C$_{34}$H$_{31}$N$_2$O$_4$ (M$^+$) 531.2284. found 531.2273.

The intermediate chloro compound was prepared as follows.

a. Preparation of Compound

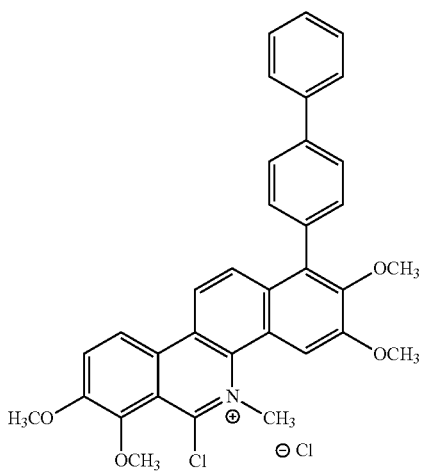 [SMILES: COc1cc2c(ccc3c4ccc(OC)c(OC)c4c(Cl)[n+](C)c23)c(-c2ccc(-c3ccccc3)cc2)c1OC ; [Cl-]]

To a suspension of the compound from Example 7 sub-part c 88 mg, 0.16 mmoles) in POCl$_3$ (3 mL) in a screw cap reaction vial fitted with a septum was Heated to 80° C. for 4 hours until all starting material consumed. The reaction was monitored by NMR. The vial was cooled to room temperature and excess of POCl$_3$ was removed under reduced pressure at 55° C. to provide the desired 6-chloro-5-alkylbenzo[c] phenanthridinium chloride derivative.

Example 25

Preparation of Compound

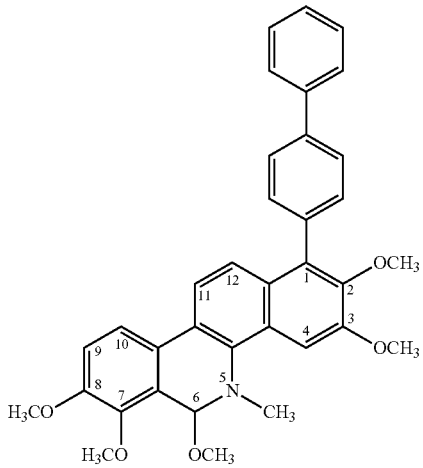 [SMILES: COc1ccc2c(c1OC)C(OC)N(C)c1c-2ccc2c(-c3ccc(-c4ccccc4)cc3)c(OC)c(OC)cc12]

A red colored methanolic solution of the compound from Example 24 sub-part a was treated with sodium methoxide in methanol until the solution became colorless. The colorless mixture was concentrated under reduced pressure and the residue extracted with chloroform. The chloroform solution was filtered and concentrated to dryness to provide the title compound.

Comparative Examples

Comparative Example 1

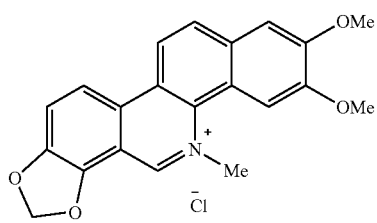 [SMILES: COc1cc2ccc3c4ccc5c(c4c[n+](C)c3c2cc1OC)OCO5 ; [Cl-]]

Using a reduction procedure similar to the one described in Example 3, the title compound was prepared from the corresponding cyclic amide;
The intermediate cyclic amide was prepared as follows.
a. Preparation of Compound

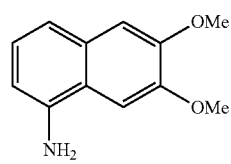

Using a precedure similar to that described in Example 3, sub-part g the corresponding nitro compound was converted to the corresponding amino compound;
b. Preparation of Compound

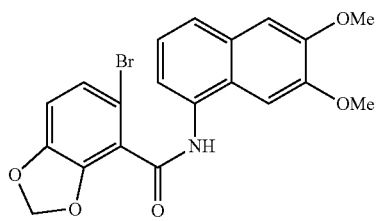 [SMILES: COc1cc2cccc(NC(=O)c3c(Br)ccc4c3OCO4)c2cc1OC]

Using a precedure similar to that described in Example 3, sub-part h the amino compound was allowed to react with the acid chloride of commercially available 2,3-methylenedioxy-6-bromobenzoic acid to provide the corresponding amide; $^1$H NMR (CDCl$_3$) δ 3.99 (s, 3H), 4.00 (s, 3H), 6.11 (s, 2H), 6.79 (d, J=7.8, 1H), 7.16 (m, 2H), 7.38 (m, 2H), 7.61-7.71 (m, 2H), 7.83 (s, 1H)
c. Preparation of Compound

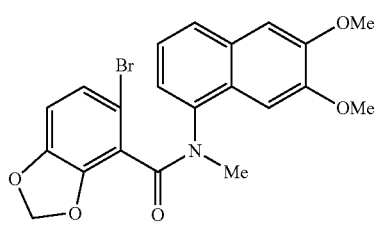 [SMILES: COc1cc2cccc(N(C)C(=O)c3c(Br)ccc4c3OCO4)c2cc1OC]

Using a precedure similar to that described in Example 3, sub-part i the amide was methylated to provide the corresponding methyl amide; $^1$H NMR (CDCl$_3$) δ 3.34-3.57 (m, 3H, N—CH$_3$), 3.97-4.05 (m, 6H, 2×OCH$_3$), 4.96-6.17 (m, 2H, OCH$_2$O), 6.33-7.68 (m, 7H, aromatic).

d. Preparation of Compound

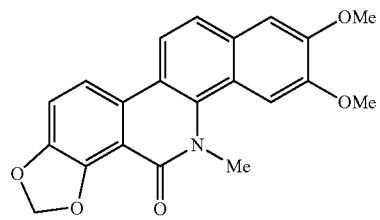 [SMILES: COc1cc2ccc3c4ccc5c(c4c(=O)n(C)c3c2cc1OC)OCO5]

Using a precedure similar to that described in Example 3, sub-part j the methyl amide was cyclized to provide the corresponding cyclic amide; $^1$H NMR (CDCl$_3$) δ 3.96 (s, 3H), 4.03 (s, 3H), 4.04 (s, 3H), 6.27 (s, 2H), 7.16 (s, 1H), 7.23 (d, J=10.0, 1H), 7.52 (s, 1H), 7.56 (d, J=10.0, 1H), 7.76 (d, J=8.8, 1H), 7.99 (d, J=8.9, 1H)

Comparative Example 2

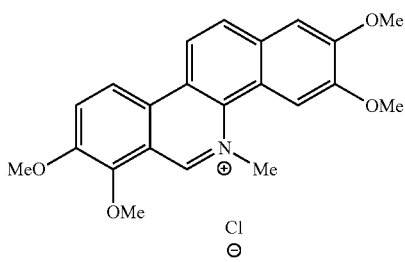 [SMILES: COc1cc2ccc3c4ccc(OC)c(OC)c4c[n+](C)c3c2cc1OC ; [Cl-]]

Using a reduction procedure similar to the one described in Example 3, the title compound was prepared from the corresponding cyclic amide; $^1$H NMR (400 MHz) (DMSO-d$_6$) δ 4.04 (s, 3H), 4.10 (s, 3H), 4.13 (s, 3H), 4.20 (s, 3H), 5.10 (s, 3H), 7.83 (s, 1H), 8.17 (s, 1H), 8.31 (d, J=8.0 Hz, 1H), 8.37 (d, J=8.0 Hz, 1H), 8.85 (m, 2H), 10.14 (s, 1H). calculated: C$_{22}$H$_{22}$NO$_4$, 364.1549. found: 364.1542.

The intermediate cyclic amide was prepared as follows.
a. Preparation of Compound

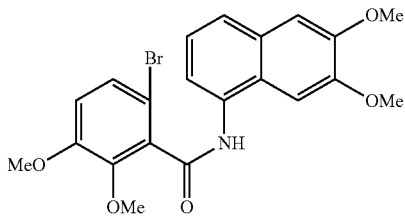 [SMILES: COc1cc2cccc(NC(=O)c3c(Br)ccc(OC)c3OC)c2cc1OC]

Using a precedure similar to that described in Example 3, sub-part h 6,7-dimethoxynaphthylamine was allowed to react with the acid chloride of commercially available 2,3-dimethoxy-6-bromobenzoic acid to provide the corresponding amide; $^1$H NMR (400 MHz) (CDCl$_3$) δ 3.93 (s, 3H), 3.99 (s, 3H), 4.03 (s, 3H), 4.05 (s, 3H), 6.91 (d, J=8.0 Hz, 1H), 7.28 (s, 1H), 7.36-7.43 (m, 2H), 7.47 (s, 1H), 7.55 (bs, 1H), 7.66 (m, 2H).

b. Preparation of Compound

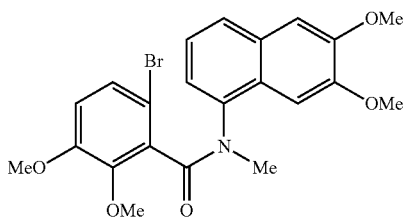 [SMILES: COc1cc2cccc(N(C)C(=O)c3c(Br)ccc(OC)c3OC)c2cc1OC]

Using a precedure similar to that described in Example 3, sub-part i the amide was methylated to provide the corresponding methyl amide; $^1$H NMR (400 MHz) (CDCl$_3$) δ 3.15-4.09 (m, 15H), 6.50-7.43 (m, 7H).

c. Preparation of Compound

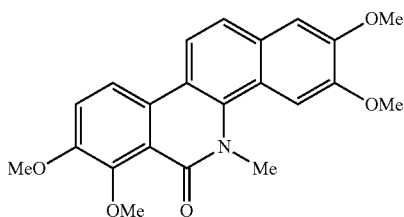 [SMILES: COc1cc2ccc3c4ccc(OC)c(OC)c4c(=O)n(C)c3c2cc1OC]

Using a precedure similar to that described in Example 3, sub-part j the methyl amide was cyclized to provide the corresponding cyclic amide; $^1$H NMR (400 MHz) (CDCl$_3$) δ 3.99 (s, 3H), 4.01 (s, 3H), 4.06 (s, 3H), 4.07 (s, 3H), 4.11 (s, 3H), 7.20 (s, 1H), 7.42 (d, J=8.0 Hz, 1H), 7.54 (s, 1H), 7.59 (d, J=12 Hz, 1H), 8.03 (d, J=4.0 Hz, 1H), 8.05 (d, J=4.0 Hz, 1H).

We claim:

1. A compound of formula I:

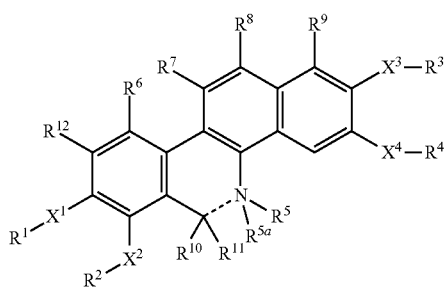

wherein:
- the bond represented by - - - is a single or double bond;
- when the bond represented by - - - is a single bond $R^5$, $R^{5a}$, $R^{10}$ and $R^{11}$ can have any of the values defined below; when the bond represented by - - - is a double bond $R^5$ can be absent or have any of the values defined below, $R^{10}$ can have any of the values defined below, and $R^{5a}$ and $R^{11}$ are absent;
- $X^1$, $X^2$, $X^3$ and $X^4$ are each independently O, S or NR$^e$;
- $R^1$ and $R^2$ are each independently, (C$_1$-C$_6$)alkyl, substituted (C$_1$-C$_6$)alkyl, (C$_1$-C$_6$)alkanoyl or —C(=O)NR$^f$R$^g$ or $R^1$ and $R^2$ together with the atoms to which they are attached form a 5 to 7 membered ring;
- $R^3$ and $R^4$ are each independently, (C$_1$-C$_6$)alkyl, (C$_1$-C$_6$)alkanoyl or —C(=O)NR$^f$R$^g$ oz or $R^3$ and $R^4$ together with the atoms to which they are attached form a 5 to 7 membered ring;
- $R^5$ is H, (C$_1$-C$_6$)alkyl, or substituted (C$_1$-C$_6$)alkyl; or $R^5$ and $R^{10}$ taken together with the atoms to which they are attached form an optionally substituted 5, 6, or 7 membered heterocyclic ring; and $R^{5a}$ is H, (C$_1$-C$_6$)alkyl, substituted (C$_1$-C$_6$)alkyl, or absent;
- at least one of $R^6$, $R^7$, $R^8$, $R^9$ and $R^{12}$ is substituted alkyl, optionally substituted alkenyl, optionally substituted alkynyl, optionally substituted cycloalkyl, optionally substituted arylalkyl, optionally substituted heteroarylalkyl, optionally substituted aryl, optionally substituted arylalkanoyl, R$^h$, or optionally substituted heteroaryl, wherein substituted alkyl is an alkyl group with 1 to 5 substituent groups independently selected from cycloalkyl, substituted cycloalkyl, cyano, halo, hydroxyl, oxo, carboxy, aryloxy, heteroaryloxy, heterocylooxy, and —NR$^a$R$^b$, wherein R$^a$ and R$^b$ may be the same or different and are chosen from hydrogen, alkyl, arylalkyl, heteroarylalkyl, cycloalkyl, substituted cycloalkyl, aryl, heteroaryl and heterocyclic; or R$^a$ and R$^b$ together with the nitrogen atom to which they are attached form a morpholino, piperazino, pyrrolidino, or piperidino; and the remainder of $R^6$, $R^7$, $R^8$, $R^9$ and $R^{12}$ are independently H, halo, nitro, —NR$^c$R$^d$ optionally substituted alkyl, optionally substituted arylalkyl, optionally substituted heteroarylalkyl, optionally substituted aryl, or optionally substituted heteroaryl or $R^{12}$ is —X$^{13}$—R$^{13}$ wherein X$^{13}$ is O, S or NR$^e$ and R$^{13}$ is (C$_1$-C$_6$)alkyl, substituted (C$_1$-C$_6$)alkyl, (C$_1$-C$_6$)alkanoyl or —C(=O)NR$^f$R$^g$ or R$^{13}$ and $R^1$ together with the atoms to which they are attached form a 5 to 7 membered ring;
- $R^{10}$ is H, optionally substituted (C$_1$-C$_6$)alkyl optionally substituted (C$_1$-C$_6$)alkoxy, optionally substituted (C$_1$-C$_6$)alkyl-S(=O)$_n$—, optionally substituted aryloxy, optionally substituted aryl, CN, NR$^p$R$^q$, or optionally substituted aryl-S(=O)$_n$—, wherein n is 0, 1, or 2; and $R^{11}$ is H or optionally substituted (C$_1$-C$_6$)alkyl; or $R^{10}$ and $R^{11}$ together with the carbon to which they are attached form a carbonyl group; or $R^{10}$ and $R^5$ taken together with the atoms to which they are attached form an optionally substituted 5, 6, or 7 membered heterocyclic ring;
- each R$^c$ and R$^d$ is independently H, (C$_1$-C$_6$)alkyl, aryl, heteroaryl, aryl(C$_1$-C$_6$)alkyl, or heteroaryl(C$_1$-C$_6$)alkyl; or R$^c$ and R$^d$ together with the nitrogen to which they are attached form a morpholino, piperazino, pyrrolidino or piperidino;
- R$^e$ is H or (C$_1$-C$_6$)alkyl;
- R$^f$ and R$^g$ are each independently H, aryl, heteroaryl, aryl(C$_1$-C$_6$)alkyl, heteroaryl(C$_1$-C$_6$)alkyl, or (C$_1$-C$_6$)alkyl; or R$^f$ and R$^g$ together with the nitrogen to which they are attached form a morpholino, piperazino, pyrrolidino or piperidino;
- each R$^h$ is independently selected from an aryl optionally substituted with one or more R$^k$, an alkyl substituted with one or more heterocycle, and an alkyl substituted with one or more substituted heterocycle;
- each R$^k$ is independently alkyl, substituted alkyl, alkoxy, substituted alkoxy, heteroaryl, heterocycle, or —S(O)$_2$NR$^m$R$^n$;
- each R$^m$ and R$^n$ is independently H, (C$_1$-C$_6$)alkyl, aryl, heteroaryl, aryl(C$_1$-C$_6$)alkyl, or heteroaryl(C$_1$-C$_6$)alkyl; or R$^m$ and R$^n$ together with the nitrogen to which they are attached form a morpholino, piperazino, pyrrolidino or piperidino; and
- each R$^p$ and R$^q$ is independently H, (C$_1$-C$_6$)alkyl, aryl, heteroaryl, aryl(C$_1$-C$_6$)alkyl, or heteroaryl(C$_1$-C$_6$)alkyl;

or $R^p$ and $R^q$ together with the nitrogen to which they are attached form a morpholino, piperazino, pyrrolidino or piperidino; and when the nitrogen attached to $R^5$ is a positively charged quaternary nitrogen, the compound is associated with a suitable counterion $X^-$;

or a salt thereof;

provided $R^8$ is not 2-oxopropyl when $R^6$, $R^9$, and $R^{12}$ are each hydrogen, $-X^1-R^1$ and $-X^2-R^2$ are each methoxy, $X^3$ and $X^4$ are each O, $R^3$ and $R^4$ together form a methylenedioxy, which when taken together with the attached atoms forms a five-membered ring, and the bond represented by - - - is a double bond;

provided $R^7$ is not carboxy or C(O)Cl when $R^6$, $R^9$, and $R^{12}$ are each hydrogen, $-X^1-R^1$ and $-X^2-R^2$ are each methoxy or methylenedioxy, $-X^3-R^3$ and $-X^4-R^4$ are each methoxy or methylenedioxy, and the bond represented by - - - is a double bond.

2. A compound of formula I as described in claim 1 wherein:

the bond represented by - - - is a single or double bond;

when the bond represented by - - - is a single bond $R^5$, $R^{5a}$, $R^{10}$ and $R^{11}$ can have any of the values defined below;

when the bond represented by - - - is a double bond $R^5$ can be absent or have any of the values defined below, $R^{10}$ can have any of the values defined below, and $R^{5a}$ and $R^{11}$ are absent;

$X^1$, $X^2$, $X^3$ and $X^4$ are each independently O, S or $NR^e$;

$R^1$ and $R^2$ are each independently, $(C_1-C_6)$alkyl, $(C_1-C_6)$alkanoyl or $-C(=O)NR^fR^g$ or $R^1$ and $R^2$ together with the atoms to which they are attached form a 5 to 7 membered ring;

$R^3$ and $R^4$ are each independently, $(C_1-C_6)$alkyl, $(C_1-C_6)$alkanoyl or $-C(=O)NR^fR^g$ or $R^3$ and $R^4$ together with the atoms to which they are attached form a 5 to 7 membered ring;

$R^5$ is H or $(C_1-C_6)$alkyl, which $(C_1-C_6)$alkyl is optionally substituted with one or more groups independently selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^aR^b$;

$R^{5a}$ is H, $(C_1-C_6)$alkyl, or absent, wherein the $(C_1-C_6)$alkyl is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^aR^b$;

$R^{10}$ is H, $(C_1-C_6)$alkyl, $(C_1-C_6)$alkoxy, $(C_1-C_6)$alkylthio, aryloxy, or aryl-$S(=O)_n-$, wherein n is 0, 1, or 2; and $R^{11}$ is H or $(C_1-C_6)$alkyl, wherein any $(C_1-C_6)$alkyl $(C_1-C_6)$alkoxy, and $(C_1-C_6)$alkylthio of $R^{10}$ and $R^{11}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^aR^b$, and wherein any wherein any aryloxy, or arylthio of $R^{10}$ and $R^{11}$ is optionally substituted with one or more groups selected from halo, cyano, $C_1-C_6$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^aR^b$; or $R^{10}$ and $R^{11}$ together with the carbon to which they are attached form a carbonyl group;

at least one of $R^6$, $R^7$, $R^8$, $R^9$ and $R^{12}$ is aryl, heteroaryl, aryl($C_1-C_6$)alkyl, heteroaryl($C_1-C_6$)alkyl, or aryl($C_1$-$C_6$)alkanoyl; and the remainder of $R^6$, $R^7$, $R^8$, $R^9$ and $R^{12}$ are independently H, halo, nitro, $-NR^cR^d$, $(C_1-C_6)$alkyl, aryl, heteroaryl, aryl($C_1-C_6$)alkyl, heteroaryl($C_1-C_6$)alkyl, $(C_1-C_6)$alkanoyl or $-C(=O)NR^aR^b$, wherein the $(C_1-C_6)$alkyl, aryl, heteroaryl, aryl($C_1-C_6$)alkyl and heteroaryl($C_1-C_6$)alkyl of $R^6$, $R^7$, $R^8$, $R^9$ and $R^{12}$ are optionally substituted with or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^aR^b$;

each $R^a$ and $R^b$ is independently H, $(C_1-C_6)$alkyl, aryl, heteroaryl, aryl($C_1-C_6$)alkyl, or heteroaryl($C_1-C_6$)alkyl; or $R^a$ and $R^b$ together with the nitrogen to which they are attached form a morpholino, piperazino, pyrrolidino or piperidino;

each $R^c$ and $R^d$ is independently H, $(C_1-C_6)$alkyl, aryl, heteroaryl, aryl($C_1-C_6$)alkyl, or heteroaryl($C_1-C_6$)alkyl; or $R^c$ and $R^d$ together with the nitrogen to which they are attached form a morpholino, piperazino, pyrrolidino or piperidino;

$R^e$ is H or $(C_1-C_6)$alkyl;

$R^f$ and $R^g$ are each independently H, $(C_1-C_6)$alkyl, aryl, heteroaryl, aryl($C_1-C_6$)alkyl, or heteroaryl($C_1-C_6$)alkyl; or $R^f$ and $R^g$ together with the nitrogen to which they are attached form a morpholino, piperazino, pyrrolidino or piperidino; and when the nitrogen attached to $R^5$ is a positively charged quaternary nitrogen, the compound is associated with a suitable counterion $X^-$;

or a salt thereof.

3. The compound of claim 1 which is a compound of the following formula Ia:

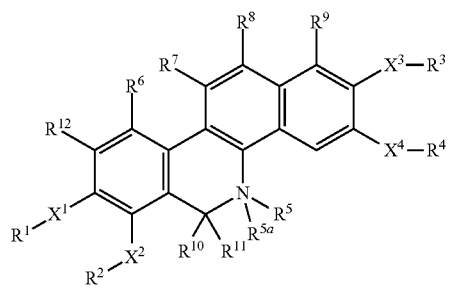

or a salt thereof.

4. The compound of claim 1 which is a compound of the following formula Ib:

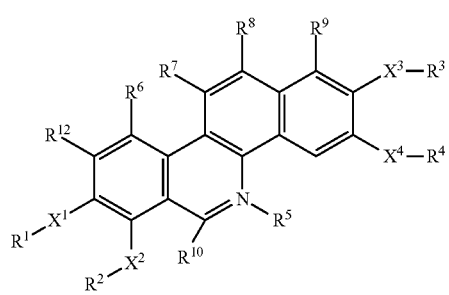

or a salt thereof.

5. The compound of claim 1 which is a compound of the following formula Ic:

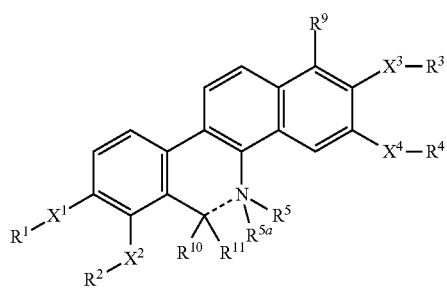

or a salt thereof.

6. The compound of claim 1 which is a compound of the following formula Id:

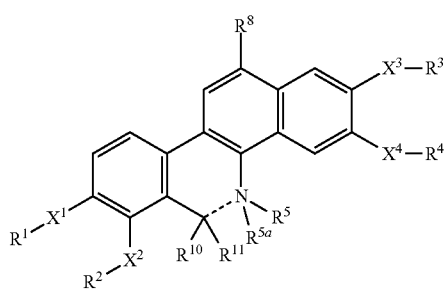

or a salt thereof.

7. The compound of claim 1 which is a compound of the following formula Ie:

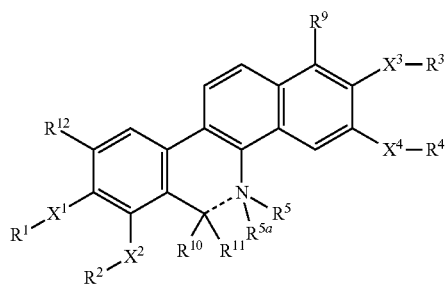

or a salt thereof.

8. The compound of claim 1 which is a compound of the following formula If:

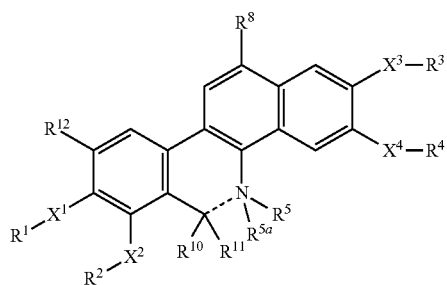

or a salt thereof.

9. The compound of claim 1 which is a compound of the following formula Ig:

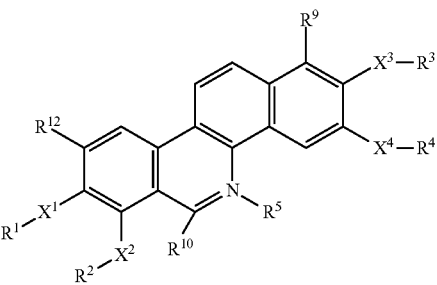

or a salt thereof.

10. The compound of claim 1 which is a compound of the following formula Ih:

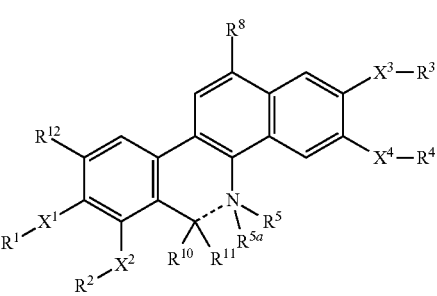

or a salt thereof.

11. The compound:

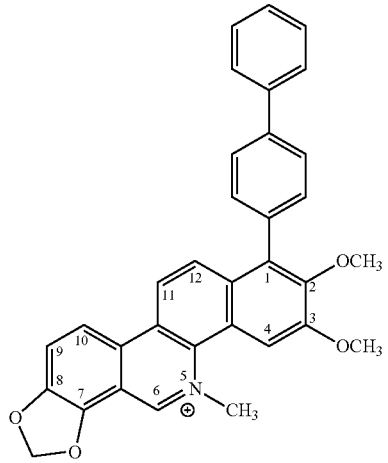

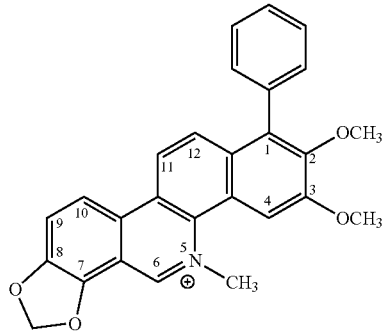

123
-continued
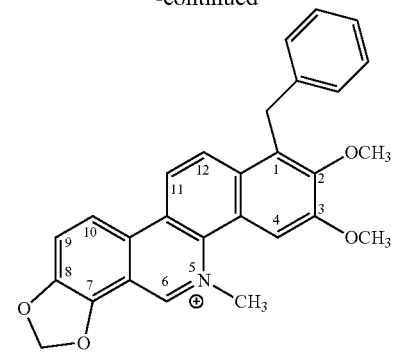
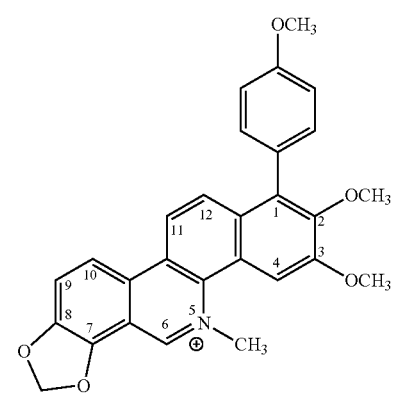
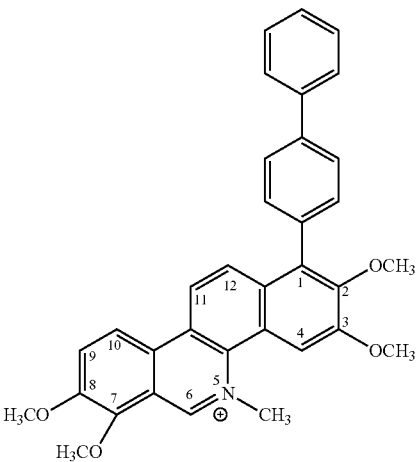
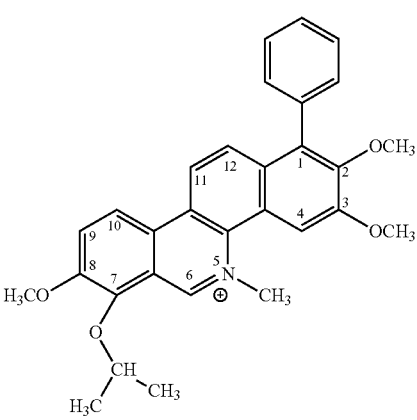
124
-continued
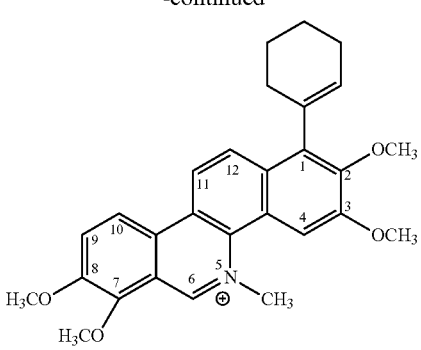
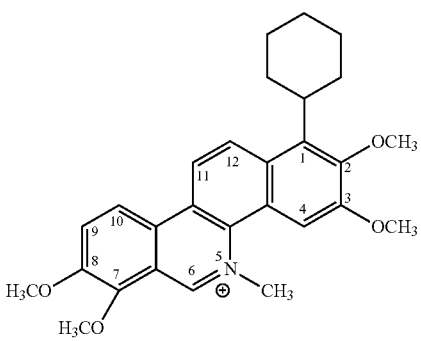
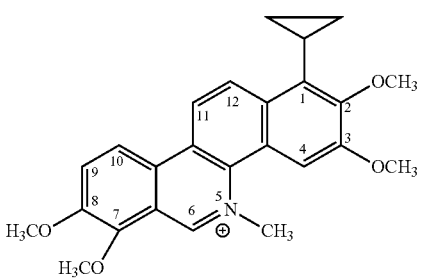
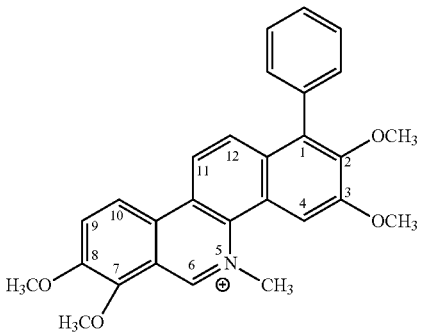

125
-continued
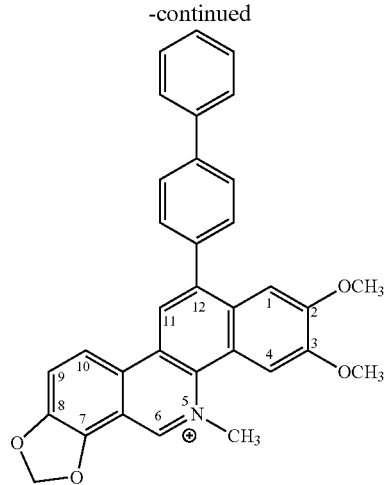
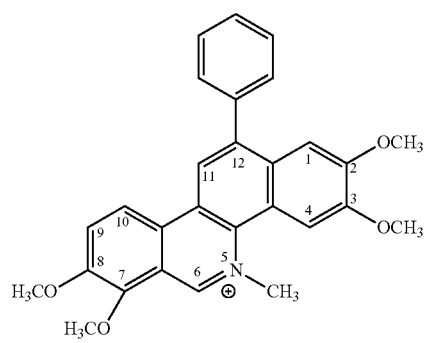
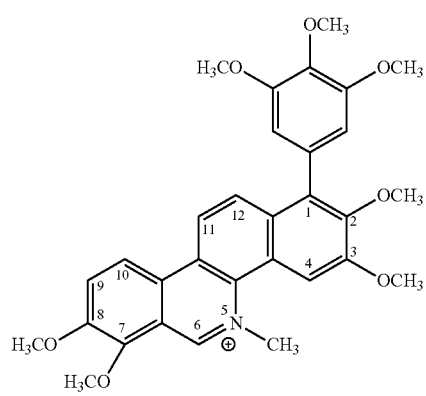
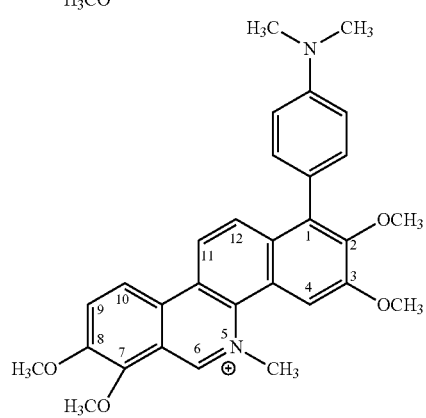
126
-continued
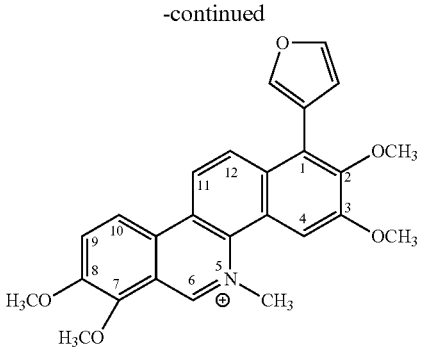
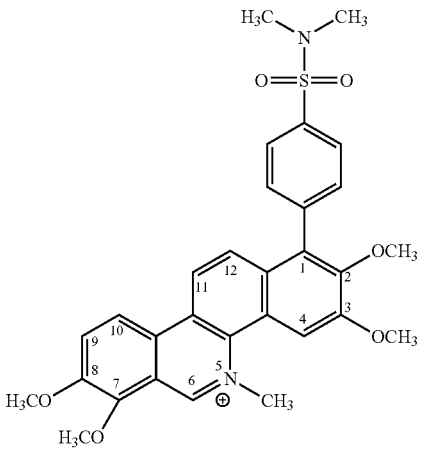
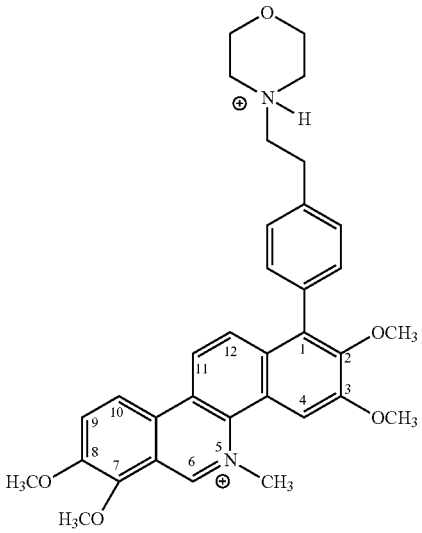

-continued
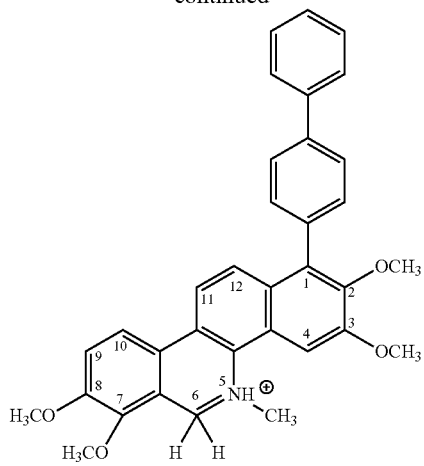
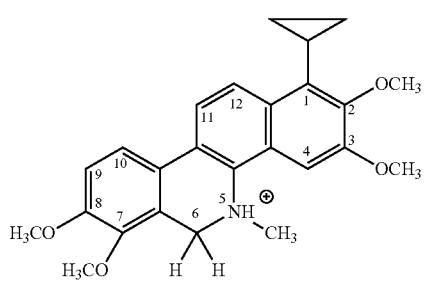
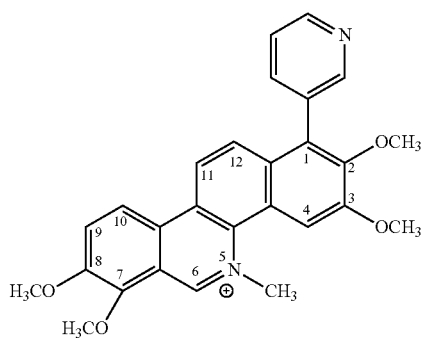
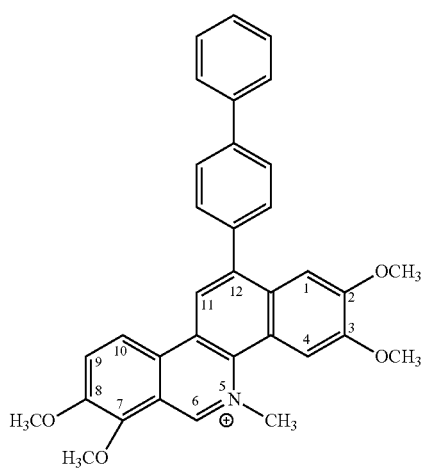
-continued
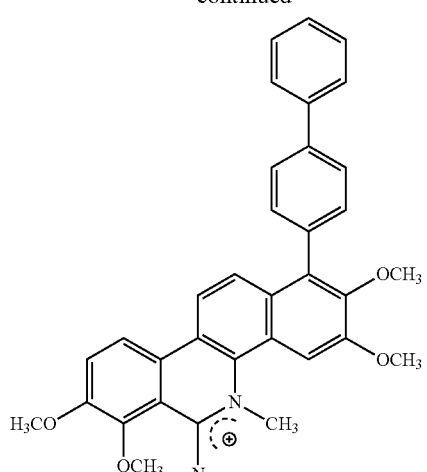
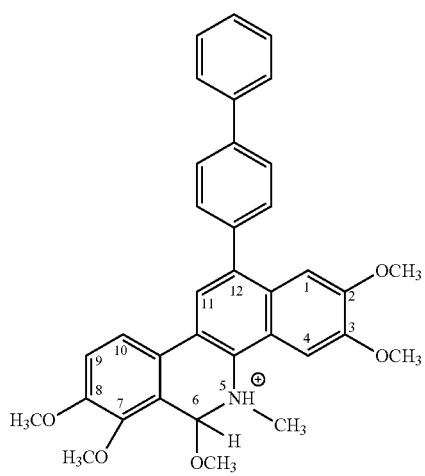
which is associated with one or more a pharmaceutically acceptable counterions; or a salt thereof.
12. The compound of claim 1 having a structure:
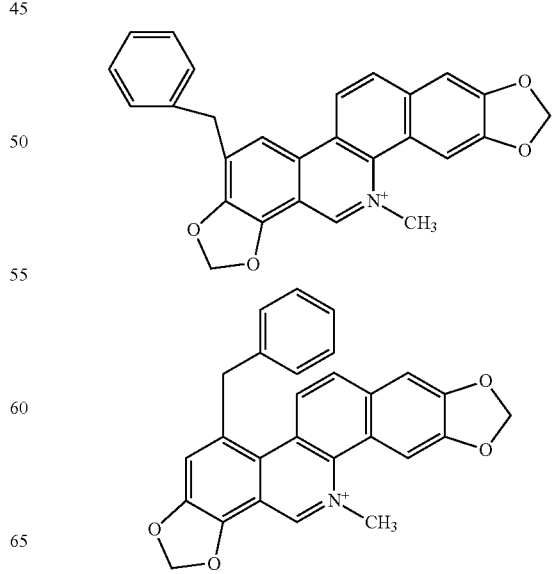

129
-continued
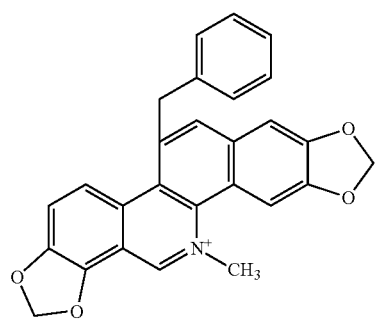
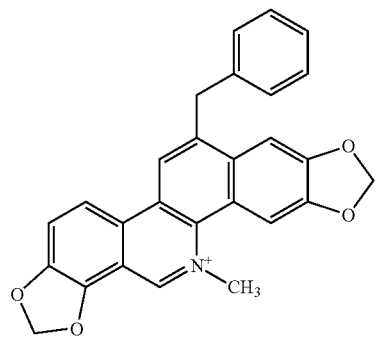
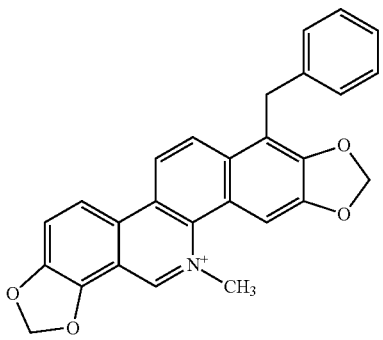
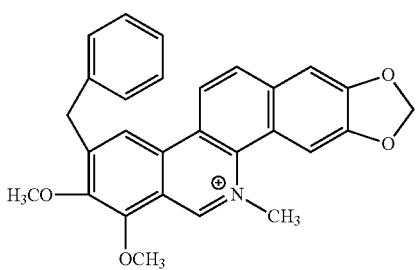
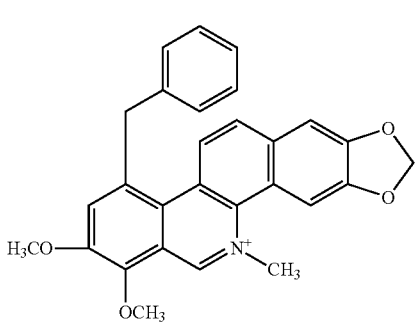
130
-continued
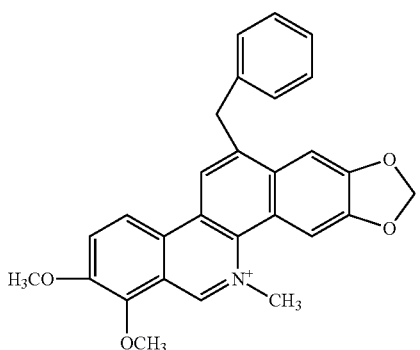
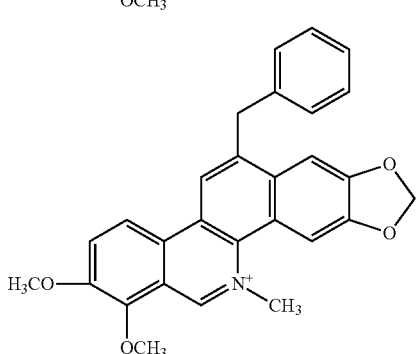
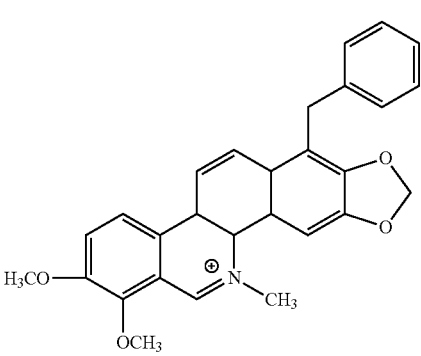
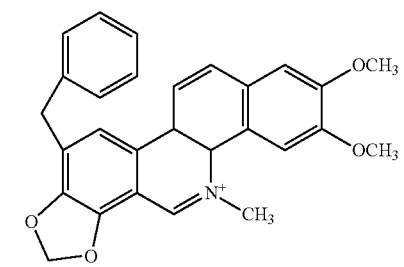
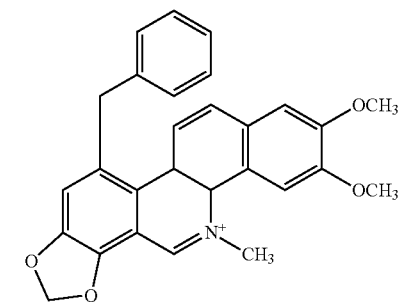

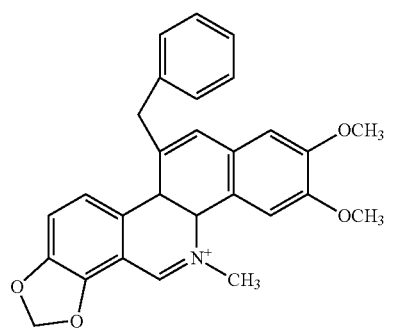
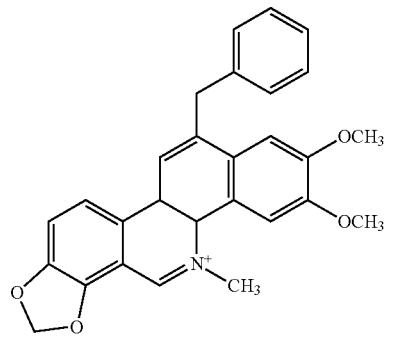
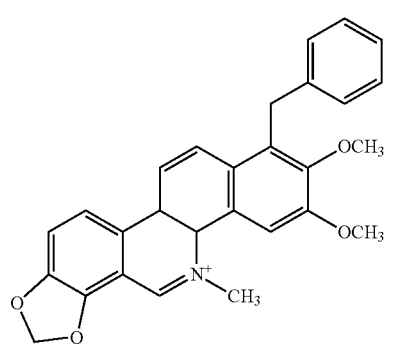
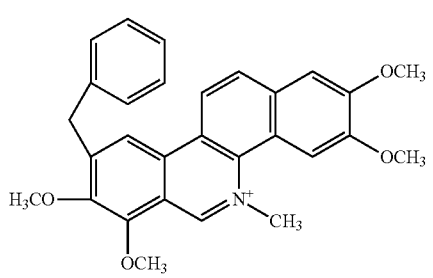
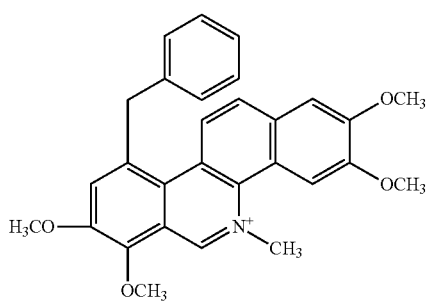
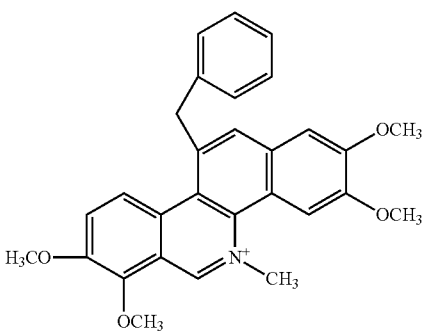
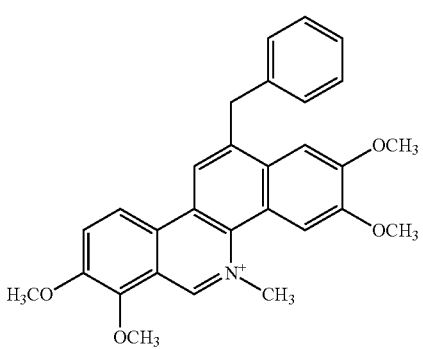
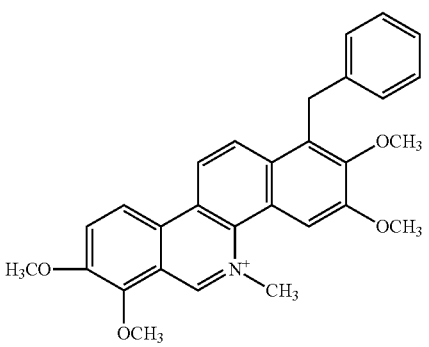 [SMILES: COc1cc2c(ccc3c4ccc(OC)c(OC)c4c[n+](C)c23)c(Cc2ccccc2)c1OC]
or
13. The compound of claim 1 having a structure:
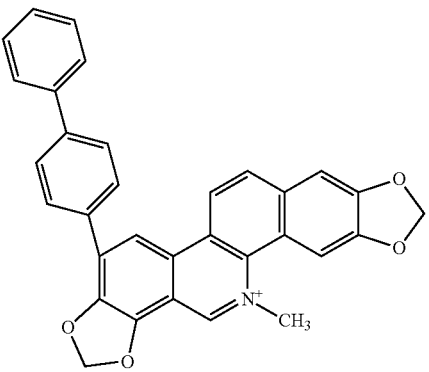

133
-continued
134
-continued
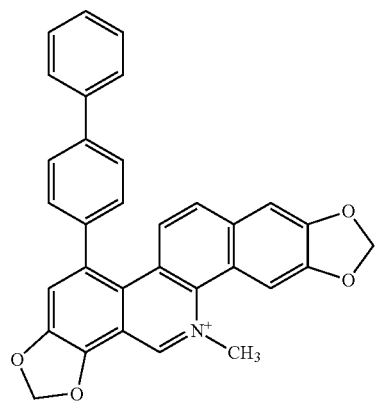
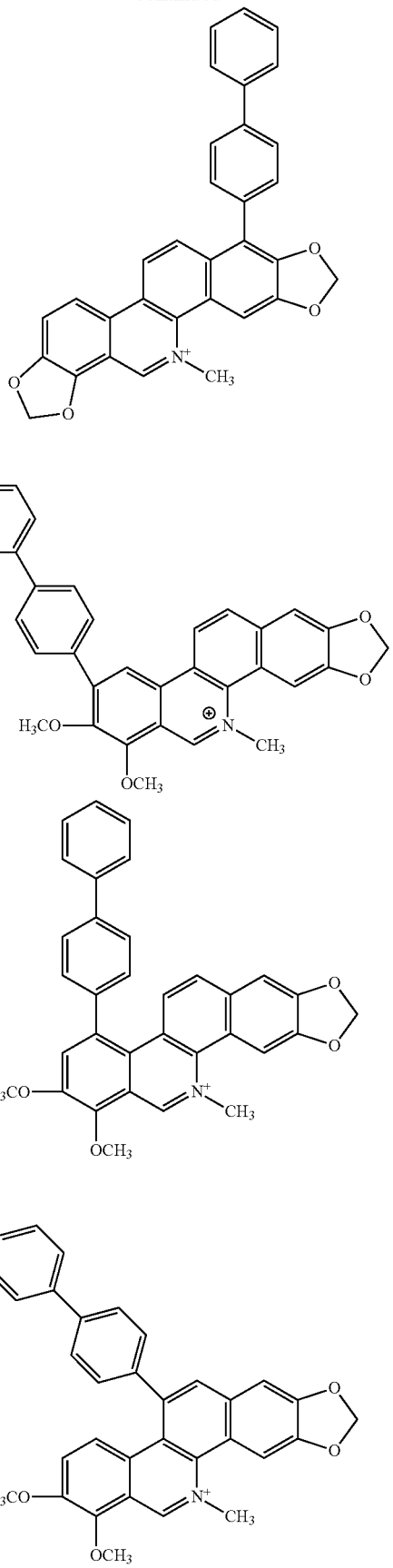

135
-continued
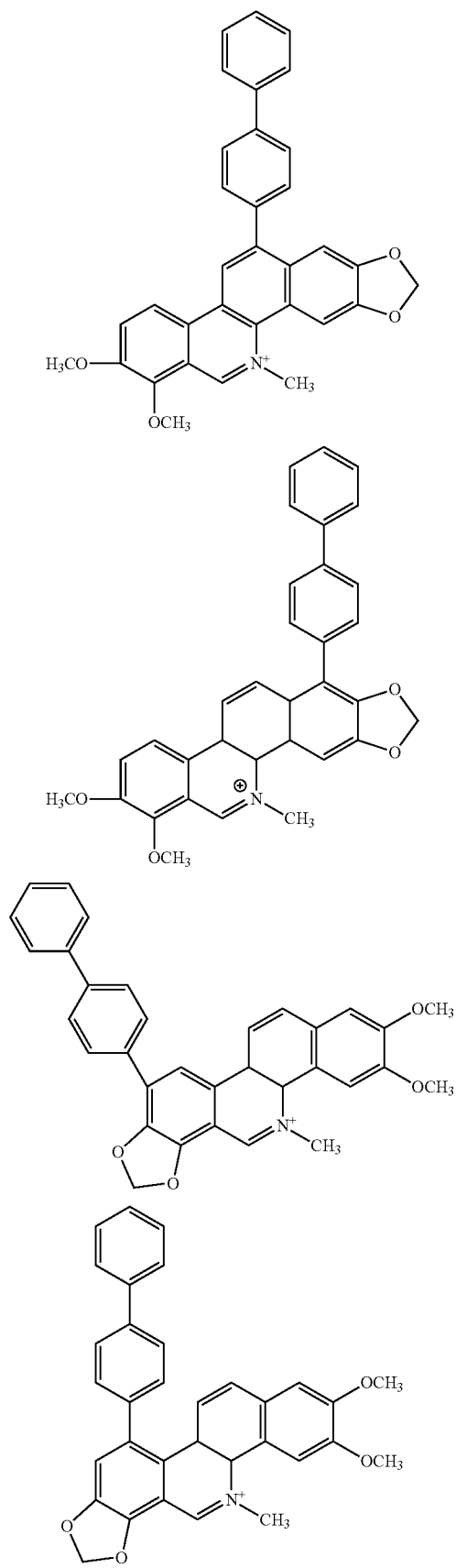
136
-continued
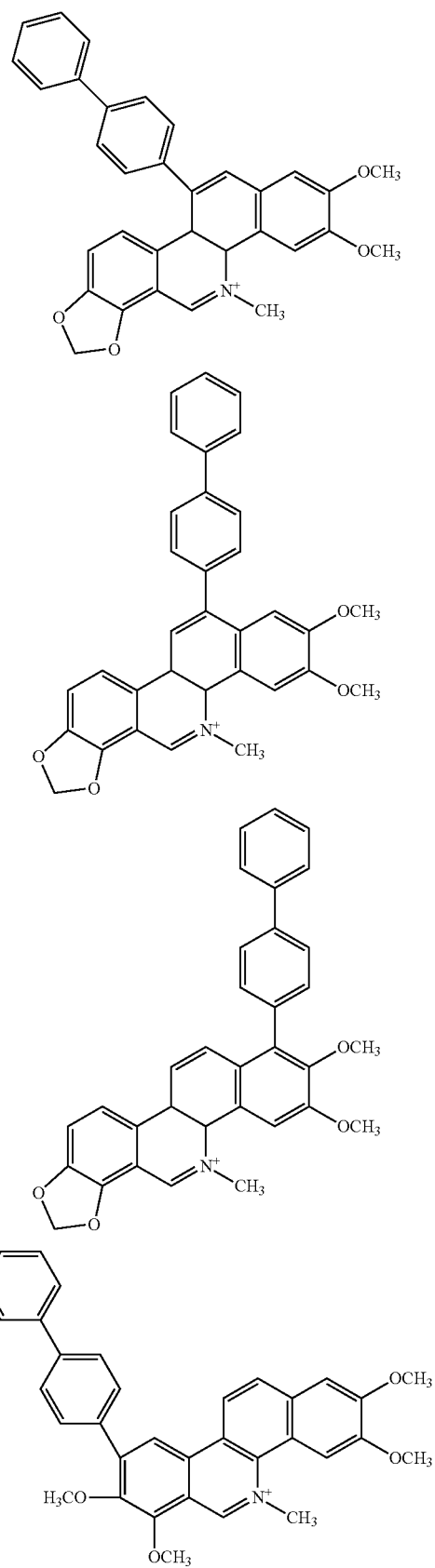

137
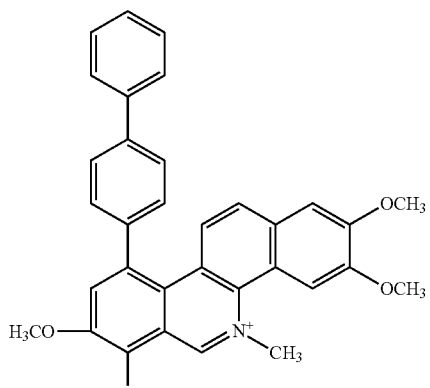
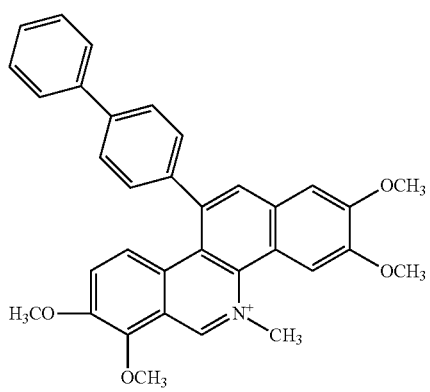
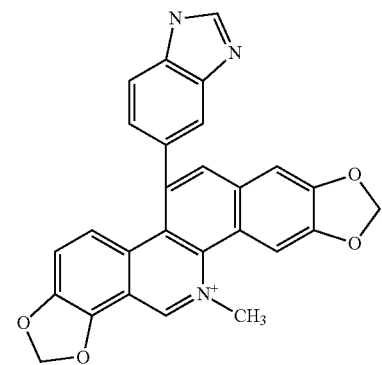
or
138
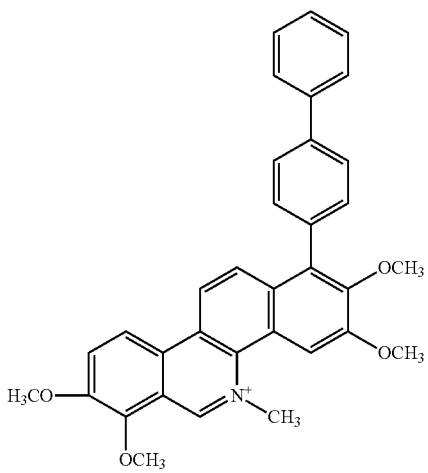 [SMILES: COc1cc2c(ccc3c4ccc(OC)c(OC)c4c[n+](C)c23)c(-c2ccc(-c3ccccc3)cc2)c1OC]
14. The compound of claim 1 having the structure:
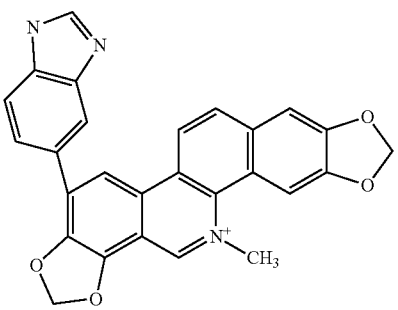
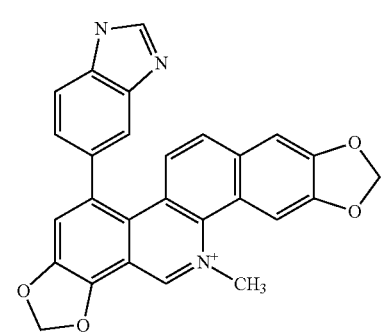
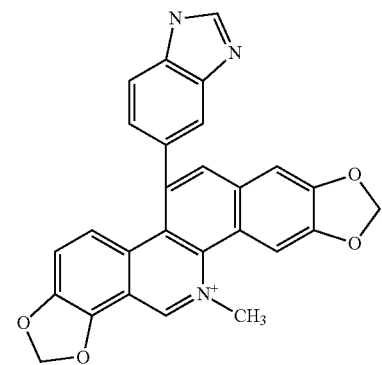

139
-continued
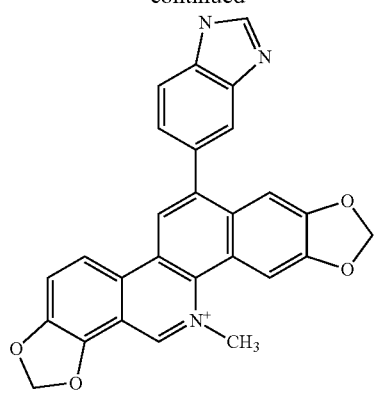
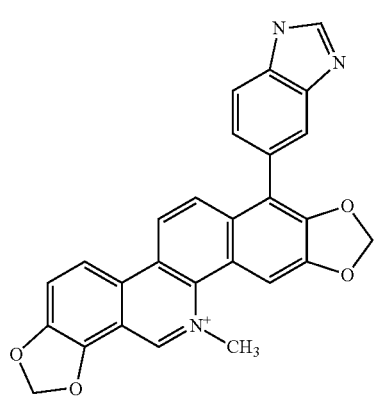
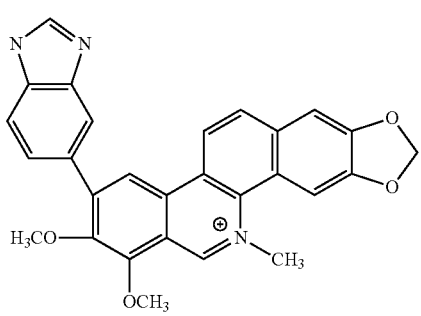
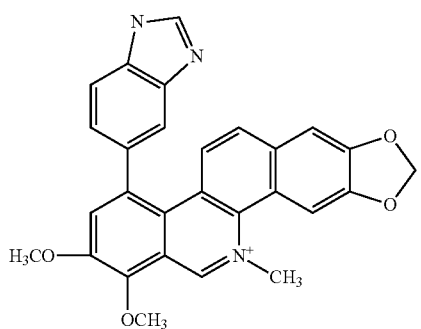
140
-continued
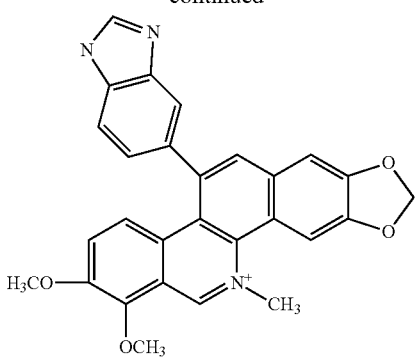
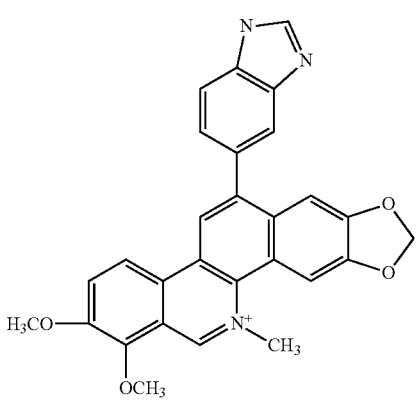
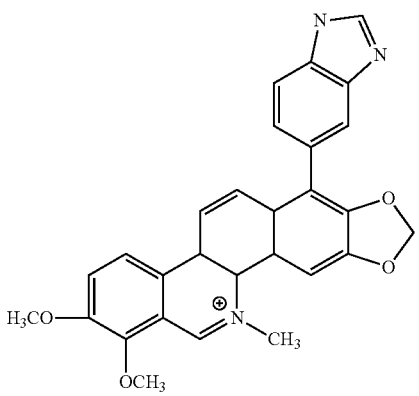
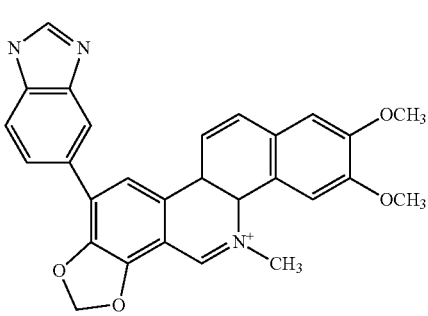

-continued

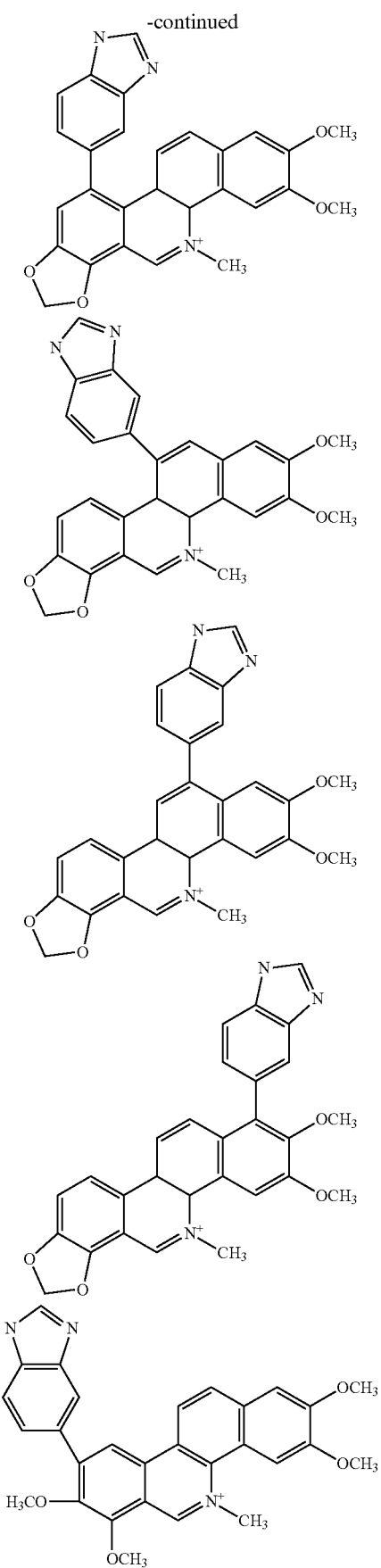

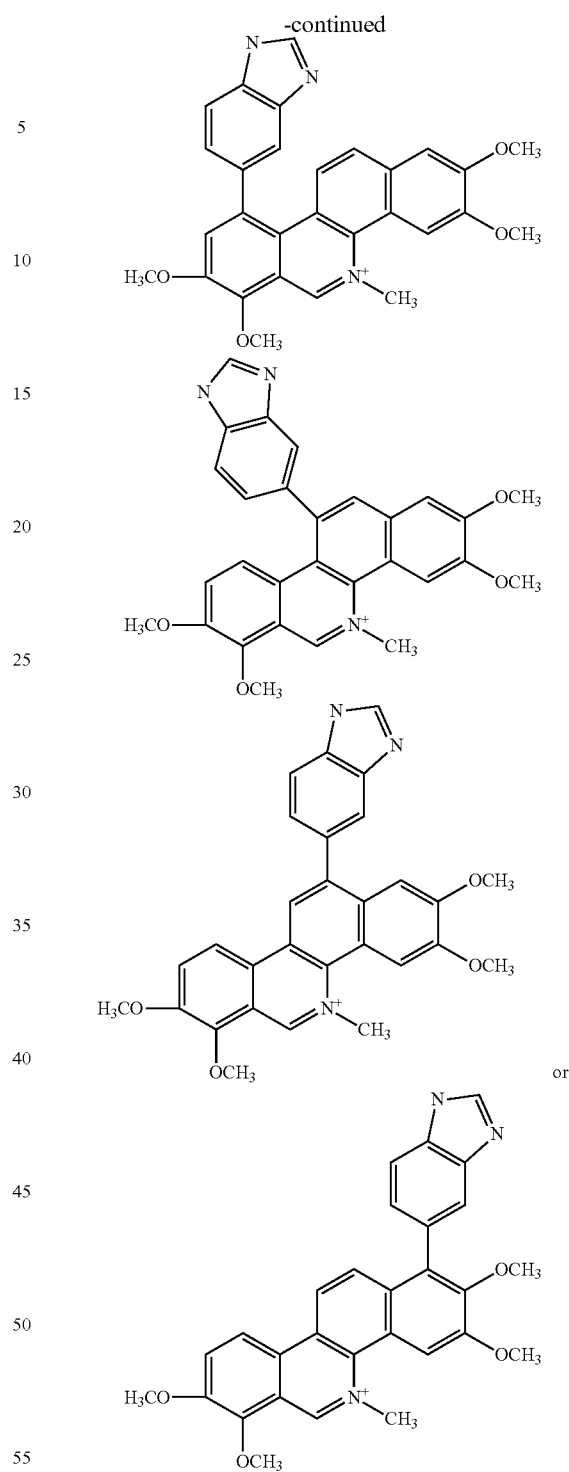

which is associated with one or more a pharmaceutically acceptable counterions; or a salt thereof.

15. A composition comprising a compound of formula I or a pharmaceutically acceptable salt thereof as described in claim 1; and a pharmaceutically acceptable carrier.

16. A method for treating a bacterial infection selected from *Staphylococcus aureus*, Methicillin-resistant *S. aureus*, *Enterococcus faecalis*, *Bacillus subtilis*, *Propionibacterium acnes*, and *Clostridium difficile*, in an animal comprising administering to the animal a compound of the formula I:

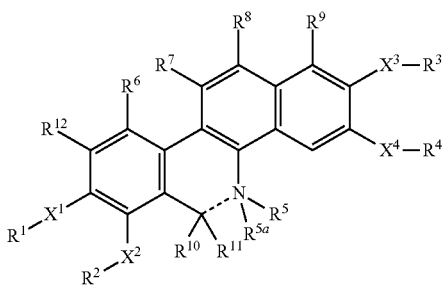

wherein:
  the bond represented by - - - is a single or double bond;
  when the bond represented by - - - is a single bond $R^5$, $R^{5a}$, $R^{10}$ and $R^{11}$ can have any of the values defined below; when the bond represented by - - - is a double bond $R^5$ can be absent or have any of the values defined below, $R^{10}$ can have any of the values defined below, and $R^{5a}$ and $R^{11}$ are absent;
  $X^1$, $X^2$, $X^3$ and $X^4$ are each independently O, S or $NR^e$;
  $R^1$ and $R^2$ are each independently, $(C_1-C_6)$alkyl, substituted $(C_1-C_6)$alkyl, $(C_1-C_6)$alkanoyl or $-C(=O)NR^fR^g$ or $R^1$ and $R^2$ together with the atoms to which they are attached form a 5 to 7 membered ring;
  $R^3$ and $R^4$ are each independently, $(C_1-C_6)$alkyl, $(C_1-C_6)$alkanoyl or $-C(=O)NR^fR^g$ or $R^3$ and $R^4$ together with the atoms to which they are attached form a 5 to 7 membered ring;
  $R^5$ is H, $(C_1-C_6)$alkyl, or substituted $(C_1-C_6)$alkyl; or $R^5$ and $R^{10}$ taken together with the atoms to which they are attached form a 5, 6, or 7 membered heterocyclic ring; and
  $R^{5a}$ is H, $(C_1-C_6)$alkyl, substituted $(C_1-C_6)$alkyl, or absent;
  at least one of $R^6$, $R^7$, $R^8$, $R^9$ and $R^{12}$ is substituted alkyl, optionally substituted alkenyl, optionally substituted alkynyl, optionally substituted cycloalkyl, optionally substituted arylalkyl, optionally substituted heteroarylalkyl, optionally substituted aryl, optionally substituted arylalkanoyl, $R^h$, or optionally substituted heteroaryl, wherein substituted alkyl is an alkyl group with 1 to 5 substituent groups independently selected from cycloalkyl, substituted cycloalkyl, alkoxycarbonyl, cyano, halo, hydroxyl, oxo, carboxy, aryloxy, heteroaryloxy, heterocyclooxy, nitro, and $-NR^aR^b$, wherein $R^a$ and $R^b$ may be the same or different and are chosen from hydrogen, alkyl, arylalkyl, heteroarylalkyl, cycloalkyl, substituted cycloalkyl, aryl, heteroaryl and heterocyclic; and the remainder of $R^6$, $R^7$, $R^8$, $R^9$ and $R^{12}$ are independently H, halo, nitro, $-NR^cR^d$ optionally substituted alkyl, optionally substituted arylalkyl, optionally substituted heteroarylalkyl, optionally substituted aryl, or optionally substituted heteroaryl or $R^{12}$ is $-X^{13}-R^{13}$ wherein $X^{13}$ is O, S or $NR^e$ and $R^{13}$ is $(C_1-C_6)$alkyl, substituted $(C_1-C_6)$alkyl, $(C_1-C_6)$alkanoyl or $-C(=O)NR^fR^g$ or $R^{13}$ and $R^1$ together with the atoms to which they are attached form a 5 to 7 membered ring;
  $R^{10}$ is H, optionally substituted $(C_1-C_6)$alkyl optionally substituted $(C_1-C_6)$alkoxy, optionally substituted $(C_1-C_6)$alkyl-$S(=O)_n-$, optionally substituted aryloxy, optionally substituted aryl, CN, $NR^pR^q$, or optionally substituted aryl-$S(=O)_n-$, wherein n is 0, 1, or 2; and
  $R^{11}$ is H or optionally substituted $(C_1-C_6)$alkyl; or $R^{10}$ and $R^{11}$ together with the carbon to which they are attached form a carbonyl group; or $R^{10}$ and $R^5$ taken together with the atoms to which they are attached form a 5, 6, or 7 membered heterocyclic ring;
  each $R^c$ and $R^d$ is independently H, $(C_1-C_6)$alkyl, aryl, heteroaryl, aryl$(C_1-C_6)$alkyl, or heteroaryl$(C_1-C_6)$alkyl; or $R^c$ and $R^d$ together with the nitrogen to which they are attached form a morpholino, piperazino, pyrrolidino or piperidino;
  $R^e$ is H or $(C_1-C_6)$alkyl;
  $R^f$ and $R^g$ are each independently H, aryl, heteroaryl, aryl$(C_1-C_6)$alkyl, heteroaryl$(C_1-C_6)$alkyl, or $(C_1-C_6)$alkyl; or $R^f$ and $R^g$ together with the nitrogen to which they are attached form a morpholino, piperazino, pyrrolidino or piperidino;
  each $R^h$ is independently selected from an aryl optionally substituted with one or more $R^k$, an alkyl substituted with one or more heterocycle, and an alkyl substituted with one or more substituted heterocycle;
  each $R^k$ is independently alkyl, substituted alkyl, alkoxy, substituted alkoxy, heteroaryl, heterocycle, or $-S(O)_2NR^mR^n$;
  each $R^m$ and $R^n$ is independently H, $(C_1-C_6)$alkyl, aryl, heteroaryl, aryl$(C_1-C_6)$alkyl, or heteroaryl$(C_1-C_6)$alkyl; or $R^m$ and $R^n$ together with the nitrogen to which they are attached form a morpholino, piperazino, pyrrolidino or piperidino; and
  each $R^p$ and $R^q$ is independently H, $(C_1-C_6)$alkyl, aryl, heteroaryl, aryl$(C_1-C_6)$alkyl, or heteroaryl$(C_1-C_6)$alkyl; or $R^p$ and $R^q$ together with the nitrogen to which they are attached form a morpholino, piperazino, pyrrolidino or piperidino; and
  when the nitrogen attached to $R^5$ is a positively charged quaternary nitrogen, the compound is associated with a suitable counterion $X^-$;
  or a salt thereof.

17. A method for inhibiting bacterial cell division comprising contacting a bacterial cell (in vitro or in vivo) with a compound as described in claim 1, wherein the bacterial cell is selected from *Staphylococcus aureus*, Methicillin-resistant *S. aureus, Enterococcus faecalis, Bacillus subtilis, Propionibacterium acnes*, and *Clostridium difficile.*

18. A method for inhibiting FtsZ Z-ring formation within a bacterial cell comprising contacting the bacterial cell (in vitro or in vivo) with a compound as described in claim 1, wherein the bacterial cell is selected from *Staphylococcus aureus*, Methicillin-resistant *S. aureus, Enterococcus faecalis, Bacillus subtilis, Propionibacterium acnes*, and *Clostridium difficile.*

19. A method for inhibiting polymerization of a FtsZ protein within a bacterial cell comprising contacting the bacterial cell (in vitro or in vivo) with a compound as described in claim 1, wherein the bacterial cell is selected from *Staphylococcus aureus*, Methicillin-resistant *S. aureus, Enterococcus faecalis, Bacillus subtilis, Propionibacterium acnes*, and *Clostridium difficile.*

20. A method for binding a compound of formula I or a salt thereof to a GTP binding pocket of a FtsZ protein within a *Bacillus subtilis* bacterial cell comprising contacting the bacterial cell (in vitro or in vivo) with a compound as described in claim 1.

* * * * *